(12) United States Patent
Xiang et al.

(10) Patent No.: US 12,195,479 B2
(45) Date of Patent: Jan. 14, 2025

(54) FIVE- AND SIX-MEMBERED COMPOUND, AND PREPARATION METHOD THEREFOR AND PHARMACEUTICAL COMPOSITION AND USE THEREOF

(71) Applicant: HANGZHOU POLYMED BIOPHARMACEUTICALS, INC., Zhejiang (CN)

(72) Inventors: Jason Shaoyun Xiang, Zhejiang (CN); Lei Wu, Zhejiang (CN); Rui Xu, Zhejiang (CN); Qiang Zhang, Zhejiang (CN); Gang Yang, Zhejiang (CN); Michael Xiang, Zhejiang (CN); Mixue Tong, Zhejiang (CN); Camille Xiang, Zhejiang (CN); Yuxin Liu, Zhejiang (CN); Suyue Wang, Zhejiang (CN); Rui Yang, Zhejiang (CN)

(73) Assignee: HANGZHOU POLYMED BIOPHARMACEUTICALS, INC., Zhejiang (CN)

( * ) Notice: Subject to any disclaimer, the term of this patent is extended or adjusted under 35 U.S.C. 154(b) by 0 days.

(21) Appl. No.: 18/544,546

(22) Filed: Dec. 19, 2023

(65) Prior Publication Data

US 2024/0208993 A1  Jun. 27, 2024

Related U.S. Application Data

(63) Continuation-in-part of application No. PCT/CN2022/141282, filed on Dec. 23, 2022.

(30) Foreign Application Priority Data

Dec. 23, 2021 (CN) .......................... 202111593577.4
Dec. 6, 2022  (CN) .......................... 202211580672.5

(51) Int. Cl.
| | | |
|---|---|---|
| C07D 498/08 | (2006.01) | |
| A61K 31/422 | (2006.01) | |
| A61K 31/437 | (2006.01) | |
| A61K 31/439 | (2006.01) | |
| A61K 31/4439 | (2006.01) | |
| A61K 31/4545 | (2006.01) | |
| A61K 31/496 | (2006.01) | |

(Continued)

(52) U.S. Cl.
CPC .......... *C07D 498/08* (2013.01); *A61K 31/422* (2013.01); *A61K 31/437* (2013.01); *A61K 31/439* (2013.01); *A61K 31/4439* (2013.01); *A61K 31/4545* (2013.01); *A61K 31/496* (2013.01); *A61K 31/4985* (2013.01); *A61K 31/5377* (2013.01); *A61K 31/5386* (2013.01); *A61P 35/02* (2018.01); *C07D 401/14* (2013.01); *C07D 413/14* (2013.01); *C07D 417/14* (2013.01); *C07D 471/04* (2013.01); *C07D 471/08* (2013.01); *C07D 487/04* (2013.01); *C07D 491/107* (2013.01); *C07D 493/08* (2013.01); *C07D 498/04* (2013.01); *C07D 513/04* (2013.01); *C07D 519/00* (2013.01)

(58) Field of Classification Search
CPC ..................................................... C07D 498/08
USPC ........................................................ 514/230.5
See application file for complete search history.

(56) References Cited

U.S. PATENT DOCUMENTS 6,031,095 A * 2/2000 Nelson ................ C07D 413/10
546/14

FOREIGN PATENT DOCUMENTS

| CN | 106456619 A | 2/2017 |
|---|---|---|
| CN | 106458982 A | 2/2017 |

(Continued)

OTHER PUBLICATIONS

International Search Report for PCT/CN2022/141282, 8 pages.

*Primary Examiner* — Niloofar Rahmani
(74) *Attorney, Agent, or Firm* — Dority & Manning, P.A.

(57) ABSTRACT

A five-membered-fused six-membered compound, and a preparation method therefor and a pharmaceutical composition and the use thereof. The five- and six-membered compound is a compound as shown in formula I, II or III. The compound has an inhibitory effect on FLT3 and/or IRAK4.

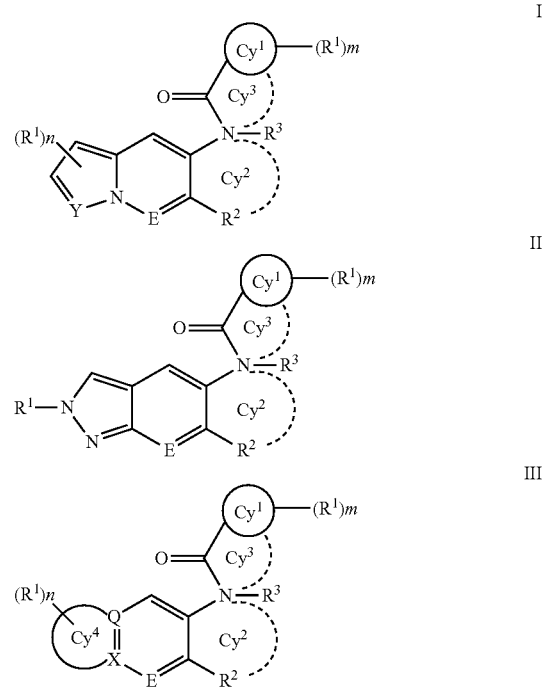

12 Claims, No Drawings

(51) Int. Cl.
  *A61K 31/4985* (2006.01)
  *A61K 31/5377* (2006.01)
  *A61K 31/5386* (2006.01)
  *A61P 35/02* (2006.01)
  *C07D 401/14* (2006.01)
  *C07D 413/14* (2006.01)
  *C07D 417/14* (2006.01)
  *C07D 471/04* (2006.01)
  *C07D 471/08* (2006.01)
  *C07D 487/04* (2006.01)
  *C07D 491/107* (2006.01)
  *C07D 493/08* (2006.01)
  *C07D 498/04* (2006.01)
  *C07D 513/04* (2006.01)
  *C07D 519/00* (2006.01)

(56) References Cited

FOREIGN PATENT DOCUMENTS

| | | |
|---|---|---|
| CN | 108024971 A | 5/2018 |
| CN | 108026065 A | 5/2018 |
| CN | 110691589 A | 1/2020 |
| CN | 111225911 A | 6/2020 |
| CN | 113278017 A | 8/2021 |
| CN | 113646305 A | 11/2021 |
| WO | WO2017023941 A1 | 2/2017 |
| WO | WO2020264499 A1 | 12/2020 |

* cited by examiner

FIVE- AND SIX-MEMBERED COMPOUND, AND PREPARATION METHOD THEREFOR AND PHARMACEUTICAL COMPOSITION AND USE THEREOF

CROSS-REFERENCE TO RELATED APPLICATIONS

The present application is a Continuation-in-part Application of International Application No. PCT/CN2022/141282, filed on Dec. 23, 2022, which claims the right of the priorities of Chinese patent application 2021115935774 filed on Dec. 23, 2021 and Chinese patent application 2022115806725 filed on Dec. 6, 2022. The contents of the above Chinese patent applications are incorporated herein by reference in their entireties.

TECHNICAL FIELD

The present disclosure relates to a five-membered-fused six-membered compound, and a preparation method therefor and a pharmaceutical composition and a use thereof.

BACKGROUND

FMS-like tyrosine kinase 3 (FLT3) is a type III receptor tyrosine kinase, and its mutation is one of the most common genetic alterations and poor prognostic factors in patients with acute myeloid leukemia (AML). The primary types of FLT3 mutations are internal tandem duplications (FLT3-ITD) in the juxtamembrane domain and point mutations or deletions in the tyrosine kinase domain (FLT3-TKD), which account for approximately 30% of AML patients (Kiyoi H, Kawashima N, Ishikawa Y. FLT3 mutations in acute myeloid leukemia: Therapeutic paradigm beyond inhibitor development. Cancer Sci. 2020 February; 111(2):312-322). Mutation caused overactivation of FLT3 induces abnormalities in multiple intracellular signaling pathways (such as RAS, PI3K, and STATS), leading to the survival, proliferation, differentiation, and resistance to apoptosis of hematopoietic cells. In addition, the prognostic role of FLT3-ITD in patients newly diagnosed FLT3-ITD mutated AML can be influenced by factors such as the ratio of mutant-wild-type alleles, insertion sites, ITD length, karyotype, and the presence of NPM1 gene mutations (Daver N, Schlenk R F, Russell N H, Levis M J. Targeting FLT3 mutations in AML: review of current knowledge and evidence. Leukemia. 2019 February; 33(2):299-312. doi: 10.1038/s41375-018-0357-9). Due to the limited improvement in prognosis with high-dose chemotherapy and allogeneic hematopoietic stem cell transplantation and the fact that patients have short survival periods and are prone to relapse, FLT3 kinase inhibitors have become a research hotspot in the treatment of AML. The first generation of FTL3 inhibitors are broad-spectrum inhibitors, such as Lestaurtinib, Sunitinib, Sorafenib, Ponatinib, and Midostaurin, which can inhibit a number of kinases. However, their efficacy is not satisfactory, and no clear therapeutic effect has been observed when used in combination with chemotherapy. Moreover, their use significantly increases toxicity. For example, the efficacy of Midostaurin as a monotherapy is not satisfactory, but it can be used in combination with Cytarabine, Daunorubicin, and Cytarabine (approved by the FDA) for the treatment of adult AML with FLT3 mutations. The second generation of FLT3 kinase inhibitors such as Gilteritinib, Crenolanib, and Quizartinib are more selective, more active and less toxic, but still have certain off-target effects.

Currently, three FLT3 inhibitors (Quizartinib, Gilteritinib, Midostaurin) have been approved for marketing in Japan and/or the United States, and are used as a monotherapy or in combination with conventional chemotherapy drugs to treat AML patients. These inhibitors have shown good therapeutic responses in clinical practice and have improved the prognosis of AML patients to a certain extent. When used as a monotherapy, disease relapses quickly, and target-dependent and non-target-dependent drug resistance has developed. Target-dependent mutations are commonly seen in activation loops (such as aspartate 835, D835) and gating residues (such as phenylalanine 691, F691), wherein D835 mutation is the most common target resistance mutation site. The activation of related signaling pathways can also compensate for the inhibition of the FLT3 signaling pathway. Some researchers have reduced the proportion of non-target drug resistance by directly inhibiting related signaling pathways (such as PI3K/AKT and/or RAS/MEK/MAPK) or using combination therapy to jointly inhibit cell survival-related signaling pathways, but the effects are still somewhat limited (Rabik C A, Wang J, Pratilas C A. FLT3-IRAK dual targeting: an exciting new therapeutic option guided by adaptive activation of immune response pathways. Ann Transl Med. 2020 April; 8(7):511). After Quizartinib and Gilteritinib were administered for a period of time, no significant inhibition of tumor cells was seen, although a decrease in pFLT3 and pSTAT5 expression was seen. It can also be seen in relapsed cases that the phosphorylation level of IRAK4 is increased in most cases. When an IRAK4 inhibitor is used in combination, a decrease in tumor cell survival rate is observed, suggesting that IRAK4 could serve as a target for non-target drug resistance.

Interleukin-1 receptor-associated kinases (IRAKs) are serine/threonine protein kinases that belong to the tyrosine-like kinase (TLK) family, of which IRAK1 and IRAK4 have kinase activity. IRAKs are located downstream of the toll like receptor and IL-1R pathways and play an important role in innate immune signaling Stimulation of TLRs can recruit MYD88 and activates the receptor complex, which then forms a complex with IRAK4 to activate IRAK1. Subsequently, TRAF6 is activated by IRAK1, leading to NF-kB activation. Abnormal activation of the IRAK pathway in tumor cells can further promote disease progression through the inflammatory response in the tumor microenvironment (Gummadi V R, Boruah A, Ainan B R, Vare B R, Manda S, Gondle H P, Kumar S N, Mukherjee S, Gore S T, Krishnamurthy N R, Marappan S, Nayak S S, Nellore K, Balasubramanian W R, Bhumireddy A, Giri S, Gopinath S, Samiulla D S, Daginakatte G, Basavaraju A, Chelur S, Eswarappa R, Belliappa C, Subramanya H S, Booher R N, Ramachandra M, Samajdar S. Discovery of CA-4948, an Orally Bioavailable IRAK4 Inhibitor for Treatment of Hematologic Malignancies. ACS Med Chem Left. 2020 Oct. 14; 11(12):2374-2381). The development of a dual-target compound for FLT3/IRAK4 has potential clinical application value and is anticipated to improve patient prognosis and reduce the likelihood of drug resistance.

BRIEF SUMMARY OF THE INVENTION

The present disclosure provides a five-membered-fused six-membered compound, and a preparation method therefor and a pharmaceutical composition and a use thereof. The compound of the present disclosure has an inhibitory effect on FLT3 and/or IRAK4 as well as potential clinical application value, and is anticipated to improve patient prognosis and reduce the likelihood of drug resistance.

The present disclosure provides a five-membered-fused six-membered compound of formula I or a pharmaceutically acceptable salt thereof,

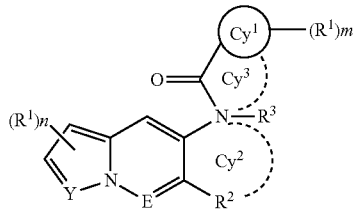

wherein
Y is N or CH;
E is N or CH;
n is 1, 2, or 3;
m is 1, 2, or 3;
$R^3$ is hydrogen or $R^3$ is absent; when $R^3$ is absent, N and the atom on ring $Cy^1$, together with the atoms to which they are attached, form ring $Cy^3$, or N and the atom on $R^2$, together with the atoms to which they are attached, form ring $Cy^2$;
ring $Cy^1$ is a 5-membered heteroaromatic ring, the heteroatom of the 5-membered heteroaromatic ring is selected from one or more than one of N, S, and O, and the number of heteroatoms is 1, 2, or 3;
ring $Cy^2$ is a 5- to 9-membered heterocyclic ring; the heteroatom of the 5- to 9-membered heterocyclic ring is selected from one or more than one of N, S, and O, and the number of heteroatoms is 1, 2, or 3, and at least one heteroatom is N;
ring $Cy^3$ is an oxo-5- to 9-membered heterocyclic ring; the heteroatom of the oxo-5- to 9-membered heterocyclic ring is selected from one or more than one of N, S, and O, and the number of heteroatoms is 1, 2, or 3, and at least one heteroatom is N;
each $R^1$ is independently hydrogen, halogen, nitro, cyano, hydroxyl,

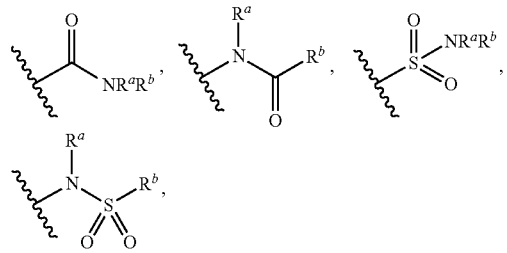

$-SO_2-R^a$, $-SO-R^a$,

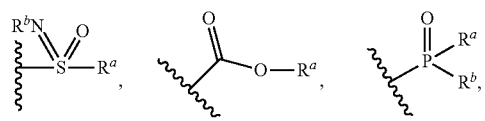

unsubstituted 3- to 11-membered heterocycloalkyl, 3- to 11-membered heterocycloalkyl substituted by one or more than one $R^{1-1}$, unsubstituted 3- to 10-membered cycloalkyl, 3- to 10-membered cycloalkyl substituted by one or more than one $R^{1-2}$,

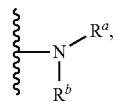

unsubstituted $C_{1-6}$ alkyl, $C_{1-6}$ alkyl substituted by one or more than one $R^{1-4}$, unsubstituted 6- to 10-membered aryl, 6- to 10-membered aryl substituted by one or more than one $R^{1-5}$, unsubstituted 5- to 10-membered heteroaryl, 5- to 10-membered heteroaryl substituted by one or more than one $R^{1-6}$, unsubstituted $C_{1-6}$ alkoxy, $C_{1-6}$ alkoxy substituted by one or more than one $R^{1-7}$, hydroxyl substituted by $R^{1-8}$, or $-O-COR^a$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;
$R^{1-1}$, $R^{1-2}$, $R^{1-4}$, $R^{1-5}$, $R^{1-6}$, and $R^{1-7}$ are each independently deuterium, halogen, oxo,

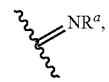

hydroxyl, unsubstituted 3- to 11-membered heterocycloalkyl, 3- to 11-membered heterocycloalkyl substituted by one or more than one $R^{1-1-1}$,

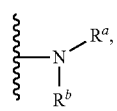

cyano, unsubstituted $C_{1-6}$ alkoxy, $C_{1-6}$ alkoxy substituted by one or more than one $R^{1-1-3}$,

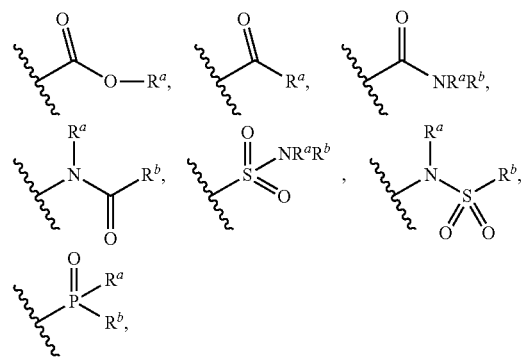

unsubstituted $C_{1-6}$ alkyl, $C_{1-6}$ alkyl substituted by one or more than one $R^{1-1-4}$, unsubstituted 3- to 10-membered cycloalkyl, 3- to 10-membered cycloalkyl substituted by one or more than one $R^{1-1-5}$, $-SO_2-R^a$, $-SO-R^a$,

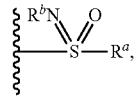

unsubstituted 6- to 10-membered aryl, 6- to 10-membered aryl substituted by one or more than one $R^{1-1-8}$, unsubstituted 5- to 10-membered heteroaryl, or 5- to 10-membered heteroaryl substituted by one or more than one $R^{1-1-7}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{1-8}$ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{1-1-1}$, $R^{1-1-3}$, $R^{1-1-4}$, $R^{1-1-5}$, $R^{1-1-7}$, and $R^{1-1-8}$ are each independently deuterium, unsubstituted $C_{1-6}$ alkyl, $C_{1-6}$ alkyl substituted by one or more than one halogen, halogen, oxo,

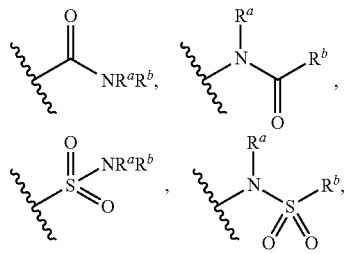

or hydroxyl;

$R^2$ is hydrogen, halogen, cyano, hydroxyl, nitro,

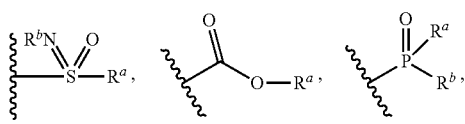

—SO$_2$—$R^a$, —SO—$R^a$,

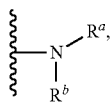

unsubstituted 3- to 11-membered heterocycloalkyl, 3- to 11-membered heterocycloalkyl substituted by one or more than one $R^{2-1}$, unsubstituted 3- to 10-membered cycloalkyl, 3- to 10-membered cycloalkyl substituted by one or more than one $R^{2-2}$,

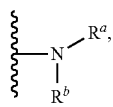

unsubstituted $C_{1-6}$ alkyl, $C_{1-6}$ alkyl substituted by one or more than one $R^{2-4}$, unsubstituted 6- to 10-membered aryl, 6- to 10-membered aryl substituted by one or more than one $R^{2-5}$, unsubstituted 5- to 10-membered heteroaryl, 5- to 10-membered heteroaryl substituted by one or more than one $R^{2-6}$, hydroxyl substituted by $R^{2-8}$, unsubstituted $C_{1-6}$ alkoxy, $C_{1-6}$ alkoxy substituted by one or more than one $R^{2-7}$, or —O—COR$^a$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{2-1}$, $R^{2-2}$, $R^{2-4}$, $R^{2-5}$, $R^{2-6}$, and $R^{2-7}$ are each independently deuterium, halogen, oxo, hydroxyl, unsubstituted 3- to 11-membered heterocycloalkyl, 3- to 11-membered heterocycloalkyl substituted by one or more than one $R^{2-1-1}$,

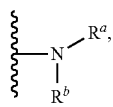

cyano, unsubstituted $C_{1-6}$ alkoxy, $C_{1-6}$ alkoxy substituted by one or more than one $R^{2-1-3}$,

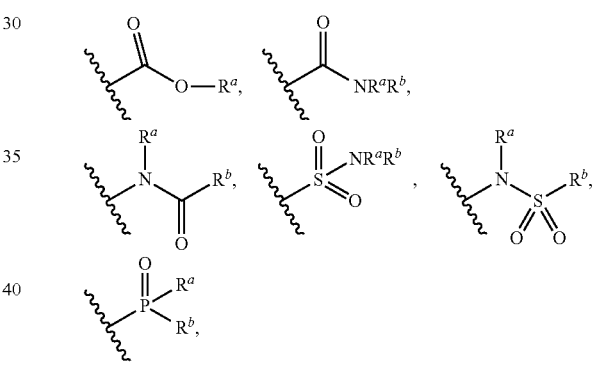

unsubstituted $C_{1-6}$ alkyl, $C_{1-6}$ alkyl substituted by one or more than one $R^{2-1-4}$, unsubstituted 3- to 10-membered cycloalkyl, 3- to 10-membered cycloalkyl substituted by one or more than one $R^{2-1-5}$, —SO$_2$—$R^a$, —SO—$R^a$,

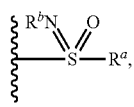

6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{2-8}$ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{2-1-1}$, $R^{2-1-3}$, $R^{2-1-4}$, and $R^{2-1-5}$ are each independently deuterium, unsubstituted $C_{1-6}$ alkyl, $C_{1-6}$ alkyl substituted by one or more than one halogen, halogen, oxo, or hydroxyl;

each $R^4$ is independently hydrogen, halogen, unsubstituted 5- to 10-membered heteroaryl, 5- to 10-membered heteroaryl substituted by one or more than one $R^{4-1}$, unsubstituted $C_{1-6}$ alkyl, $C_{1-6}$ alkyl substituted by one or more than one $R^{4-2}$, unsubstituted 3- to 11-membered heterocycloalkyl, 3- to 11-membered heterocycloalkyl substituted by one or more than one $R^{4-3}$, unsubstituted 3- to 10-membered cycloalkyl, 3- to 10-membered cycloalkyl substituted by one or more than one $R^{4-4}$, unsubstituted 6- to 10-membered aryl, or 6- to 10-membered aryl substituted by one or more than one $R^{4-5}$; the heteroatom of the 3- to 11-membered heterocycloalkyl is selected from one or more than one of N, S, or O, and the number of heteroatoms is 1, 2, or 3; the heteroatom of the 5- to 10-membered heteroaryl is selected from one or more than one of N, S, or O, and the number of heteroatoms is 1, 2, or 3;

$R^{4-1}$ and $R^{4-5}$ are each independently halogen,

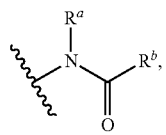

unsubstituted $C_{1-6}$ alkoxy, $C_{1-6}$ alkoxy substituted by one or more than one $R^{4-1-1}$,

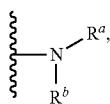

cyano, oxo, hydroxyl, unsubstituted $C_{1-6}$ alkyl, $C_{1-6}$ alkyl substituted by one or more than one $R^{4-1-3}$, unsubstituted 3- to 10-membered cycloalkyl, 3- to 10-membered cycloalkyl substituted by one or more than one $R^{4-1-4}$, unsubstituted 3- to 11-membered heterocycloalkyl, or 3- to 11-membered heterocycloalkyl substituted by one or more than one $R^{4-1-5}$; the heteroatom of the 3- to 11-membered heterocycloalkyl is selected from one or more than one of N, S, and O, and the number of heteroatoms is 1, 2, or 3; $R^{4-2}$, $R^{4-3}$, and $R^{4-4}$ are each independently hydroxyl, halogen, unsubstituted $C_{1-6}$ alkyl, $C_{1-6}$ alkyl substituted by one or more than one halogen,

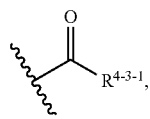

oxo, or

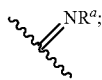

$R^{4-1-1}$, $R^{4-1-3}$, $R^{4-1-4}$, and $R^{4-1-5}$ are each independently halogen, hydroxyl, 3- to 10-membered cycloalkyl, 3- to 11-membered heterocycloalkyl, unsubstituted $C_{1-6}$ alkyl, $C_{1-6}$ alkyl substituted by one or more than one halogen, unsubstituted $C_{1-6}$ alkoxy, or $C_{1-6}$ alkoxy substituted by one or more than one halogen;

$R^{4-3-1}$ is H, $C_{1-6}$ alkyl, or $C_{1-6}$ alkoxy;

$R^a$ and $R^b$ are each independently H, unsubstituted $C_{1-6}$ alkyl, $C_{1-6}$ alkyl substituted by one or more than one $R^{a-1}$, unsubstituted 3- to 10-membered cycloalkyl, 3- to 10-membered cycloalkyl substituted by one or more than one $R^{a-2}$, unsubstituted 3- to 11-membered heterocycloalkyl, 3- to 11-membered heterocycloalkyl substituted by one or more than one $R^{a-3}$, unsubstituted 6- to 10-membered aryl, 6- to 10-membered aryl substituted by one or more than one $R^{a-4}$, unsubstituted 5- to 10-membered heteroaryl, or 5-to 10-membered heteroaryl substituted by one or more than one $R^{a-5}$; or, $R^a$ and $R^b$, together with the atom to which they are attached, form a 3- to 11-membered heterocyclic ring; the heteroatom of the 3- to 11-membered heterocycloalkyl is selected from one or more than one of N, S, or O, and the number of heteroatoms is 1, 2, or 3; the heteroatom of the 5- to 10-membered heteroaryl is selected from one or more than one of N, S, and O, and the number of heteroatoms is 1, 2, or 3;

$R^{a-1}$, $R^{a-2}$, $R^{a-3}$, $R^{a-4}$, and $R^{a-5}$ are each independently halogen, cyano, hydroxyl, nitro, $C_{1-6}$ alkyl, $C_{1-6}$ alkoxy, 3- to 10-membered cycloalkyl, 3- to 11-membered heterocycloalkyl, 6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5-to 10-membered heteroaryl is selected from one or more than one of N, S, and O, and the number of heteroatoms is 1, 2, or 3.

The present disclosure provides a five-membered-fused six-membered compound of formula I or a pharmaceutically acceptable salt thereof,

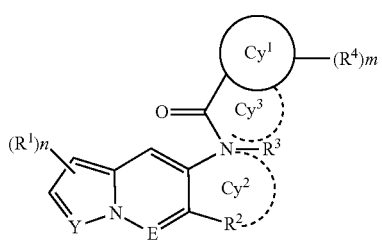

I wherein
Y is N or CH;
E is N or CH;
n is 1, 2, or 3;
m is 1, 2, or 3;
$R^3$ is hydrogen or $R^3$ is absent; when $R^3$ is absent, N and the atom on ring $Cy^1$, together with the atoms to which they are attached, form ring Cy³, or N and the atom on R² , together with the atoms to which they are attached, form ring Cy²;

ring Cy¹ is a 5-membered heteroaromatic ring, the heteroatom of the 5-membered heteroaromatic ring is selected from one or more than one of N, S, and O, and the number of heteroatoms is 1, 2, or 3;

ring Cy² is a 5- to 9-membered heterocyclic ring; the heteroatom of the 5- to 9-membered heterocyclic ring is selected from one or more than one of N, S, and O, and the number of heteroatoms is 1, 2, or 3, and at least one heteroatom is N;

ring Cy³ is an oxo-5- to 9-membered heterocyclic ring; the heteroatom of the oxo-5- to 9-membered heterocyclic ring is selected from one or more than one of N, S, and O, and the number of heteroatoms is 1, 2, or 3, and at least one heteroatom is N;

each R¹ is independently hydrogen, halogen, nitro, cyano, hydroxyl,

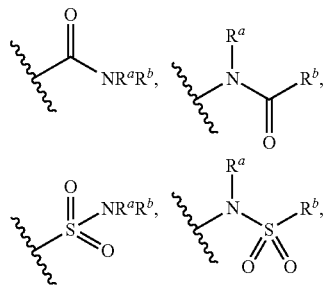

—SO₂-Rᵃ, —SO—Rᵃ,

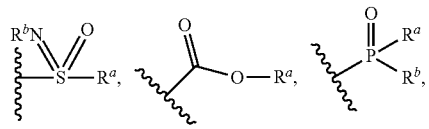

unsubstituted 3- to 11-membered heterocycloalkyl, 3- to 11-membered heterocycloalkyl substituted by one or more than one R¹⁻¹, unsubstituted 3- to 10-membered cycloalkyl, 3- to 10-membered cycloalkyl substituted by one or more than one R¹⁻²,

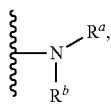

unsubstituted C₁₋₆ alkyl or C₁₋₆ alkyl substituted by one or more than one R¹⁻⁴, unsubstituted 6- to 10-membered aryl, 6- to 10-membered aryl substituted by one or more than one R¹⁻⁵, unsubstituted 5- to 10-membered heteroaryl, 5- to 10-membered heteroaryl substituted by one or more than one R¹⁻⁶, unsubstituted C₁₋₆ alkoxy, C₁₋₆ alkoxy substituted by one or more than one R¹⁻⁷, hydroxyl substituted by R¹⁻⁸, or —O—CORᵃ; the heteroatom of the 3- to 11-membered heterocycloalkyl is selected from one or more than one of N, S, and O, and the number of heteroatoms is 1, 2, or 3; the hetero atom of the 5- to 10-membered heteroaryl is selected from one or more than one of N, S, and O, and the number of heteroatoms is 1, 2, or 3;

R¹⁻¹, R¹⁻², R¹⁻⁴, R¹⁻⁵, R¹⁻⁶, and R¹⁻⁷ are each independently halogen, oxo,

hydroxyl, unsubstituted 3- to 11-membered heterocycloalkyl, 3- to 11-membered heterocycloalkyl substituted by one or more than one R¹⁻¹⁻¹,

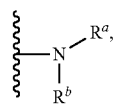

cyano, unsubstituted C₁₋₆ alkoxy, C₁₋₆ alkoxy substituted by one or more than one R¹⁻¹⁻³,

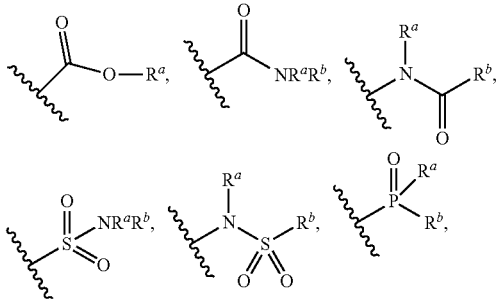

unsubstituted C₁₋₆ alkyl, C₁₋₆ alkyl substituted by one or more than one R¹⁻¹⁻⁴, unsubstituted 3- to 10-membered cycloalkyl, 3- to 10-membered cycloalkyl substituted by one or more than one R¹⁻¹⁻⁵, —SO₂—Rᵃ, —SO—Rᵃ,

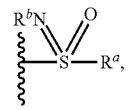

unsubstituted 6- to 10-membered aryl, 6- to 10-membered aryl substituted by one or more than one R¹⁻¹⁻⁸, unsubstituted 5- to 10-membered heteroaryl, or 5- to 10-membered heteroaryl substituted by one or more than one R¹⁻¹⁻⁷; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

R¹⁻⁸ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3; R¹⁻¹⁻¹, R¹⁻¹⁻³, R¹⁻¹⁻⁴, R¹⁻¹⁻⁵, R¹⁻¹⁻⁷, and $R^{1-1-8}$ are each independently unsubstituted $C_{1-6}$ alkyl, $C_{1-6}$ alkyl substituted by one or more than one halogen, halogen, oxo,

or hydroxyl;

$R^2$ is hydrogen, halogen, cyano, hydroxyl, nitro,

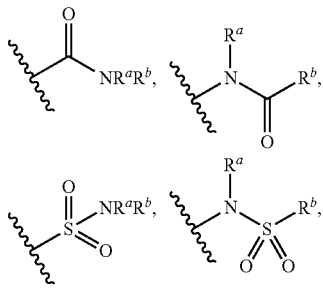

—SO$_2$—R$^a$, —SO—R$^a$,

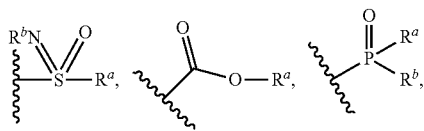

unsubstituted 3- to 11-membered heterocycloalkyl, 3- to 11-membered heterocycloalkyl substituted by one or more than one $R^{2-1}$, unsubstituted 3- to 10-membered cycloalkyl, 3- to 10-membered cycloalkyl substituted by one or more than one $R^{2-2}$,

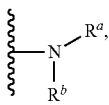

unsubstituted $C_{1-6}$ alkyl, $C_{1-6}$ alkyl substituted by one or more than one $R^{2-4}$, unsubstituted 6- to 10-membered aryl, 6- to 10-membered aryl substituted by one or more than one $R^{2-5}$, unsubstituted 5-to 10-membered heteroaryl, 5- to 10-membered heteroaryl substituted by one or more than one $R^{2-6}$, hydroxyl substituted by $R^{2-8}$, unsubstituted $C_{1-6}$ alkoxy, $C_{1-6}$ alkoxy substituted by one or more than one $R^{2-7}$, or —O—COR$^a$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{2-1}$, $R^{2-2}$, $R^{2-4}$, $R^{2-5}$, $R^{2-6}$, and $R^{2-7}$ are each independently halogen, oxo, hydroxyl, unsubstituted 3- to 11-membered heterocycloalkyl, 3- to 11-membered heterocycloalkyl substituted by one or more than one $R^{2-1-1}$,

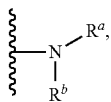

cyano, unsubstituted $C_{1-6}$ alkoxy, $C_{1-6}$ alkoxy substituted by one or more than one $R^{2-1-3}$,

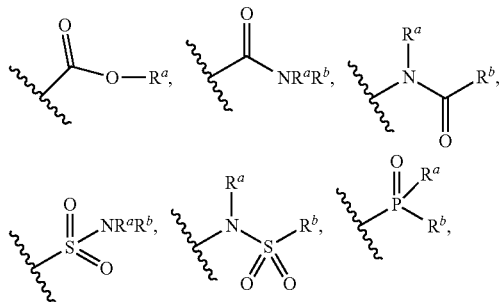

unsubstituted $C_{1-6}$ alkyl, $C_{1-6}$ alkyl substituted by one or more than one $R^{2-1-4}$, unsubstituted 3- to 10-membered cycloalkyl, 3- to 10-membered cycloalkyl substituted by one or more than one $R^{2-1-5}$, —SO$_2$—R$^a$, —SO—R$^a$,

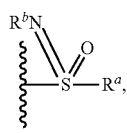

6-to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{2-8}$ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{2-1-1}$, $R^{2-1-3}$, $R^{2-1-4}$, and $R^{2-1-5}$ are each independently unsubstituted $C_{1-6}$ alkyl, or $C_{1-6}$ alkyl substituted by one or more than one halogen, halogen, oxo, or hydroxyl;

each $R^4$ is independently hydrogen, halogen, unsubstituted 5- to 10-membered heteroaryl, 5- to 10-membered heteroaryl substituted by one or more than one $R^{4-1}$, unsubstituted $C_{1-6}$ alkyl, $C_{1-6}$ alkyl substituted by one or more than one $R^{4-2}$, unsubstituted 3- to 11-membered heterocycloalkyl, 3- to 11-membered heterocycloalkyl substituted by one or more than one $R^{4-3}$, unsubstituted 3- to 10-membered cycloalkyl, 3- to 10-membered cycloalkyl substituted by one or more than one $R^{4-4}$, unsubstituted 6- to 10-membered aryl, or 6- to 10-membered aryl substituted by one or more than one $R^{4-5}$; the heteroatom of the 3- to 11-membered heterocycloalkyl is selected from one or more than one of N, S, or O, and the number of heteroatoms is 1, 2, or 3; the heteroatom of the 5- to 10-membered heteroaryl is selected from one or more than one of N, S, or O, and the number of heteroatoms is 1, 2, or 3;

$R^{4-1}$ and $R^{4-5}$ are each independently halogen,

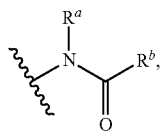

unsubstituted $C_{1-6}$ alkoxy, $C_{1-6}$ alkoxy substituted by one or more than one $R^{4-1-1}$,

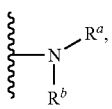

cyano, oxo, hydroxyl, unsubstituted $C_{1-6}$ alkyl, $C_{1-6}$ alkyl substituted by one or more than one $R^{4-1-3}$, unsubstituted 3- to 10-membered cycloalkyl, 3- to 10-membered cycloalkyl substituted by one or more than one $R^{4-1-4}$, unsubstituted 3- to 11-membered heterocycloalkyl, or 3- to 11-membered heterocycloalkyl substituted by one or more than one $R^{4-1-5}$; the heteroatom of the 3- to 11-membered heterocycloalkyl is selected from one or more than one of N, S, and O, and the number of heteroatoms is 1, 2, or 3;

$R^{4-2}$, $R^{4-3}$, and $R^{4-4}$ are each independently hydroxyl, halogen, unsubstituted $C_{1-6}$ alkyl, $C_{1-6}$ alkyl substituted by one or more than one halogen,

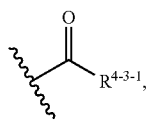

oxo, or

$R^{4-1-1}$, $R^{4-1-3}$, $R^{4-1-4}$, and $R^{4-1-5}$ are each independently halogen, hydroxyl, 3- to 10-membered cycloalkyl, 3- to 11-membered heterocycloalkyl, unsubstituted $C_{1-6}$ alkyl, $C_{1-6}$ alkyl substituted by one or more than one halogen, unsubstituted $C_{1-6}$ alkoxy, or $C_{1-6}$ alkoxy substituted by one or more than one halogen;

$R^{4-3-1}$ is H, $C_{1-6}$ alkyl, or $C_{1-6}$ alkoxy;

$R^a$ and $R^b$ are each independently H, unsubstituted $C_{1-6}$ alkyl, $C_{1-6}$ alkyl substituted by one or more than one $R^{a-1}$, unsubstituted 3- to 10-membered cycloalkyl, 3- to 10-membered cycloalkyl substituted by one or more than one $R^{a-2}$, unsubstituted 3- to 11-membered heterocycloalkyl, 3- to 11-membered heterocycloalkyl substituted by one or more than one $R^{a-3}$, unsubstituted 6- to 10-membered aryl, 6- to 10-membered aryl substituted by one or more than one $R^{a-4}$, unsubstituted 5- to 10-membered heteroaryl, or 5-to 10-membered heteroaryl substituted by one or more than one $R^{a-5}$; or, $R^a$ and $R^b$, together with the atom to which they are attached, form a 3- to 11-membered heterocyclic ring; the heteroatom of the 3- to 11-membered heterocycloalkyl is selected from one or more than one of N, S, or O, and the number of heteroatoms is 1, 2, or 3; the heteroatom of the 5- to 10-membered heteroaryl is selected from one or more than one of N, S, and O, and the number of heteroatoms is 1, 2, or 3;

$R^{a-1}$, $R^{a-2}$, $R^{a-3}$, $R^{a-4}$, and $R^{a-5}$ are each independently halogen, cyano, hydroxyl, nitro, $C_{1-6}$ alkyl, $C_{1-6}$ alkoxy, 3- to 10-membered cycloalkyl, 3- to 11-membered heterocycloalkyl, 6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5-to 10-membered heteroaryl is selected from one or more than one of N, S, and O, and the number of heteroatoms is 1, 2, or 3.

In a preferred embodiment, in the compound of formula I or the pharmaceutically acceptable salt thereof, some groups can be defined as follows, and other groups can be defined as described in any of the above embodiments (hereinafter referred to as "in a preferred embodiment"): ring $Cy^2$ is a 5- to 6-membered heterocyclic ring; the heteroatom of the 5- to 6-membered heterocyclic ring is N, and the number of heteroatoms is 1, 2, or 3.

In a preferred embodiment, ring $Cy^3$ is an oxo-5- to 9-membered heterocyclic ring; the heteroatom of the oxo-5- to 9-membered heterocyclic ring is N, and the number of heteroatoms is 1, 2, or 3.

In a preferred embodiment, each $R^1$ is $C_{1-6}$ alkyl substituted by one or more than one $R^{1-4}$, unsubstituted 3- to 10-membered cycloalkyl, 3- to 10-membered cycloalkyl substituted by one or more than one $R^{1-2}$, unsubstituted 3- to 11-membered heterocycloalkyl, or 3- to 11-membered heterocycloalkyl substituted by one or more than one $R^{1-1}$; the heteroatom of the 3- to 11-membered heterocycloalkyl is selected from one or two of N, S, and O, and the number of heteroatoms is 1, 2, or 3.

In a preferred embodiment, $R^{1-1}$, $R^{1-2}$, and $R^{1-4}$ are each independently halogen, oxo, hydroxyl,

unsubstituted $C_{1-6}$ alkoxy, $C_{1-6}$ alkoxy substituted by one or more than one $R^{1-1-3}$

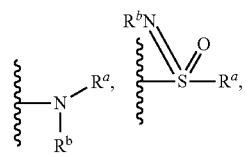

—$SO_2$-$C_{1-6}$ alkyl, unsubstituted $C_{1-6}$ alkyl, $C_{1-6}$ alkyl substituted by one or more than one $R^{1-1-4}$, unsubstituted 3- to 10-membered cycloalkyl, 3- to 10-membered cycloalkyl substituted by one or more than one $R^{1-1-5}$, unsubstituted 3- to 10-membered heterocycloalkyl, or 3- to 10-membered heterocycloalkyl substituted by one or more than one $R^{1-1-1}$; the heteroatom of the 3- to 10-membered heterocycloalkyl is one or two of N, S, and O, and the number of heteroatoms is 1, 2, or 3.

In a preferred embodiment, $R^{1-1}$, $R^{1-2}$, and $R^{1-4}$ are each independently deuterium, halogen, oxo, hydroxyl,

unsubstituted $C_{1-6}$ alkoxy, $C_{1-6}$ alkoxy substituted by one or more than one $R^{1-1-3}$,

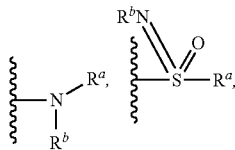

—$SO_2$-$C_{1-6}$ alkyl, unsubstituted $C_{1-6}$ alkyl, $C_{1-6}$ alkyl substituted by one or more than one $R^{1-1-4}$, unsubstituted 3- to 10-membered cycloalkyl, 3- to 10-membered cycloalkyl substituted by one or more than one $R^{1-1-5}$, unsubstituted 3- to 10-membered heterocycloalkyl, or 3- to 10-membered heterocycloalkyl substituted by one or more than one $R^{1-1-1}$; the heteroatom of the 3- to 10-membered heterocycloalkyl is one or two of N, S, and O, and the number of heteroatoms is 1, 2, or 3.

In a preferred embodiment, each $R^{1-1-1}$ is independently hydroxyl, unsubstituted $C_{1-6}$ alkyl, $C_{1-6}$ alkyl substituted by one or more than one halogen, oxo,

or halogen.

In a preferred embodiment, each $R^{1-1-1}$ is independently deuterium, hydroxyl, unsubstituted $C_{1-6}$ alkyl, $C_{1-6}$ alkyl substituted by one or more than one halogen, oxo,

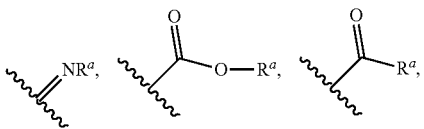

or halogen.

In a preferred embodiment, each $R^{1-1-3}$ is independently hydroxyl or halogen.

In a preferred embodiment, each $R^{1-1-4}$ is independently hydroxyl or halogen.

In a preferred embodiment, each $R^{1-1-5}$ is independently hydroxyl or halogen.

In a preferred embodiment, each $R^{1-1-3}$ is independently deuterium, hydroxyl, or halogen.

In a preferred embodiment, each $R^{1-1-4}$ is independently deuterium, hydroxyl, or halogen.

In a preferred embodiment, each $R^{1-1-5}$ is independently deuterium, hydroxyl, or halogen.

In a preferred embodiment, $R^2$ is hydrogen, hydroxyl, halogen, cyano, unsubstituted 3- to 10-membered heterocycloalkyl, 3- to 10-membered heterocycloalkyl substituted by one or more than one $R^{2-1}$, unsubstituted 3- to 8-membered cycloalkyl, 3- to 8-membered cycloalkyl substituted by one or more than one $R^{2-2}$, unsubstituted $C_{1-6}$ alkyl, $C_{1-6}$ alkyl substituted by one or more than one $R^{2-4}$, unsubstituted $C_{1-6}$ alkoxy, $C_{1-6}$ alkoxy substituted by one or more than one $R^{2-7}$, or hydroxyl substituted by $R^{2-8}$; the heteroatom of the 3- to 10-membered heterocycloalkyl is selected from one or two of N and O, and the number of heteroatoms is 1, 2, or 3.

In a preferred embodiment, $R^{2-1}$, $R^{2-2}$, $R^{2-4}$, and $R^{2-7}$ are each independently oxo, hydroxyl, halogen, 3- to 6-membered cycloalkyl, 3- to 6-membered heterocycloalkyl, unsubstituted $C_{1-6}$ alkyl, or $C_{1-6}$ alkyl substituted by one or more than one halogen.

In a preferred embodiment, $R^{2-1}$, $R^{2-2}$, $R^{2-4}$, and $R^{2-7}$ are each independently deuterium, oxo, hydroxyl, halogen, 3- to 6-membered cycloalkyl, 3- to 6-membered heterocycloalkyl, unsubstituted $C_{1-6}$ alkyl, or $C_{1-6}$ alkyl substituted by one or more than one halogen.

In a preferred embodiment, $R^{2-8}$ is 3- to 6-membered cycloalkyl or 3- to 6-membered heterocycloalkyl; the heteroatom of the 3- to 6-membered heterocycloalkyl is selected from one or more than one of N, S, and O, and the number of heteroatoms is 1, 2, or 3.

In a preferred embodiment, each $R^4$ is independently hydrogen, halogen, unsubstituted $C_{1-6}$ alkyl, $C_{1-6}$ alkyl substituted by one or more than one halogen, unsubstituted phenyl, phenyl substituted by one or more than one $R^{4-5}$, unsubstituted 5- to 6-membered heteroaryl, 5- to 6-membered heteroaryl substituted by one or more than one $R^{4-1}$, unsubstituted 3- to 6-membered heterocycloalkyl, or 3- to 6-membered heterocycloalkyl substituted by one or more than one $R^{4-3}$; the heteroatom of the 3- to 6-membered heterocycloalkyl is selected from one or more than one of N, S, and O, and the number of heteroatoms is 1, 2, or 3; the heteroatom of the 5- to 6-membered heteroaryl is selected from one or more than one of N, S, and O, and the number of heteroatoms is 1, 2, or 3.

In a preferred embodiment, each $R^{4-1}$ is independently oxo, hydroxyl, unsubstituted $C_{1-6}$ alkyl, or $C_{1-6}$ alkyl substituted by one or more than one halogen.

In a preferred embodiment, each $R^{4-3}$ is independently halogen, unsubstituted $C_{1-6}$ alkyl, $C_{1-6}$ alkyl substituted by one or more than one halogen,

or oxo.

In a preferred embodiment, each $R^{4-5}$ is independently oxo, hydroxyl, unsubstituted $C_{1-6}$ alkyl, or $C_{1-6}$ alkyl substituted by one or more than one halogen.

In a preferred embodiment, each $R^{4-3-1}$ is $C_{1-6}$ alkyl or $C_{1-6}$ alkoxy.

In a preferred embodiment, $R^a$ and $R^b$ are each independently hydrogen, unsubstituted $C_{1-6}$ alkyl, $C_{1-6}$ alkyl substituted by one or more than one $R^{a-1}$; or, $R^a$ and $R^b$, together with the atom to which they are attached, form a 3- to 6-membered heterocyclic ring; the heteroatom of the 3- to 6-membered heterocyclic ring is selected from one or more than one of N, S, and O, and the number of heteroatoms is 1, 2, or 3.

In a preferred embodiment, each $R^{a-1}$ is independently $C_{1-6}$ alkyl, halogen, or hydroxyl.

In a preferred embodiment, n is 1.

In a preferred embodiment, m is 1.

In a preferred embodiment, Y is N.

In a preferred embodiment, E is CH.

In a preferred embodiment, $R^3$ is hydrogen.

In a preferred embodiment, $R^1$ is $C_{1-6}$ alkyl substituted by one or more than one $R^{1-4}$, unsubstituted 3- to 10-membered cycloalkyl, 3- to 10-membered cycloalkyl substituted by one or more than one $R^{1-2}$, unsubstituted 3- to 10-membered heterocycloalkyl, or 3- to 10-membered heterocycloalkyl substituted by one or more than one $R^{1-1}$; the heteroatom of the 3- to 10-membered heterocycloalkyl is one or more than one of N, O, or S, and the number of heteroatoms is 1 or 2.

In a preferred embodiment, $R^1$ is $C_{1-6}$ alkyl substituted by one or more than one $R^{1-4}$, unsubstituted 3- to 6-membered cycloalkyl, 3- to 6-membered cycloalkyl substituted by one or more than one $R^{1-2}$, unsubstituted 3- to 6-membered heterocycloalkyl, or 3- to 6-membered heterocycloalkyl substituted by one or more than one $R^{1-1}$; the heteroatom of the 3- to 6-membered heterocycloalkyl is one of N, O, or S, and the number of heteroatoms is 1.

In a preferred embodiment, $R^1$ is

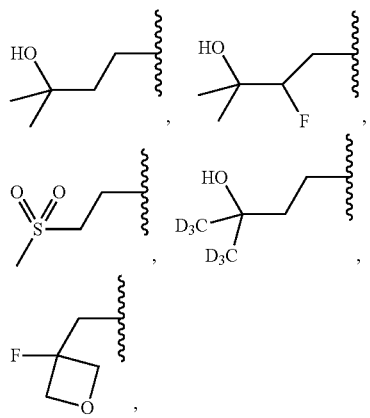

3- to 6-membered cycloalkyl substituted by one hydroxyl group, 6-membered cycloalkyl substituted by one —SO$_2$-$C_{1-6}$ alkyl group, or

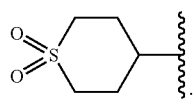

In a preferred embodiment, $R^{1-1}$, $R^{1-2}$, and $R^{1-4}$ are each independently deuterium, oxo, hydroxyl,

halogen,

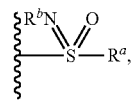

—SO$_2$-$C_{1-6}$ alkyl, unsubstituted $C_{1-6}$ alkyl, $C_{1-6}$ alkyl substituted by one or more than one $R^{1-1-4}$, unsubstituted 3- to 10-membered cycloalkyl, 3- to 10-membered cycloalkyl substituted by one or more than one $R^{1-1-5}$, unsubstituted 3- to 10-membered heterocycloalkyl, or 3- to 10-membered heterocycloalkyl substituted by one or more than one $R^{1-1-1}$; the heteroatom of the 3- to 10-membered heterocycloalkyl is one or more than one of N, O, or S, and the number of heteroatoms is 1, 2, or 3.

In a preferred embodiment, $R^{1-1}$, $R^{1-2}$, and $R^{1-4}$ are each independently deuterium, hydroxyl,

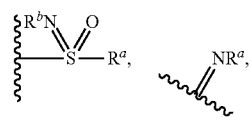

oxo, halogen, —SO$_2$-$C_{1-6}$ alkyl, unsubstituted $C_{1-6}$ alkyl, $C_{1-6}$ alkyl substituted by one or more than one $R^{1-1-4}$, unsubstituted 3- to 6-membered cycloalkyl, 3- to 6-membered cycloalkyl substituted by one or more than one $R^{1-1-5}$, unsubstituted 3- to 6-membered heterocycloalkyl, or 3- to 6-membered heterocycloalkyl substituted by one or more than one $R^{1-1-1}$; the heteroatom of the 3- to 6-membered heterocycloalkyl is one of N, O, or S, and the number of heteroatoms is 1.

In a preferred embodiment, each $R^{1-1}$ is independently oxo,

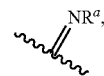

unsubstituted $C_{1-6}$ alkyl, or $C_{1-6}$ alkyl substituted by one or more than one $R^{1-1-4}$.

In a preferred embodiment, each $R^{1-2}$ is independently halogen, hydroxyl, or —SO$_2$-$C_{1-6}$ alkyl.

In a preferred embodiment, each $R^{1-4}$ is independently deuterium, hydroxyl,

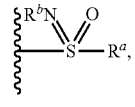

halogen, —SO$_2$-$C_{1-6}$ alkyl, unsubstituted $C_{1-6}$ alkyl, $C_{1-6}$ alkyl substituted by one or more than one $R^{1-1-4}$, unsubstituted 3- to 6-membered heterocycloalkyl, or 3- to 6-membered heterocycloalkyl substituted by one or more than one $R^{1-1-1}$; the heteroatom of the 3- to 6-membered heterocycloalkyl is one of N, O, or S, and the number of heteroatoms is 1.

In a preferred embodiment, each $R^{1-1-1}$ is independently oxo or hydroxyl.

In a preferred embodiment, each $R^{1-1-1}$ is independently oxo, halogen, or hydroxyl.

In a preferred embodiment, each $R^{1-1-4}$ is independently halogen.

In a preferred embodiment, each $R^{1-1-5}$ is independently hydroxyl.

In a preferred embodiment, $R^2$ is unsubstituted 3- to 6-membered heterocycloalkyl, 3- to 6-membered heterocycloalkyl substituted by one or more than one $R^{2-1}$, unsubstituted $C_{3-6}$ cycloalkyl, $C_{3-6}$ cycloalkyl substituted by one or more than one $R^{2-2}$, unsubstituted $C_{1-6}$ alkoxy, $C_{1-6}$ alkoxy substituted by one or more than one $R^{2-7}$, unsubstituted $C_{1-6}$ alkyl, $C_{1-6}$ alkyl substituted by one or more than one $R^{2-4}$, or hydroxyl substituted by $R^{2-8}$; the heteroatom of the 3- to 6-membered heterocycloalkyl is selected from one or two of N and O, and the number of heteroatoms is 1 or 2.

In a preferred embodiment, $R^2$ is unsubstituted 3- to 6-membered heterocycloalkyl, 3- to 6-membered heterocycloalkyl substituted by one or more than one $R^{2-1}$, unsubstituted $C_{1-6}$ alkoxy, $C_{1-6}$ alkoxy substituted by one or more than one $R^{2-7}$, unsubstituted $C_{1-6}$ alkyl, or $C_{1-6}$ alkyl substituted by one or more than one $R^{2-4}$; the heteroatom of the 3- to 6-membered heterocycloalkyl is selected from N and/or O, and the number of heteroatoms is 1 or 2.

In a preferred embodiment, $R^2$ is unsubstituted $C_{1-6}$ alkoxy, $C_{1-6}$ alkoxy substituted by one or more than one $R^{2-7}$, unsubstituted $C_{1-6}$ alkyl, or $C_{1-6}$ alkyl substituted by one or more than one $R^{2-4}$.

In a preferred embodiment, $R^{2-8}$ is 3- to 6-membered cycloalkyl or 3- to 6-membered heterocycloalkyl; the heteroatom of the 3- to 6-membered heterocycloalkyl is selected from one of N and O, and the number of heteroatoms is 1.

In a preferred embodiment, each $R^{2-1}$ is independently hydroxyl or halogen.

In a preferred embodiment, each $R^{2-2}$ is independently hydroxyl.

In a preferred embodiment, each $R^{2-4}$ is independently hydroxyl.

In a preferred embodiment, each $R^{2-7}$ is independently halogen.

In a preferred embodiment, each $R^{2-4}$ is independently deuterium, halogen, or hydroxyl.

In a preferred embodiment, each $R^{2-7}$ is independently deuterium or halogen.

In a preferred embodiment, each $R^4$ is independently hydrogen, halogen, unsubstituted $C_{1-6}$ alkyl, $C_{1-6}$ alkyl substituted by one or more than one halogen, unsubstituted 5- to 6-membered heteroaryl, 5- to 6-membered heteroaryl substituted by one or more than one $R^{4-1}$, unsubstituted phenyl, phenyl substituted by one or more than one $R^{4-5}$, unsubstituted 3- to 6-membered heterocycloalkyl, or 3- to 6-membered heterocycloalkyl substituted by one or more than one $R^{4-3}$, the heteroatom of the 5- to 6-membered heteroaryl is N, and the number of heteroatoms is 1, 2, or 3; the heteroatom of the 3- to 6-membered heterocycloalkyl is selected from one or more than one of N, S, and O, and the number of heteroatoms is 1 or 2 (preferably each $R^4$ is independently unsubstituted 5- to 6-membered heteroaryl or 5- to 6-membered heteroaryl substituted by one or more than one $R^{4-1}$ the heteroatom of the 5- to 6-membered heteroaryl is N, and the number of heteroatoms is 1 or 2).

In a preferred embodiment, each $R^4$ is independently unsubstituted pyridyl or pyridyl substituted by one or more than one $R^{4-1}$.

In a preferred embodiment, $R^{4-1}$ and $R^{4-5}$ are each independently unsubstituted $C_{1-6}$ alkyl or $C_{1-6}$ alkyl substituted by one or more than one halogen.

In a preferred embodiment, each $R^{4-1}$ is independently unsubstituted $C_{1-6}$ alkyl or $C_{1-6}$ alkyl substituted by one, two, or three halogens.

In a preferred embodiment, each $R^{4-3}$ is independently halogen, unsubstituted $C_{1-6}$ alkyl, or $C_{1-6}$ alkyl substituted by one or more than one halogen.

In a preferred embodiment, $R^a$ and $R^b$ are each independently H or $C_{1-6}$ alkyl; or, $R^a$ and $R^b$, together with the atom to which they are attached, form a 3- to 6-membered heterocyclic ring; the heteroatom of the 3- to 6-membered heterocyclic ring is S, and the number of heteroatoms is 1.

In a preferred embodiment, the five-membered-fused six-membered compound of formula I is a compound of formula I-a

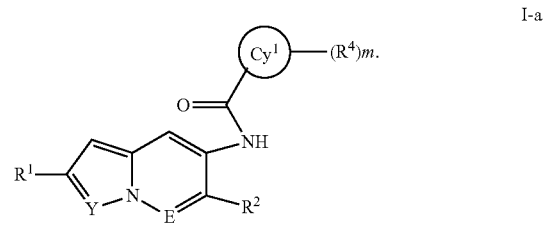

I-a

In a preferred embodiment, the five-membered-fused six-membered compound of formula I is a compound of formula I-b

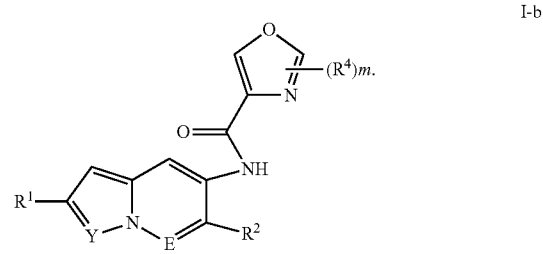

I-b

In a preferred embodiment, the five-membered-fused six-membered compound of formula I is a compound of formula I-c

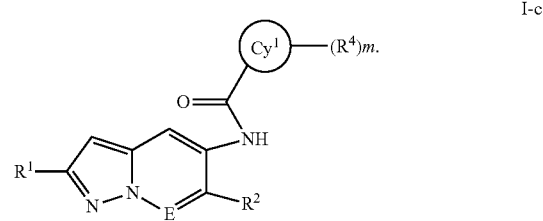

I-c

In a preferred embodiment, $R^1$ is

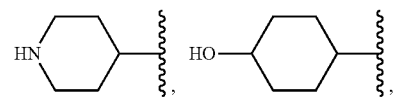

-continued
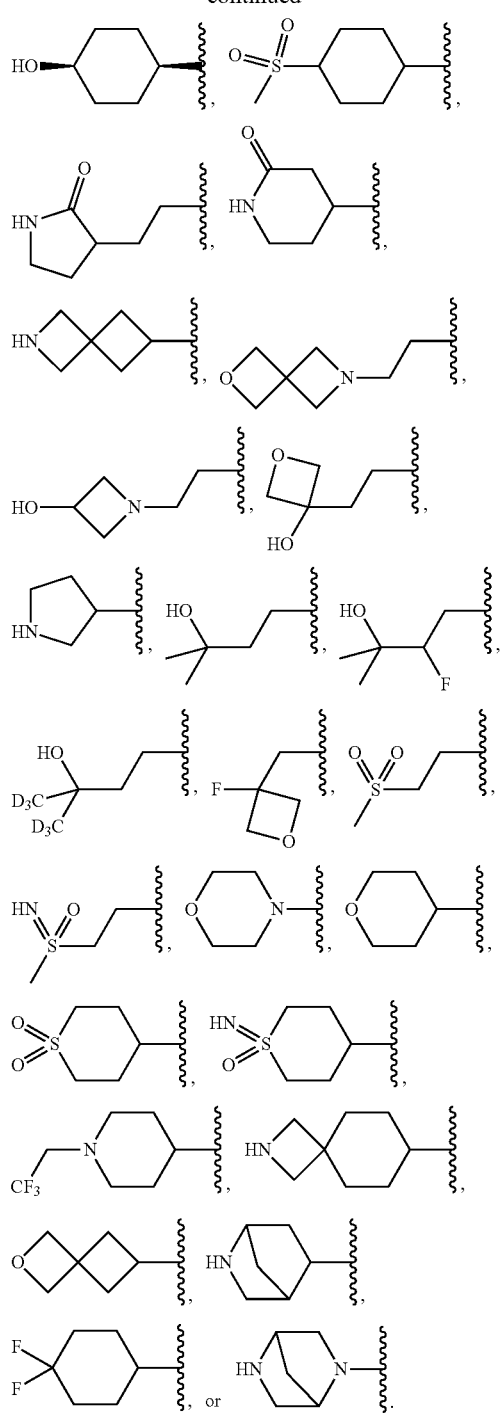
In a preferred embodiment,
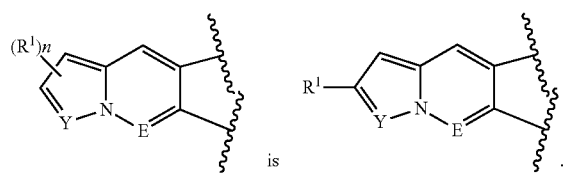 is
In a preferred embodiment, $R^2$ is methoxy, isopropoxy, trifluoromethoxy, hydroxyl, —OCD$_3$,
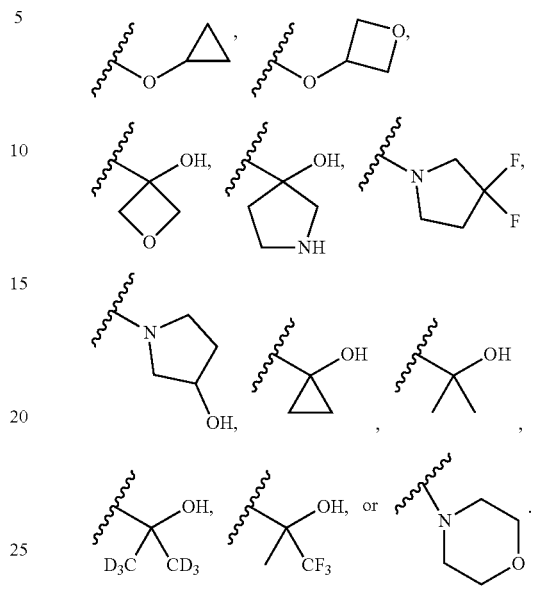
In a preferred embodiment, each $R^4$ is independently hydrogen, bromine, trifluoromethyl,
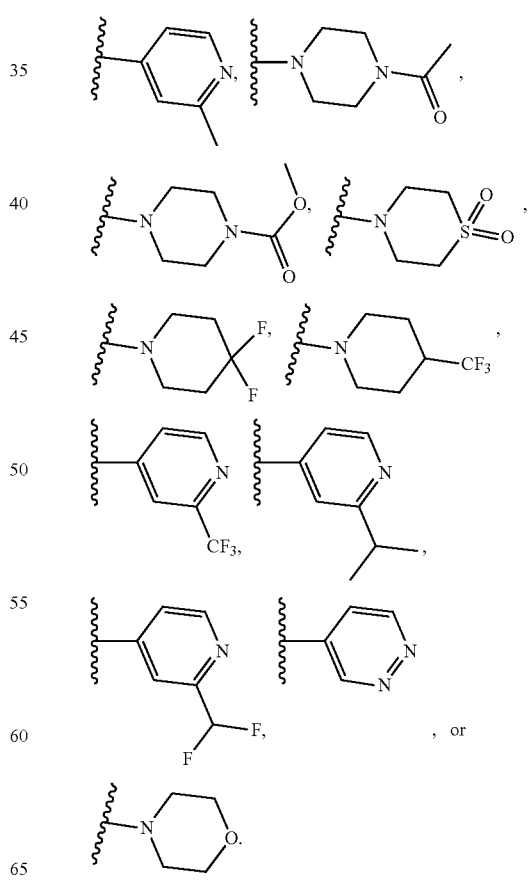

In a preferred embodiment, ring Cy¹ is
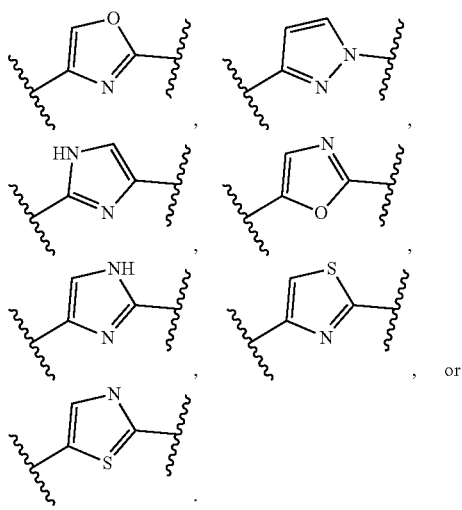
In a preferred embodiment, ring Cy¹ is
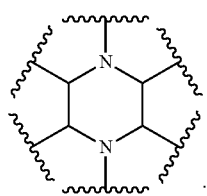 [SMILES: *C1C(*)N(*)C(*)C(*)N1*]
In a preferred embodiment, ring Cy³ is
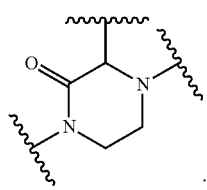 [SMILES: *C1C(=O)N(*)CCN1*]
In a preferred embodiment,
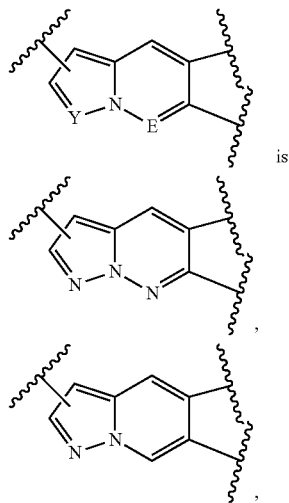 is
-continued
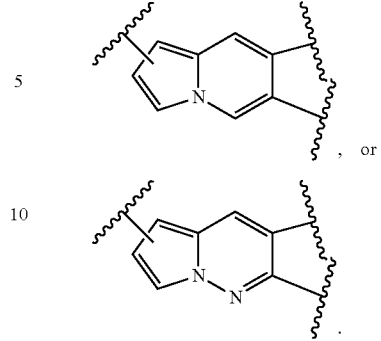
In a preferred embodiment, the five-membered-fused six-membered compound of formula I or the pharmaceutically acceptable salt thereof is any one of the following compounds,
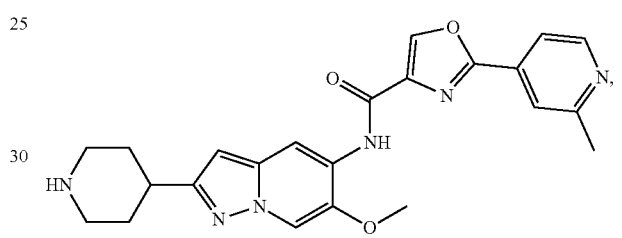
II-3
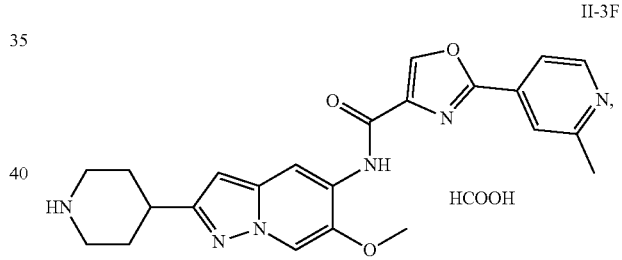
II-3F
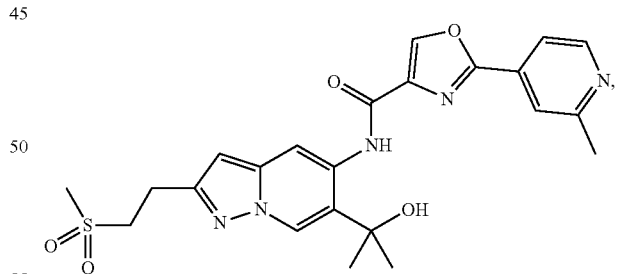
II-18
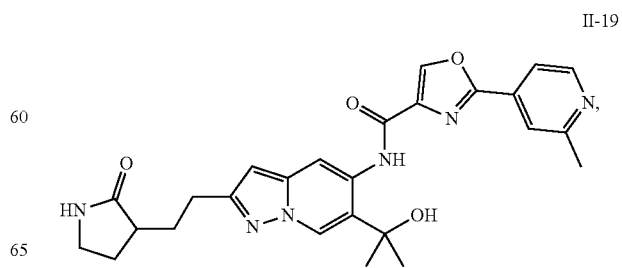
II-19

-continued
II-20
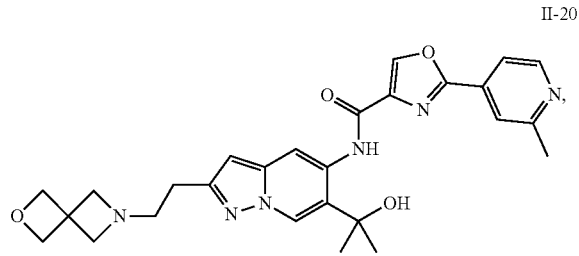
II-21
II-22
II-23
II-24
II-25
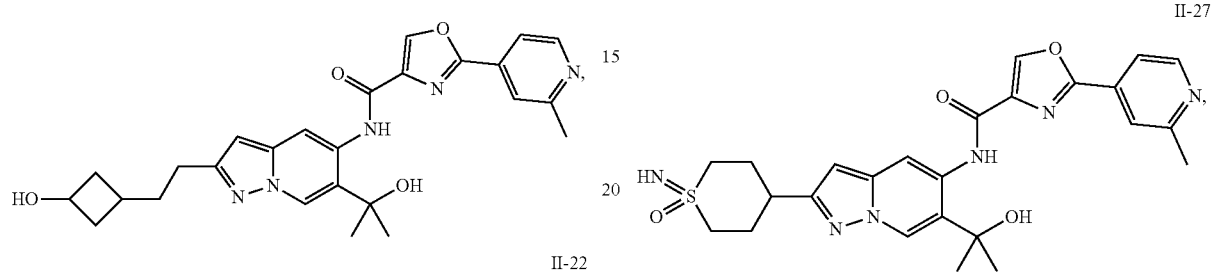
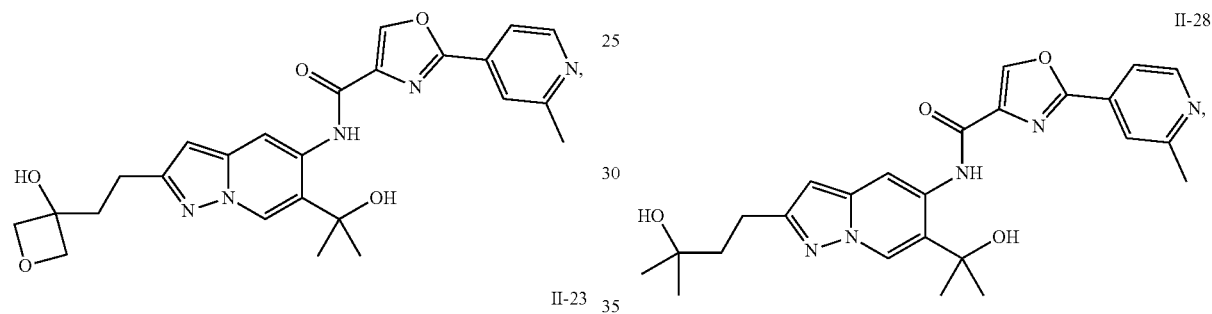
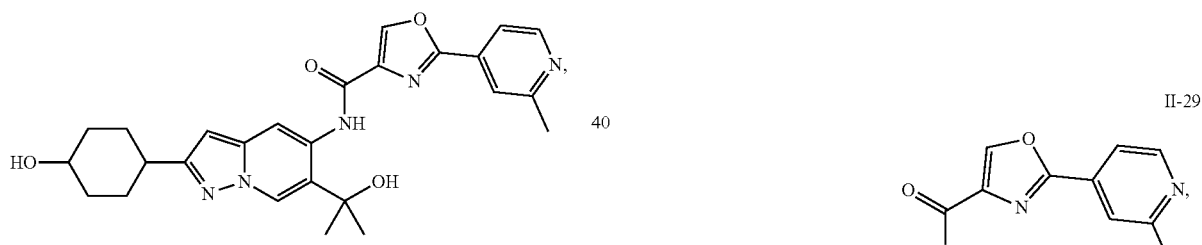
-continued
II-26
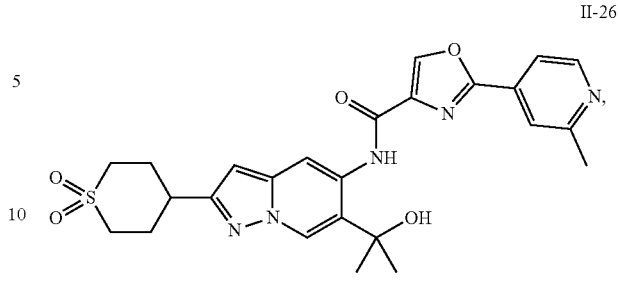
II-27
II-28
II-29
II-30
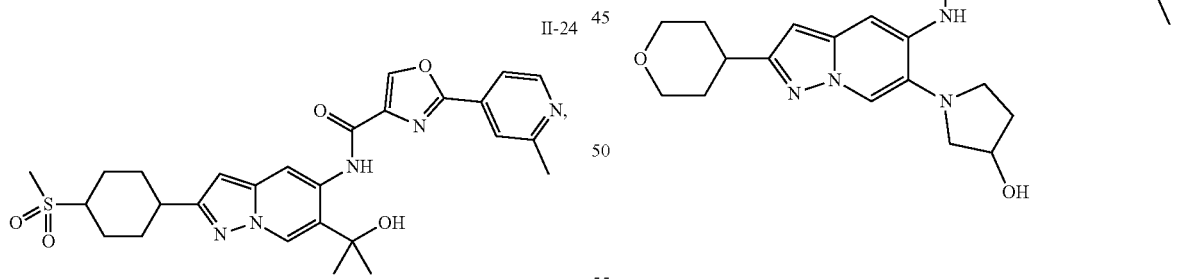
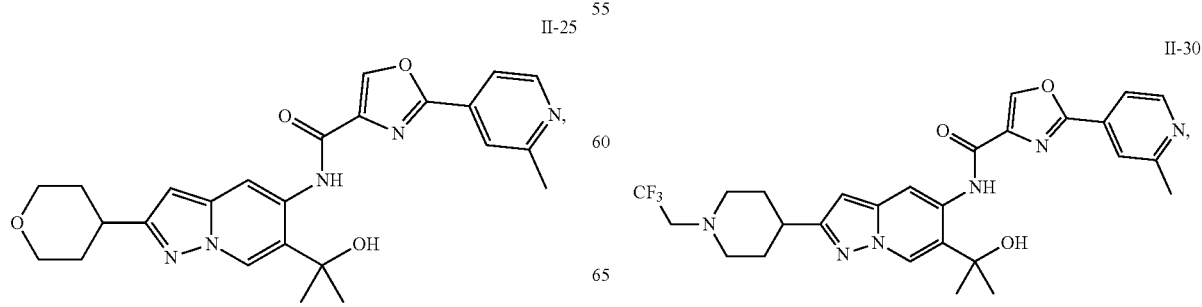

II-31
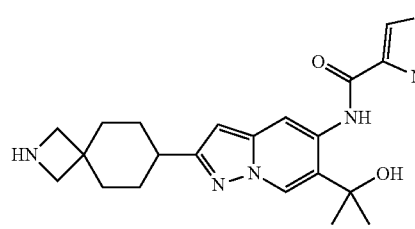
II-32
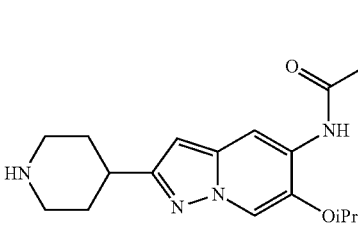
II-33
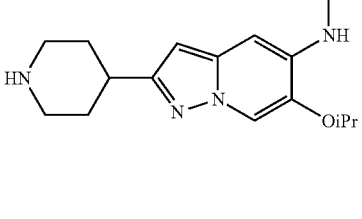
II-34
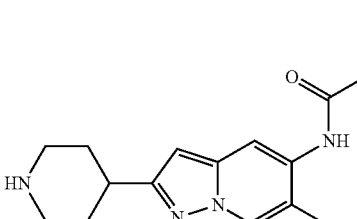
II-35
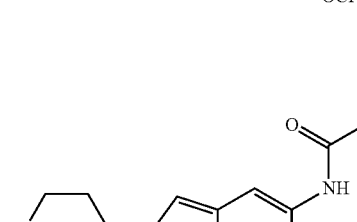
II-36
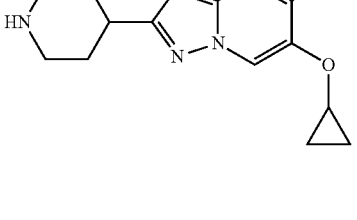
II-37
II-38
II-39
II-40
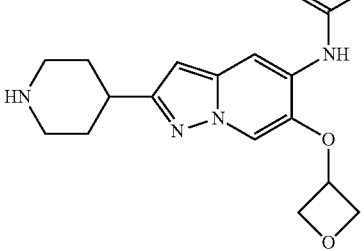

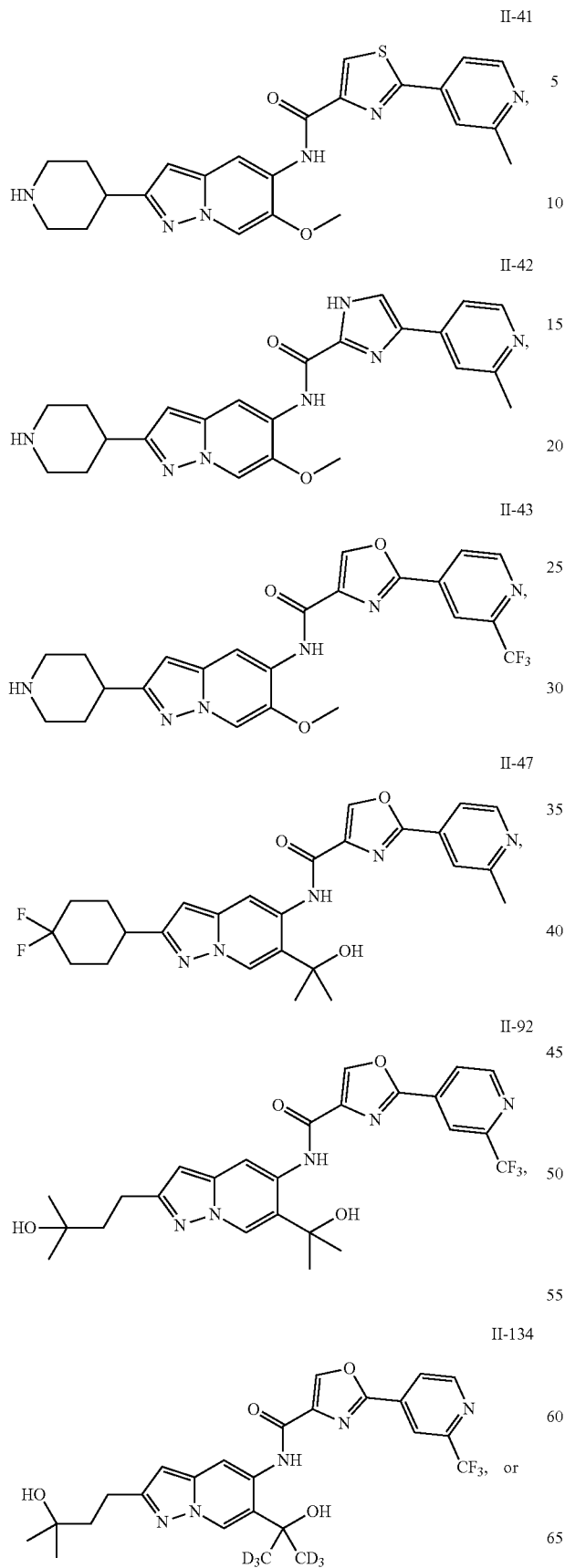

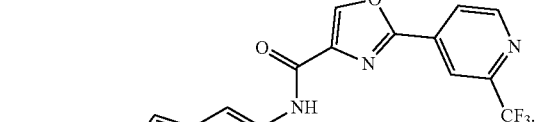

The present disclosure provides a five-membered-fused six-membered compound of formula II or a pharmaceutically acceptable salt thereof,

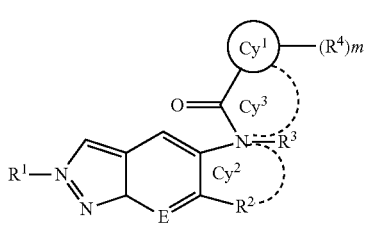

wherein m is 1, 2, or 3;
E is N or CH;
ring $Cy^1$ is a 5-membered heteroaromatic ring; the heteroatom of the 5-membered heteroaromatic ring is selected from one or more than one of N, S, and O, and the number of heteroatoms is 1, 2, or 3;
$R^3$ is hydrogen or $R^3$ is absent; when $R^3$ is absent, N and the atom on ring $Cy^1$, together with the atoms to which they are attached, form ring $Cy^3$, or N and the atom on $R^2$, together with the atoms to which they are attached, form ring $Cy^2$;
ring $Cy^2$ is a 5- to 9-membered heterocyclic ring; the heteroatom of the 5- to 9-membered heterocyclic ring is selected from one or more than one of N, S, and O, and the number of heteroatoms is 1, 2, or 3, and at least one heteroatom is N;
ring $Cy^3$ is an oxo-5- to 9-membered heterocyclic ring; the heteroatom of the oxo-5- to 9-membered heterocyclic ring is selected from one or more than one of N, S, and O, and the number of heteroatoms is 1, 2, or 3, and at least one heteroatom is N;
each $R^1$ is independently hydrogen, halogen, nitro, cyano, hydroxyl,

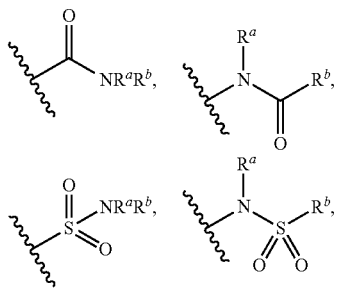

—SO$_2$—R$^a$, —SO—R$^a$,

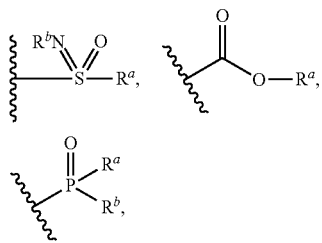

unsubstituted 3- to 11-membered heterocycloalkyl, 3- to 11-membered heterocycloalkyl substituted by one or more than one R$^{1-1}$, 3- to 10-membered cycloalkyl substituted by one or more than one R$^{1-2}$,

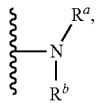

C$_{1-6}$ alkyl substituted by one or more than one R$^{1-4}$, unsubstituted 6- to 10-membered aryl, 6- to 10-membered aryl substituted by one or more than one R$^{1-5}$, unsubstituted 5- to 10-membered heteroaryl, 5- to 10-membered heteroaryl substituted by one or more than one R$^{1-6}$, unsubstituted C$_{1-6}$ alkoxy, C$_{1-6}$ alkoxy substituted by one or more than one R$^{1-7}$, hydroxyl substituted by R$^{1-8}$, or —O—COR$^a$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

R$^{1-1}$, R$^{1-2}$, R$^{1-4}$, R$^{1-5}$, R$^{1-6}$, and R$^{1-7}$ are each independently deuterium, halogen, oxo,

hydroxyl, unsubstituted 3- to 11-membered heterocycloalkyl, 3- to 11-membered heterocycloalkyl substituted by one or more than one R$^{1-1-1}$,

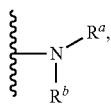

cyano, unsubstituted C$_{1-6}$ alkoxy, C$_{1-6}$ alkoxy substituted by one or more than one R$^{1-1-3}$

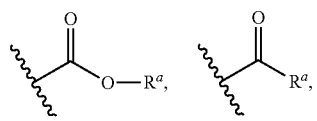

unsubstituted C$_{1-6}$ alkyl, C$_{1-6}$ alkyl substituted by one or more than one R$^{1-1-4}$, unsubstituted 3- to 10-membered cycloalkyl, 3- to 10-membered cycloalkyl substituted by one or more than one R$^{1-1-5}$, —SO$_2$—R$^a$, —SO—R$^a$,

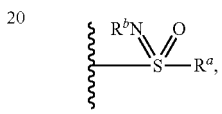

unsubstituted 6- to 10-membered aryl, 6- to 10-membered aryl substituted by one or more than one R$^{1-1-8}$ unsubstituted 5- to 10-membered heteroaryl, or 5- to 10-membered heteroaryl substituted by one or more than one R$^{1-1-7}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

R$^{1-8}$ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3; R$^{1-1-1}$, R$^{1-1-3}$, R$^{1-1-4}$, R$^{1-1-5}$, R$^{1-1-7}$, and R$^{1-1-8}$ are each independently deuterium, unsubstituted C$_{1-6}$ alkyl, C$_{1-6}$ alkyl substituted by one or more than one halogen, halogen, oxo,

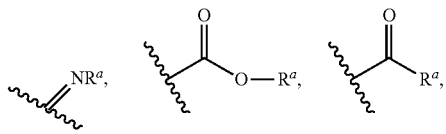

or hydroxyl;

R$^2$ is unsubstituted 3- to 11-membered heterocycloalkyl, 3- to 11-membered heterocycloalkyl substituted by one or more than one R$^{2-1}$, unsubstituted 3- to 8-membered cycloalkyl, 3- to 8-membered cycloalkyl substituted by one or more than one R$^{2-2}$, unsubstituted C$_{1-6}$ alkoxy, C$_{1-6}$ alkoxy substituted by one or more than one R$^{2-7}$, hydroxyl substituted by R$^{2-8}$, or C$_{1-6}$ alkyl substituted by one or more than one R$^{2-4}$; the heteroatom of the 3- to 11-membered heterocycloalkyl is selected from one or more than one of N, S, and O, and the number of heteroatoms is 1, 2, or 3;

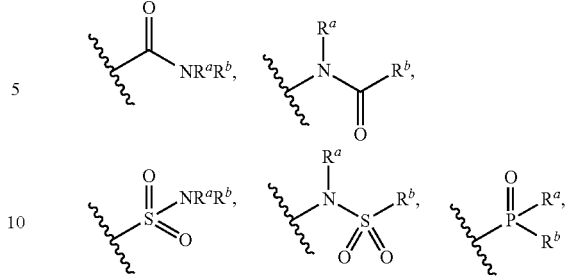

$R^{2-1}$ and $R^{2-7}$ are each independently deuterium, hydroxyl, halogen, oxo, unsubstituted $C_{1-6}$ alkyl, $C_{1-6}$ alkyl substituted by one or more than one halogen, 3- to 10-membered cycloalkyl, unsubstituted 3- to 8-membered heterocycloalkyl, or 3- to 8-membered heterocycloalkyl substituted by one or more than one $R^{2-1-1}$; the heteroatom of the 3- to 8-membered heterocycloalkyl is selected from one or more than one of N, S, and O, and the number of heteroatoms is 1, 2, or 3;

each $R^{2-2}$ is independently deuterium, halogen, hydroxyl, or hydroxyl substituted by 3- to 8-membered heterocycloalkyl; the heteroatom of the 3- to 8-membered heterocycloalkyl is selected from one or more than one of N, S, and O, and the number of heteroatoms is 1, 2, or 3;

each $R^{2-4}$ is independently deuterium, halogen, hydroxyl, or hydroxyl substituted by 3- to 8-membered heterocycloalkyl; the heteroatom of the 3- to 8-membered heterocycloalkyl is selected from one or more than one of N, S, and O, and the number of heteroatoms is 1, 2, or 3;

$R^{2-8}$ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

each $R^{2-1-1}$ is independently hydroxyl, halogen, oxo, $C_{1-6}$ alkyl, 3- to 10-membered cycloalkyl, or 3- to 8-membered heterocycloalkyl; the heteroatom of the 3- to 8-membered heterocycloalkyl is selected from one or more than one of N, S, and O, and the number of heteroatoms is 1, 2, or 3;

when $R^2$ is unsubstituted 3- to 7-membered monoheterocycloalkyl or 3- to 7-membered monoheterocycloalkyl substituted by one or more than one $R^{2-1}$, and $R^1$ is $C_{1-6}$ alkyl substituted by one or more than one $R^{1-4}$; each $R^{1-4}$ is independently deuterium, halogen, hydroxyl, unsubstituted 3- to 11-membered heterocycloalkyl, 3- to 11-membered heterocycloalkyl substituted by one or more than one $R^{1-1-1}$,

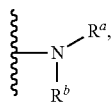

cyano,

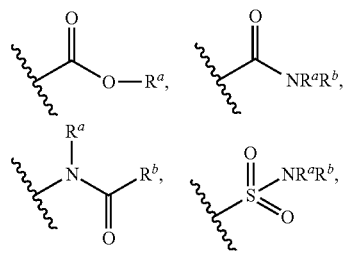

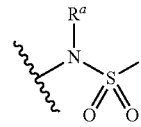

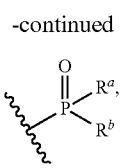

unsubstituted 3- to 10-membered cycloalkyl, 3- to 10-membered cycloalkyl substituted by one or more than one $R^{1-1-5}$, —$SO_2$—$R^a$, —SO—$R^a$,

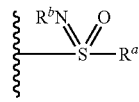

unsubstituted 6- to 10-membered aryl, 6- to 10-membered aryl substituted by one or more than one $R^{1-1-8}$, unsubstituted 5- to 10-membered heteroaryl, or 5- to 10-membered heteroaryl substituted by one or more than one $R^{1-1-7}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^a$ and $R^b$ are each independently H, unsubstituted $C_{1-6}$ alkyl, $C_{1-6}$ alkyl substituted by one or more than one $R^{a-1}$, unsubstituted 3- to 10-membered cycloalkyl, 3- to 10-membered cycloalkyl substituted by one or more than one $R^{a-2}$, unsubstituted 3- to 11-membered heterocycloalkyl, 3- to 11-membered heterocycloalkyl substituted by one or more than one $R^{a-3}$, unsubstituted 6- to 10-membered aryl, 6- to 10-membered aryl substituted by one or more than one $R^{a-4}$, unsubstituted 5- to 10-membered heteroaryl, or 5-to 10-membered heteroaryl substituted by one or more than one $R^{a-5}$;

or, $R^a$ and $R^b$, together with the atom to which they are attached, form a 3- to 11-membered heterocyclic ring; the heteroatom of the 3- to 11-membered heterocycloalkyl is selected from one or more than one of N, S, and O, and the number of heteroatoms is 1, 2, or 3; the heteroatom of the 3- to 11-membered heterocyclic ring is selected from one or more than one of N, S, and O, and the number of heteroatoms is 1, 2, or 3;

$R^{a-1}$, $R^{a-2}$, $R^{a-3}$, $R^{a-4}$, and $R^{a-5}$ are each independently halogen, cyano, hydroxyl, nitro, $C_{1-6}$ alkyl, $C_{1-6}$ alkoxy, 3- to 10-membered cycloalkyl, 3- to 11-membered heterocycloalkyl, 6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5-to 10-membered heteroaryl is selected from one or more than one of N, S, and O, and the number of heteroatoms is 1, 2, or 3;

each $R^4$ is independently unsubstituted 5- to 10-membered heteroaryl, 5- to 10-membered heteroaryl substituted by one or more than one $R^{4-1}$, unsubstituted 6- to 10-membered aryl, 6- to 10-membered aryl substituted by one or more than one $R^{4-5}$, unsubstituted 3- to 11-membered heterocycloalkyl, or 3- to 11-membered heterocycloalkyl substituted by one or more than one $R^{4-3}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{4-1}$ and $R^{4-5}$ are each independently halogen,

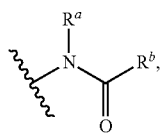

unsubstituted $C_{1-6}$ alkoxy, $C_{1-6}$ alkoxy substituted by one or more than one $R^{4-1-1}$,

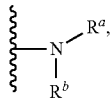

cyano, oxo, hydroxyl, unsubstituted $C_{1-6}$ alkyl, $C_{1-6}$ alkyl substituted by one or more than one $R^{4-1-3}$, unsubstituted 3- to 10-membered cycloalkyl, 3- to 10-membered cycloalkyl substituted by one or more than one $R^{4-1-4}$, unsubstituted 3- to 11-membered heterocycloalkyl, or 3- to 11-membered heterocycloalkyl substituted by one or more than one $R^{4-1-5}$; the heteroatom of the 3- to 11-membered heterocycloalkyl is selected from one or more than one of N, S, and O, and the number of heteroatoms is 1, 2, or 3;

each $R^{4-3}$ is independently hydroxyl, halogen, unsubstituted $C_{1-6}$ alkyl, $C_{1-6}$ alkyl substituted by one or more than one halogen,

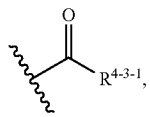

or oxo;

$R^{4-1-1}$, $R^{4-1-3}$, $R^{4-1-4}$, and $R^{4-1-5}$ are each independently halogen, hydroxyl, 3- to 10-membered cycloalkyl, 3- to 11-membered heterocycloalkyl, unsubstituted $C_{1-6}$ alkyl, $C_{1-6}$ alkyl substituted by one or more than one halogen, unsubstituted $C_{1-6}$ alkoxy, or $C_{1-6}$ alkoxy substituted by one or more than one halogen; the heteroatom of the 3- to 11-membered heterocycloalkyl is selected from one or more than one of N, S, or O, and the number of heteroatoms is 1, 2, or 3;

each $R^{4-3-1}$ is hydrogen, $C_{1-6}$ alkyl, or $C_{1-6}$ alkoxy.

The present disclosure provides a five-membered-fused six-membered compound of formula II or a pharmaceutically acceptable salt thereof,

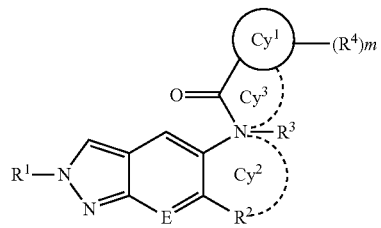

wherein m is 1, 2, or 3;

E is N or CH;

ring $Cy^1$ is a 5-membered heteroaromatic ring; the heteroatom of the 5-membered heteroaromatic ring is selected from one or more than one of N, S, and O, and the number of heteroatoms is 1, 2, or 3;

$R^3$ is hydrogen or $R^3$ is absent; when $R^3$ is absent, N and the atom on ring $Cy^1$, together with the atoms to which they are attached, form ring $Cy^3$, or N and the atom on $R^2$, together with the atoms to which they are attached, form ring $Cy^2$;

ring $Cy^2$ is a 5- to 9-membered heterocyclic ring; the heteroatom of the 5- to 9-membered heterocyclic ring is selected from one or more than one of N, S, and O, and the number of heteroatoms is 1, 2, or 3, and at least one heteroatom is N;

ring $Cy^3$ is an oxo-5- to 9-membered heterocyclic ring; the heteroatom of the oxo-5- to 9-membered heterocyclic ring is selected from one or more than one of N, S, and O, and the number of heteroatoms is 1, 2, or 3, and at least one heteroatom is N;

each $R^1$ is independently hydrogen, halogen, nitro, cyano, hydroxyl,

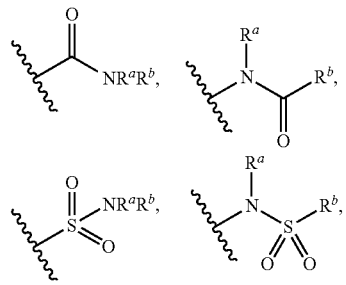

$-SO_2-R^a$, $-SO-R^a$,

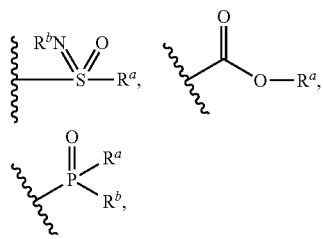

unsubstituted 3- to 11-membered heterocycloalkyl, 3- to 11-membered heterocycloalkyl substituted by one or more than one $R^{1-1}$, unsubstituted 3- to 10-membered cycloalkyl, 3- to 10-membered cycloalkyl substituted by one or more than one $R^{1-2}$,

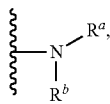

unsubstituted $C_{1-6}$ alkyl or $C_{1-6}$ alkyl substituted by one or more than one $R^{1-4}$, unsubstituted 6- to 10-membered aryl, 6- to 10-membered aryl substituted by one or more than one $R^{1-5}$, unsubstituted 5- to 10-membered heteroaryl, 5- to 10-membered heteroaryl substituted by one or more than one $R^{1-6}$, unsubstituted $C_{1-6}$ alkoxy, $C_{1-6}$ alkoxy substituted by one or more than one $R^{1-7}$, hydroxyl substituted by $R^{1-8}$, or —O—COR$^a$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{1-1}$, $R^{1-2}$, $R^{1-4}$, $R^{1-5}$, $R^{1-6}$, and $R^{1-7}$ are each independently halogen, oxo,

hydroxyl, unsubstituted 3- to 11-membered heterocycloalkyl, 3- to 11-membered heterocycloalkyl substituted by one or more than one $R^{1-1-1}$ cyano,

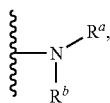

unsubstituted $C_{1-6}$ alkoxy, $C_{1-6}$ alkoxy substituted by one or more than one $R^{1-1-3}$,

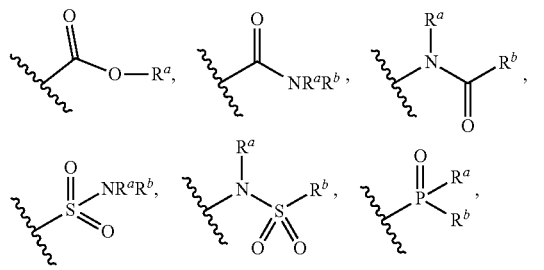

unsubstituted $C_{1-6}$ alkyl, $C_{1-6}$ alkyl substituted by one or more than one $R^{1-1-4}$, unsubstituted 3- to 10-membered cycloalkyl, 3- to 10-membered cycloalkyl substituted by one or more than one $R^{1-1-5}$, —SO$_2$—R$^a$, —SO—R$^a$,

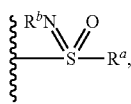

unsubstituted 6- to 10-membered aryl, 6- to 10-membered aryl substituted by one or more than one $R^{1-1-8}$, unsubstituted 5- to 10-membered heteroaryl, or 5- to 10-membered heteroaryl substituted by one or more than one $R^{1-1-7}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{1-8}$ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3; $R^{1-1-1}$, $R^{1-1-3}$, $R^{1-1-4}$, $R^{1-1-5}$, $R^{1-1-7}$, and $R^{1-1-8}$ are each independently unsubstituted $C_{1-6}$ alkyl, $C_{1-6}$ alkyl substituted by one or more than one halogen, halogen, oxo,

or hydroxyl;

$R^2$ is unsubstituted 3- to 11-membered heterocycloalkyl, 3- to 11-membered heterocycloalkyl substituted by one or more than one $R^{2-1}$, unsubstituted 3- to 8-membered cycloalkyl, 3- to 8-membered cycloalkyl substituted by one or more than one $R^{2-2}$, unsubstituted $C_{1-6}$ alkoxy, $C_{1-6}$ alkoxy substituted by one or more than one $R^{2-7}$, hydroxyl substituted by $R^{2-8}$, or $C_{1-6}$ alkyl substituted by one or more than one $R^{2-4}$; the heteroatom of the 3- to 11-membered heterocycloalkyl is selected from one or more than one of N, S, and O, and the number of heteroatoms is 1, 2, or 3;

$R^{2-1}$ and $R^{2-7}$ are each independently hydroxyl, halogen, oxo, unsubstituted $C_{1-6}$ alkyl, $C_{1-6}$ alkyl substituted by one or more than one halogen, 3- to 10-membered cycloalkyl, unsubstituted 3- to 8-membered heterocycloalkyl, or 3- to 8-membered heterocycloalkyl substituted by one or more than one $R^{2-1-1}$; the heteroatom of the 3- to 8-membered heterocycloalkyl is selected from one or more than one of N, S, and O, and the number of heteroatoms is 1, 2, or 3;

each $R^{2-2}$ is independently halogen, hydroxyl or hydroxyl substituted by 3- to 8-membered heterocycloalkyl; the heteroatom of the 3- to 8-membered heterocycloalkyl is selected from one or more than one of N, S, and O, and the number of heteroatoms is 1, 2, or 3;

each $R^{2-4}$ is independently halogen, hydroxyl, or hydroxyl substituted by 3- to 8-membered heterocycloalkyl; the heteroatom of the 3- to 8-membered heterocycloalkyl is selected from one or more than one of N, S, and O, and the number of heteroatoms is 1, 2, or 3;

$R^{2-8}$ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

each $R^{2-1-1}$ is independently hydroxyl, halogen, oxo, $C_{1-6}$ alkyl, 3- to 10-membered cycloalkyl, or 3- to 8-membered heterocycloalkyl; the heteroatom of the 3- to 8-membered heterocycloalkyl is selected from one or more than one of N, S, and O, and the number of heteroatoms is 1, 2, or 3;

when $R^2$ is unsubstituted 3- to 7-membered monoheterocycloalkyl, 3- to 7-membered monoheterocycloalkyl substituted by one or more than one $R^{2-1}$, unsubstituted 3- to 6-membered cycloalkyl, or 3- to 6-membered cycloalkyl substituted by one or more than one $R^{2-2}$, and $R^1$ is $C_{1-6}$ alkyl substituted by one or more than one $R^{1-4}$; each $R^{1-4}$ is independently halogen,

unsubstituted 3- to 11-membered heterocycloalkyl, 3- to 11-membered heterocycloalkyl substituted by one or more than one $R^{1-1-1}$,

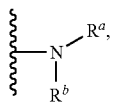

cyano,

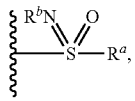

3- to 10-membered cycloalkyl substituted by one or more than one $R^{1-1-5}$, —$SO_2$—$R^a$, —SO—$R^a$,

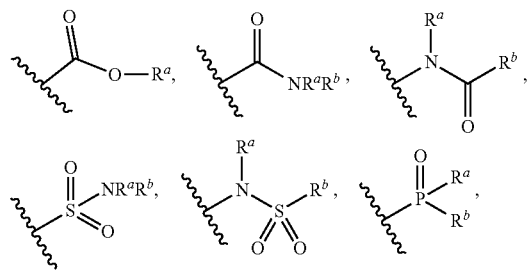

unsubstituted 6- to 10-membered aryl, 6- to 10-membered aryl substituted by one or more than one $R^{1-1-8}$, unsubstituted 5- to 10-membered heteroaryl, or 5- to 10-membered heteroaryl substituted by one or more than one $R^{1-1-7}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^a$ and $R^b$ are each independently H, unsubstituted $C_{1-6}$ alkyl, $C_{1-6}$ alkyl substituted by one or more than one $R^{a-1}$, unsubstituted 3- to 10-membered cycloalkyl, 3- to 10-membered cycloalkyl substituted by one or more than one $R^{a-2}$, unsubstituted 3- to 11-membered heterocycloalkyl, 3- to 11-membered heterocycloalkyl substituted by one or more than one $R^{a-3}$, unsubstituted 6- to 10-membered aryl, 6- to 10-membered aryl substituted by one or more than one $R^{a-4}$, unsubstituted 5- to 10-membered heteroaryl, or 5-to 10-membered heteroaryl substituted by one or more than one $R^{a-5}$;

or, $R^a$ and $R^b$, together with the atom to which they are attached, form a 3- to 11-membered heterocyclic ring; the heteroatom of the 3- to 11-membered heterocycloalkyl is selected from one or more than one of N, S, and O, and the number of heteroatoms is 1, 2, or 3; the heteroatom of the 3- to 11-membered heterocyclic ring is selected from one or more than one of N, S, and O, and the number of heteroatoms is 1, 2, or 3; $R^{a-1}$, $R^{a-2}$, $R^{a-3}$, $R^{a-4}$, and $R^{a-5}$ are each independently halogen, cyano, hydroxyl, nitro, $C_{1-6}$ alkyl, $C_{1-6}$ alkoxy, 3- to 10-membered cycloalkyl, 3- to 11-membered heterocycloalkyl, 6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5-to 10-membered heteroaryl is selected from one or more than one of N, S, and O, and the number of heteroatoms is 1, 2, or 3;

each $R^4$ is independently unsubstituted 5- to 10-membered heteroaryl, 5- to 10-membered heteroaryl substituted by one or more than one $R^{4-1}$, unsubstituted 6- to 10-membered aryl, 6- to 10-membered aryl substituted by one or more than one $R^{4-5}$, unsubstituted 3- to 11-membered heterocycloalkyl, 3- to 11-membered heterocycloalkyl substituted by one or more than one $R^{4-3}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{4-1}$ and $R^{4-5}$ are each independently halogen,

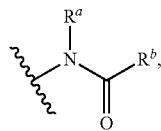

unsubstituted $C_{1-6}$ alkoxy, $C_{1-6}$ alkoxy substituted by one or more than one $R^{4-1-1}$,

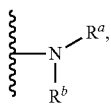

cyano, oxo, hydroxyl, unsubstituted $C_{1-6}$ alkyl, $C_{1-6}$ alkyl substituted by one or more than one $R^{4-1-3}$, unsubstituted 3- to 10-membered cycloalkyl, 3- to 10-membered cycloalkyl substituted by one or more than one $R^{4-1-4}$, unsubstituted 3- to 11-membered heterocycloalkyl, or 3- to 11-membered heterocycloalkyl substituted by one or more than one $R^{4-1-5}$; the heteroatom of the 3- to 11-membered heterocycloalkyl is selected from one or more than one of N, S, and O, and the number of heteroatoms is 1, 2, or 3;

each $R^{4-3}$ is independently hydroxyl, halogen, unsubstituted $C_{1-6}$ alkyl, $C_{1-6}$ alkyl substituted by one or more than one halogen,

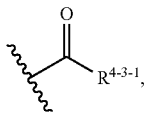

or oxo;

$R^{4-1-1}$, $R^{4-1-3}$, $R^{4-1-4}$, and $R^{4-1-5}$ are each independently halogen, hydroxyl, 3- to 10-membered cycloalkyl, 3- to 11-membered heterocycloalkyl, unsubstituted $C_{1-6}$ alkyl, $C_{1-6}$ alkyl substituted by one or more than one halogen, unsubstituted $C_{1-6}$ alkoxy, or $C_{1-6}$ alkoxy substituted by one or more than one halogen;

each $R^{4-3-1}$ is hydrogen, $C_{1-6}$ alkyl, or $C_{1-6}$ alkoxy.

In a preferred embodiment, in the compound of formula II or the pharmaceutically acceptable salt thereof, some groups can be defined as follows, and other groups can be defined as described in any of the above embodiments (hereinafter referred to as "in a preferred embodiment"): ring $Cy^1$ is a 5-membered heteroaromatic ring; the heteroatom of the 5-membered heteroaromatic ring is selected from one or two of N, S, and O, and the number of heteroatoms is 1, 2, or 3.

When $R^2$ is unsubstituted 3- to 7-membered monoheterocycloalkyl, 3- to 7-membered monoheterocycloalkyl substituted by one or more than one $R^{2-1}$, unsubstituted 3- to 6-membered cycloalkyl, 3- to 6-membered cycloalkyl substituted by one or more than one $R^{2-2}$, and $R^1$ is $C_{1-6}$ alkyl substituted by one or more than one $R^{1-4}$; each $R^{1-4}$ is independently halogen, unsubstituted 3- to 11-membered heterocycloalkyl, 3- to 11-membered heterocycloalkyl substituted by one or more than one $R^{1-1-1}$,

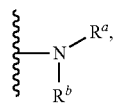

cyano,

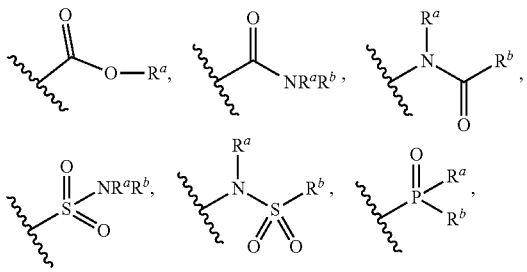

3- to 10-membered cycloalkyl substituted by one or more than one $R^{1-1-5}$, $-SO_2-R^a$, $-SO-R^a$,

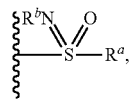

unsubstituted 6- to 10-membered aryl, 6- to 10-membered aryl substituted by one or more than one $R^{1-1-8}$, unsubstituted 5- to 10-membered heteroaryl, or 5- to 10-membered heteroaryl substituted by one or more than one $R^{1-1-7}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

In a preferred embodiment, ring Cy t is a 5- to 6-membered heterocyclic ring; the heteroatom of the 5- to 6-membered heterocyclic ring is N, and the number of heteroatoms is 1, 2, or 3.

In a preferred embodiment, ring $Cy^3$ is an oxo-5- to 9-membered heterocyclic ring; the heteroatom of the oxo-5- to 9-membered heterocyclic ring is N, and the number of heteroatoms is 1, 2, or 3.

In a preferred embodiment, $R^1$ is $C_{1-6}$ alkyl substituted by one or more than one $R^{1-4}$, 3- to 10-membered cycloalkyl substituted by one or more than one $R^{1-2}$, unsubstituted 3- to 11-membered heterocycloalkyl, or 3- to 11-membered heterocycloalkyl substituted by one or more than one $R^{1-1}$; the heteroatom of the 3- to 11-membered heterocycloalkyl is selected from one or two of N, S, and O, and the number of heteroatoms is 1, 2, or 3.

In a preferred embodiment, $R^1$ is $C_{1-6}$ alkyl substituted by one or more than one $R^{1-4}$, unsubstituted 3- to 10-membered cycloalkyl, 3- to 10-membered cycloalkyl substituted by one or more than one $R^{1-2}$, unsubstituted 3- to 11-membered heterocycloalkyl, or 3- to 11-membered heterocycloalkyl substituted by one or more than one $R^{1-1}$; the heteroatom of the 3- to 11-membered heterocycloalkyl is selected from one or two of N, S, and O, and the number of heteroatoms is 1, 2, or 3.

In a preferred embodiment, $R^{1-1}$, $R^{1-2}$, and $R^{1-4}$ are each independently deuterium, halogen, oxo, hydroxyl,

unsubstituted $C_{1-6}$ alkoxy, $C_{1-6}$ alkoxy substituted by one or more than one $R^{1-1-3}$,

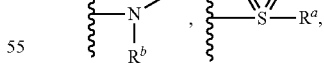

$-SO_2$-$C_{1-6}$ alkyl, unsubstituted $C_{1-6}$ alkyl, $C_{1-6}$ alkyl substituted by one or more than one $R^{1-1-4}$, unsubstituted 3- to 10-membered cycloalkyl, 3- to 10-membered cycloalkyl substituted by one or more than one $R^{1-1-5}$, unsubstituted 3- to 10-membered heterocycloalkyl, or 3- to 10-membered heterocycloalkyl substituted by one or more than one $R^{1-1-1}$; the heteroatom of the 3- to 10-membered heterocycloalkyl is one or two of N, S, and O, and the number of heteroatoms is 1, 2, or 3.

In a preferred embodiment, $R^{1-1}$, $R^{1-2}$, and $R^{1-4}$ are each independently halogen, oxo, hydroxyl,

unsubstituted $C_{1-6}$ alkoxy, $C_{1-6}$ alkoxy substituted by one or more than one $R^{1-1-3}$,

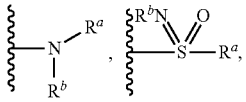

—SO$_2$—C$_{1-6}$ alkyl, unsubstituted $C_{1-6}$ alkyl, $C_{1-6}$ alkyl substituted by one or more than one $R^{1-1-4}$, unsubstituted 3- to 10-membered cycloalkyl, 3- to 10-membered cycloalkyl substituted by one or more than one $R^{1-1-5}$, unsubstituted 3- to 10-membered heterocycloalkyl, or 3- to 10-membered heterocycloalkyl substituted by one or more than one $R^{1-1-1}$; the heteroatom of the 3- to 10-membered heterocycloalkyl is one or two of N, S, and O, and the number of heteroatoms is 1, 2, or 3.

In a preferred embodiment, each $R^{1-1-1}$ is independently hydroxyl, unsubstituted $C_{1-6}$ alkyl, $C_{1-6}$ alkyl substituted by one or more than one halogen, oxo,

or halogen.

In a preferred embodiment, each $R^{1-1-1}$ is independently deuterium, hydroxyl, unsubstituted $C_{1-6}$ alkyl, $C_{1-6}$ alkyl substituted by one or more than one halogen, oxo,

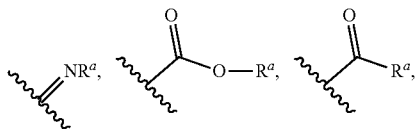

or halogen.

In a preferred embodiment, each $R^{1-1-1}$ is independently hydroxyl, unsubstituted $C_{1-6}$ alkyl, $C_{1-6}$ alkyl substituted by one or more than one halogen, oxo,

or halogen.

In a preferred embodiment, each $R^{1-1-3}$ is independently deuterium, hydroxyl, or halogen.

In a preferred embodiment, each $R^{1-1-4}$ is independently deuterium, hydroxyl, or halogen.

In a preferred embodiment, each $R^{1-1-5}$ is independently deuterium, hydroxyl, or halogen.

In a preferred embodiment, $R^2$ is unsubstituted 3- to 10-membered heterocycloalkyl, 3- to 10-membered hetero-cycloalkyl substituted by one or more than one $R^{2-1}$, unsubstituted 3- to 6-membered cycloalkyl, 3- to 6-membered cycloalkyl substituted by one or more than one $R^{2-2}$, unsubstituted $C_{1-6}$ alkyl, $C_{1-6}$ alkyl substituted by one or more than one $R^{2-4}$, unsubstituted $C_{1-6}$ alkoxy, $C_{1-6}$ alkoxy substituted by one or more than one $R^{2-7}$, or hydroxyl substituted by $R^{2-8}$; the heteroatom of the 3- to 10-membered heterocycloalkyl is selected from one or two of N and O, and the number of heteroatoms is 1, 2, or 3.

In a preferred embodiment, $R^{2-1}$ and $R^{2-7}$ are each independently deuterium, oxo, hydroxyl, halogen, unsubstituted $C_{1-6}$ alkyl, $C_{1-6}$ alkyl substituted by one or more than one halogen, 3- to 6-membered cycloalkyl, or 3- to 8-membered heterocycloalkyl; the heteroatom of the 3- to 8-membered heterocycloalkyl is selected from one or more than one of N, S, and O, and the number of heteroatoms is 1 or 2.

In a preferred embodiment, $R^{2-1}$ and $R^{2-2}$ are each independently deuterium, oxo, hydroxyl, halogen, unsubstituted $C_{1-6}$ alkyl, $C_{1-6}$ alkyl substituted by one or more than one halogen, 3- to 6-membered cycloalkyl, or 3- to 8-membered heterocycloalkyl; the heteroatom of the 3- to 8-membered heterocycloalkyl is selected from one or more than one of N, S, and O, and the number of heteroatoms is 1 or 2.

In a preferred embodiment, each $R^{2-2}$ is independently deuterium, halogen, hydroxyl, or hydroxyl substituted by 3- to 8-membered heterocycloalkyl; the heteroatom of the 3- to 8-membered heterocycloalkyl is selected from one or more than one of N, S, and O, and the number of heteroatoms is 1 or 2.

In a preferred embodiment, each $R^{2-2}$ is independently hydroxyl, hydroxyl substituted by 3- to 8-membered heterocycloalkyl; the heteroatom of the 3- to 8-membered heterocycloalkyl is selected from one or more than one of N, S, and O, and the number of heteroatoms is 1 or 2.

In a preferred embodiment, each $R^{2-4}$ is independently deuterium, halogen, hydroxyl, or hydroxyl substituted by 3- to 8-membered heterocycloalkyl; the heteroatom of the 3- to 8-membered heterocycloalkyl is selected from one or more than one of N, S, and O, and the number of heteroatoms is 1 or 2.

In a preferred embodiment, each $R^{2-4}$ is independently hydroxyl, hydroxyl substituted by 3- to 8-membered heterocycloalkyl; the heteroatom of the 3- to 8-membered heterocycloalkyl is selected from one or more than one of N, S, and O, and the number of heteroatoms is 1 or 2.

In a preferred embodiment, $R^{2-8}$ is 3- to 6-membered cycloalkyl or 3- to 6-membered heterocycloalkyl; the heteroatom of the 3- to 6-membered heterocycloalkyl is selected from one or more than one of N, S, and O, and the number of heteroatoms is 1, 2, or 3.

In a preferred embodiment, each $R^4$ is independently unsubstituted phenyl, phenyl substituted by one or more than one $R^{4-5}$, unsubstituted 5- to 6-membered heteroaryl, 5- to 6-membered heteroaryl substituted by one or more than one $R^{4-1}$, unsubstituted 3- to 6-membered heterocycloalkyl, or 3- to 6-membered heterocycloalkyl substituted by one or more than one $R^{4-3}$; the heteroatom of the 3- to 6-membered heterocycloalkyl is selected from one or more than one of N, S, and O, and the number of heteroatoms is 1, 2, or 3; the heteroatom of the 5- to 6-membered heteroaryl is selected from one or more than one of N, S, or O, and the number of heteroatoms is 1, 2, or 3.

In a preferred embodiment, $R^{4-1}$ and $R^{4-5}$ are each independently oxo, hydroxyl, $C_{1-6}$ alkyl, or $C_{1-6}$ alkyl substituted by one or more than one halogen.

In a preferred embodiment, each $R^{4-3}$ is independently halogen, unsubstituted $C_{1-6}$ alkyl, $C_{1-6}$ alkyl substituted by one or more than one halogen,

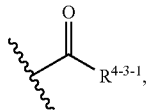

or oxo.

In a preferred embodiment, each $R^{4-3-1}$ is independently $C_{1-6}$ alkyl or $C_{1-6}$ alkoxy.

In a preferred embodiment, E is CH.

In a preferred embodiment, $R^a$ and $R^b$ are each independently H or $C_{1-6}$ alkyl; or, $R^a$ and $R^b$, together with the atom to which they are attached, form a 3- to 6-membered heterocyclic ring; the heteroatom of the 3- to 6-membered heterocyclic ring is S, and the number of heteroatoms is 1.

In a preferred embodiment, when $R^2$ is unsubstituted 3- to 7-membered monoheterocycloalkyl, 3-to 7-membered monoheterocycloalkyl substituted by one or more than one $R^{2-1}$, and $R^1$ is $C_{1-6}$ alkyl substituted by one or more than one $R^{1-4}$; each $R^{1-4}$ is independently deuterium, hydroxyl, halogen, unsubstituted 3- to 8-membered heterocycloalkyl, 3- to 8-membered heterocycloalkyl substituted by one or more than one $R^{1-1-1}$, 3- to 10-membered cycloalkyl substituted by one or more than one $R^{1-1-5}$, $-SO_2-R^a$, or

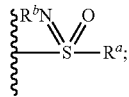

the heteroatom of the 3- to 8-membered heterocycloalkyl is selected from one or two of N and O, and the number of heteroatoms is 1 or 2.

In a preferred embodiment, when $R^2$ is unsubstituted 3- to 7-membered monoheterocycloalkyl, 3-to 7-membered monoheterocycloalkyl substituted by one or more than one $R^{2-1}$, unsubstituted 3- to 6-membered cycloalkyl, or 3- to 6-membered cycloalkyl substituted by one or more than one $R^{2-2}$, and $R^1$ is $C_{1-6}$ alkyl substituted by one or more than one $R^{1-4}$; each $R^{1-4}$ is independently halogen,

unsubstituted 3- to 8-membered heterocycloalkyl, or 3- to 8-membered heterocycloalkyl substituted by one or more than one $R^{1-1-1}$, 3- to 10-membered cycloalkyl substituted by one or more than one $R^{1-1-5}$, $-SO_2-R^a$, $-SO-R^a$, or

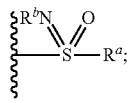

the heteroatom of the 3- to 8-membered heterocycloalkyl is selected from one or two of N and O, and the number of heteroatoms is 1 or 2.

In a preferred embodiment, m is 1.

In a preferred embodiment, $R^3$ is hydrogen.

In a preferred embodiment, $R^1$ is $C_{1-6}$ alkyl substituted by one or more than one $R^{1-4}$, 3- to 10-membered cycloalkyl substituted by one or more than one $R^{1-2}$, unsubstituted 3- to 10-membered heterocycloalkyl, or 3- to 10-membered heterocycloalkyl substituted by one or more than one $R^{1-1}$; the heteroatom of the 3- to 10-membered heterocycloalkyl is one or more than one of N, O, or S, and the number of heteroatoms is 1 or 2.

In a preferred embodiment, $R^1$ is $C_{1-6}$ alkyl substituted by one or more than one $R^{1-4}$, unsubstituted 3- to 10-membered cycloalkyl, 3- to 10-membered cycloalkyl substituted by one or more than one $R^{1-2}$, unsubstituted 3- to 10-membered heterocycloalkyl, or 3- to 10-membered heterocycloalkyl substituted by one or more than one $R^{1-1}$; the heteroatom of the 3- to 10-membered heterocycloalkyl is one or more than one of N, O, or S, and the number of heteroatoms is 1 or 2.

In a preferred embodiment, $R^1$ is $C_{1-6}$ alkyl substituted by one or more than one $R^{1-4}$, unsubstituted 3- to 6-membered cycloalkyl, 3- to 6-membered cycloalkyl substituted by one or more than one $R^{1-2}$, unsubstituted 3- to 8-membered heterocycloalkyl, or 3- to 8-membered heterocycloalkyl substituted by one or more than one $R^{1-1}$; the heteroatom of the 3- to 8-membered heterocycloalkyl is one of N, O, or S, and the number of heteroatoms is 1.

In a preferred embodiment, $R^1$ is

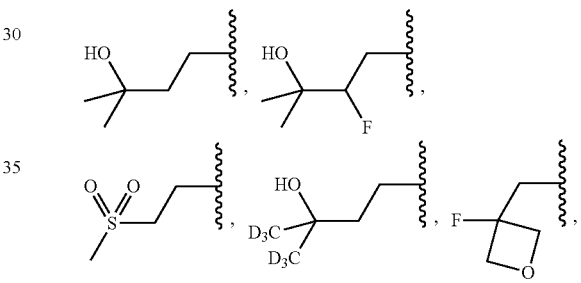

3- to 6-membered cycloalkyl substituted by one hydroxyl group, 6-membered cycloalkyl substituted by one $-SO_2-C_{1-6}$ alkyl group, or

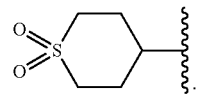

In a preferred embodiment, $R^{1-1}$, $R^{1-2}$, and $R^{1-4}$ are each independently deuterium, oxo, hydroxyl,

halogen, $-SO_2-C_{1-6}$ alkyl,

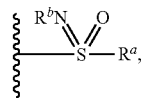

unsubstituted $C_{1-6}$ alkyl, $C_{1-6}$ alkyl substituted by one or more than one $R^{1-1-4}$, unsubstituted 3- to 10-membered cycloalkyl, 3- to 10-membered cycloalkyl substituted by one or more than one $R^{1-1-5}$, unsubstituted 3- to 10-membered heterocycloalkyl, or 3- to 10-membered heterocycloalkyl substituted by one or more than one $R^{1-1-1}$; the heteroatom of the 3- to 10-membered heterocycloalkyl is one or more than one of N, O, or S, and the number of heteroatoms is 1, 2, or 3.

In a preferred embodiment, $R^{1-1}$, $R^{1-2}$, and $R^{1-4}$ are each independently deuterium, hydroxyl,

oxo, halogen,

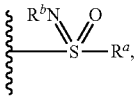

—$SO_2$-$C_{1-6}$ alkyl, unsubstituted $C_{1-6}$ alkyl, $C_{1-6}$ alkyl substituted by one or more than one $R^{1-1-4}$ unsubstituted 3- to 6-membered cycloalkyl, 3- to 6-membered cycloalkyl substituted by one or more than one $R^{1-1-5}$, unsubstituted 3- to 6-membered heterocycloalkyl, or 3- to 6-membered heterocycloalkyl substituted by one or more than one $R^{1-1-1}$; the heteroatom of the 3- to 6-membered heterocycloalkyl is one of N, O, or S, and the number of heteroatoms is 1.

In a preferred embodiment, each $R^{1-1}$ is independently oxo,

unsubstituted $C_{1-6}$ alkyl, $C_{1-6}$ alkyl substituted by one or more than one $R^{1-1-4}$, unsubstituted 3- to 6-membered heterocycloalkyl, or 3- to 6-membered heterocycloalkyl substituted by one or more than one $R^{1-1-1}$; the heteroatom of the 3- to 6-membered heterocycloalkyl is one of N, O, or S, and the number of heteroatoms is 1.

In a preferred embodiment, each $R^{1-2}$ is independently halogen, hydroxyl, or —$SO_2$—$C_{1-6}$ alkyl.

In a preferred embodiment, each $R^{1-4}$ is independently deuterium, hydroxyl,

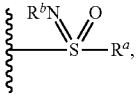

halogen, —$SO_2$-$C_{1-6}$ alkyl, unsubstituted $C_{1-6}$ alkyl, $C_{1-6}$ alkyl substituted by one or more than one $R^{1-1-4}$, unsubstituted 3- to 6-membered heterocycloalkyl, or 3- to 6-membered heterocycloalkyl substituted by one or more than one $R^{1-1-1}$; the heteroatom of the 3- to 6-membered heterocycloalkyl is one of N, O, or S, and the number of heteroatoms is 1.

In a preferred embodiment, each $R^{1-1-1}$ is independently oxo, halogen,

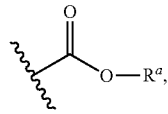

or hydroxyl.

In a preferred embodiment, each $R^{1-1-4}$ is independently halogen.

In a preferred embodiment, each $R^{1-1-5}$ is independently hydroxyl.

In a preferred embodiment, $R^2$ is unsubstituted 3- to 8-membered heterocycloalkyl, 3- to 8-membered heterocycloalkyl substituted by one or more than one $R^{2-1}$, unsubstituted $C_{3-6}$ cycloalkyl, $C_{3-6}$ cycloalkyl substituted by one or more than one $R^{2-2}$, unsubstituted $C_{1-6}$ alkoxy, $C_{1-6}$ alkoxy substituted by one or more than one $R^{2-7}$, unsubstituted $C_{1-6}$ alkyl, $C_{1-6}$ alkyl substituted by one or more than one $R^{2-4}$, or hydroxyl substituted by $R^{2-8}$; the heteroatom of the 3- to 8-membered heterocycloalkyl is selected from one or two of N and O, and the number of heteroatoms is 1 or 2.

In a preferred embodiment, $R^2$ is unsubstituted 3- to 6-membered heterocycloalkyl, 3- to 6-membered heterocycloalkyl substituted by one or more than one $R^{2-1}$, unsubstituted $C_{1-6}$ alkoxy, $C_{1-6}$ alkoxy substituted by one or more than one $R^{2-7}$, unsubstituted $C_{1-6}$ alkyl, or $C_{1-6}$ alkyl substituted by one or more than one $R^{2-4}$; the heteroatom of the 3- to 6-membered heterocycloalkyl is selected from N and/or O, and the number of heteroatoms is 1 or 2.

In a preferred embodiment, $R^2$ is unsubstituted $C_{1-6}$ alkoxy, $C_{1-6}$ alkoxy substituted by one or more than one $R^{2-7}$, unsubstituted $C_{1-6}$ alkyl, or $C_{1-6}$ alkyl substituted by one or more than one $R^{2-4}$.

In a preferred embodiment, $R^{2-8}$ is 3- to 6-membered cycloalkyl or 3- to 6-membered heterocycloalkyl; the heteroatom of the 3- to 6-membered heterocycloalkyl is selected from one of N and O, and the number of heteroatoms is 1.

In a preferred embodiment, each $R^{2-1}$ is independently hydroxyl or halogen.

In a preferred embodiment, each $R^{2-2}$ is independently hydroxyl.

In a preferred embodiment, each $R^{2-4}$ is independently deuterium, hydroxyl, or halogen.

In a preferred embodiment, each $R^{2-7}$ is independently deuterium or halogen.

In a preferred embodiment, $R^4$ is unsubstituted phenyl, phenyl substituted by one or more than one $R^{4-5}$, unsubstituted 5- to 6-membered heteroaryl, 5- to 6-membered heteroaryl substituted by one or more than one $R^{4-1}$, unsubstituted 3- to 6-membered heterocycloalkyl, or 3- to 6-membered heterocycloalkyl substituted by one or more than one $R^{4-3}$; the heteroatom of the 5- to 6-membered heteroaryl is N, and the number of heteroatoms is 1, 2, or 3; the heteroatom of the 3- to 6-membered heterocycloalkyl is selected from one or more than one of N, S, and O, and the number of heteroatoms is 1 or 2 (preferably each $R^4$ is independently unsubstituted 5- to 6-membered heteroaryl, or 5- to 6-membered heteroaryl substituted by one or more than one $R^{4-1}$, the heteroatom of the 5- to 6-membered heteroaryl is N, and the number of heteroatoms is 1 or 2).

In a preferred embodiment, each $R^4$ is independently unsubstituted pyridyl, or pyridyl substituted by one or more than one $R^{4-1}$.

In a preferred embodiment, $R^{4-1}$ and $R^{4-5}$ are each independently unsubstituted $C_{1-6}$ alkyl, or $C_{1-6}$ alkyl substituted by one or more than one halogen.

In a preferred embodiment, each $R^{4-1}$ is independently unsubstituted $C_{1-6}$ alkyl, or $C_{1-6}$ alkyl substituted by one, two, or three halogens.

In a preferred embodiment, each $R^{4-3}$ is independently halogen, unsubstituted $C_{1-6}$ alkyl, $C_{1-6}$ alkyl substituted by one or more than one halogen, oxo, or

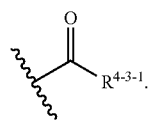

In a preferred embodiment, each $R^{4-3-1}$ is independently $C_{1-6}$ alkyl or $C_{1-6}$ alkoxy.

In a preferred embodiment, the five-membered-fused six-membered compound of formula II is a compound of formula II-a, a compound of formula II-b, a compound of formula II-c, or a compound of formula II-d, II-a

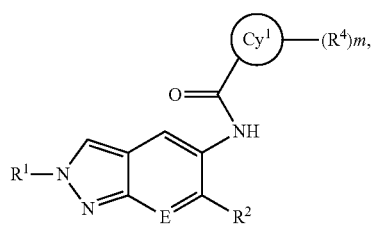

II-b

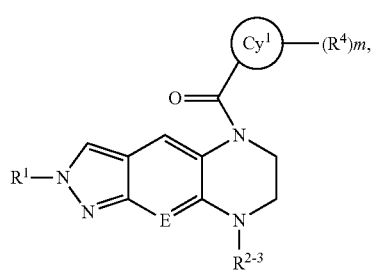

II-c

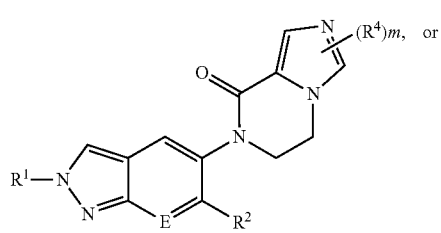

II-d

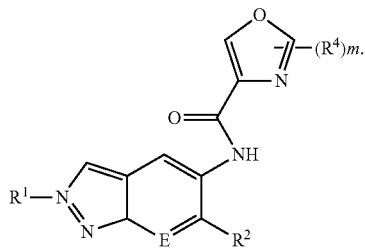

In a preferred embodiment, $R^1$ is

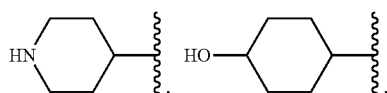

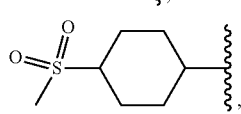

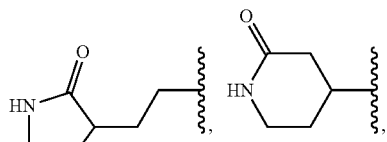

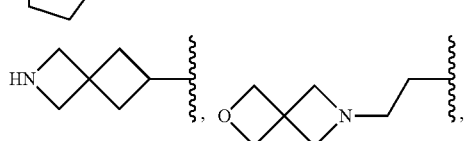

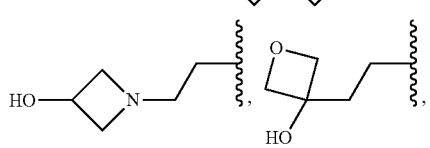

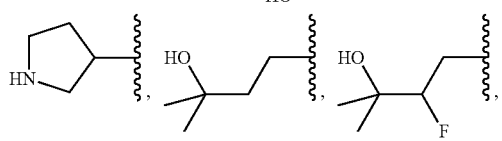

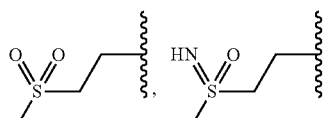

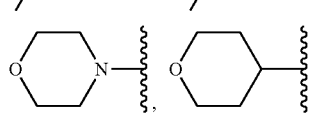

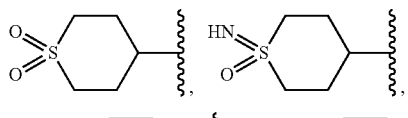

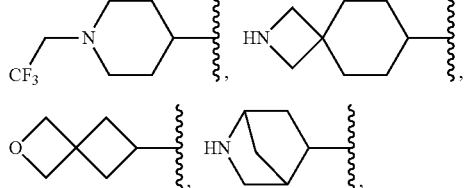

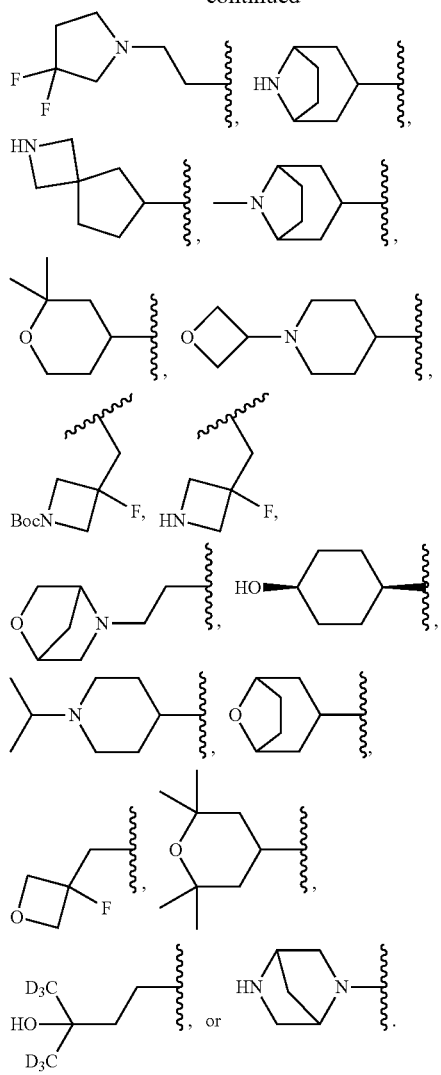
In a preferred embodiment, $R^2$ is methoxy, —$OCD_3$, isopropoxy, trifluoromethoxy,
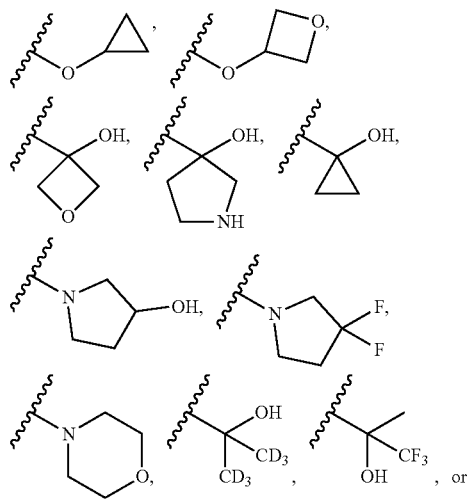
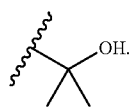
In a preferred embodiment, each $R^4$ is independently
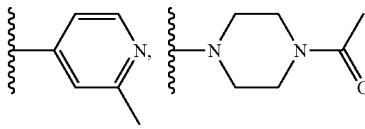
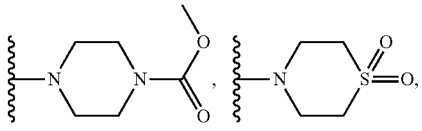
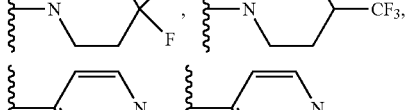
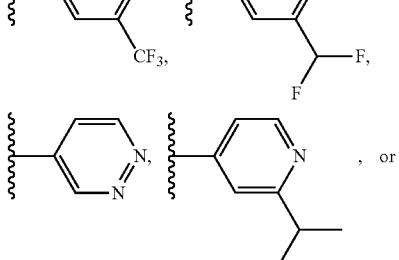
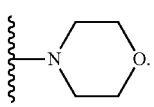
In a preferred embodiment, ring $Cy^1$ is
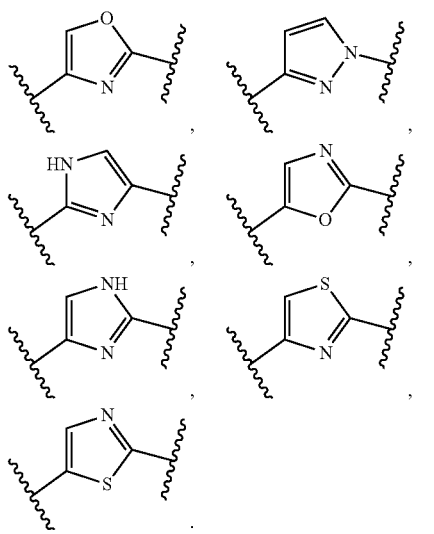

In a preferred embodiment, the five-membered-fused six-membered compound of formula II or the pharmaceutically acceptable salt thereof is any one of the following compounds,
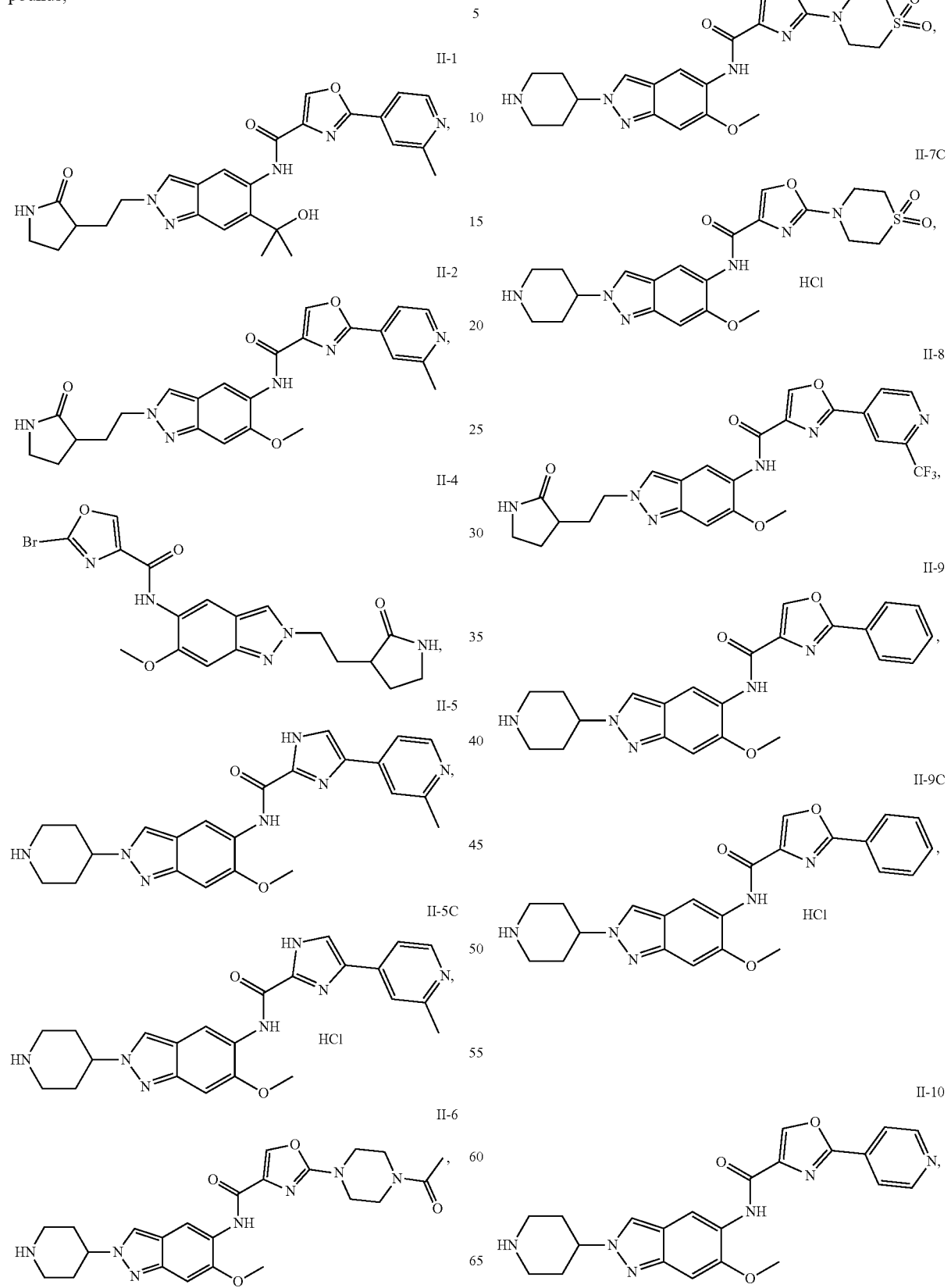

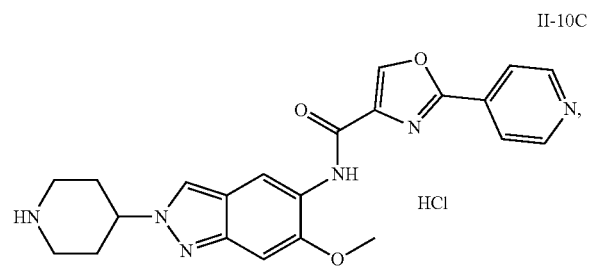
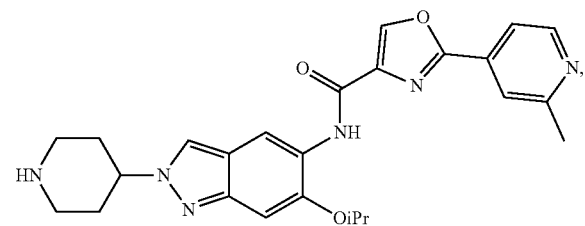
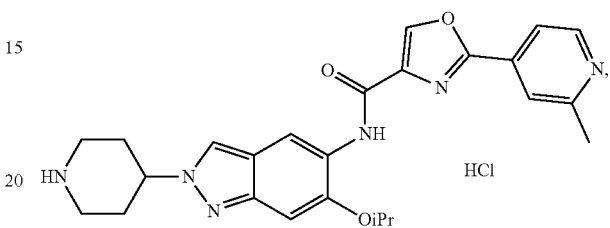
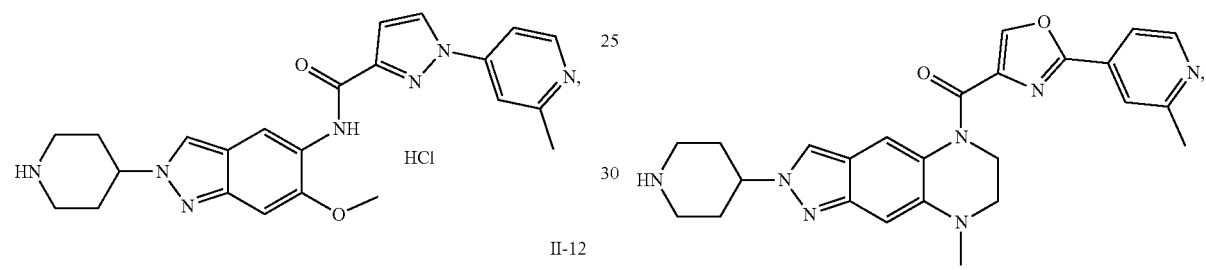
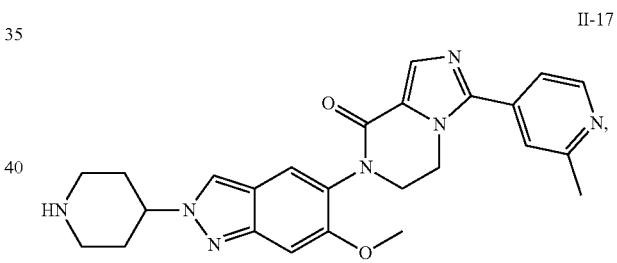
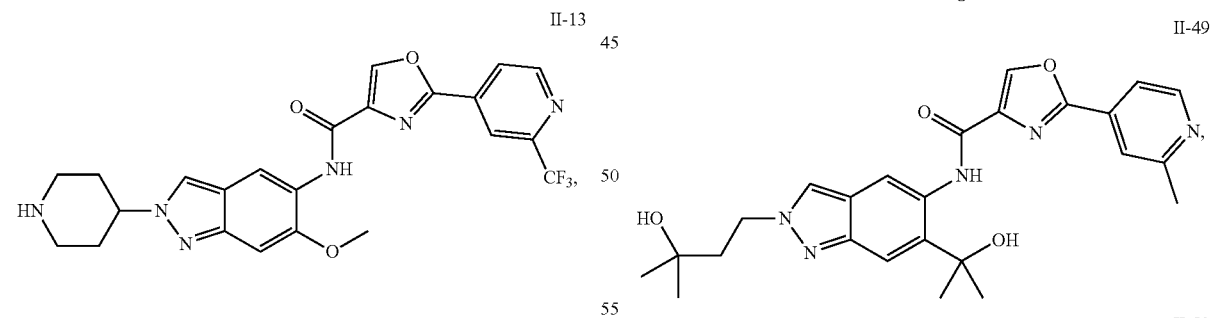
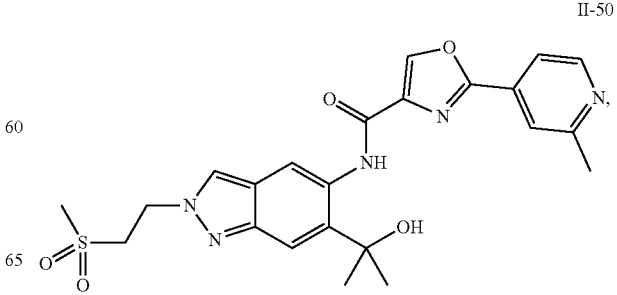

II-51 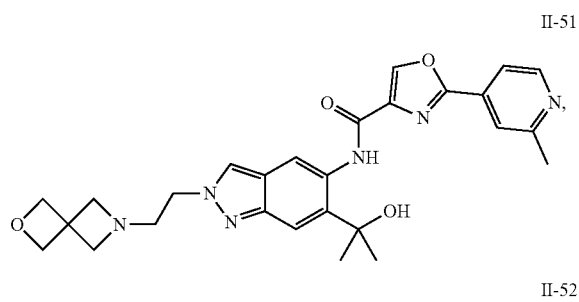
II-52 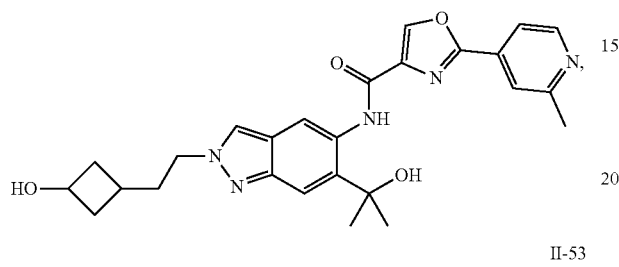
II-53 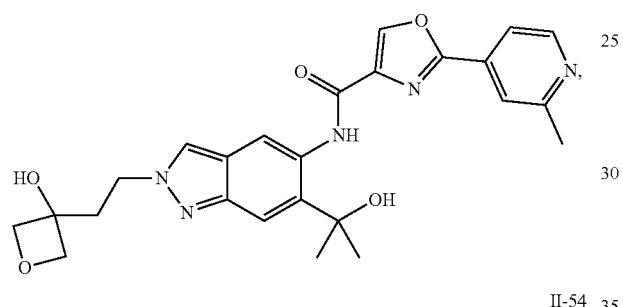
II-54 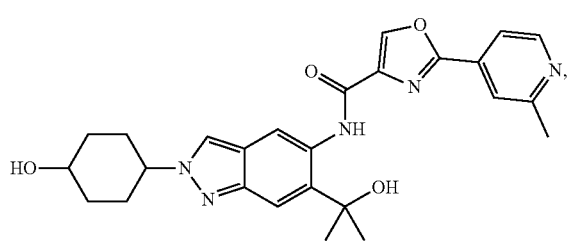
II-55 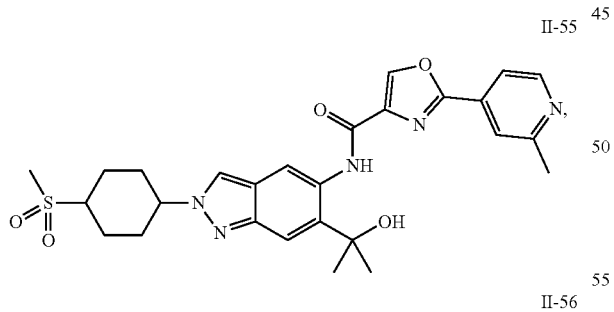
II-56 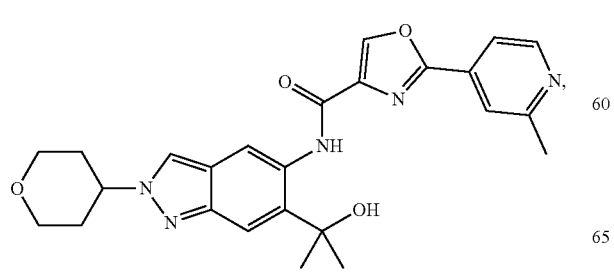
II-57 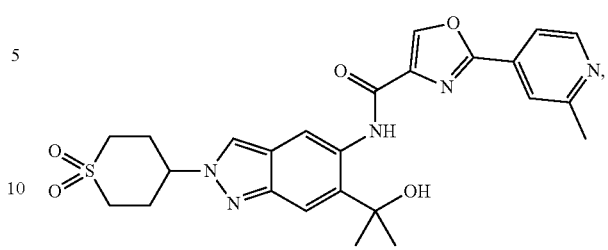
II-58 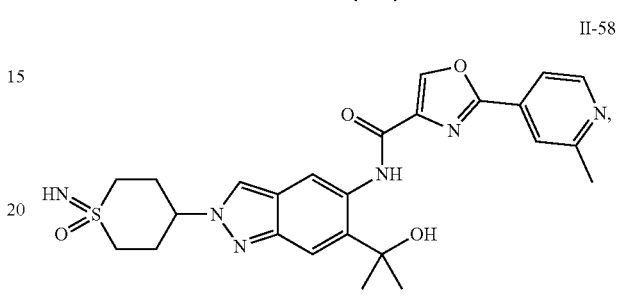
II-59
II-60
II-61 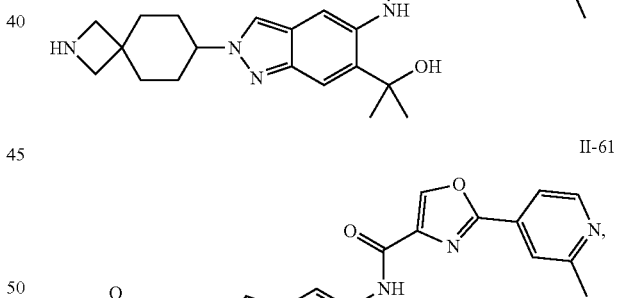
II-62 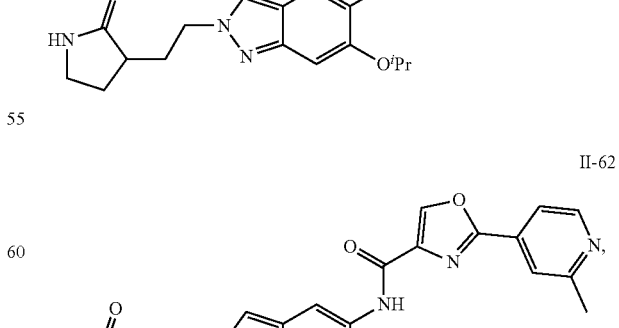

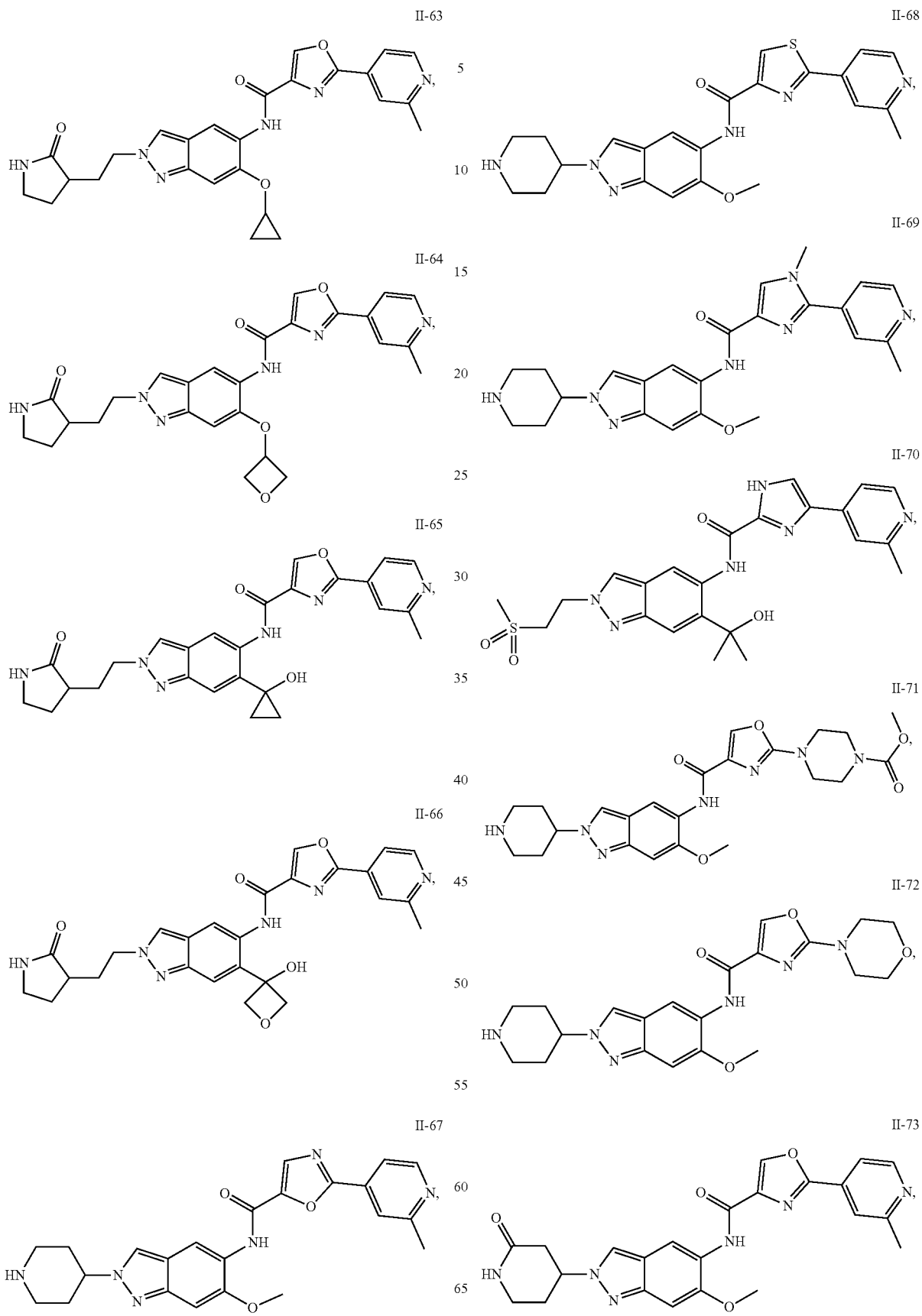

II-74
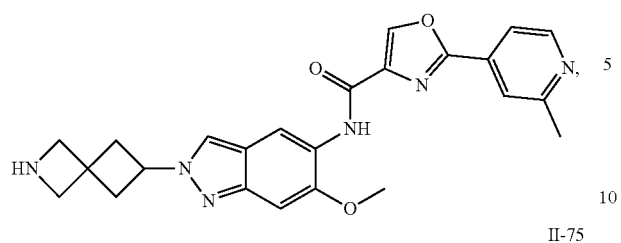
II-94
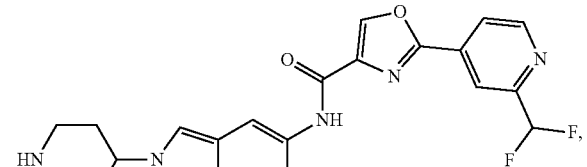
II-75
II-94C
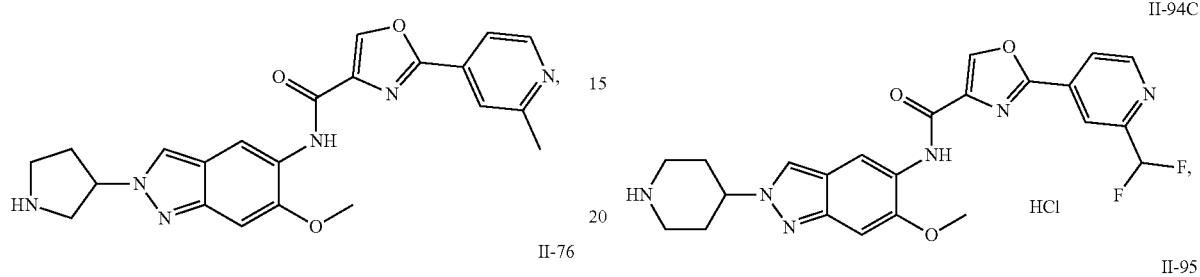
II-76
II-95
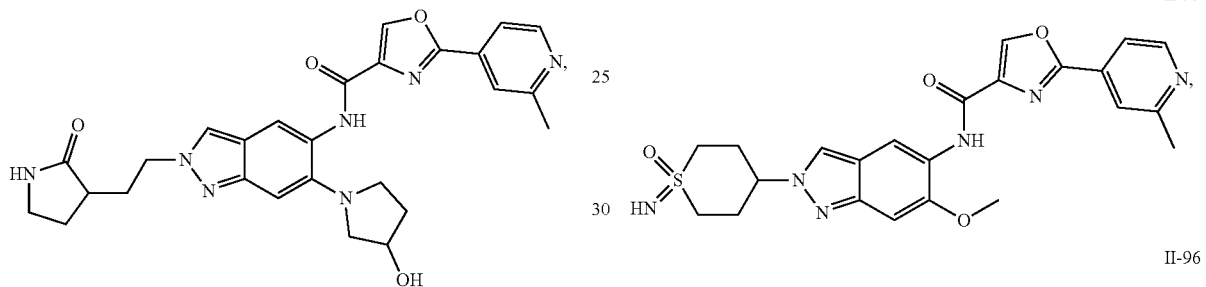
II-77
II-96
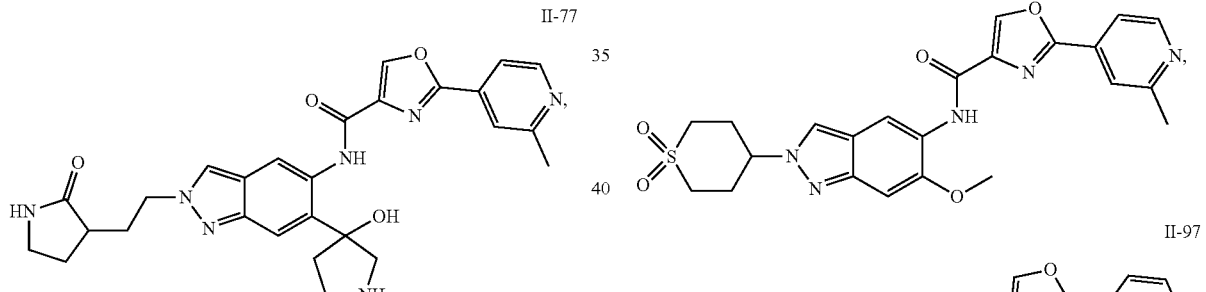
II-78
II-97
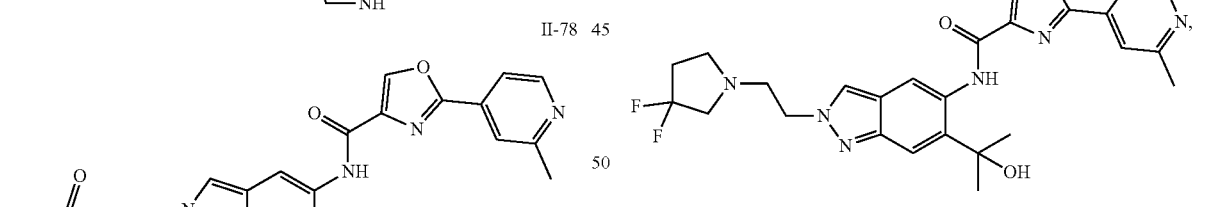
II-93
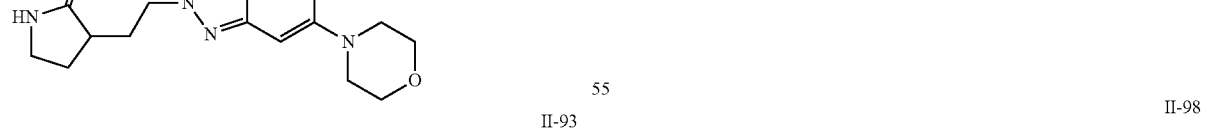
II-98
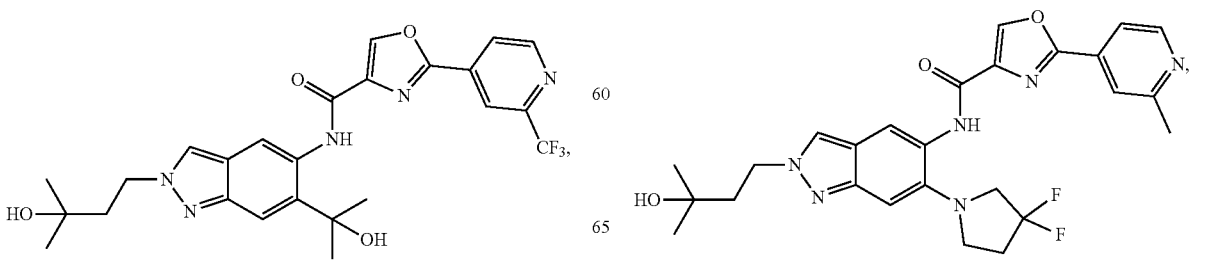

-continued
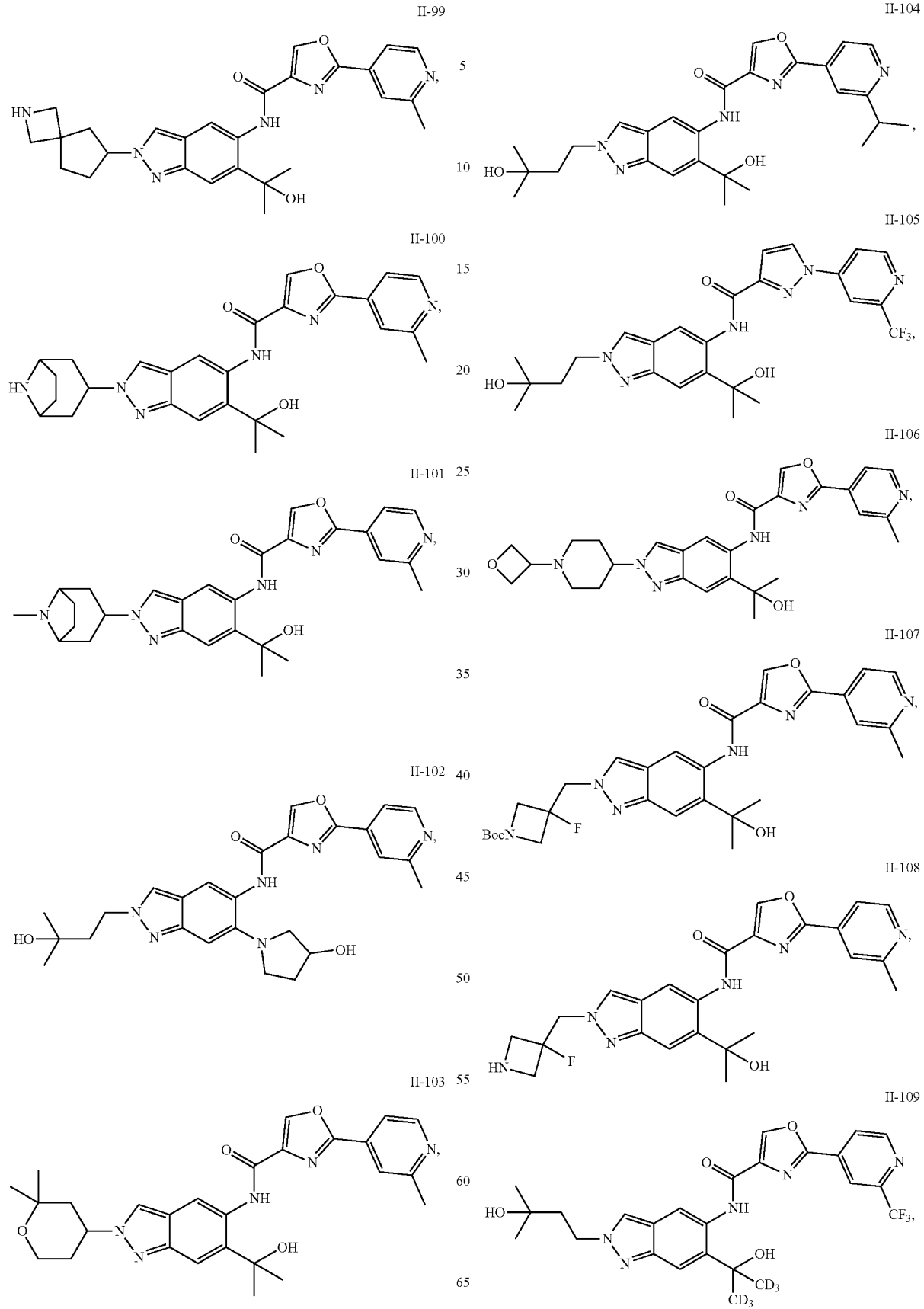

-continued
II-110
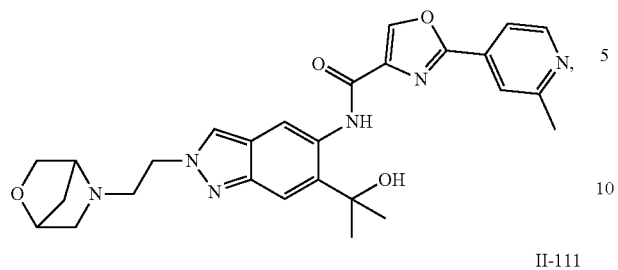
II-111
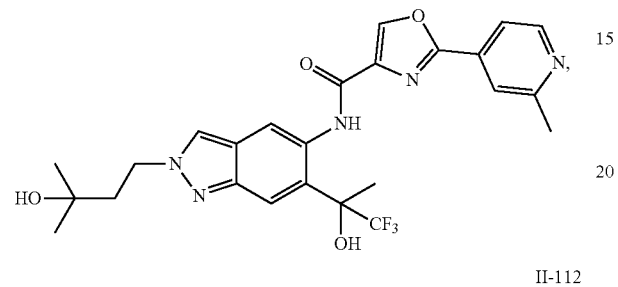
II-112
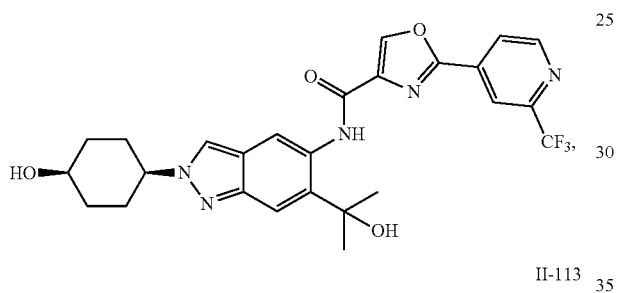
II-113
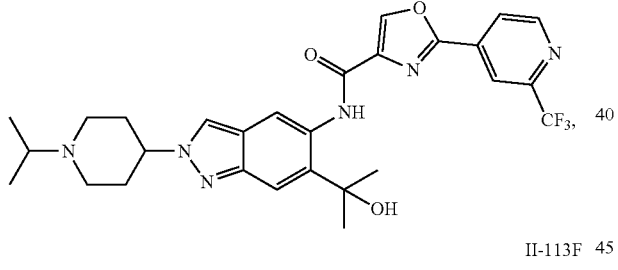
II-113F
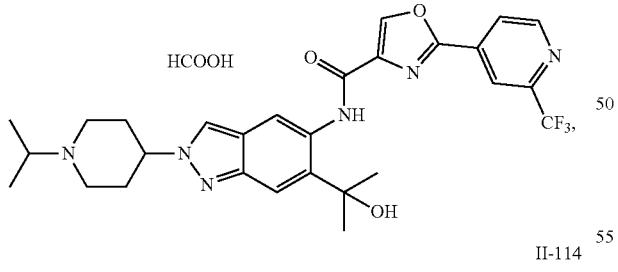
II-114
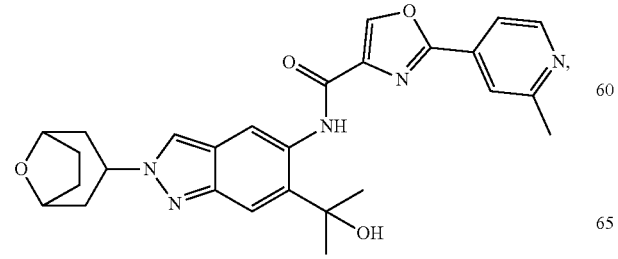
-continued
II-115
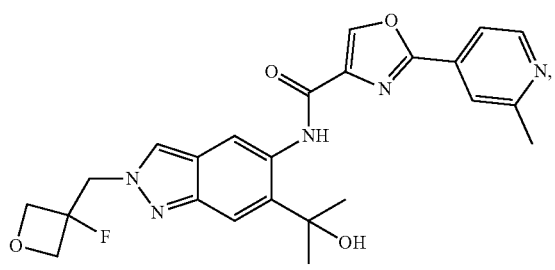
II-116
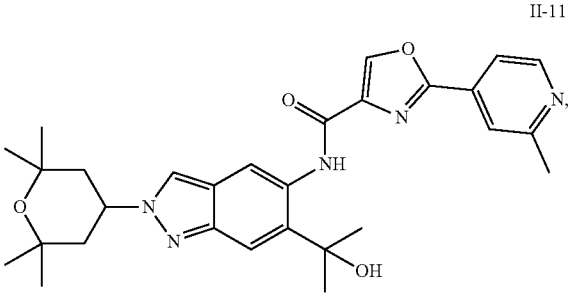
II-117
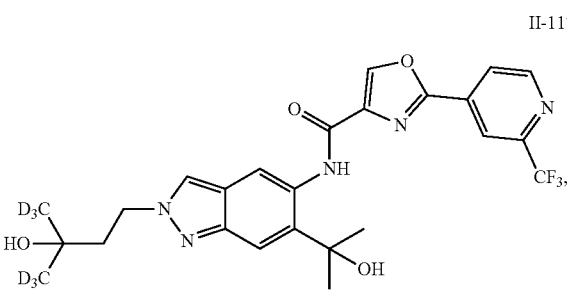
II-118
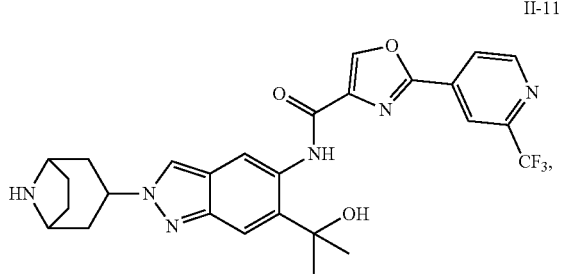
II-119
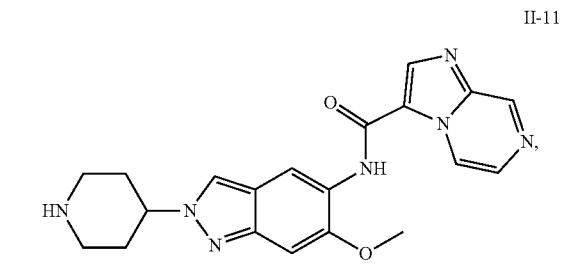
II-119C
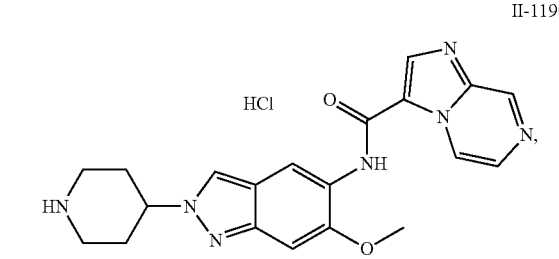

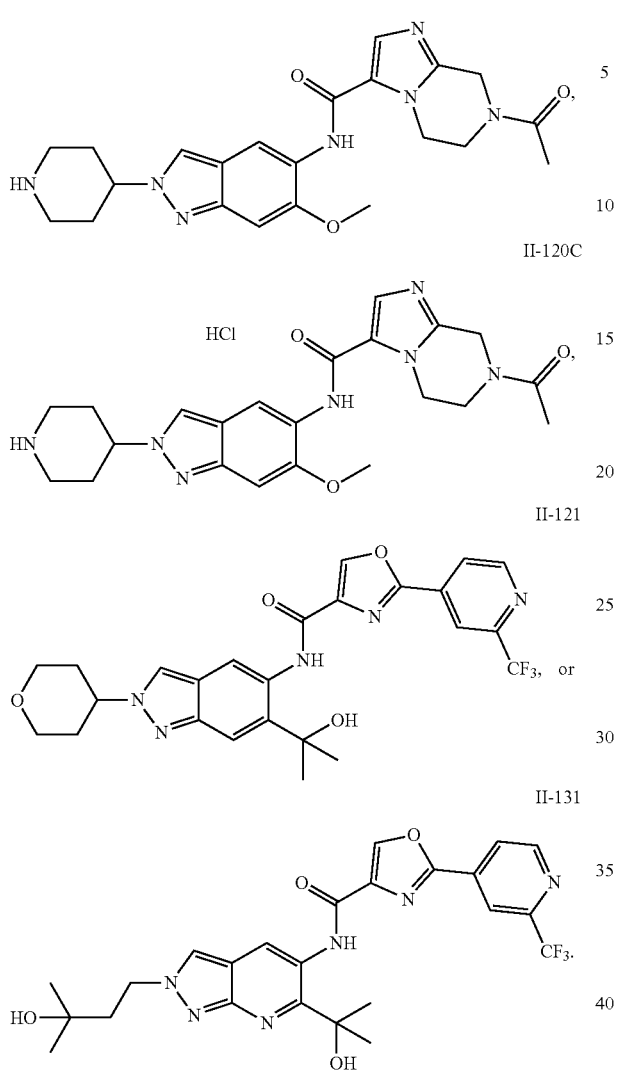

The present disclosure provides a five-membered-fused six-membered compound of formula III or a pharmaceutically acceptable salt thereof,

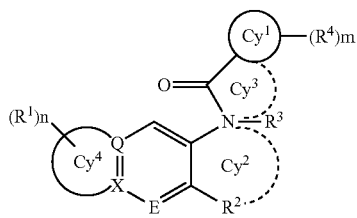

wherein ring $Cy^4$ is an imidazole ring, an oxazole ring, a thiazole ring, a 5-membered heterocyclic ring, or an oxo-5-membered heterocyclic ring; the heteroatom of the 5-membered heterocyclic ring is selected from one or more than one of N, S, and O, the number of heteroatoms is 1, 2, or 3;

n is 1, 2, or 3; m is 1, 2, or 3;

X is N or C; Q is N or C; E is N or CH;

$R^3$ is hydrogen or $R^3$ is absent; when $R^3$ is absent, N and the atom on ring $Cy^1$, together with the atoms to which they are attached, form ring $Cy^3$, or N and the atom on $R^2$, together with the atoms to which they are attached, form ring $Cy^2$;

ring $Cy^1$ is a 5-membered heteroaromatic ring; the heteroatom of the 5-membered heteroaromatic ring is selected from one or more than one of N, S, and O, and the number of heteroatoms is 1, 2, or 3;

ring $Cy^2$ is a 5- to 9-membered heterocyclic ring; the heteroatom of the 5- to 9-membered heterocyclic ring is selected from one or more than one of N, S, and O, and the number of heteroatoms is 1, 2, or 3, and at least one heteroatom is N;

ring $Cy^3$ is an oxo-5- to 9-membered heterocyclic ring; the heteroatom of the oxo-5- to 9-membered heterocyclic ring is selected from one or more than one of N, S, and O, and the number of heteroatoms is 1, 2, or 3, and at least one heteroatom is N;

each $R^1$ is independently $C_{1-6}$ alkyl substituted by one or more than one $R^{1-4}$, unsubstituted 3- to 10-membered cycloalkyl, 3- to 10-membered cycloalkyl substituted by one or more than one $R^{1-2}$, unsubstituted 3- to 11-membered heterocycloalkyl, or 3- to 11-membered heterocycloalkyl substituted by one or more than one $R^{1-1}$; the heteroatom of the 3- to 11-membered heterocycloalkyl is selected from one or more than one of N, O, and S, and the number of heteroatoms is 1, 2, or 3;

each $R^{1-4}$ is independently unsubstituted 3- to 8-membered heterocycloalkyl, 3- to 8-membered heterocycloalkyl substituted by one or more than one $R^{1-1-1}$, deuterium, hydroxyl, halogen, unsubstituted 3- to 10-membered cycloalkyl, 3- to 10-membered cycloalkyl substituted by one or more than one $R^{1-1-5}$,

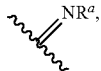

or —$SO_2$-$C_{1-6}$ alkyl; the heteroatom of the 3- to 8-membered heterocycloalkyl is N and/or O, and the number of heteroatoms is 1, 2, or 3;

each $R^{1-1}$ is independently deuterium, halogen, oxo, hydroxyl,

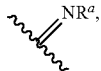

unsubstituted 3- to 8-membered heterocycloalkyl, 3- to 8-membered heterocycloalkyl substituted by one or more than one $R^{1-1-1}$, unsubstituted $C_{1-6}$ alkyl, $C_{1-6}$ alkyl substituted by one or more than one halogen, 3- to 10-membered cycloalkyl, or 6- to 10-membered aryl; the heteroatom of the 3- to 8-membered heterocycloalkyl is N, and the number of heteroatoms is 1, 2, or 3;

each $R^{1-2}$ is independently deuterium, hydroxyl, halogen, unsubstituted $C_{1-6}$ alkyl, $C_{1-6}$ alkyl substituted by one or more than one halogen,

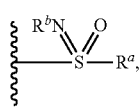

or —SO$_2$-C$_{1-6}$ alkyl;

each R$^{1-1-1}$ is independently C$_{1-6}$ alkyl, oxo, halogen,

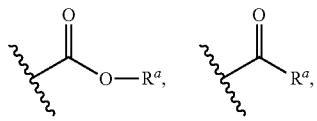

or hydroxyl;

each R$^{1-1-5}$ is independently unsubstituted C$_{1-6}$ alkyl, C$_{1-6}$ alkyl substituted by one or more than one halogen, halogen, oxo, or hydroxyl;

when

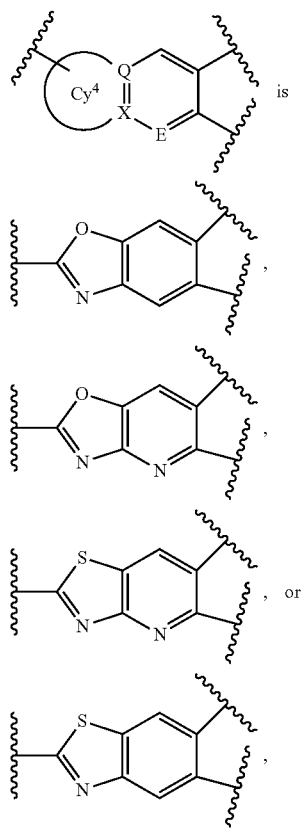

and each R$^1$ is independently unsubstituted 3- to 11-membered heterocycloalkyl or 3- to 11-membered heterocycloalkyl substituted by one or more than one R$^{1-1}$, the five-membered-fused six-membered compound of formula III satisfies one or more than one of the following conditions:

(1) at least one R$^1$ is unsubstituted 3- to 11-membered heterocycloalkyl, 3- to 11-membered heterocycloalkyl substituted by one or more than one R$^{1-1}$,

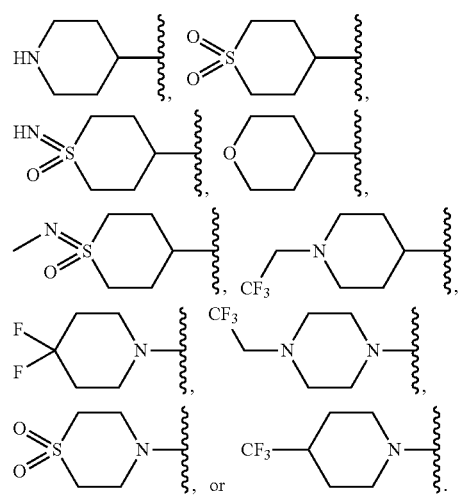

and the 3- to 11-membered heterocycloalkyl is bicyclic;

(2) at least one R$^4$ is

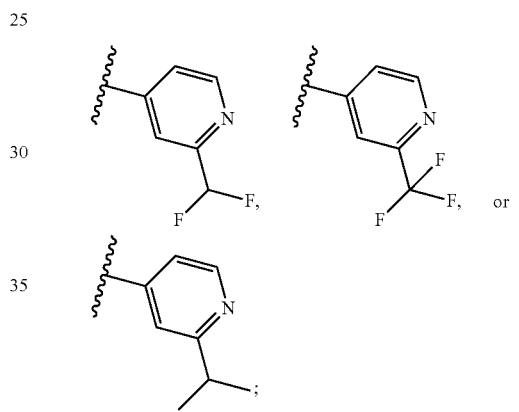

(3) R$^2$ is —OCD$_3$,

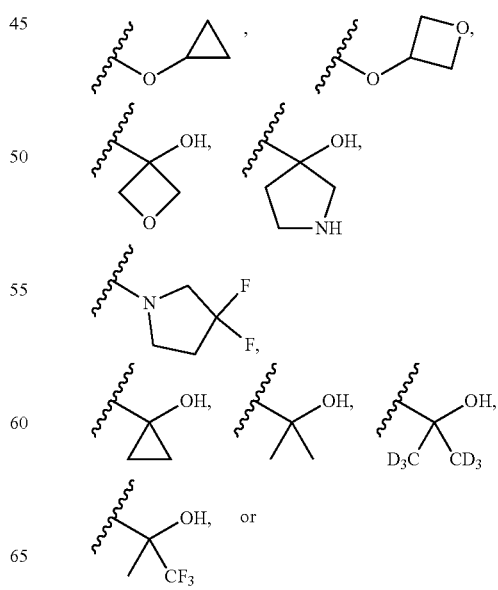

-continued

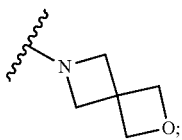

and (4) ring Cy$^1$ is a 5-membered heteroaromatic ring; the heteroatom of the 5-membered heteroaromatic ring is N, and the number of heteroatoms is 2;

R$^2$ is unsubstituted 3- to 11-membered heterocycloalkyl, 3- to 11-membered heterocycloalkyl substituted by one or more than one R$^{2-1}$, unsubstituted 3- to 8-membered cycloalkyl, 3- to 8-membered cycloalkyl substituted by one or more than one R$^{2-2}$, unsubstituted C$_{1-6}$ alkoxy, C$_{1-6}$ alkoxy substituted by one or more than one R$^{2-7}$, hydroxyl substituted by R$^{2-8}$, or C$_{1-6}$ alkyl substituted by one or more than one R$^{2-4}$; the heteroatom of the 3- to 11-membered heterocycloalkyl is selected from one or more than one of N, S, and O, and the number of heteroatoms is 1, 2, or 3;

R$^{2-1}$, R$^{2-2}$, and R$^{2-7}$ are each independently deuterium, hydroxyl, halogen, oxo, unsubstituted C$_{1-6}$ alkyl, C$_{1-6}$ alkyl substituted by one or more than one halogen, 3- to 10-membered cycloalkyl, unsubstituted 3- to 8-membered heterocycloalkyl, or 3- to 8-membered heterocycloalkyl substituted by one or more than one R$^{2-1-1}$; the heteroatom of the 3- to 8-membered heterocycloalkyl is selected from one or more than one of N, S, and O, and the number of heteroatoms is 1, 2, or 3;

each R$^{2-4}$ is independently deuterium, halogen, hydroxyl, or hydroxyl substituted by 3- to 8-membered heterocycloalkyl; the heteroatom of the 3- to 8-membered heterocycloalkyl is selected from one or more than one of N, S, and O, and the number of heteroatoms is 1, 2, or 3;

R$^{2-8}$ is 3- to 10-membered cycloalkyl or 3- to 11-membered heterocycloalkyl; the heteroatom of the 3- to 11-membered heterocycloalkyl is selected from one or more than one of N, S, and O, and the number of heteroatoms is 1, 2, or 3;

each R$^{2-1-1}$ is independently deuterium, hydroxyl, halogen, oxo, C$_{1-6}$ alkyl, 3- to 10-membered cycloalkyl, or 3- to 8-membered heterocycloalkyl; the heteroatom of the 3- to 8-membered heterocycloalkyl is selected from one or more than one of N, S, and O, and the number of heteroatoms is 1, 2, or 3;

when R$^2$ is unsubstituted C$_{1-6}$ alkoxy or C$_{1-6}$ alkoxy substituted by one or more than one R$^{2-7}$; each R$^1$ is independently C$_{1-6}$ alkyl substituted by one or more than one R$^{1-4}$, 3- to 10-membered cycloalkyl substituted by one or more than one hydroxyl or halogen, 3- to 10-membered cycloalkyl substituted by one or more than one —SO$_2$—R$^a$,

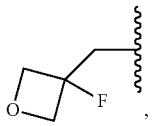

unsubstituted 3- to 8-membered heterocycloalkyl, or 3- to 8-membered heterocycloalkyl substituted by one or more than one R$^{1-1-1}$, and each R$^{1-4}$ is independently hydroxyl, deuterium, halogen, unsubstituted 3- to 8-membered N- or S-heterocycloalkyl, 3- to 8-membered N- or S-heterocycloalkyl substituted by one or more than one R$^{1-1-1}$, unsubstituted 3- to 6-membered cycloalkyl, 3- to 6-membered cycloalkyl substituted by one or more than one R$^{1-1-5}$, SO$_2$—R$^a$, —SO—R$^a$, or

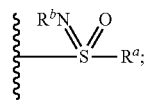

the heteroatom of the 3- to 8-membered heterocycloalkyl is N and/or S, the number of heteroatoms is 1, 2, or 3;

when R$^2$ is unsubstituted 6-membered monoheterocycloalkyl, 6-membered monoheterocycloalkyl substituted by one or more than one R$^{2-1}$, or unsubstituted 3- to 6-membered cycloalkyl, and each R$^1$ is independently C$_{1-6}$ alkyl substituted by one or more than one R$^{1-4}$; each R$^{1-4}$ is independently unsubstituted 3- to 8-membered heterocycloalkyl, 3- to 8-membered heterocycloalkyl substituted by one or more than one R$^{1-1-1}$, deuterium, halogen, unsubstituted 3- to 10-membered cycloalkyl, 3- to 10-membered cycloalkyl substituted by one or more than one R$^{1-1-5}$, or

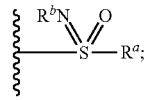

the heteroatom of the 3- to 8-membered heterocycloalkyl is N and/or O, and the number of heteroatoms is 1, 2, or 3;

each R$^4$ is independently unsubstituted 5- to 10-membered heteroaryl, 5- to 10-membered heteroaryl substituted by one or more than one R$^{4-1}$, unsubstituted 6- to 10-membered aryl, 6- to 10-membered aryl substituted by one or more than one R$^{4-5}$, unsubstituted 3- to 11-membered heterocycloalkyl, or 3- to 11-membered heterocycloalkyl substituted by one or more than one R$^{4-3}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

R$^{4-1}$ and R$^{4-5}$ are each independently halogen,

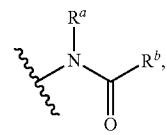

unsubstituted C$_{1-6}$ alkoxy, C$_{1-6}$ alkoxy substituted by one or more than one R$^{4-1-1}$,

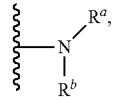

cyano, oxo, hydroxyl, unsubstituted $C_{1-6}$ alkyl, $C_{1-6}$ alkyl substituted by one or more than one $R^{4-1-3}$, unsubstituted 3- to 10-membered cycloalkyl, 3- to 10-membered cycloalkyl substituted by one or more than one $R^{4-1-4}$, unsubstituted 3- to 11-membered heterocycloalkyl, or 3- to 11-membered heterocycloalkyl substituted by one or more than one $R^{4-1-5}$; the heteroatom of the 3- to 11-membered heterocycloalkyl is selected from one or more than one of N, S, and O, and the number of heteroatoms is 1, 2, or 3;

each $R^{4-3}$ is independently hydroxyl, halogen, unsubstituted $C_{1-6}$ alkyl, $C_{1-6}$ alkyl substituted by one or more than one halogen,

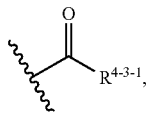

or oxo;

$R^{4-1-1}$, $R^{4-1-3}$, $R^{4-1-4}$, and $R^{4-1-5}$ are each independently halogen, hydroxyl, 3- to 10-membered cycloalkyl, 3- to 11-membered heterocycloalkyl, unsubstituted $C_{1-6}$ alkyl, $C_{1-6}$ alkyl substituted by one or more than one halogen, unsubstituted $C_{1-6}$ alkoxy, or $C_{1-6}$ alkoxy substituted by one or more than one halogen; the heteroatom of the 3- to 11-membered heterocycloalkyl is selected from one or more than one of N, S, or O, and the number of heteroatoms is 1, 2, or 3;

each $R^{4-3-1}$ is hydrogen, $C_{1-6}$ alkyl, or $C_{1-6}$ alkoxy;

$R^a$ and $R^b$ are each independently H, unsubstituted $C_{1-6}$ alkyl, $C_{1-6}$ alkyl substituted by one or more than one $R^{a-1}$, unsubstituted 3- to 10-membered cycloalkyl, 3- to 10-membered cycloalkyl substituted by one or more than one $R^{a-2}$, unsubstituted 3- to 11-membered heterocycloalkyl, 3- to 11-membered heterocycloalkyl substituted by one or more than one $R^{a-3}$, unsubstituted 6- to 10-membered aryl, 6- to 10-membered aryl substituted by one or more than one $R^{a-4}$, unsubstituted 5- to 10-membered heteroaryl, or 5-to 10-membered heteroaryl substituted by one or more than one $R^{a-5}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

or, $R^a$ and $R^b$, together with the atom to which they are attached, form a 3- to 11-membered heterocyclic ring; the heteroatom of the 3- to 11-membered heterocycloalkyl is selected from one or more than one of N, S, and O, and the number of heteroatoms is 1, 2, or 3; $R^{a-1}$, $R^{a-2}$, $R^{a-3}$, $R^{a-4}$, and $R^{a-5}$ are each independently halogen, cyano, hydroxyl, nitro, $C_{1-6}$ alkyl, $C_{1-6}$ alkoxy, 3- to 10-membered cycloalkyl, 3- to 11-membered heterocycloalkyl, 6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5-to 10-membered heteroaryl is selected from one or more than one of N, S, and O, and the number of heteroatoms is 1, 2, or 3.

The present disclosure provides a five-membered-fused six-membered compound of formula III or a pharmaceutically acceptable salt thereof,

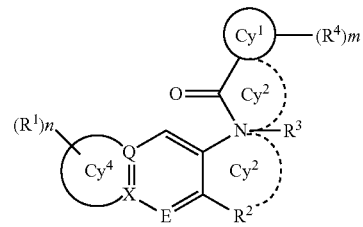

wherein ring $Cy^4$ is an imidazole ring, a 5-membered heterocyclic ring, or an oxo-5-membered heterocyclic ring; the heteroatom of the 5-membered heterocyclic ring is selected from one or more than one of N, S, and O, the number of heteroatoms is 1, 2, or 3;

n is 1, 2, or 3; m is 1, 2, or 3;

X is N or C; Q is N or C; E is N or CH;

$R^3$ is hydrogen or $R^3$ is absent; when $R^3$ is absent, N and the atom on ring $Cy^1$, together with the atoms to which they are attached, form ring $Cy^3$, or N and the atom on $R^2$, together with the atoms to which they are attached, form ring $Cy^2$;

ring $Cy^1$ is a 5-membered heteroaromatic ring; the heteroatom of the 5-membered heteroaromatic ring is selected from one or more than one of N, S, and O, and the number of heteroatoms is 1, 2, or 3;

ring $Cy^2$ is a 5- to 9-membered heterocyclic ring; the heteroatom of the 5- to 9-membered heterocyclic ring is selected from one or more than one of N, S, and O, and the number of heteroatoms is 1, 2, or 3, and at least one heteroatom is N;

ring $Cy^3$ is an oxo-5- to 9-membered heterocyclic ring; the heteroatom of the oxo-5- to 9-membered heterocyclic ring is selected from one or more than one of N, S, and O, and the number of heteroatoms is 1, 2, or 3, and at least one heteroatom is N;

each $R^1$ is independently $C_{1-6}$ alkyl substituted by one or more than one $R^{1-4}$, unsubstituted 3- to 10-membered cycloalkyl, 3- to 10-membered cycloalkyl substituted by one or more than one $R^{1-2}$, unsubstituted 3- to 11-membered heterocycloalkyl, or 3- to 11-membered heterocycloalkyl substituted by one or more than one $R^{1-1}$; the heteroatom of the 3- to 11-membered heterocycloalkyl is selected from one or more than one of N, O, and S, and the number of heteroatoms is 1, 2, or 3;

each $R^{1-4}$ is independently unsubstituted 3- to 8-membered heterocycloalkyl, 3- to 8-membered heterocycloalkyl substituted by one or more than one $R^{1-1-1}$, hydroxyl, halogen, unsubstituted 3- to 10-membered cycloalkyl, 3- to 10-membered cycloalkyl substituted by one or more than one $R^{1-1-5}$,

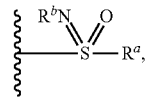

or —$SO_2$-$C_{1-6}$ alkyl; the heteroatom of the 3- to 8-membered heterocycloalkyl is N, and the number of heteroatoms is 1, 2, or 3;

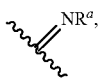

each $R^{1-1}$ is independently halogen, oxo, hydroxyl, unsubstituted 3- to 8-membered heterocycloalkyl, 3- to 8-membered heterocycloalkyl substituted by one or more than one $R^{1-1-1}$, unsubstituted $C_{1-6}$ alkyl, $C_{1-6}$ alkyl substituted by one or more than one halogen, 3- to 10-membered cycloalkyl, or 6- to 10-membered aryl; the heteroatom of the 3- to 8-membered heterocycloalkyl is N, and the number of heteroatoms is 1, 2, or 3;

each $R^{1-2}$ is independently hydroxyl, halogen, unsubstituted $C_{1-6}$ alkyl, $C_{1-6}$ alkyl substituted by one or more than one halogen,

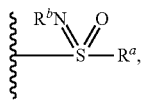

or $-SO_2\text{-}C_{1-6}$ alkyl;

each $R^{1-1-1}$ is independently $C_{1-6}$ alkyl, oxo, or hydroxyl;

each $R^{1-1-5}$ is independently unsubstituted $C_{1-6}$ alkyl, $C_{1-6}$ alkyl substituted by one or more than one halogen, halogen, oxo, or hydroxyl;

$R^2$ is unsubstituted 3- to 11-membered heterocycloalkyl, 3- to 11-membered heterocycloalkyl substituted by one or more than one $R^{2-1}$, unsubstituted 3- to 8-membered cycloalkyl, 3- to 8-membered cycloalkyl substituted by one or more than one $R^{2-2}$, unsubstituted $C_{1-6}$ alkoxy, $C_{1-6}$ alkoxy substituted by one or more than one $R^{2-7}$, hydroxyl substituted by $R^{2-8}$, or $C_{1-6}$ alkyl substituted by one or more than one $R^{2-4}$; the heteroatom of the 3- to 11-membered heterocycloalkyl is selected from one or more than one of N, S, and O, and the number of heteroatoms is 1, 2, or 3;

$R^{2-1}$, $R^{2-2}$, and $R^{2-7}$ are each independently hydroxyl, halogen, oxo, unsubstituted $C_{1-6}$ alkyl, $C_{1-6}$ alkyl substituted by one or more than one halogen, 3- to 10-membered cycloalkyl, unsubstituted 3- to 8-membered heterocycloalkyl, 3- to 8-membered heterocycloalkyl substituted by one or more than one $R^{2-1-1}$; the heteroatom of the 3- to 8-membered heterocycloalkyl is selected from one or more than one of N, S, and O, and the number of heteroatoms is 1, 2, or 3;

each $R^{2-4}$ is independently halogen, hydroxyl, or hydroxyl substituted by 3- to 8-membered heterocycloalkyl; the heteroatom of the 3- to 8-membered heterocycloalkyl is selected from one or more than one of N, S, and O, and the number of heteroatoms is 1, 2, or 3;

$R^{2-8}$ is 3- to 10-membered cycloalkyl or 3- to 11-membered heterocycloalkyl; the heteroatom of the 3- to 11-membered heterocycloalkyl is selected from one or more than one of N, S, and O, and the number of heteroatoms is 1, 2, or 3;

each $R^{2-1-1}$ is independently hydroxyl, halogen, oxo, $C_{1-6}$ alkyl, 3- to 10-membered cycloalkyl, or 3- to 8-membered heterocycloalkyl; the heteroatom of the 3- to 8-membered heterocycloalkyl is selected from one or more than one of N, S, and O, and the number of heteroatoms is 1, 2, or 3;

when $R^2$ is unsubstituted $C_{1-6}$ alkoxy or $C_{1-6}$ alkoxy substituted by one or more than one $R^{2-7}$; each $R^1$ is independently $C_{1-6}$ alkyl substituted by one or more than one $R^{1-4}$, and each $R^{1-4}$ is independently hydroxyl, $SO_2-R^a$, $-SO-R^a$, or

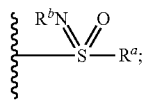

when $R^2$ is unsubstituted 6-membered monoheterocycloalkyl, 6-membered monoheterocycloalkyl substituted by one or more than one $R^{2-1}$, or unsubstituted 3- to 6-membered cycloalkyl, and each $R^1$ is independently $C_{1-6}$ alkyl substituted by one or more than one $R^{1-4}$; each $R^{1-4}$ is independently unsubstituted 3- to 8-membered heterocycloalkyl, 3- to 8-membered heterocycloalkyl substituted by one or more than one $R^{1-1-1}$, unsubstituted 3- to 10-membered cycloalkyl, 3- to 10-membered cycloalkyl substituted by one or more than one $R^{1-1-5}$, or

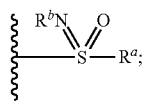

the heteroatom of the 3- to 8-membered heterocycloalkyl is N, and the number of heteroatoms is 1, 2, or 3;

each $R^4$ is independently unsubstituted 5- to 10-membered heteroaryl, 5- to 10-membered heteroaryl substituted by one or more than one $R^{4-1}$, unsubstituted 6- to 10-membered aryl, 6- to 10-membered aryl substituted by one or more than one $R^{4-5}$, unsubstituted 3- to 11-membered heterocycloalkyl, or 3- to 11-membered heterocycloalkyl substituted by one or more than one $R^{4-3}$; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^{4-1}$ and $R^{4-5}$ are each independently halogen,

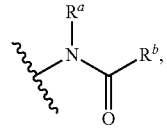

unsubstituted $C_{1-6}$ alkoxy, $C_{1-6}$ alkoxy substituted by one or more than one $R^{4-1-1}$,

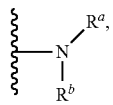

cyano, oxo, hydroxyl, unsubstituted $C_{1-6}$ alkyl, $C_{1-6}$ alkyl substituted by one or more than one $R^{4-1-3}$, unsubstituted 3- to 10-membered cycloalkyl, 3- to 10-membered cycloalkyl substituted by one or more than one $R^{4-1-4}$, unsubstituted 3- to 11-membered heterocycloalkyl, or 3- to 11-membered heterocycloalkyl substituted by one or more than one $R^{4-1-5}$; the heteroatom of the 3- to 11-membered heterocycloalkyl is selected from one or more than one of N, S, and O, and the number of heteroatoms is 1, 2, or 3;

each $R^{4-3}$ is independently hydroxyl, halogen, unsubstituted $C_{1-6}$ alkyl, $C_{1-6}$ alkyl substituted by one or more than one halogen,

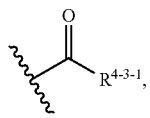

or oxo;

$R^{4-1-1}$, $R^{4-1-3}$, $R^{4-1-4}$, and $R^{4-1-5}$ are each independently halogen, hydroxyl, 3- to 10-membered cycloalkyl, 3- to 11-membered heterocycloalkyl, unsubstituted $C_{1-6}$ alkyl, $C_{1-6}$ alkyl substituted by one or more than one halogen, unsubstituted $C_{1-6}$ alkoxy, or $C_{1-6}$ alkoxy substituted by one or more than one halogen; the heteroatom of the 3- to 11-membered heterocycloalkyl is selected from one or more than one of N, S, or O, and the number of heteroatoms is 1, 2, or 3;

each $R^{4-3-1}$ is hydrogen, $C_{1-6}$ alkyl, or $C_{1-6}$ alkoxy;

$R^a$ and $R^b$ are each independently H, unsubstituted $C_{1-6}$ alkyl, $C_{1-6}$ alkyl substituted by one or more than one $R^{a-1}$, unsubstituted 3- to 10-membered cycloalkyl, 3- to 10-membered cycloalkyl substituted by one or more than one $R^{a-2}$, unsubstituted 3- to 11-membered heterocycloalkyl, 3- to 11-membered heterocycloalkyl substituted by one or more than one $R^{a-3}$, unsubstituted 6- to 10-membered aryl, 6- to 10-membered aryl substituted by one or more than one $R^{a-4}$, unsubstituted 5- to 10-membered heteroaryl, or 5-to 10-membered heteroaryl substituted by one or more than one $R^{a-5}$;

or, $R^a$ and $R^b$, together with the atom to which they are attached, form a 3- to 11-membered heterocyclic ring; the heteroatom of the 3- to 11-membered heterocycloalkyl is selected from one or more than one of N, S, and O, and the number of heteroatoms is 1, 2, or 3; the heteroatom of the 3- to 11-membered heterocyclic ring is selected from one or more than one of N, S, and O, and the number of heteroatoms is 1, 2, or 3;

$R^{a-1}$, $R^{a-2}$, $R^{a-3}$, $R^{a-4}$, and $R^{a-5}$ are each independently halogen, cyano, hydroxyl, nitro, $C_{1-6}$ alkyl, $C_{1-6}$ alkoxy, 3- to 10-membered cycloalkyl, 3- to 11-membered heterocycloalkyl, 6- to 10-membered aryl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5-to 10-membered heteroaryl is selected from one or more than one of N, S, and O, and the number of heteroatoms is 1, 2, or 3.

In a preferred embodiment, in the five-membered-fused six-membered compound of formula III or the pharmaceutically acceptable salt thereof, some groups can be defined as follows, and other groups can be defined as described in any of the above embodiments (hereinafter referred to as "in a preferred embodiment"): ring $Cy^4$ is an imidazole ring, an oxazole ring, a thiazole ring, a 5-membered heterocyclic ring, or an oxo-5-membered heterocyclic ring; the heteroatom of the 5-membered heterocyclic ring is O, the number of heteroatoms is 1, the heteroatom of the oxo-5-membered heterocyclic ring is N, the number of heteroatoms is 1.

In a preferred embodiment, ring $Cy^4$ is an imidazole ring, a 5-membered heterocyclic ring, or an oxo-5-membered heterocyclic ring; the heteroatom of the 5-membered heterocyclic ring is O, the number of heteroatoms is 1, the heteroatom of the oxo-5-membered heterocyclic ring is N, the number of heteroatoms is 1.

In a preferred embodiment, ring $Cy^1$ is a 5-membered heteroaromatic ring; the heteroatom of the 5-membered heteroaromatic ring is selected from one or two of N, S, and O, and the number of heteroatoms is 1, 2, or 3.

In a preferred embodiment, ring $Cy^2$ is a 5- to 6-membered heterocyclic ring; the heteroatom of the 5- to 6-membered heterocyclic ring is N, and the number of heteroatoms is 1, 2, or 3.

In a preferred embodiment, ring $Cy^3$ is an oxo-5- to 9-membered heterocyclic ring; the heteroatom of the oxo-5- to 9-membered heterocyclic ring is N, and the number of heteroatoms is 1, 2, or 3.

In a preferred embodiment, each $R^1$ is independently $C_{1-6}$ alkyl substituted by one or more than one $R^{1-4}$, unsubstituted 3- to 10-membered cycloalkyl, 3- to 10-membered cycloalkyl substituted by one or more than one $R^{1-2}$, unsubstituted 3- to 11-membered heterocycloalkyl, or 3- to 11-membered heterocycloalkyl substituted by one or more than one $R^{1-1}$; the heteroatom of the 3- to 11-membered heterocycloalkyl is selected from one or two of N, O, and S, and the number of heteroatoms is 1 or 2.

In a preferred embodiment, each $R^{1-4}$ is independently unsubstituted 3- to 8-membered heterocycloalkyl, 3- to 8-membered heterocycloalkyl substituted by one or more than one $R^{1-1-1}$, hydroxyl, halogen, unsubstituted 3- to 10-membered cycloalkyl, 3- to 10-membered cycloalkyl substituted by one or more than one $R^{1-1-5}$, or —$SO_2$-$C_{1-6}$ alkyl; the heteroatom of the 3- to 8-membered heterocycloalkyl is N, and the number of heteroatoms is 1, 2, or 3.

In a preferred embodiment, each $R^{1-4}$ is independently deuterium, unsubstituted 3- to 8-membered heterocycloalkyl, 3- to 8-membered heterocycloalkyl substituted by one or more than one $R^{1-1-1}$, hydroxyl, halogen, unsubstituted 3- to 10-membered cycloalkyl, 3- to 10-membered cycloalkyl substituted by one or more than one $R^{1-1-5}$,

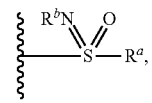

or —$SO_2$-$C_{1-6}$ alkyl; the heteroatom of the 3- to 8-membered heterocycloalkyl is one or two of N, S, or O, and the number of heteroatoms is 1, 2, or 3.

In a preferred embodiment, each $R^{1-1}$ is independently oxo, hydroxyl,

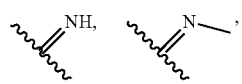

unsubstituted $C_{1-6}$ alkyl, or $C_{1-6}$ alkyl substituted by one or more than one halogen.

In a preferred embodiment, each $R^{1-1}$ is independently halogen, oxo, hydroxyl,

unsubstituted 3- to 8-membered heterocycloalkyl, 3- to 8-membered heterocycloalkyl substituted by one or more than one $R^{1-1-1}$, unsubstituted $C_{1-6}$ alkyl, or $C_{1-6}$ alkyl substituted by one or more than one halogen; the heteroatom of the 3- to 8-membered heterocycloalkyl is N, and the number of heteroatoms is 1, 2, or 3.

In a preferred embodiment, each $R^{1-2}$ is independently hydroxyl or halogen.

In a preferred embodiment, each $R^{1-2}$ is independently hydroxyl, —SO$_2$-C$_{1-6}$ alkyl, or halogen.

In a preferred embodiment, each $R^{1-1-1}$ is independently $C_{1-6}$ alkyl, oxo, or hydroxyl.

In a preferred embodiment, each $R^{1-1-1}$ is independently deuterium, unsubstituted $C_{1-6}$ alkyl, $C_{1-6}$ alkyl substituted by one or more than one halogen, oxo,

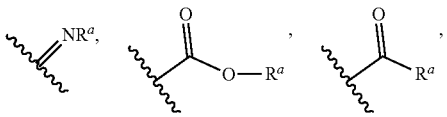

halogen, or hydroxyl.

In a preferred embodiment, $R^2$ is unsubstituted 3- to 11-membered heterocycloalkyl, 3- to 11-membered heterocycloalkyl substituted by one or more than one $R^{2-1}$, unsubstituted 3- to 6-membered cycloalkyl, 3- to 6-membered cycloalkyl substituted by one or more than one $R^{2-2}$, unsubstituted $C_{1-6}$ alkyl, $C_{1-6}$ alkyl substituted by one or more than one $R^{2-4}$, hydroxyl substituted by $R^{2-8}$, unsubstituted $C_{1-6}$ alkoxy, or $C_{1-6}$ alkoxy substituted by one or more than one $R^{2-7}$; the heteroatom of the 3- to 11-membered heterocycloalkyl is selected from one or two of N and O, and the number of heteroatoms is 1 or 2.

In a preferred embodiment, $R^{2-1}$ and $R^{2-2}$ are each independently oxo, hydroxyl, unsubstituted $C_{1-6}$ alkyl, or $C_{1-6}$ alkyl substituted by one or more than one halogen.

In a preferred embodiment, $R^{2-1}$ and $R^{2-2}$ are each independently deuterium, oxo, halogen, hydroxyl, unsubstituted $C_{1-6}$ alkyl, or $C_{1-6}$ alkyl substituted by one or more than one halogen.

In a preferred embodiment, each $R^{2-4}$ is independently halogen, hydroxyl, or hydroxyl substituted by 3- to 8-membered heterocycloalkyl; the heteroatom of the 3- to 8-membered heterocycloalkyl is selected from one or two of N, S, and O, and the number of heteroatoms is 1 or 2.

In a preferred embodiment, each $R^{2-4}$ is independently deuterium, halogen, hydroxyl, or hydroxyl substituted by 3- to 8-membered heterocycloalkyl; the heteroatom of the 3- to 8-membered heterocycloalkyl is selected from one or two of N, S, and O, and the number of heteroatoms is 1 or 2.

In a preferred embodiment, $R^{2-8}$ is 3- to 6-membered cycloalkyl or 3- to 6-membered heterocycloalkyl; the heteroatom of the 3- to 6-membered heterocycloalkyl is selected from one or two of N and O, and the number of heteroatoms is 1 or 2.

In a preferred embodiment, each $R^{2-7}$ is independently halogen.

In a preferred embodiment, each $R^{2-7}$ is independently deuterium or halogen.

In a preferred embodiment, each $R^4$ is independently unsubstituted phenyl, phenyl substituted by one or more than one $R^{4-5}$, unsubstituted 5- to 6-membered heteroaryl, 5- to 6-membered heteroaryl substituted by one or more than one $R^{4-1}$, unsubstituted 3- to 6-membered heterocycloalkyl, or 3- to 6-membered heterocycloalkyl substituted by one or more than one $R^{4-3}$; the heteroatom of the 5- to 6-membered heteroaryl is N, and the number of heteroatoms is 1, 2, or 3; the heteroatom of the 3- to 6-membered heterocycloalkyl is selected from one or more than one of N, S, and O, and the number of heteroatoms is 1 or 2.

In a preferred embodiment, $R^{4-1}$ and $R^{4-5}$ are each independently unsubstituted $C_{1-6}$ alkyl, or $C_{1-6}$ alkyl substituted by one or more than one halogen.

In a preferred embodiment, each $R^{4-3}$ is independently halogen, unsubstituted $C_{1-6}$ alkyl, or $C_{1-6}$ alkyl substituted by one or more than one halogen.

In a preferred embodiment, ring $Cy^1$ is a 5-membered heteroaromatic ring; the heteroatom of the 5-membered heteroaromatic ring is selected from one or two of N and O, and the number of heteroatoms is 2.

In a preferred embodiment, ring $Cy^2$ is a 5- to 6-membered heterocyclic ring; the heteroatom of the 5- to 6-membered heterocyclic ring is N, and the number of heteroatoms is 1 or 2.

In a preferred embodiment, ring $Cy^3$ is an oxo-5- to 6-membered heterocyclic ring; the heteroatom of the oxo-5- to 6-membered heterocyclic ring is N, and the number of heteroatoms is 1 or 2.

In a preferred embodiment, each $R^1$ is independently $C_{1-6}$ alkyl substituted by one or more than one $R^{1-4}$, unsubstituted 3- to 6-membered cycloalkyl, 3- to 6-membered cycloalkyl substituted by one or more than one $R^{1-2}$, unsubstituted 3- to 6-membered heterocycloalkyl, or 3- to 6-membered heterocycloalkyl substituted by one or more than one $R^{1-1}$; the heteroatom of the 3- to 6-membered heterocycloalkyl is one or two of N, O, or S, and the number of heteroatoms is 1 or 2.

In a preferred embodiment, each $R^1$ is independently $C_{1-6}$ alkyl substituted by one or more than one $R^{1-4}$, unsubstituted 3- to 6-membered cycloalkyl, 3- to 6-membered cycloalkyl substituted by one or more than one $R^{1-2}$, unsubstituted 3- to 8-membered heterocycloalkyl, or 3- to 8-membered heterocycloalkyl substituted by one or more than one $R^{1-1}$; the heteroatom of the 3- to 8-membered heterocycloalkyl is selected from one or two of N, O, or S, and the number of heteroatoms is 1 or 2.

In a preferred embodiment, $R^1$ is $C_{1-6}$ alkyl substituted by one or more than one $R^{1-4}$, unsubstituted 3- to 6-membered cycloalkyl, 3- to 6-membered cycloalkyl substituted by one or more than one $R^{1-2}$, unsubstituted 3- to 6-membered heterocycloalkyl, or 3- to 6-membered heterocycloalkyl substituted by one or more than one $R^{1-1}$; the heteroatom of the 3- to 6-membered heterocycloalkyl is selected from one or two of N, O, or S, and the number of heteroatoms is 1 or 2.

In a preferred embodiment, $R^1$ is

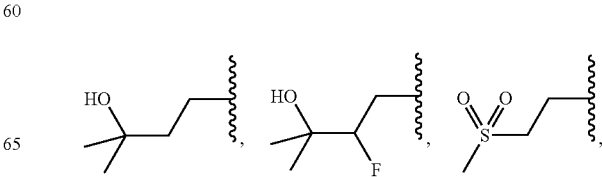

-continued

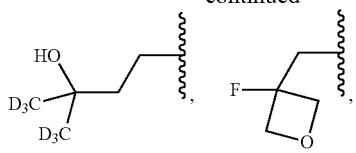

3- to 6-membered cycloalkyl substituted by one hydroxyl group, 6-membered cycloalkyl substituted by one —SO$_2$-C$_{1-6}$ alkyl group,

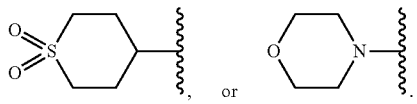

In a preferred embodiment, R$^{1-1}$, R$^{1-2}$, and R$^{1-4}$ are each independently deuterium, hydroxyl,

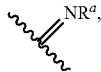

oxo, halogen,

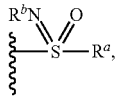

—SO$_2$-C$_{1-6}$ alkyl, unsubstituted C$_{1-6}$ alkyl, C$_{1-6}$ alkyl substituted by one or more than one R$^{1-1-4}$, unsubstituted 3- to 6-membered cycloalkyl, 3- to 6-membered cycloalkyl substituted by one or more than one R$^{1-1-5}$, unsubstituted 3- to 6-membered heterocycloalkyl, or 3- to 6-membered heterocycloalkyl substituted by one or more than one R$^{1-1-1}$; the heteroatom of the 3- to 6-membered heterocycloalkyl is one of N, O, or S, and the number of heteroatoms is 1.

In a preferred embodiment, each R$^{1-1}$ is independently oxo,

unsubstituted C$_{1-6}$ alkyl, C$_{1-6}$ alkyl substituted by one or more than one R$^{1-1-4}$, unsubstituted 3- to 6-membered heterocycloalkyl, or 3- to 6-membered heterocycloalkyl substituted by one or more than one R$^{1-1-1}$; the heteroatom of the 3- to 6-membered heterocycloalkyl is one of N, O, or S, and the number of heteroatoms is 1.

In a preferred embodiment, each R$^{1-2}$ is independently halogen, hydroxyl, or —SO$_2$-C$_{1-6}$ alkyl.

In a preferred embodiment, each R$^{1-4}$ is independently deuterium, hydroxyl,

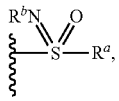

halogen, —SO$_2$-C$_{1-6}$ alkyl, unsubstituted C$_{1-6}$ alkyl, C$_{1-6}$ alkyl substituted by one or more than one R$^{1-1-4}$, unsubstituted 3- to 8-membered heterocycloalkyl, or 3- to 8-membered heterocycloalkyl substituted by one or more than one R$^{1-1-1}$; the heteroatom of the 3- to 8-membered heterocycloalkyl is one of N, O, or S, and the number of heteroatoms is 1.

In a preferred embodiment, each R$^{1-4}$ is independently unsubstituted 3- to 8-membered heterocycloalkyl, 3- to 8-membered heterocycloalkyl substituted by one or more than one R$^{1-1-1}$, deuterium, hydroxyl, halogen, unsubstituted 3- to 6-membered cycloalkyl, 3- to 6-membered cycloalkyl substituted by one or more than one R$^{1-1-1}$, or —SO$_2$-C$_{1-6}$ alkyl; the heteroatom of the 3- to 8-membered heterocycloalkyl is N, and the number of heteroatoms is 1.

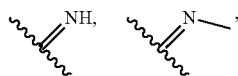

In a preferred embodiment, each R$^{1-1}$ is independently halogen, oxo, hydroxyl, unsubstituted C$_{1-6}$ alkyl, or C$_{1-6}$ alkyl substituted by one or more than one halogen.

In a preferred embodiment, each R$^{1-2}$ is independently hydroxyl or halogen.

In a preferred embodiment, each R$^{1-1-1}$ is independently C$_{1-6}$ alkyl or hydroxyl.

In a preferred embodiment, each R$^{1-1-1}$ is independently unsubstituted C$_{1-6}$ alkyl, C$_{1-6}$ alkyl substituted by one or more than one halogen, halogen, or hydroxyl.

In a preferred embodiment, R$^2$ is unsubstituted 3- to 7-membered heterocycloalkyl, 3- to 7-membered heterocycloalkyl substituted by one or more than one R$^{2-1}$, unsubstituted 3- to 6-membered cycloalkyl, 3- to 6-membered cycloalkyl substituted by one or more than one R$^{2-2}$, unsubstituted C$_{1-6}$ alkyl, C$_{1-6}$ alkyl substituted by one or more than one R$^{2-4}$, unsubstituted C$_{1-6}$ alkoxy, or C$_{1-6}$ alkoxy substituted by one or more than one R$^{2-7}$; the heteroatom of the 3- to 7-membered heterocycloalkyl is selected from one or two of N and O, and the number of heteroatoms is 1 or 2.

In a preferred embodiment, R$^2$ is unsubstituted 5- to 6-membered heterocycloalkyl, 5- to 6-membered heterocycloalkyl substituted by one or more than one R$^{2-1}$, C$_{1-6}$ alkyl substituted by one or more than one R$^{2-4}$, unsubstituted C$_{1-6}$ alkoxy, or C$_{1-6}$ alkoxy substituted by one or more than one R$^{2-7}$; the heteroatom of the 5- to 6-membered heterocycloalkyl is selected from one or two of N and O, and the number of heteroatoms is 1 or 2.

In a preferred embodiment, R$^2$ is unsubstituted 5- to 6-membered heterocycloalkyl, 5- to 6-membered heterocycloalkyl substituted by one or more than one R$^{2-1}$, C$_{1-6}$ alkyl substituted by one or more than one R$^{2-4}$, or unsubstituted C$_{1-6}$ alkoxy, or C$_{1-6}$ alkoxy substituted by one or more than one R$^{2-7}$; the heteroatom of the 5- to 6-membered heterocycloalkyl is N, and the number of heteroatoms is 1.

In a preferred embodiment, R$^{2-1}$ and R$^{2-2}$ are each independently hydroxyl.

In a preferred embodiment, each R$^{2-1}$ is independently hydroxyl or halogen.

In a preferred embodiment, in R$^2$, the 3- to 11-membered heterocycloalkyl is a spiro ring or a five-membered monocyclic ring.

In a preferred embodiment, each R$^{2-4}$ is independently hydroxyl.

In a preferred embodiment, each $R^{2-4}$ is independently hydroxyl, deuterium, or halogen.

In a preferred embodiment, each $R^{2-7}$ is independently halogen.

In a preferred embodiment, each $R^{2-7}$ is independently halogen or deuterium.

In a preferred embodiment, each $R^4$ is independently unsubstituted 5- to 6-membered heteroaryl, 5- to 6-membered heteroaryl substituted by one or more than one $R^{4-1}$, unsubstituted phenyl, or phenyl substituted by one or more than one $R^{4-5}$; the heteroatom of the 5- to 6-membered heteroaryl is N, and the number of heteroatoms is 1 or 2.

In a preferred embodiment, each $R^4$ is independently unsubstituted pyridyl or pyridyl substituted by one or more than one $R^{4-1}$.

In a preferred embodiment, $R^{4-1}$ and $R^{4-5}$ are each independently unsubstituted $C_{1-6}$ alkyl or $C_{1-6}$ alkyl substituted by one or more than one fluorine.

In a preferred embodiment, each $R^{4-1}$ is independently unsubstituted $C_{1-6}$ alkyl or $C_{1-6}$ alkyl substituted by one, two, or three halogens.

In a preferred embodiment, the five-membered-fused six-membered compound of formula III is a compound of formula III-a, a compound of formula III-d, a compound of formula III-e, or a compound of formula III-b,

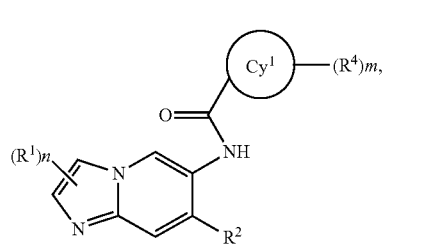

III-a

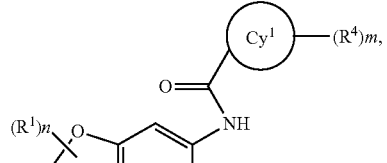

III-d

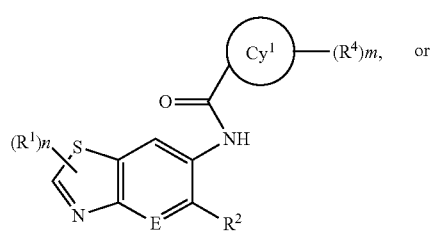

III-e

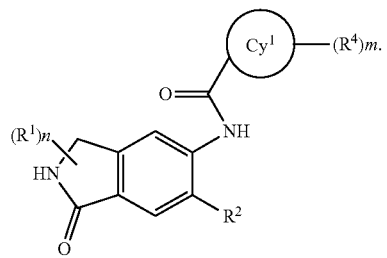

III-b

In a preferred embodiment, the five-membered-fused six-membered compound of formula III is a compound of formula III-c, a compound of formula III-f, or a compound of formula III-g,

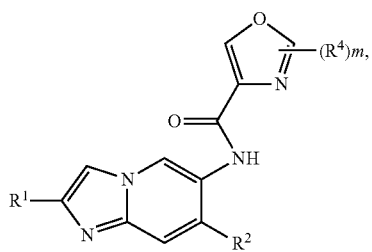

III-c

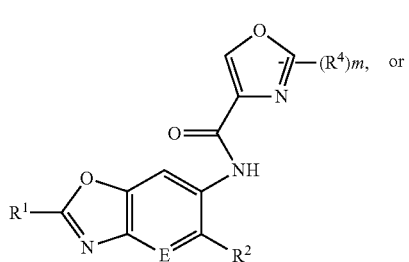

III-f

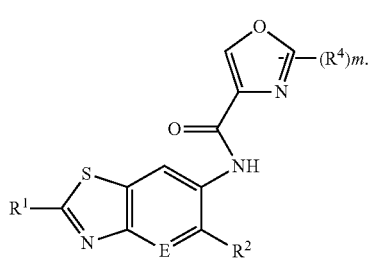

III-g

In a preferred embodiment, each $R^1$ is independently

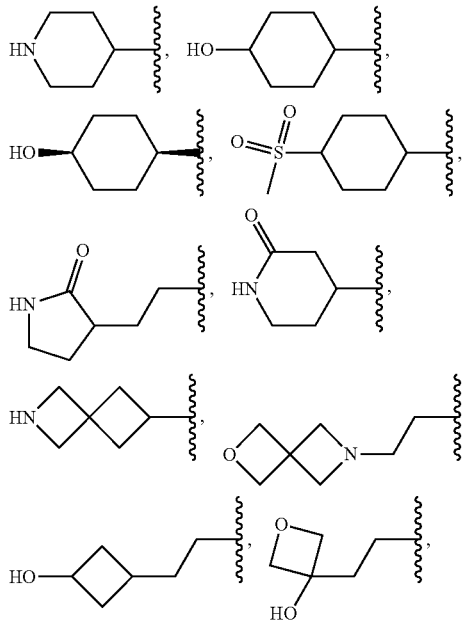

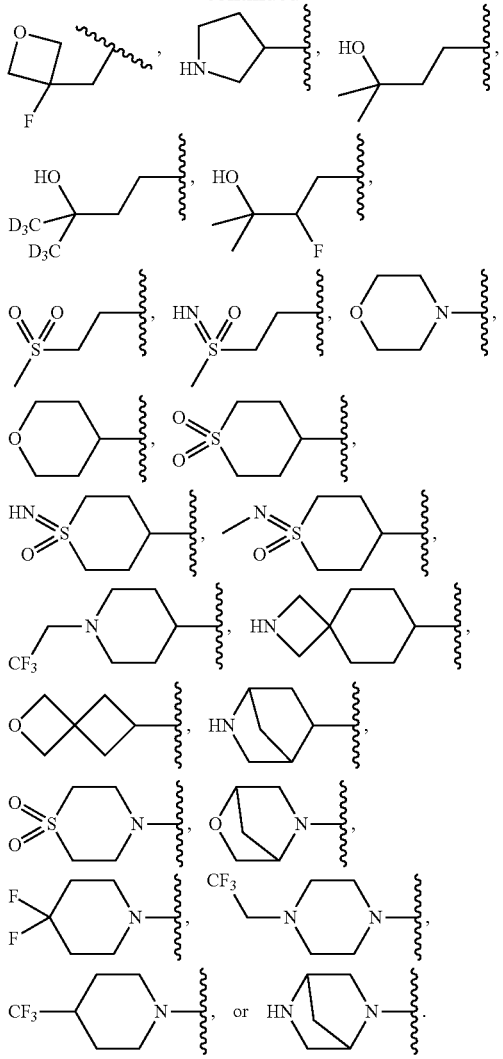
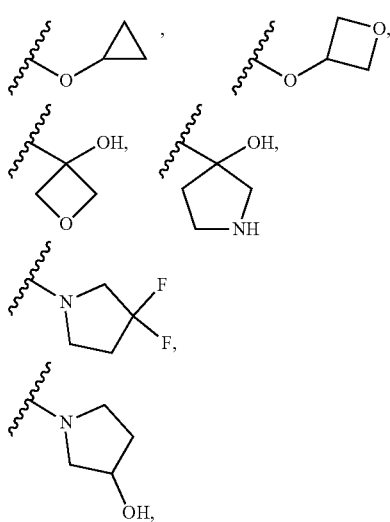
In a preferred embodiment, $R^2$ is methoxy, —OCD$_3$, isopropoxy, trifluoromethoxy, hydroxyl,
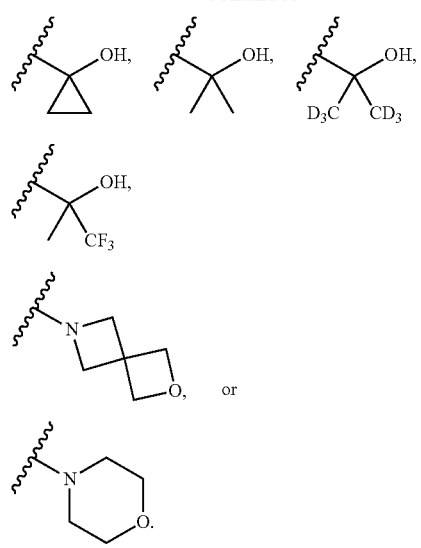
In a preferred embodiment, each $R^4$ is independently hydrogen, bromine, trifluoromethyl,
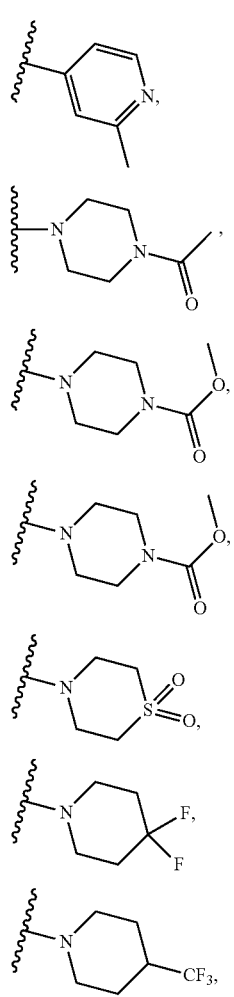

-continued
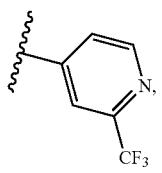
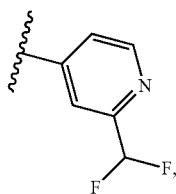
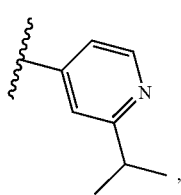
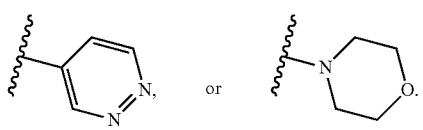
In a preferred embodiment, ring Cy¹ is
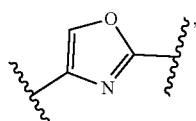 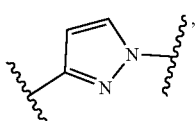
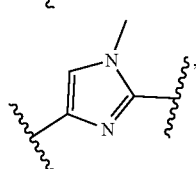 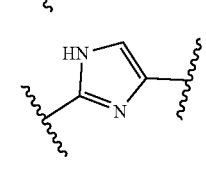
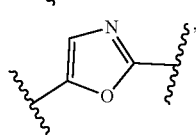 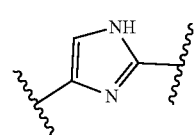
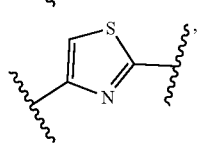 or 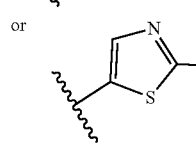
In a preferred embodiment, ring Cy² is
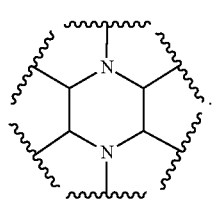 [SMILES: *C1C(*)N(*)C(*)C(*)N1*]
In a preferred embodiment, ring Cy³ is
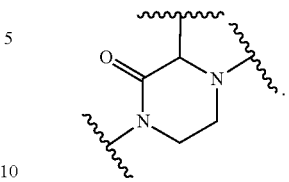
In a preferred embodiment,
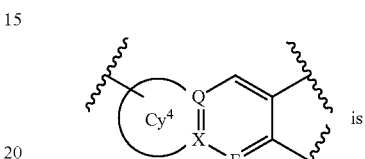 is
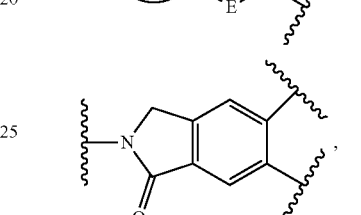
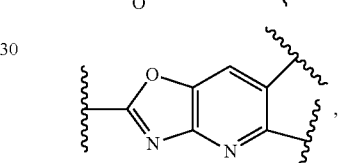
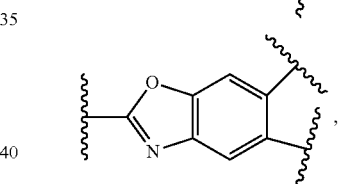
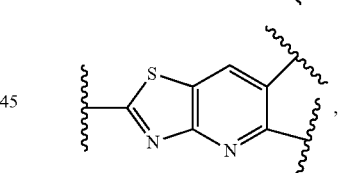
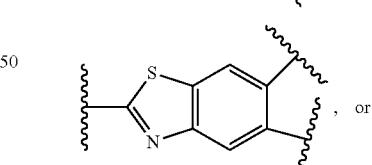, or
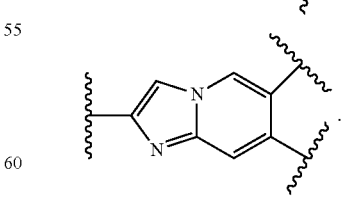
In a preferred embodiment, the five-membered-fused six-membered compound of formula III or the pharmaceutically acceptable salt thereof is any one of the following compounds,

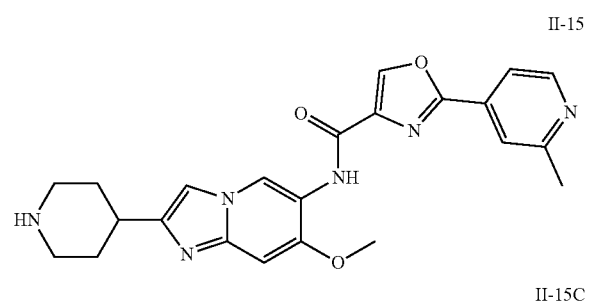
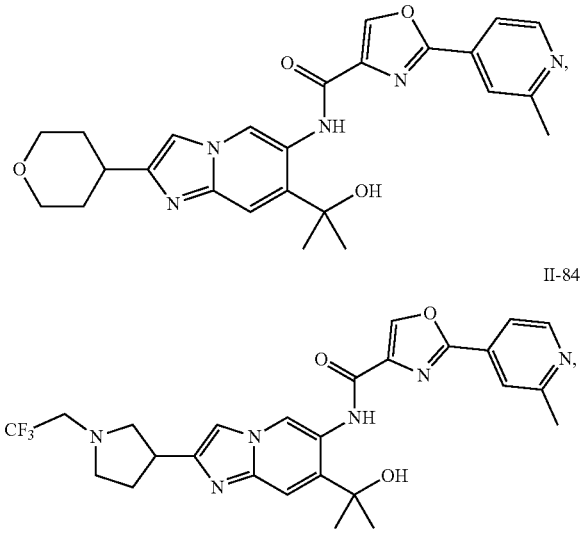

II-89
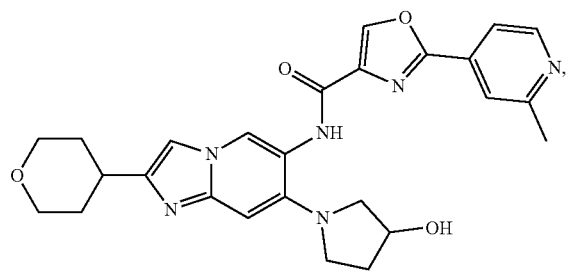
II-124
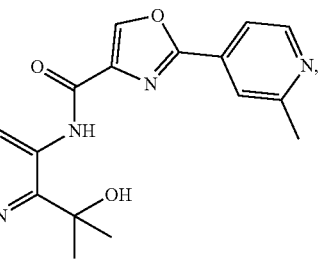
II-90
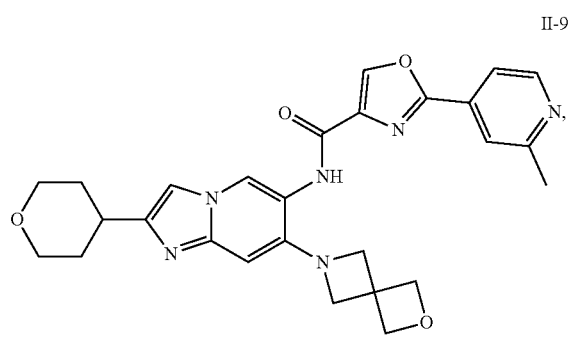
II-125
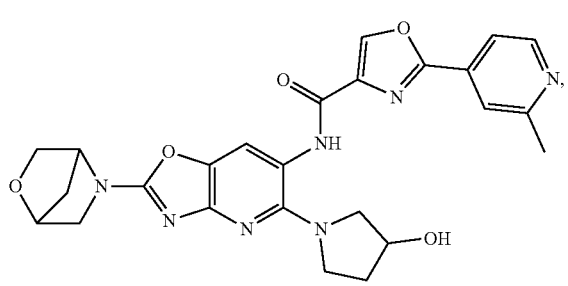
II-91
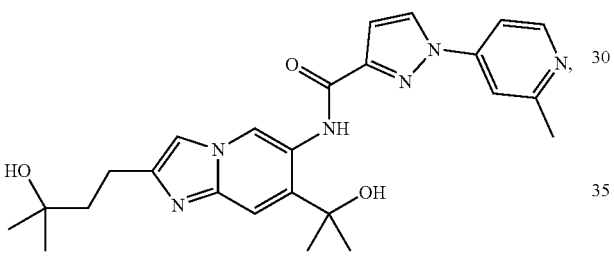
II-126
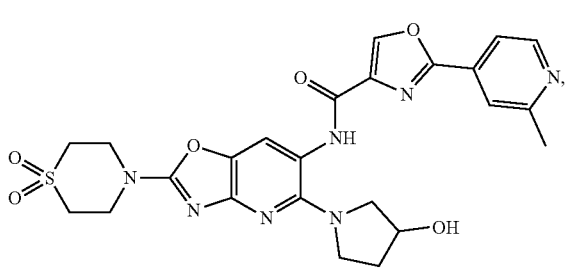
II-122
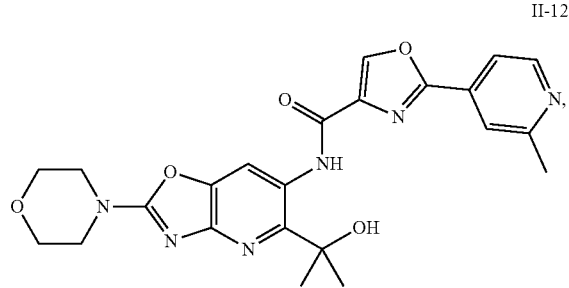
II-127
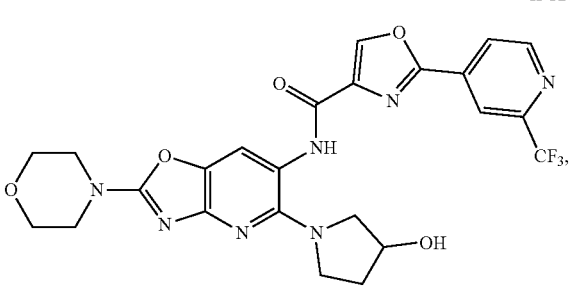
II-123
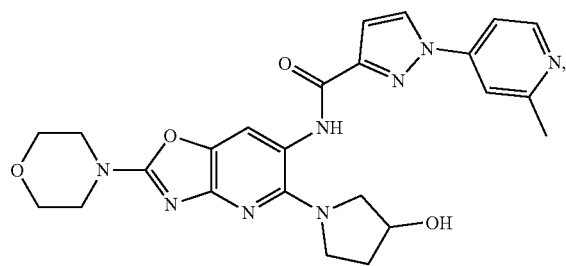
II-128
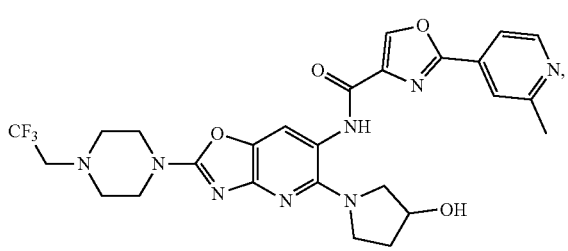

II-129
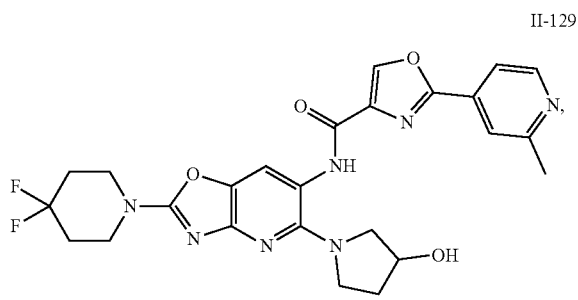

II-130
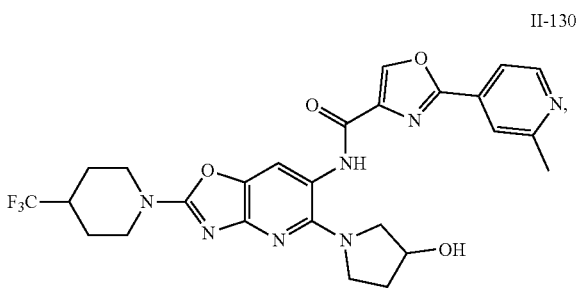

II-132
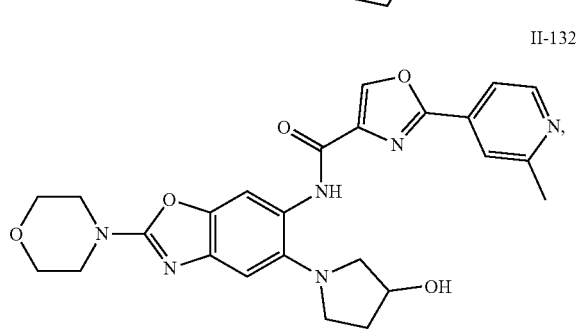

II-133
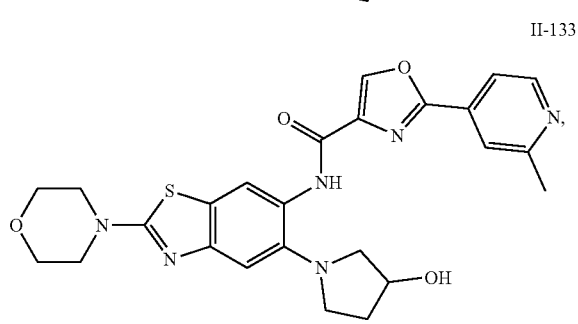

II-136
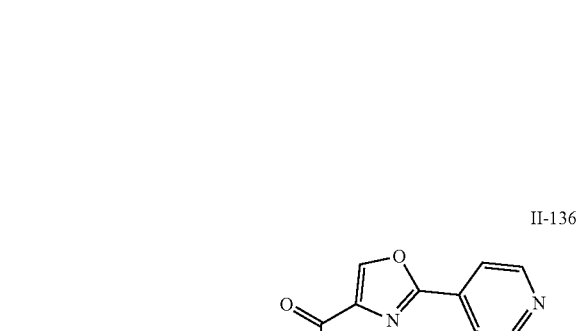

II-137
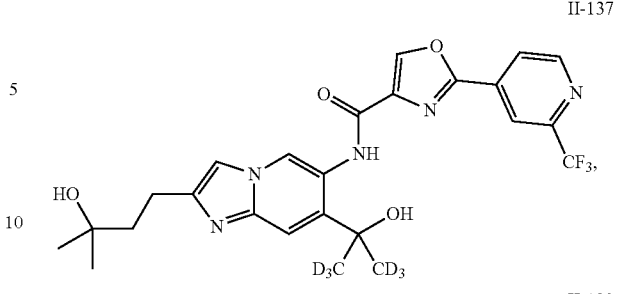

II-138
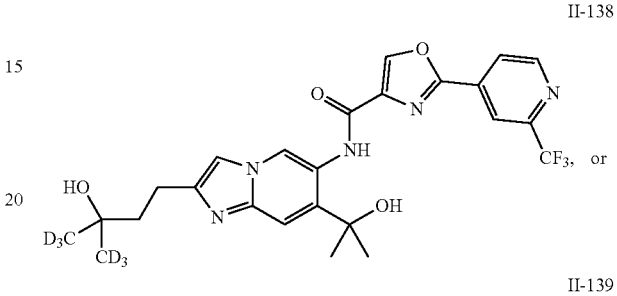

II-139
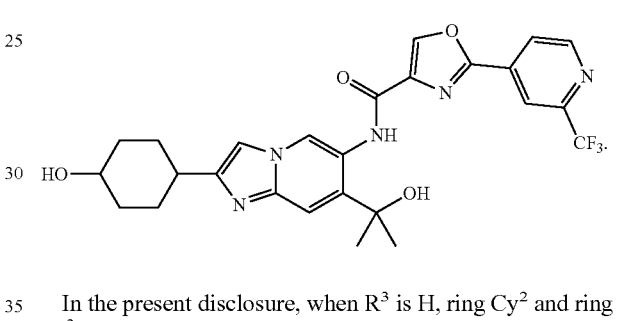

In the present disclosure, when $R^3$ is H, ring $Cy^2$ and ring $Cy^3$ are absent.

In the present disclosure, in ring $Cy^1$, the heteroatom of the 5-membered heteroaromatic ring is selected from one or more than one of N, S, and O, and the number of heteroatoms is 2; the 5-membered heteroaromatic ring is preferably an oxazole ring, a pyrazole ring, a thiazole ring, or an imidazole ring, such as

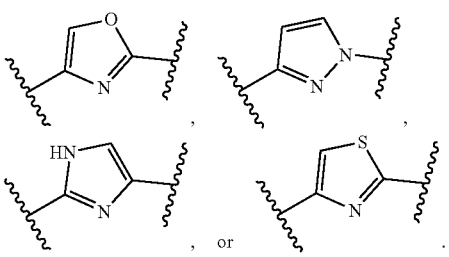

In the present disclosure, in ring $Cy^2$, the 5- to 9-membered heterocyclic ring may be a 6-membered heterocyclic ring, the heteroatom of the 6-membered heterocyclic ring is N, and the number of heteroatoms is 1 or 2; preferably, the 5- to 9-membered heterocyclic ring is a piperazine ring or a piperidine ring.

In the present disclosure, in ring $Cy^3$, the oxo-5- to 9-membered heterocyclic ring is a 6-membered heterocyclic ring, the heteroatom of the 6-membered heterocyclic ring is N, and the number of heteroatoms is 1 or 2; preferably, the oxo-5- to 9-membered heterocyclic ring is an oxo-piperazine ring or an oxo-piperidine ring, such as

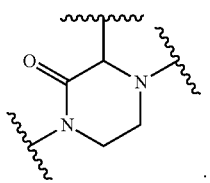 [SMILES: *C1C(=O)N(*)CCN1*]

In the present disclosure, when $R^1$ is halogen, the halogen is fluorine, chlorine, bromine, or iodine.

In the present disclosure, when $R^1$ is unsubstituted 3- to 11-membered heterocycloalkyl or 3- to 11-membered heterocycloalkyl substituted by one or more than one $R^{1-1}$, the 3- to 11-membered heterocycloalkyl may be 3- to 9-membered heterocycloalkyl, and the 3- to 9-membered heterocycloalkyl is preferably piperidinyl, tetrahydropyrrolyl, 2-azaspiro[3.3]heptyl, 2-oxaspiro[3.3]heptyl, morpholinyl, tetrahydropyranyl, azabicyclo[2.2.1]heptyl, tetrahydrothiopyranyl, 2-azaspiro[3.5]nonyl, diazabicyclo[2.2.1]heptyl, azabicyclo[3.2.1]octyl, azaspiro[3.4]octyl, or oxabicyclo[3.2.1]octyl; preferably, each $R^{1-1}$ is independently halogen, hydroxyl, oxo,

or $C_{1-6}$ alkyl substituted by one or more than one halogen or heterocycloalkyl; the unsubstituted 3- to 11-membered heterocycloalkyl or the 3-to 11-membered heterocycloalkyl substituted by one or more than one $R^{1-1}$ is preferably

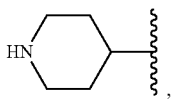

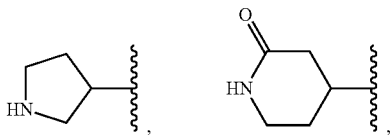

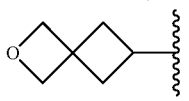

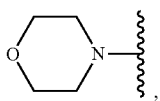

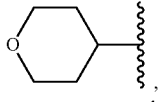

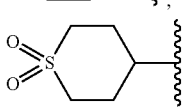

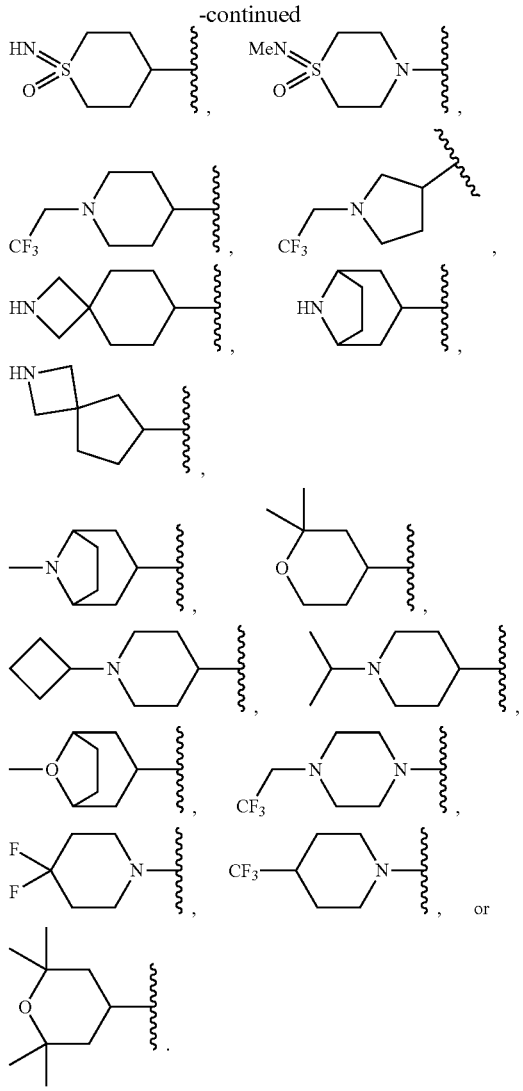

In the present disclosure, when $R^1$ is unsubstituted 3- to 10-membered cycloalkyl or 3- to 10-membered cycloalkyl substituted by one or more than one $R^{1-2}$, the 3- to 10-membered cycloalkyl may be $C_{3-6}$ cycloalkyl, which may also be cyclopropyl, cyclobutyl, cyclopentyl, or cyclohexyl, such as cyclopropyl, cyclobutyl, or cyclohexyl; each $R^{1-2}$ is independently and preferably —$SO_2$—$R^a$, halogen, or hydroxyl, $R^a$ is $C_{1-6}$ alkyl; the unsubstituted 3- to 10-membered cycloalkyl or the 3- to 10-membered cycloalkyl substituted by one or more than one $R^{1-2}$ is preferably

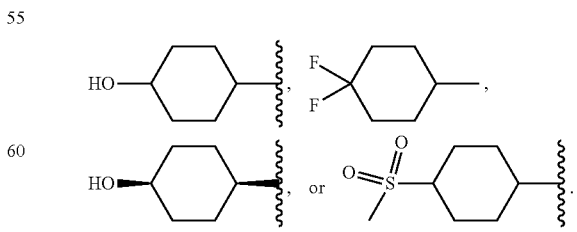

In the present disclosure, when $R^1$ is unsubstituted $C_{1-6}$ alkyl or $C_{1-6}$ alkyl substituted by one or more than one $R^{1-4}$, the $C_{1-6}$ alkyl may be methyl, ethyl, n-propyl, isopropyl, n-butyl, isobutyl, primary butyl, sec-butyl, tert-butyl, n-pentyl, isopentyl, primary pentyl, sec-pentyl, tert-pentyl, or neopentyl, and may also be methyl, ethyl, n-propyl, isopropyl, or isopentyl; each $R^{1-4}$ is independently and preferably deuterium, halogen, hydroxyl, —SO$_2$—R$^a$,

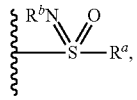

3- to 6-membered cycloalkyl substituted by hydroxyl, 3- to 8-membered heterocycloalkyl substituted by hydroxyl, 3- to 8-membered heterocycloalkyl substituted by oxo, 3- to 8-membered heterocycloalkyl substituted by halogen and Boc, or 3- to 8-membered heterocycloalkyl substituted by halogen; the heteroatom of the 3- to 8-membered heterocycloalkyl is preferably N and/or O, the number of heteroatoms is 1 or 2, R$^a$ is C$_{1-6}$ alkyl, and R$^b$ is hydrogen; the unsubstituted C$_{1-6}$ alkyl or the C$_{1-6}$ alkyl substituted by one or more than one $R^{1-4}$ is preferably

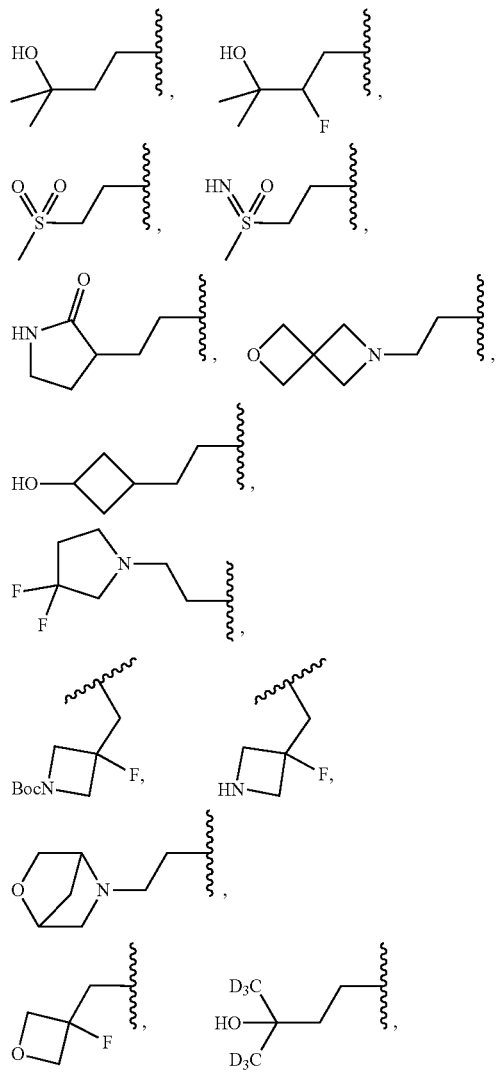

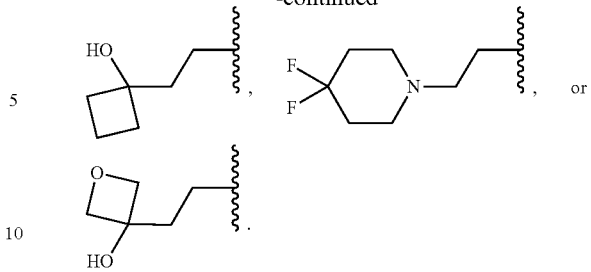

In the present disclosure, when $R^{1-1}$, $R^{1-2}$, $R^{1-4}$, $R^{1-5}$, $R^{1-6}$, and $R^{1-7}$ are each independently halogen, the halogen may be fluorine, chlorine, bromine, or iodine, such as fluorine.

In the present disclosure, when $R^{1-1}$, $R^{1-2}$, $R^{1-4}$, $R^{1-5}$, $R^{1-6}$, and $R^{1-7}$ are each independently unsubstituted 3- to 11-membered heterocycloalkyl or 3- to 11-membered heterocycloalkyl substituted by one or more than one $R^{1-1-1}$, the 3- to 11-membered heterocycloalkyl is preferably 3- to 7-membered heterocycloalkyl, and the heteroatom of the 3- to 11-membered heterocycloalkyl is preferably N and/or O, and the number of heteroatoms is 1 or 2; the 3- to 11-membered heterocycloalkyl is preferably tetrahydropyrrolyl, oxetanyl, or spiroheptyl containing oxygen and/or nitrogen, such as

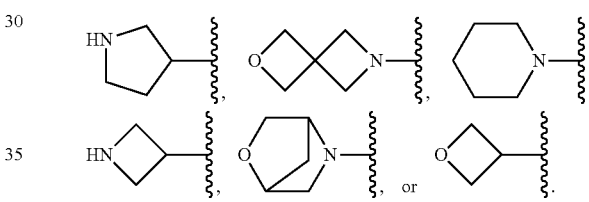

In the present disclosure, when $R^{1-1}$, $R^{1-2}$, $R^{1-4}$, $R^{1-5}$, $R^{1-6}$, and $R^{1-7}$ are each independently unsubstituted C$_{1-6}$ alkyl or C$_{1-6}$ alkyl substituted by one or more than one $R^{1-1-4}$, the C$_{1-6}$ alkyl may be C$_{1-4}$ alkyl, which may also be methyl, ethyl, n-propyl, isopropyl, n-butyl, isobutyl, primary butyl, sec-butyl, or tert-butyl, which may also be isopropyl, methyl, or ethyl.

In the present disclosure, when each $R^{1-1-1}$ is independently C$_{1-6}$ alkyl, the C$_{1-6}$ alkyl may be C$_{1-4}$ alkyl, which may also be methyl, ethyl, n-propyl, isopropyl, n-butyl, isobutyl, primary butyl, sec-butyl, or tert-butyl, which may also be methyl or ethyl.

In the present disclosure, when R$^2$ is halogen, the halogen may be fluorine, chlorine, bromine, or iodine.

In the present disclosure, when R$^2$ is unsubstituted 3- to 11-membered heterocycloalkyl or 3- to 11-membered heterocycloalkyl substituted by one or more than one $R^{2-1}$, the 3- to 11-membered heterocycloalkyl may be 3- to 8-membered heterocycloalkyl, and the heteroatom of the 3- to 11-membered heterocycloalkyl is preferably N and/or O, and the number of heteroatoms is 1 or 2; the 3- to 11-membered heterocycloalkyl is preferably piperidinyl, tetrahydropyrrolyl, 2-azaspiro[3.3]heptyl, 2-oxaspiro[3.3]heptyl, morpholinyl, tetrahydropyranyl, oxetanyl, azabicyclo[2.2.1]heptyl, or diazabicyclo[2.2.1]heptyl; each $R^{2-1}$ is independently and preferably halogen, oxo, or hydroxyl, and the unsubstituted 3- to 8-membered heterocycloalkyl or the 3- to 8-membered heterocycloalkyl substituted by one or more than one $R^{2-1}$ is preferably

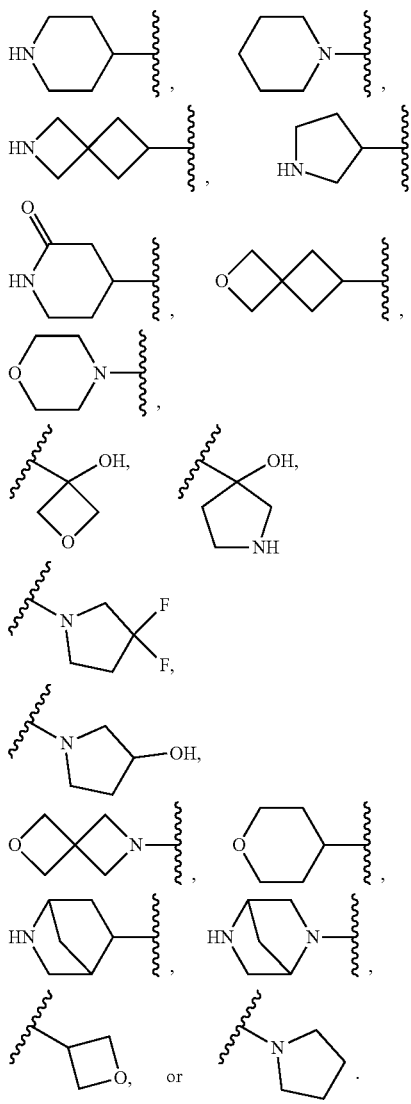

In the present disclosure, when R² is unsubstituted 3- to 10-membered cycloalkyl or 3- to 10-membered cycloalkyl substituted by one or more than one R²⁻², the 3- to 10-membered cycloalkyl may be $C_{3-6}$ cycloalkyl, which may also be cyclopropyl, cyclobutyl, cyclopentyl, or cyclohexyl, such as cyclopropyl, cyclobutyl, or cyclohexyl; each $R^{2-2}$ is independently and preferably halogen or hydroxyl; the unsubstituted 3- to 10-membered cycloalkyl or the 3- to 10-membered cycloalkyl substituted by one or more than one $R^{2-2}$ is preferably

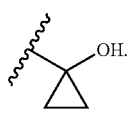 [SMILES: *C1(O)CC1]

In the present disclosure, when R² is unsubstituted $C_{1-6}$ alkyl, or $C_{1-6}$ alkyl substituted by one or more than one $R^{2-4}$, the $C_{1-6}$ alkyl may be methyl, ethyl, n-propyl, isopropyl, n-butyl, isobutyl, primary butyl, sec-butyl, tert-butyl, n-pentyl, isopentyl, primary pentyl, sec-pentyl, tert-pentyl, or neopentyl, and may also be methyl, ethyl, n-propyl, isopropyl, or isopentyl; each $R^{2-4}$ is independently and preferably deuterium, halogen, hydroxyl, $-SO_2-R^a$, or

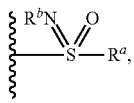

$R^a$ is $C_{1-6}$ alkyl, and $R^b$ is hydrogen; the unsubstituted $C_{1-6}$ alkyl, or $C_{1-6}$ alkyl substituted by one or more than one $R^{2-4}$ may be

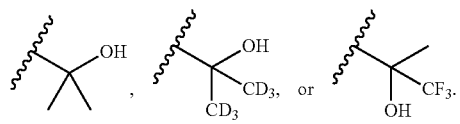

In the present disclosure, when R² is unsubstituted $C_{1-6}$ alkoxy or $C_{1-6}$ alkoxy substituted by one or more than one $R^{2-7}$, the $C_{1-6}$ alkoxy may be $C_{1-4}$ alkoxy, which may also be methoxy, ethoxy, n-propoxy, isopropoxy, n-butoxy, isobutoxy, primary butoxy, sec-butoxy, or tert-butoxy, and which may also be methoxy, ethoxy, or isopropoxy; each $R^{2-7}$ is independently and preferably deuterium or halogen; the unsubstituted $C_{1-6}$ alkoxy or $C_{1-6}$ alkoxy substituted by one or more than one $R^{2-7}$ is preferably methoxy, isopropoxy, deuterated methoxy, or trifluoromethoxy.

In the present disclosure, when R² is hydroxyl substituted by $R^{2-8}$, the $R^{2-8}$ may be 3- to 6-membered cycloalkyl or 3- to 6-membered heterocycloalkyl, and the heteroatom of the 3- to 6-membered heterocycloalkyl is oxygen, the number of heteroatoms is 1; the hydroxyl substituted by $R^{2-8}$ is preferably

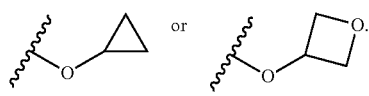

In the present disclosure, when $R^{2-1}$, $R^{2-2}$, $R^{2-4}$, $R^{2-5}$, $R^{2-6}$, and $R^{2-7}$ are each independently halogen, the halogen may be fluorine, chlorine, bromine, or iodine, such as fluorine.

In the present disclosure, when $R^{2-1}$, $R^{2-2}$, $R^{2-4}$, $R^{2-5}$, $R^{2-6}$, and $R^{2-7}$ are each independently unsubstituted 3- to 11-membered heterocycloalkyl or 3- to 11-membered heterocycloalkyl substituted by one or more than one $R^{2-1-1}$, the 3- to 11-membered heterocycloalkyl may be 5- to 8-membered heterocycloalkyl, and the heteroatom of the 3- to 11-membered heterocycloalkyl is preferably N and/or O, and the number of heteroatoms is 1 or 2; the unsubstituted 3- to 11-membered heterocycloalkyl or 3- to 11-membered heterocycloalkyl substituted by one or more than one $R^{2-1-1}$ is preferably tetrahydropyrrolyl, oxetanyl, or spiroheptyl containing one oxygen atom and/or one nitrogen atom, such as

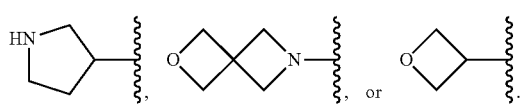

In the present disclosure, when each $R^{2-1-1}$ is independently $C_{1-6}$ alkyl, the $C_{1-6}$ alkyl may be $C_{1-4}$ alkyl, which may also be methyl, ethyl, n-propyl, isopropyl, n-butyl, isobutyl, primary butyl, sec-butyl, or tert-butyl, which may also be methyl or ethyl;

In the present disclosure, when $R^4$ is unsubstituted 5- to 10-membered heteroaryl or 5- to 10-membered heteroaryl substituted by one or more than one $R^{4-1}$, the 5- to 10-membered heteroaryl may be 6-membered heteroaryl, and the 6-membered heteroaryl is preferably pyridazinyl or pyridyl; each $R^{4-1}$ is independently and preferably $C_{1-6}$ alkyl or $C_{1-6}$ alkyl substituted by one or more than one halogen; the unsubstituted 5- to 10-membered heteroaryl or the 5- to 10-membered heteroaryl substituted by one or more than one $R^{4-1}$ is preferably

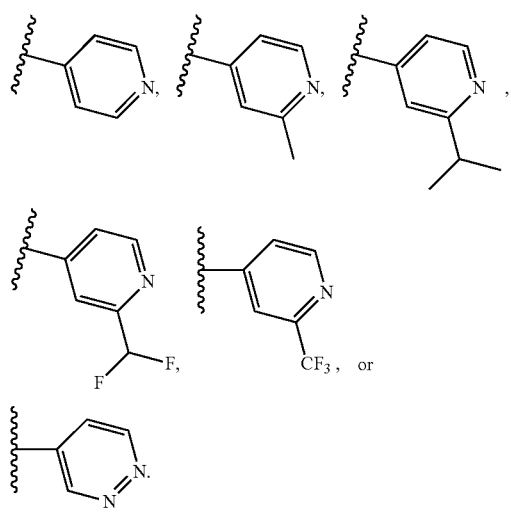

In the present disclosure, when $R^4$ is unsubstituted 6- to 10-membered aryl or 6- to 10-membered aryl substituted by one or more than one $R^{4-5}$, the 6- to 10-membered aryl may be phenyl; each $R^{4-5}$ is independently and preferably $C_{1-6}$ alkyl or $C_{1-6}$ alkyl substituted by one or more than one halogen.

In the present disclosure, when $R^4$ is unsubstituted 3- to 11-membered heterocycloalkyl or 3- to 11-membered heterocycloalkyl substituted by one or more than one $R^{4-3}$, the 3- to 11-membered heterocycloalkyl is 6-membered heterocycloalkyl, preferably piperazinyl, piperidinyl, thiomorpholinyl, or morpholinyl; each $R^{4-3}$ is independently and preferably halogen, $C_{1-6}$ alkyl, $C_{1-6}$ alkyl substituted by one or more than one halogen, oxo, or

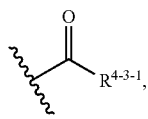

and $R^{4-3-1}$ is hydrogen, $C_{1-6}$ alkyl, or $C_{1-6}$ alkoxy; the unsubstituted 3- to 11-membered heterocycloalkyl or 3- to 11-membered heterocycloalkyl substituted by one or more than one $R^{4-3}$ is more preferably

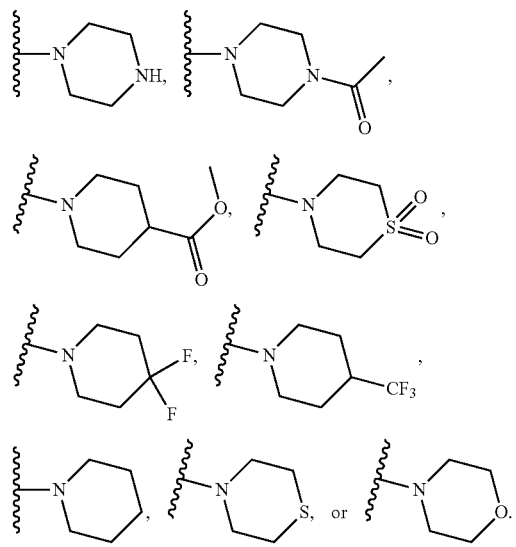

In the present disclosure, when each $R^4$ is independently halogen, the halogen is fluorine, chlorine, bromine, or iodine, such as bromine.

In the present disclosure, when $R^{4-1}$ is unsubstituted $C_{1-6}$ alkyl or $C_{1-6}$ alkyl substituted by one or more than one halogen, the $C_{1-6}$ alkyl may be $C_{1-4}$ alkyl, which may also be methyl, ethyl, n-propyl, isopropyl, n-butyl, isobutyl, primary butyl, sec-butyl, or tert-butyl, and which may also be isopropyl, methyl, or ethyl; the halogen may be fluorine, chlorine, bromine, or iodine, such as fluorine; the unsubstituted $C_{1-6}$ alkyl, or $C_{1-6}$ alkyl substituted by one or more than one halogen is preferably $C_{1-6}$ alkyl substituted by fluorine, such as difluoromethyl or trifluoromethyl.

In the present disclosure, when $R^{4-3}$ is $C_{1-6}$ alkyl, the $C_{1-6}$ alkyl may be $C_{1-4}$ alkyl, which may also be methyl, ethyl, n-propyl, isopropyl, n-butyl, isobutyl, primary butyl, sec-butyl, or tert-butyl, which may also be methyl or ethyl.

In the present disclosure, when $R^{4-3-1}$ is $C_{1-6}$ alkyl, the $C_{1-6}$ alkyl may be $C_{1-4}$ alkyl, which may also be methyl, ethyl, n-propyl, isopropyl, n-butyl, isobutyl, primary butyl, sec-butyl, or tert-butyl, which may also be methyl or ethyl.

In the present disclosure, when ring $Cy^4$ is a 5-membered heterocyclic ring, the heteroatom of the 5-membered heterocyclic ring is selected from one or two of N, S, and O, and the number of heteroatoms is 1 or 2, such as

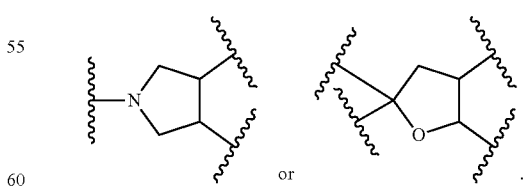

In the present disclosure, when ring $Cy^4$ is an oxo-5-membered heterocyclic ring; the heteroatom of the oxo-5-membered heterocyclic ring is selected from one or two of N and S, and the number of heteroatoms is 1 or 2, the oxo-5-membered heterocyclic ring is preferably

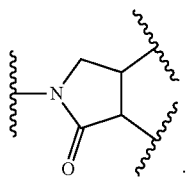 [SMILES: *C1CN(*)C(=O)C1*]

In the present disclosure, when $R^a$ and $R^b$, together with the atom to which they are attached, form a 3- to 11-membered heterocyclic ring, the 3- to 11-membered heterocyclic ring may be 3- to 6-membered heterocycloalkyl; the heteroatom of the 3- to 6-membered heterocycloalkyl is preferably N, O, or S, and the number of heteroatoms is 1; the 3- to 11-membered heterocyclic ring may be

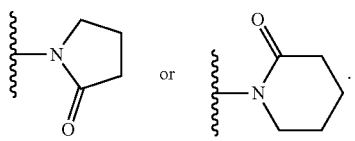 [SMILES: *N1CCCC1=O ; *N1CCCCC1=O]

In the present disclosure,

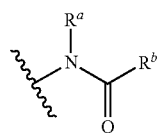

is preferably

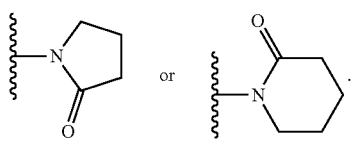 [SMILES: *N1CCCC1=O ; *N1CCCCC1=O]

In the present disclosure, —SO$_2$—R$^a$ is preferably

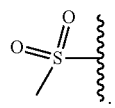

In the present disclosure,

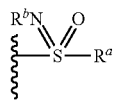

is preferably

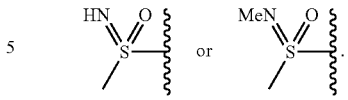

In the present disclosure,

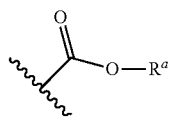

is preferably

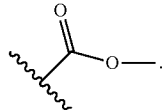 [SMILES: *C(=O)OC]

In the present disclosure,

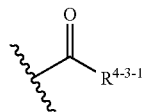

is preferably

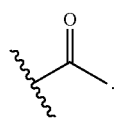

The present disclosure also provides a preparation method for a five-membered-fused six-membered compound of formula I, formula II, or formula III,
wherein the preparation method for the five-membered-fused six-membered compound of formula I comprises the following steps: a compound of formula I-A and a compound of formula I-B undergo a condensation reaction as shown below in a solvent with the presence of a base and a condensing agent,

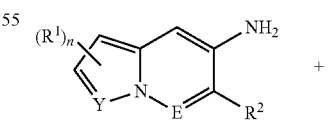
I-A

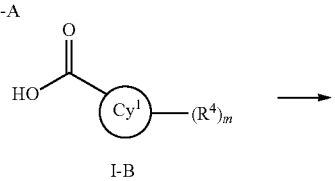
I-B

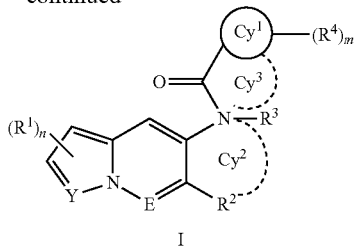

I

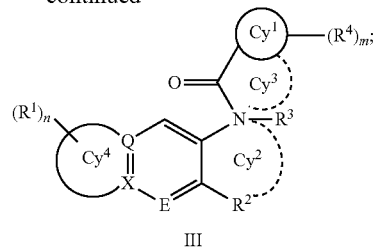

III

R³ is hydrogen, and n, m, Y, E, R³, ring Cy¹, ring Cy², ring Cy³, R¹, R², and R⁴ are as defined above;

the preparation method for the five-membered-fused six-membered compound of formula II comprises the following steps: a compound of formula II-A and a compound of formula I-B undergo a condensation reaction as shown below in a solvent with the presence of a base and a condensing agent,

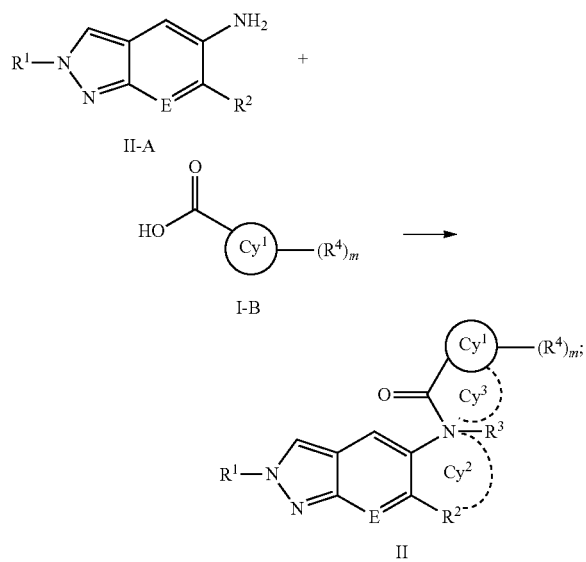

R³ is hydrogen, and n, m, E, R³, ring Cy¹, ring Cy², ring Cy³, R¹, R² and R⁴ are as defined above;

the preparation method for the five-membered-fused six-membered compound of formula III comprises the following steps: a compound of formula III-A and a compound of formula III-B undergo a condensation reaction as shown below in a solvent with the presence of a base and a condensing agent,

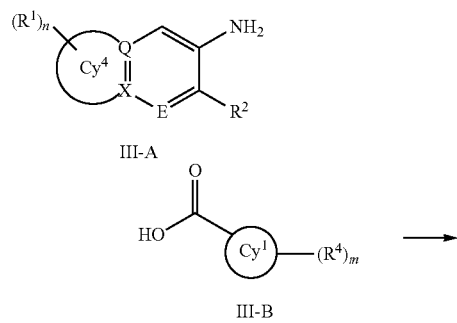

R³ is hydrogen, and n, m, E, X, Q, R³, ring Cy¹, ring Cy², ring Cy³, ring Cy⁴, R¹, R², and R⁴ are as defined above.

In the present disclosure, the solvent is a conventional solvent for such reactions in the art, preferably an amide solvent, and more preferably DMF, such as anhydrous DMF.

In the present disclosure, the amount of the solvent is a conventional amount of the solvent in the art. Preferably, the solvent has a volume molar ratio of (20-5):1 mL/mmol with the compound of formula I-A, the compound of formula II-A, or the compound of formula III-A, such as 12:1 mL/mmol or 12.5:1 mL/mmol.

In the present disclosure, the base is a conventional base for such reactions in the art, preferably a nitrogen-containing organic base, such as N,N-diisopropylethylamine.

In the present disclosure, the amount of the base is a conventional amount of the base in the art. Preferably, the base has a molar ratio of (1-5):1 with the compound of formula I-A, the compound of formula II-A, or the compound of formula III-A, such as 1.5:1, 2:1, or 3:1.

In the present disclosure, the condensing agent is a condensing agent used for such reactions in the art, which is preferably a phosphate condensing agent, such as bromo-tris-pyrrolidino-phosphonium hexafluorophosphate or 2-(7-azabenzotriazol-1-yl)-N,N,N',N'-tetramethyluronium hexafluorophosphate.

In the present disclosure, the amount of the condensing agent is a conventional amount of the condensing agent in the art. Preferably, the condensing agent has a molar ratio of (1-2):1 with the compound of formula I-A, the compound of formula II-A, or the compound of formula III-A, such as 1:1, 1.2:1, 1.3:1, or 1.5:1.

In the present disclosure, the reaction temperature of the condensation reaction is a conventional reaction temperature in the art, preferably −10° C. to 30° C., such as 0° C.

The present disclosure also provides a pharmaceutical composition comprising the five-membered-fused six-membered compound of formula I, formula II, or formula III, or the pharmaceutically acceptable salt thereof, or the pharmaceutically acceptable salt thereof, and a pharmaceutical excipient.

The present disclosure also provides a pharmaceutical composition comprising the five-membered-fused six-membered compound of formula I, formula II, or formula III, or the pharmaceutically acceptable salt thereof, and a pharmaceutically acceptable carrier.

The present disclosure also provides a substance Z for use in the manufacture of an FLT3 and/or IRAK4 inhibitor or a medicament for the treatment and/or prevention of an FLT3-related and/or IRAK4-related disease, wherein the substance Z is the five-membered-fused six-membered compound of formula I, formula II, or formula III, or the pharmaceutically acceptable salt thereof.

The FLT3-related disease comprises a hematological tumor and/or a solid tumor.

The hematological tumor may be selected from one or more than one of acute lymphoblastic leukemia, acute myeloid leukemia, acute promyelocytic leukemia, chronic lymphocytic leukemia, chronic myeloid leukemia, chronic neutrophilic leukemia, acute undifferentiated leukemia, anaplastic large cell lymphoma, prolymphocytic leukemia, juvenile myelomonocytic leukemia, myelodysplastic syndrome, non-Hodgkin's lymphoma, multiple myeloma, myeloproliferative disease, mantle cell lymphoma, and de novo acute myeloid leukemia in adults;

The solid tumor may be selected from one or more than one of colorectal cancer, renal cell carcinoma, non-small cell lung cancer, bladder cancer, ovarian cancer, breast cancer, pancreatic cancer, gastric adenocarcinoma, prostate cancer, and lung cancer.

The IRAK4-related disease comprises autoimmune disease, inflammatory disease, cardiovascular disease, cancer, or central nervous system disease.

The autoimmune disease may be selected from one or more than one of rheumatoid arthritis, osteoarthritis, juvenile arthritis, multiple sclerosis, lupus, diabetes (such as type I diabetes), psoriasis, psoriatic arthritis, atopic dermatitis, chronic obstructive pulmonary disease, Crohn's disease, ulcerative colitis, and irritable bowel syndrome.

The inflammatory disease may be selected from, but not limited to, one or more than one of rheumatoid arthritis, osteoarthritis, juvenile arthritis, multiple sclerosis, lupus, diabetes (such as type I diabetes), psoriasis, psoriatic arthritis, atopic dermatitis, chronic obstructive pulmonary disease, Crohn's disease, ulcerative colitis, and irritable bowel syndrome.

The cardiovascular disease may be stroke or atherosclerosis.

The present disclosure also provides a method for treating and/or preventing an FLT3-related disease and/or an IRAK4-related disease, which comprises administering an effective amount of a substance Z to a patient, and the substance Z is the compound of formula I, II, or III or the pharmaceutically acceptable salt thereof.

The present disclosure also provides a method for treating cancer, autoimmune disease, inflammatory disease, cardiovascular disease or central nervous system disease, which comprises administering a therapeutically effective amount of the five-membered-fused six-membered compound of formula I, formula II, or formula III, or the pharmaceutically acceptable salt thereof. The cancer may be selected from hematological tumor or solid tumor.

Unless otherwise specified, the terms used in the present disclosure have the following meanings:

The terms "compound" and "pharmaceutically acceptable salt", if the tautomer exists, can exists in the form of a single tautomer or a mixture thereof, preferably in the form of predominantly more stable isomers If a linkage group is expressed as "absent", the structures on both sides of the linkage group are directly attached by a single bond, such as -A-B—C—, when B is not absent, -A-B—C— is -A-C—.

The term "¦" means presence or absence.

The term "halogen" refers to fluorine, chlorine, bromine, or iodine.

The term "oxo" refers to the substitution of hydrogen or lone pair of electrons on a non-oxygen atom by oxygen. For example,

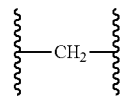

is oxo-substituted to

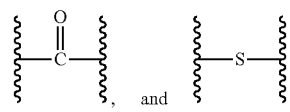

is oxo-substituted to

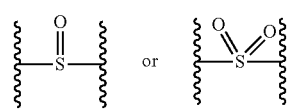

The term "cycloalkyl" refers to a saturated monocyclic group consisting only of carbon atoms with a specified number of carbon atoms (e.g., $C_3$ to $C_{10}$). The monocycloalkyl includes, but is not limited to, cyclopropyl, cyclobutyl, cyclopentyl, cyclohexyl.

The term "alkyl" refers to a straight or branched alkyl group with a specified number of carbon atoms (e.g., $C_1$ to $C_6$). The alkyl includes, but is not limited to, methyl, ethyl, n-propyl, isopropyl, n-butyl, tert-butyl, isobutyl, sec-butyl, n-pentyl, n-hexyl.

The term "heterocycloalkyl" refers to a cyclic group with a specified number of ring atoms (e.g., 3- to 11-membered, also e.g., 3- to 8-membered), a specified number of heteroatoms (e.g., 1, 2, or 3), and a specified type of heteroatom (one or more than one of N, O, and S), wherein the heteroatom may be attached to other groups as an linkage group, or may not be attached to other groups (e.g., piperidinyl may be

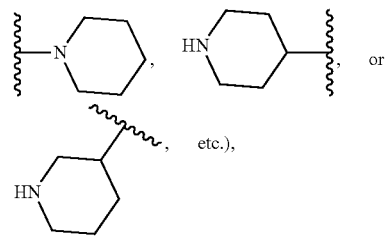

and it is a monocyclic ring, a fused ring, a bridged ring, or a spiro ring, and each ring is saturated. The heterocycloalkyl includes, but is not limited to, azetidinyl, tetrahydropyrrolyl, tetrahydrofuryl, morpholinyl, piperidinyl.

The term "heterocyclic ring" refers to a cyclic group with a specified number of ring atoms (e.g., 3- to 11-membered, also e.g., 3- to 8-membered), a specified number of heteroatoms (e.g., 1, 2, or 3), and a specified type of heteroatom (one or more than one of N, O, and S), wherein the heteroatom may be attached to other groups as an linkage group, or may not be attached to other groups (e.g., a piperidine ring may be

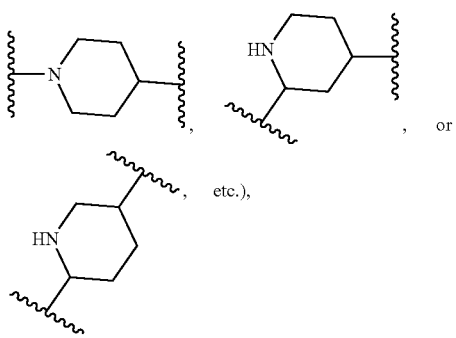

and it is a monocyclic ring, a fused ring, a bridged ring, or a spiro ring. The heterocyclic ring includes, but is not limited to, an azetidine ring, a tetrahydropyrrole ring, a tetrahydrofuran ring, a morpholine ring, a piperidinyl ring.

The term "aryl" refers to a cyclic group consisting only of carbon atoms with a specified number of carbon atoms (e.g., $C_6$ to $C_{10}$), which is a monocyclic ring or a polycyclic ring, and at least one ring is aromatic (in accordance with Huckel's rule). The aryl are attached to other moieties in the molecule through aromatic rings or non-aromatic rings. The aryl includes, but is not limited to, phenyl, naphthyl.

The term "heteroaryl" refers to a cyclic group with a specified number of ring atoms (e.g., 5- to 10-membered, also e.g., 5- to 8-membered), a specified number of heteroatoms (e.g., 1, 2, or 3), and a specified type of heteroatom (one or more than one of N, O, and S), which is a monocyclic ring or a polycyclic ring, and at least one ring is aromatic (in accordance with Huckel's rule). The heteroaryl are attached to other moieties in the molecule through aromatic rings or non-aromatic rings. The heteroaryl includes, but is not limited to, furyl, pyrrolyl, thienyl, pyrazolyl, imidazolyl, oxazolyl, thiazolyl, pyridyl, pyrimidinyl, indolyl.

The "-" at the end of a group means that the group is attached to other moieties in the molecule through this site. For example, CHs—C(=O)— refers to acetyl.

The

" "

in a structural moiety means that the structural moiety is attached to other moieties in the molecule through this site. For example,

refers to acetyl.

The term "more than one" refers to 2, 3, 4, or 5.

When any variable (such as group $R^{1-1}$) appears multiple times in the definition of a compound, their definitions are independent of each other and do not affect each other. For example, $C_{6-10}$ aryl substituted by 3 $R^{1-1}$ groups means that the $C_{6-10}$ aryl will be substituted by 3 $R^{1-1}$ groups, and the definitions of the 3 $R^{1-1}$ groups are independent of each other and do not affect each other.

The term "pharmaceutically acceptable salt" refers to a salt obtained by reacting a compound with a pharmaceutically acceptable (relatively nontoxic, safe, and suitable for use by a patient) acid or base. When the compound contains a relatively acidic functional group, a base addition salt can be obtained by contacting the free form of the compound with a sufficient amount of a pharmaceutically acceptable base in a suitable inert solvent. The pharmaceutically acceptable base addition salt includes, but is not limited to, a sodium salt, a potassium salt, a calcium salt, an aluminum salt, a magnesium salt, a bismuth salt, an ammonium salt. When the compound contains a relatively basic functional group, an acid addition salt can be obtained by contacting the free form of the compound with a sufficient amount of a pharmaceutically acceptable acid in a suitable inert solvent. The pharmaceutically acceptable acid addition salt includes, but is not limited to, hydrochloride, acetate, trifluoroacetate, sulfate, methanesulfonate. For details, see *Handbook of Pharmaceutical Salts: Properties, Selection, and Use* (P. Heinrich Stahl, 2002).

The term "pharmaceutical excipient" refers to the excipient and additive used in the production of drugs and preparation of prescriptions, and is all substances other than active ingredients included in pharmaceutical preparations. For details, see the *Pharmacopoeia of the People's Republic of China* (2020 edition) or *Handbook of Pharmaceutical EMcipients* (Raymond C Rowe, 2009).

The term "treatment" or "treat" refers to any of the following: (1) alleviating one or more than one biological manifestation of a disease; (2) interfering with one or more than one point in the biological cascade that causes the disease; (3) slowing the progression of one or more than one biological manifestation of a disease.

The term "prevention" refers to reducing the risk of developing a disease.

The term "patient" refers to any animal that has been or is about to be treated, preferably a mammal, most preferably a human. The mammal includes, but is not limited to, cattle, horses, sheep, pigs, cats, dogs, mice, rats, rabbits, guinea pigs, monkeys, humans.

As used in the specifications and claims, the singular form "a", "an" and "the" includes plural references unless the context clearly dictates otherwise.

On the basis of not violating common sense in the art, the above preferred conditions can be combined arbitrarily to obtain preferred examples of the present disclosure.

The reagent and raw material used in the present disclosure are all commercially available.

The positive and progressive effect of the present disclosure is that when the FLT3 inhibitor is used as monotherapy, the disease relapses quickly, and target-dependent and non-target-dependent drug resistance has occurred; although combined use of drugs to coinhibit signaling pathways related to cell survival can reduce the occurrence of non-target drug resistance, the effect is still limited. The compounds of the present disclosure have an inhibitory effect on FLT3 and/or IRAK4. The compounds developed in the present disclosure can be used as dual-target inhibitors of FLT3 and IRAK4, which have potential clinical application value and are anticipated to improve patient prognosis and reduce the likelihood of drug resistance.

DETAILED DESCRIPTION OF THE INVENTION

The following examples further illustrate the present disclosure, but the present disclosure is not limited thereto.

Below presents preferred embodiments of the present disclosure based on the drawings in order to illustrate the technical schemes of the present disclosure in detail.

Embodiment 1

The present disclosure is further illustrated below by means of examples, but the present disclosure is not limited to the scope of the examples. The experimental methods for which specific conditions are not indicated in the following examples are selected according to conventional methods and conditions, or according to the product instructions.

Example II-1: Synthesis of II-1

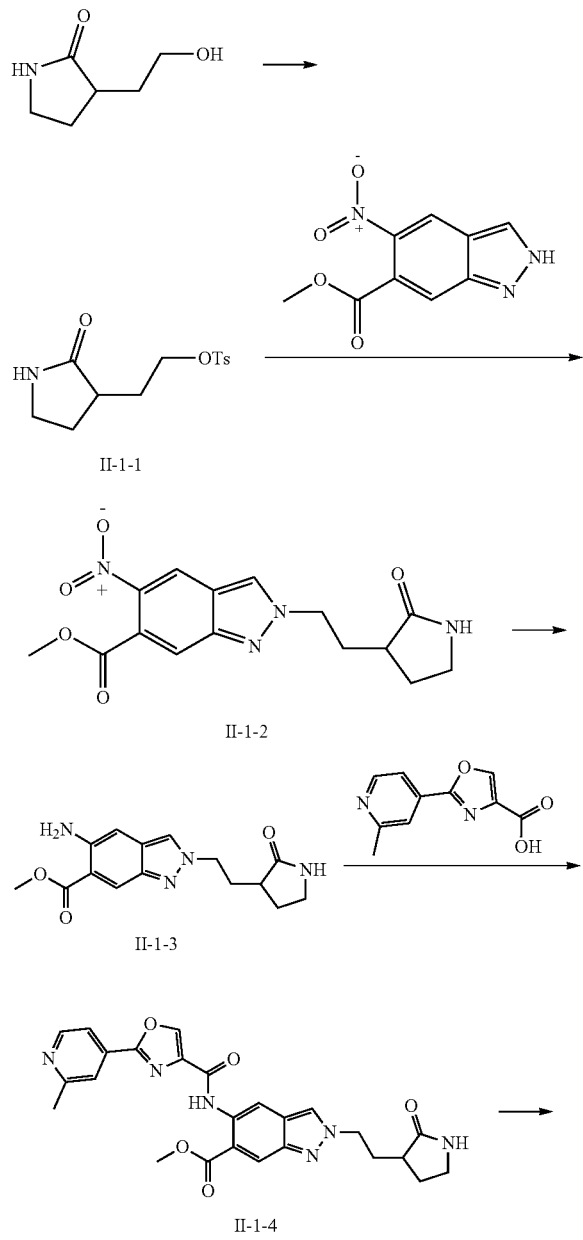

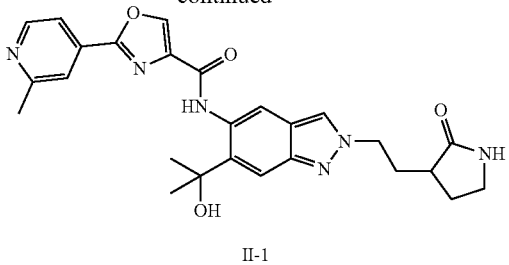

Step 1: Synthesis of II-1-1

TEA (triethylamine) (1.48 g, 14.63 mmol, 2.04 mL) was added to a mixture of 4-methylbenzenesulfonyl chloride (1.12 g, 5.85 mmol), 3-(2-hydroxyethyl)pyrrolidin-2-one (0.63 g, 4.88 mmol), DMAP (4-dimethylaminopyridine) (29.80 mg, 243.89 μmop, and anhydrous DCM (dichloromethane) (6 mL), and the reaction mixture was stirred for 4 hours at 25° C. until the reaction was complete. The reaction mixture was added with $H_2O$ (50 mL) and stirred for 5 minutes, the resulting mixture was extracted with EA (ethyl acetate) (40 mL×3), and the combined organic phases were washed with brine (20 mL), dried over anhydrous $Na_2SO_4$, filtered, and distilled under reduced pressure to obtain the white solid crude product II-1-1 (1 g, crude product), MS (ESI) m/z: 284.3 [M+H]$^+$.

Step 2: Synthesis of II-1-2

Potassium carbonate (1.46 g, 10.59 mmol, 639.02 mmol) and tetrabutylammonium bromide (4.55 g, 14.12 mmol) were added to a mixture of methyl 5-nitro-2H-indazole-6-carboxylate (780.57 mg, 3.53 mmol) and II-1-1 (2 g, 7.06 mmol) in THF (tetrahydrofuran) (10 mL), and the reaction mixture was then stirred for 20 hours at 60° C. until the reaction was complete. The reaction mixture was diluted with $H_2O$ (50 mL), and the resulting mixture was extracted with EA (ethyl acetate) (30 mL×3). The combined organic phases were washed with saturated brine (20 mL), dried over anhydrous $Na_2SO_4$, filtered, and concentrated to obtain the crude product. The crude product was purified by silica gel chromatography and eluted with DCM: MeOH=70/1 to obtain the yellow solid product II-1-2 (0.4 g, yield of 34.11%), MS (ESI) m/z: 333.3 [M+H]$^+$.

Step 3: Synthesis of II-1-3

Fe (564.7 mg, 10.11 mmol), ammonium chloride (540.84 mg, 10.11 mmol, 353.49 μL), and $H_2O$ (1 mL) were added to a mixture of II-1-2 (0.28 g, 842.58 μmol) in ethanol (3 mL), and the reaction mixture was reacted at 70° C. for 4.5 hours. The mixture was diluted with water (50 mL), extracted with EA (ethyl acetate) (30 mL×3), and the combined organic phases were washed with brine (10 mL), dried over anhydrous $Na_2SO_4$, filtered and concentrated to obtain the brown solid crude product II-1-3 (0.2 g, crude product), MS (ESI) m/z: 303.3 [M+H]$^+$.

Step 4: Synthesis of II-1-4

PyBOP (bromotripyrrolidinophosphonium hexafluorophosphate) (165.24 mg, 317.54 μmol) was added to a mixture of 2-(2-methyl-4-pyridyl)oxazole-4-carboxylic acid (64.84 mg, 317.54 μmol), II-1-3 (0.08 g, 264.61 μmol), DIPEA (i.e., N,N-diisopropylethylamine) (68.40 mg, 529.23 μmol, 92.18 μL), and anhydrous DMF (N,N-dimethylformamide, 4 mL), and the reaction mixture was stirred for 4 hours at 25° C. The reaction mixture was diluted with water (50 mL), the resulting mixture was extracted with EA (ethyl acetate) (20 mL×3), and the combined organic phases were washed with brine (20 mL), dried over anhydrous Na$_2$SO$_4$, filtered, and concentrated to obtain the yellow solid crude product II-1-4 (0.15 g, yield of 96.05%), MS (ESI) m/z: 489.5 [M+H]$^+$.

Step 5: Synthesis of II-1

A mixture of II-1-4 (0.15 g, 307.07 mmol), lithium chloride (130.17 mg, 3.07 mmol, 62.94 μL), and anhydrous THF (4 mL) was stirred and added slowly with methylmagnesium chloride (160.75 mg, 2.15 mmol) for 30 minutes at 0° C. under N$_2$ atmosphere, and the reaction mixture was stirred for another 3 hours at 0° C. Then the reaction mixture was diluted with water (50 mL), and the resulting mixture was extracted with EA (ethyl acetate) (20 mL×3). The combined organic phases were washed with brine (20 mL) and then dried over anhydrous Na$_2$SO$_4$, filtered, and concentrated to obtain the crude product. The crude product was purified by silica gel chromatography to obtain white solid product II-1 (0.014 g, yield of 9.33%), MS (ESI) m/z: 489.5 [M+H]$^+$, $^1$H NMR (500 MHz, DMSO-d$_6$) δ: 11.89 (s, 1H), 8.97 (s, 1H), 8.70 (dd, J=5.0, 1.0 Hz, 1H), 8.63 (s, 1H), 8.37 (d, J=1.0 Hz, 1H), 7.84-7.81 (m, 2H), 7.62 (s, 1H), 7.60 (s, 1H), 6.21 (s, 1H), 4.55-4.48 (m, 2H), 3.17-3.08 (m, 2H), 2.61 (s, 3H), 2.35-2.30 (m, 1H), 2.13-2.07 (m, 2H), 1.91-1.83 (m, 1H), 1.68-1.61 (m, 7H).

Example II-2: Synthesis of II-2

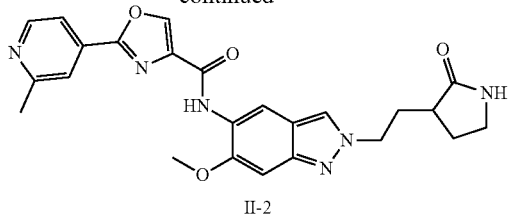

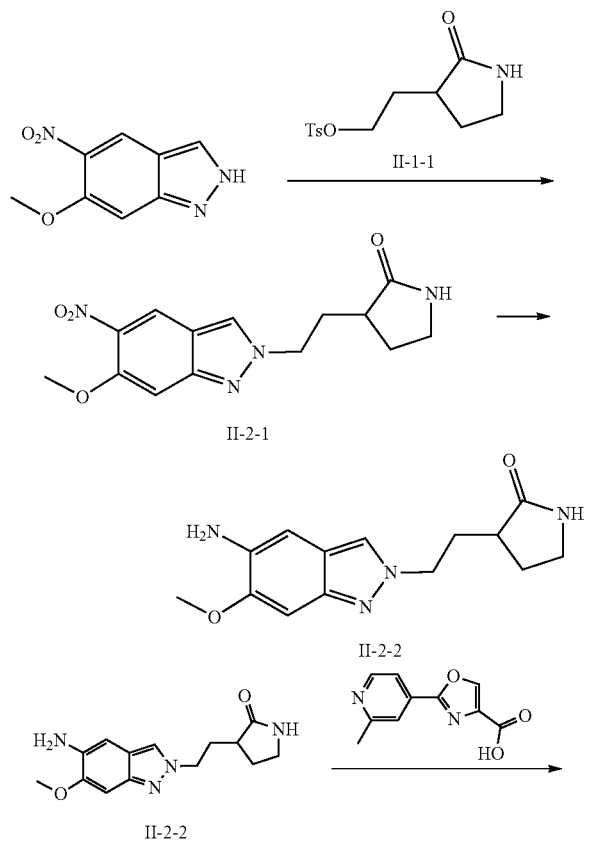

Step 1: Synthesis of II-2-1

TBAB (tetrabutylammonium bromide, 5 g, 15.5 mmol) and K$_2$CO$_3$ (2.9 g, 20.7 mmol) were added to a mixture of 6-methoxy-5-nitro-2H-indazole (1 g, 26 mmol) and II-1-1 (2.2 g, 7.8 mmol) in 1,4-dioxane (10 mL), and the reaction mixture was stirred for 16 hours at room temperature until the reaction was complete. The reaction mixture was diluted with water (10 mL), and the resulting mixture was extracted with EA (ethyl acetate) (10 mL×3). The combined organic phases were washed with brine (20 mL), dried over anhydrous Na$_2$SO$_4$, filtered, and concentrated to obtain the crude product. The crude product was purified by silica gel chromatography to obtain light yellow solid product II-2-1 (173 mg, yield of 11%), MS (ESI) m/z: 305.1 [M+H]$^+$.

Step 2: Synthesis of II-2-2

II-2-1 (173 mg, 0.57 mmol) was dissolved in methanol (5 mL), then Pd/C (10%, 20 mg) was added thereto, the system was replaced with H$_2$ three times, and the mixture was reacted for 12 hours at room temperature until the reaction was complete. The reaction mixture was filtered to remove the Pd/C, the filter cake was washed with methanol (3 mL), and the filtrate was distilled under reduced pressure to obtain the light yellow solid product II-2-2 (156 mg, yield of 99%), MS (ESI) m/z: 275.1 [M+H]$^+$.

Step 3: Synthesis of II-2

II-2-2 (50 mg, 0.18 mmol) was dissolved in DMF (2 mL), then PyBOP (190 mg, 0.36 mmol) and DIPEA (71 mg, 0.55 mmol) were added thereto, and the reaction was stirred for 2 hours at room temperature until the reaction was complete. The reaction mixture was purified by C18 chromatography column to obtain the light yellow solid product II-2 (26 mg, yield of 31%), MS (ESI) m/z: 461.2 [M+H]$^+$, $^1$H NMR (500 MHz, DMSO-d$_6$) δ: 9.59 (s, 1H), 9.11 (s, 1H), 8.76 (d, J=5.0 Hz, 1H), 8.61 (s, 1H), 8.39 (s, 1H), 7.93 (s, 1H), 7.86 (d, J=5.0 Hz, 1H), 7.69 (s, 1H), 7.22 (s, 1H), 4.52 (m, 2H), 4.08 (s, 3H), 3.23-3.15 (m, 2H), 2.68 (s, 3H), 2.37 (m, 1H), 2.19-2.13 (m, 2H), 1.90 (m, 1H), 1.70-1.65 (m, 1H).

Example II-8: Synthesis of II-8

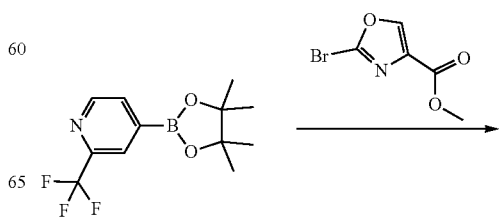

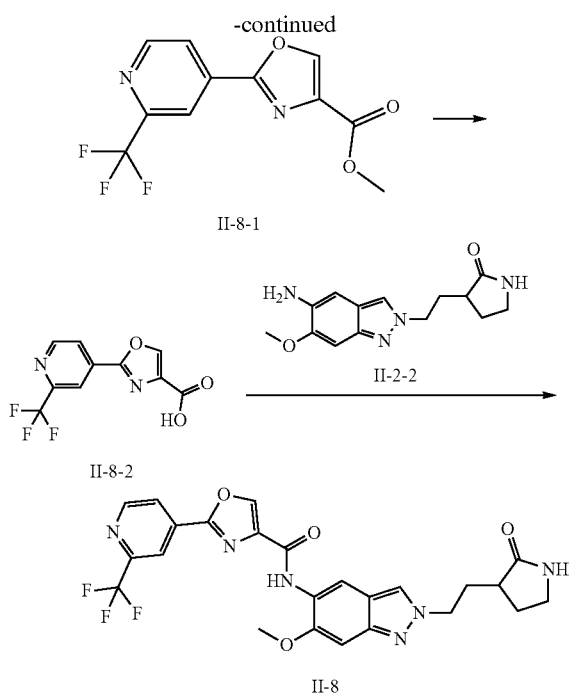

Step 1: Synthesis of II-8-1

A mixture of 4-(4,4,5,5-tetramethyl-1,3,2-dioxobenzofuran-2-yl)-2-(trifluoromethyl)pyridine (286.32 mg, 1.05 mmol), methyl 2-bromooxazole-4-carboxylate (0.18 g, 873.81 μmol), Pd(dppf)Cl$_2$ (115.24 mg, 0.16 mmol), cesium carbonate (569.41 mg, 1.75 mmol), and anhydrous 1,4-dioxane (6 mL) was stirred for 4 hours at 80° C. under nitrogen atmosphere until the reaction was complete. The reaction mixture was diluted with H$_2$O (10 mL) and extracted with EA (10 mL×3) while stirring. The combined organic phases were washed with brine (10 mL), dried over anhydrous Na$_2$SO$_4$, filtered, and concentrated in vacuum to obtain the crude product. The crude product was purified by silica gel chromatography and eluted with PE (petroleum ether)/EA=10/3 to obtain the white solid product II-8-1 (0.23 g, yield of 84.66%), MS (ESI) m/z: 272.0 [M+H]$^+$.

Step 2: Synthesis of II-8-2

Lithium hydroxide (40.48 mg, 1.69 mmol) was added to a mixture of II-8-1 (0.23 g, 845.03 μmol), H$_2$O (1 mL), and THF (3 mL), and the resulting mixture was stirred for 3 hours at 25° C. under nitrogen atmosphere until the reaction was complete. The reaction mixture was diluted with H$_2$O (10 mL) and acidified while stirring until the pH of the mixture was adjusted to 3 to 4, and the mixture was extracted with EA (10 mL×3). The combined organic phases were washed with brine (20 mL), dried over anhydrous Na$_2$SO$_4$, filtered, and concentrated in vacuum to obtain the white solid product II-8-2 (0.2 g, crude), MS (ESI) m/z: 259.0 [M+H]$^+$.

Step 3: Synthesis of II-8

A mixture of II-8-2 (67.76 mg, 262.47 μmol), II-2-2 (0.06 g, 218.72 μmol), DIPEA (56.54 mg, 437.45 μmol, 76.19 μL), anhydrous DMF (5 mL), and PYBOP (136.59 mg, 262.47 μmol) was stirred for 4 hours at 25° C. under nitrogen atmosphere until the reaction was complete. The reaction mixture was diluted with H$_2$O (10 mL) and extracted with EA (10 mL×3) while stirring. The combined organic phases were washed with brine (10 mL), dried over anhydrous Na$_2$SO$_4$, filtered, and concentrated in vacuum to obtain the crude product. The crude product was purified by C18 chromatography column to obtain the brown solid product II-8 (0.01 g, yield of 8.44%). MS (ESI) m/z: 515.1 [M+H]$^+$. $^1$H NMR (500 MHz, DMSO-d$_6$) δ: 9.56 (s, 1H), 9.15 (s, 1H), 9.04 (d, J=5 Hz, 1H), 8.51 (s, 1H), 8.36 (s, 1H), 8.33 (s, 1H), 7.62 (s, 1H), 7.16 (s, 1H), 4.55-4.42 (m, 2H), 4.00 (s, 3H), 3.18-3.14 (m, 2H), 2.20-2.09 (m, 1H), 2.08-2.00 (m, 1H), 1.88-1.81 (m, 3H).

Example II-4: Synthesis of II-4

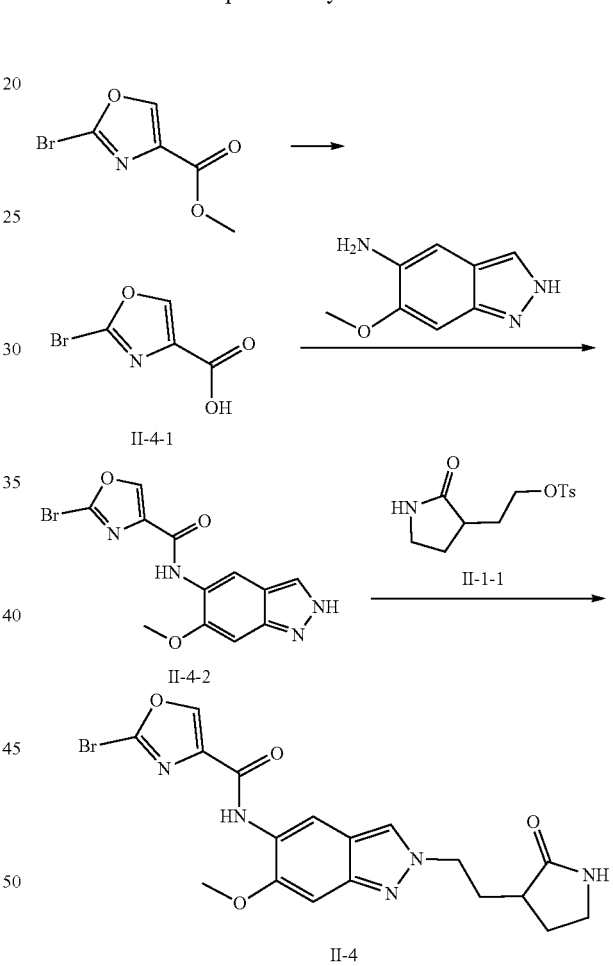

Step 1: Synthesis of II-4-1

Lithium hydroxide (46.51 mg, 1.94 mmol) was added to a mixture of methyl 2-bromooxazole-4-carboxylate (0.2 g, 970.90 μmol), H$_2$O (1 mL), and THF (3 mL), and the reaction mixture was stirred for 3 hours at 25° C. under N$_2$ atmosphere. The reaction mixture was diluted with H$_2$O (30 mL), and the pH of the resulting mixture was adjusted to 3 to 4 while stirring at 0° C., and the resulting mixture was extracted with EA (30 mL×3). The combined organic phases were washed with brine, dried over anhydrous Na$_2$SO$_4$, filtered, and concentrated under reduced pressure to obtain the white solid crude product II-4-1 (0.18 g). MS (ESI) m/z: 190.9 [M+H]+.

Step 2: Synthesis of II-4-2

PyBOP (459.23 mg, 882.48 μmol) was added to a mixture of II-4-1 (169.41 mg, 882.48 μmol), 6-methoxy-2H-indazol-5-amine (0.12 g, 735.40 μmol), anhydrous DMF (7 mL), and DIPEA (190.09 mg, 1.47 mmol, 256.18 μL), and the reaction mixture was stirred for 4 hours at 25° C. The reaction mixture was diluted with water (50 mL) and extracted with EA (20 mL×3). The combined organic phases were washed with brine (20 mL), dried over anhydrous Na$_2$SO$_4$, filtered, and concentrated under reduced pressure to obtain the crude product. The crude product was purified by silica gel chromatography and eluted with PE: EA=3:2 to obtain the yellow solid product II-4-2 (0.15 g, yield of 55.98%), MS (ESI) m/z: 338.1 [M+H]+.

Step 3: Synthesis of II-4

DIPEA (57.50 mg, 444.93 μmol, 77.50 μL) and II-1-1 (252.14 mg, 889.87 μmol) were added to a mixture of II-4-2 (0.03 g, 88.99 μmol) and anhydrous 1,4-dioxane (3 mL), and the reaction mixture was stirred for 36 hours at 100° C. The reaction mixture was diluted with water (50 mL), extracted with EA (20 mL×3), and the combined organic phases were washed with brine (20 mL), dried over anhydrous Na$_2$SO$_4$, filtered, and concentrated to obtain the crude product, and the crude product was purified by silica gel chromatography to obtain the off-white solid product II-4 (0.005 g, yield of 12.29%), MS (ESI) m/z: 449.2 [M+H]+, $^1$H NMR (500 MHz, DMSO-d$_6$) δ: 9.30 (s, 1H), 8.97 (s, 1H), 8.49 (s, 1H), 8.31 (d, J=0.9 Hz, 1H), 7.61 (s, 1H), 7.13 (s, 1H), 5.34-5.31 (m, 1H), 4.48-4.43 (m, 2H), 3.96 (s, 3H), 3.15-3.10 (m, 2H), 2.38-2.34 (m, 1H), 2.03-1.99 (m, 1H), 1.99-1.97 (m, 1H), 1.62-1.58 (m, 1H).

Example II-3F: Synthesis of II-3F

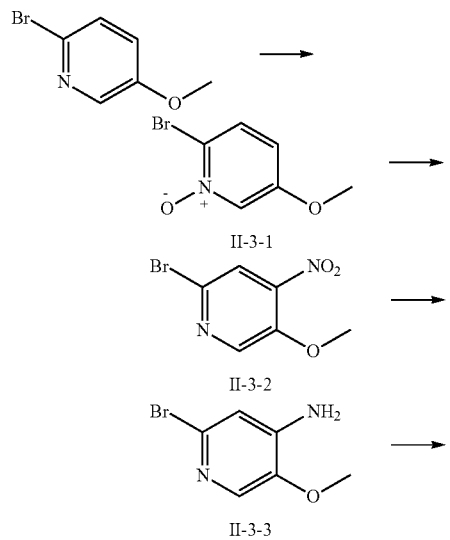

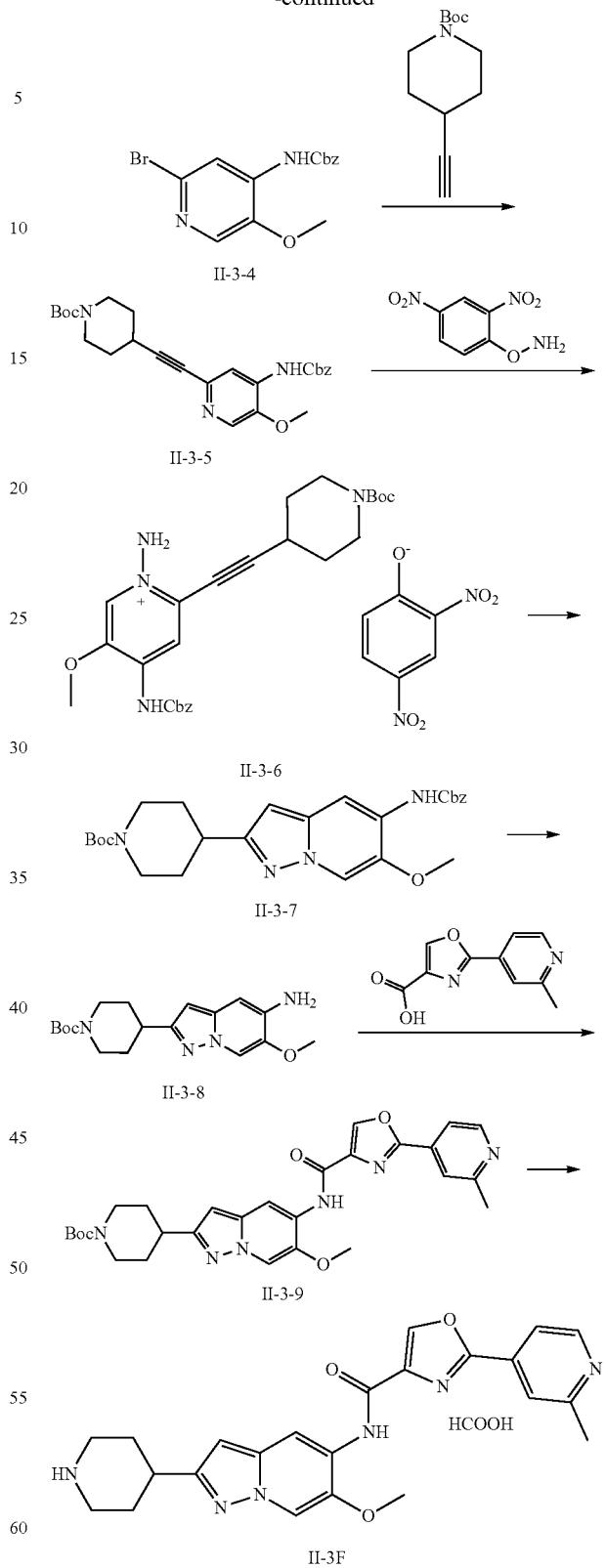

Step 1: Synthesis of II-3-1

2-Bromo-5-methoxypyridine (9.5 g, 50.53 mmol), m-CPBA (3-chloroperoxybenzoic acid) (13.0 g, 75.8 mmol), and 1,2-dichloroethane (95.0 mL) were added to a reaction flask, and then the resulting mixture was stirred for 2 hours at 60° C. The reaction mixture was cooled, the reaction was quenched by the addition of diethylamine (10.0 mL), and the reaction mixture was concentrated in vacuum. The residue was purified by silica gel column chromatography (eluent: EA/PE=1:1 to 1:0) to obtain the product II-3-1 (8.1 g, yield of 78.6%), MS (ESI) m/z: 204.0 [M+H]$^+$.

Step 2: Synthesis of II-3-2

Concentrated nitric acid (6.0 mL) was added dropwise to a stirred mixture of II-3-1 (6.0 g, 29.4 mmol) in concentrated sulfuric acid (18.0 mL) at 0° C., and the mixture was heated, stirred at 25° C., then heated to 90° C., and reacted for 2 hours. The mixture was cooled to 20° C., poured into ice, and added carefully with NaOH (40 wt. %) to adjust the pH to 14. The mixture was extracted with DCM (100.0 mL×3), then the combined organic phases were washed with saturated NaCl solution (30.0 mL), dried over anhydrous $Na_2SO_4$, filtered, and concentrated to obtain the yellow solid product II-3-2 (4.0 g, yield of 59%), MS (ESI) m/z: 233.0 [M+H]$^+$.

Step 3: Synthesis of II-3-3

Iron powder (3.4 g, 60.6 mmol) was added to a mixed suspension of II-3-2 (4.0 g, 17.3 mmol) and $NH_4Cl$ (3.27 g, 60.6 mmol) in ethanol (200.0 mL) and water (70.0 mL) at room temperature. The mixture was heated to 60° C., stirred for 2 hours, cooled to room temperature, and filtered through a diatomite pad, and the filtrate was concentrated to a volume of about 50.0 mL to form a suspension. The suspension was filtered, and the filter cake was washed with water (100 mL×2), and dried under reduced pressure over a funnel for 1 hour. The diatomite pad was washed with DCM (80.0 m×3), and the washing liquid was concentrated to dryness. The resulting crude extract was purified by column chromatography and eluted with a gradient of 0-5% MeOH/DCM to obtain the product II-3-3 (2.6 g, yield of 74%), MS (ESI) m/z: 203.0 [M+H]$^+$.

Step 4: Synthesis of II-3-4

CbzCl (benzyl chloroformate) (7.5 g, 43.9 mmol) was added to a mixture of II-3-3 (3.0 g, 14.8 mmol) and DIPEA (11.4 g, 88.7 mmol) in THF (150.0 mL). The reaction was stirred for 16 hours at 25° C. until the reaction was complete, and the reaction mixture was distilled under reduced pressure, added with EA (30.0 mL) and water (50.0 mL), and the organic phase was separated. The aqueous phase was extracted with EA (50.0 mL×3), and the combined organic phases were dried over anhydrous $Na_2SO_4$, filtered, and distilled under reduced pressure to obtain the crude product. The crude product was purified by silica gel column chromatography (eluent: PE/EA=3/1) to obtain the product II-3-4 (1.6 g, yield of 32%), MS (ESI) m/z: 336.0 [M+H]$^+$.

Step 5: Synthesis of II-3-5

II-3-4 (1.0 g, 2.98 mmol), tert-butyl 4-ethynylpiperidine-1-carboxylate (0.80 g, 3.57 mmol), TEA (4.2 g, 4.17 mmol), $Pd(PPh_3)_2Cl_2$ (bis(triphenylphosphine)palladium(II) dichloride, 0.22 g, 0.36 mmol), and CuI (0.12 g, 0.6 mmol) were added to DMF (20.0 mL), and the mixture was heated and reacted for 5 hours at 90° C. under nitrogen atmosphere. The reaction mixture was cooled to room temperature, added with saturated $NH_4C_1$ solution (50.0 mL), and the mixture was extracted with EA (50.0 mL×3). The combined organic phases were dried over anhydrous $Na_2SO_4$, filtered, and concentrated. The crude product was purified by silica gel column chromatography (DCM/MeOH=100:1 to 30:1) to obtain the product II-3-5 (1.0 g, yield of 72.5%), MS (ESI) m/z: 466.2 [M+H]$^+$.

Step 6: Synthesis of II-3-7

II-3-5 (1.0 g, 2.15 mmol) and O-(2,4-dinitrophenyl)hydroxylamine (0.86 g, 4.3 mmol) were added to MeCN (acetonitrile, 60.0 mL), and the reaction mixture was stirred for 20 hours at 50° C. until the reaction was complete. The mixture was distilled under reduced pressure to remove the solvent and obtain the crude product II-3-6.

DMF (50.0 mL) was added to the crude product II-3-6, and the mixture was stirred for 16 hours at 80° C. The reaction was quenched by the addition of a saturated $NaHCO_3$ solution, and the reaction mixture was extracted with EA. The combined organic phases were washed with saturated $NH_4C_1$ solution and brine, dried over anhydrous $Na_2SO_4$, and concentrated to obtain the crude product. The crude product was purified by silica gel column chromatography (EA/PE=100:0 to 80:20) to obtain the product II-3-7 (120 mg, yield of 11.7%), MS (ESI) m/z: 481.2 [M+H]$^+$.

Step 7: Synthesis of II-3-8

Pd/C (0.1 g) was added to a mixture of II-3-7 (120 mg, 0.25 mmol) in methanol (14.0 mL), and the reaction mixture was then stirred for 2 hours at room temperature under a normal pressure condition and $H_2$ atmosphere. The reaction mixture was filtered through diatomite and washed with 20 mL of MeOH/DCM (10:1). The filtrate was distilled under reduced pressure to obtain the product II-3-8 (70 mg, yield of 81%), MS (ESI) m/z: 347.2 [M+H]$^+$.

Step 8: Synthesis of II-3-9

DIPEA (40.0 mg, 0.31 mmol) and HATU (2-(7-azabenzotriazol-1-yl)-N,N,N',N'-tetramethyluronium hexafluorophosphate) (132.0 mg, 0.35 mmol) were added to a mixture of 2-(2-methylpyridin-4-yl)oxazole-4-carboxylic acid (53.0 mg, 0.26 mmol) in DMF (10.0 mL), and the mixture was stirred at 0° C. for 0.5 hours. Then II-3-8 (60.0 mg, 0.173 mmol) was added thereto, and the reaction mixture was stirred for 4 hours at room temperature. EtOAc (50.0 mL) and saturated $NaHCO_3$ (25.0 mL) solution were added to the reaction mixture, the mixture was extracted, and the phases were separated. The organic phase was washed with saturated $NaHCO_3$ (20.0 mL) and brine (20.0 mL), dried, filtered, and distilled under reduced pressure to obtain the crude product. The crude product was purified by silica gel column chromatography (DCM/MeOH=20:1) to obtain the product II-3-9 (60.0 mg, yield of 65%), MS (ESI) m/z: 533.2 [M+H]$^+$.

Step 9: Synthesis of II-3F

The mixture of II-3-9 (60.0 mg, 0.11 mmol) and hydrochloric acid/dioxane (4N, 2.0 mL) was stirred for 1 hour at room temperature until the reaction was complete. The mixture was concentrated under reduced pressure, and the crude product was purified by preparative HPLC (high performance liquid chromatography) to obtain the product II-3F (6.0 mg), MS (ESI) m/z: 433.2 [M+H]$^+$, $^1$H NMR (400

MHz, MeOD-d$_4$) δ: 8.74 (s, 1H), 8.63 (d, J=5.2 Hz, 1H), 8.54 (s, 2H), 8.22 (s, 1H), 7.97 (s, 1H), 7.89 (d, J=4.9 Hz, 1H), 6.38 (s, 1H), 4.08 (s, 3H), 3.52-3.41 (m, 2H), 3.10-3.24 (m, 3H), 2.65 (s, 3H), 2.34-2.20 (m, 2H), 2.05-1.86 (m, 2H).

Example II-5C: Synthesis of II-5C

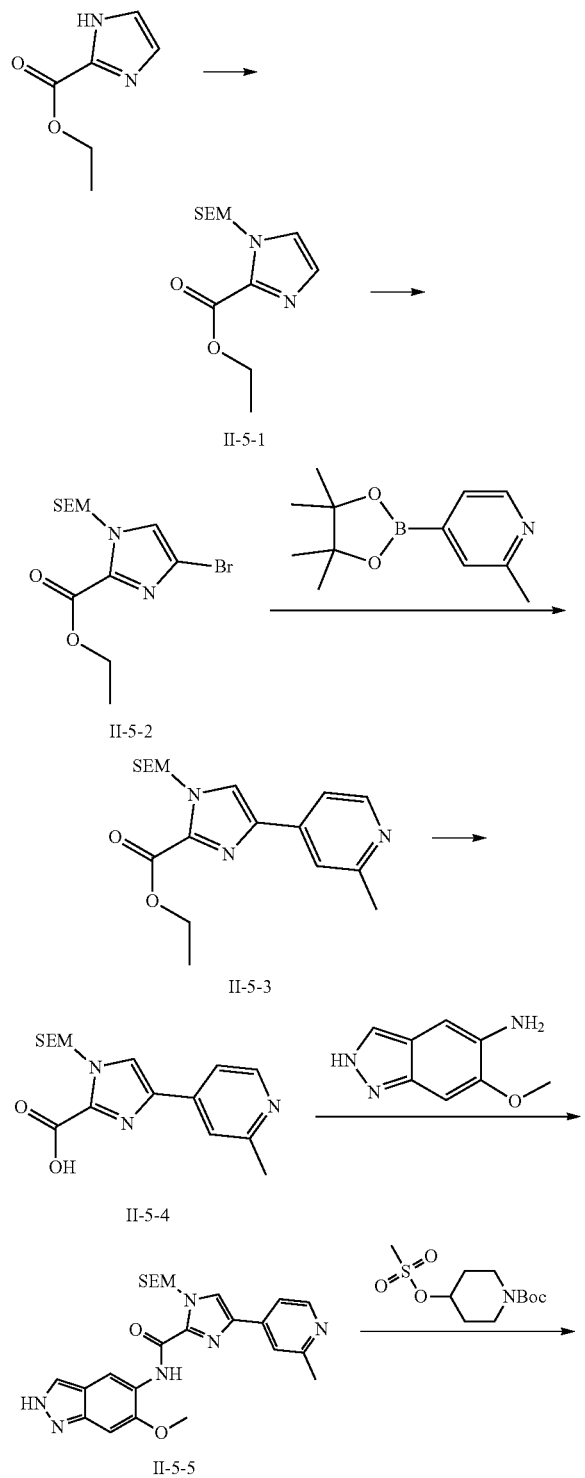

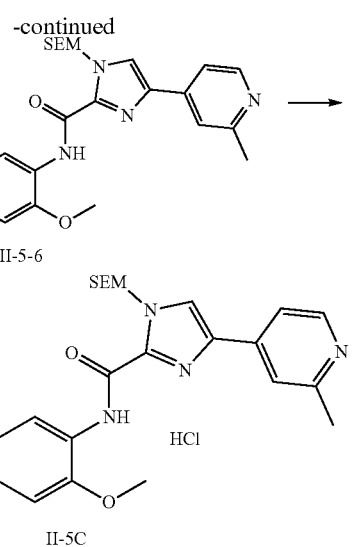

Step 1: Synthesis of II-5-1

SEMCl (trimethylsilyl)ethoxymethyl chloride, 14.96 g, 0.09 mol) and K$_2$CO$_3$ (19.7 g, 0.142 mol) were added to a mixture of ethyl 1H-imidazole-2-carboxylate (10 g, 0.071 mol) in DMF (60 mL), and the reaction mixture was stirred for 16 hours at room temperature until the reaction was complete. The reaction mixture was diluted with ethyl acetate (100 mL), the mixture was washed with water (100 mL), and the aqueous phase was extracted with ethyl acetate (100×3 mL). The combined organic phases were washed with brine (100×3 mL), dried over magnesium sulfate and filtered, and concentrated in vacuum to obtain the crude product. The crude product was purified by silica gel flash column chromatography to obtain the white solid product II-5-1 (10 g, yield of 52.6%), MS (ESI) m/z: 271.0 [M+H]$^+$.

Step 2: Synthesis of II-5-2

A DCM/DMF (50 mL, 1:1) solution containing NBS (N-bromosuccinimide, 10.68 g, 0.06 mol) was added dropwise to a mixture of II-5-1 (10 g, 0.04 mol) in DCM/DMF (50 mL, 1:1) at room temperature. After the dropwise addition was complete, the reaction mixture was stirred for 16 hours at room temperature until the reaction was complete. The reaction mixture was diluted with ethyl acetate (100 mL), the mixture was washed with water (100 mL), and the aqueous phase was extracted with ethyl acetate (100×3 mL). The combined organic phases were washed with brine (100×3 mL), dried over magnesium sulfate and filtered, and concentrated in vacuum to obtain the crude product. The crude product was purified by silica gel flash column chromatography to obtain the white solid product II-5-2 (2.17 g, yield of 14.29%), MS (ESI) m/z: 349.0 [M+H]$^+$.

Step 3: Synthesis of II-5-3

2-Methyl-4-(4,4,5,5-tetramethyl-1,3,2-dioxobenzofuran-2-yl)pyridine (1.32 g, 0.006 mol), Pd(dppf)Cl$_2$ (1,1'-bis(diphenylphosphino)ferrocene dichloropalladium(II), 0.49 g, 0.0006 mol), and K$_2$CO$_3$ (2.49 g, 0.018 mol) were added to a mixture of II-5-2 (2 g, 0.006 mol) in DMF (12 mL) under N$_2$ atmosphere. The reaction mixture was stirred for 16 hours at 85° C. until the reaction was complete. The reaction mixture was cooled to room temperature and diluted with ethyl acetate (100 mL). The mixture was washed with water (100 mL), and the aqueous phase was extracted with ethyl acetate (100×3 mL). The combined organic phases were washed with brine (100×3 mL), dried over magnesium sulfate and filtered, and concentrated under vacuum to obtain the crude product. The crude product was purified by silica gel flash column chromatography to obtain the yellow solid product II-5-3 (1.2 g, yield of 54.5%), MS (ESI) m/z: 362.0 [M+H]⁺.

Step 4: Synthesis of II-5-4

LiOH (431.1 mg, 18 mmol) and H₂O (3 mL) were added to a mixture of II-5-3 (1.3 g, 3.6 mol) in ethanol (3 mL) and THF (3 mL). The mixture was stirred for 16 hours at room temperature until the reaction was complete. The pH of the reaction mixture was adjusted with 3 M HCl to 2 to 3, and a large amount of white solid was precipitated. The mixture was filtered, and the filter cake was washed with water (60 mL), concentrated, and dried to obtain the white solid product II-5-4 (700 mg, yield of 58.3%), MS (ESI) m/z: 334.0 [M+H]+.

Step 5: Synthesis of II-5-5

A mixture of II-5-4 (600 mg, 1.8 mmol), 6-methoxy-2H-indazol-5-amine (195.6 mg, 1.2 mmol), HATU (1.1 g, 2.88 mmol), and DIPEA (620.35 mg, 4.8 mmol) in DMF (30 mL) was stirred for 16 hours at room temperature until the reaction was complete. Ethyl acetate (30 mL) and water (30 mL) were added to the reaction mixture, the mixture was extracted, the phases were separated, and then the aqueous phase was extracted with ethyl acetate (30×3 mL). The combined organic phases were washed with brine (30×3 mL), dried over magnesium sulfate, filtered, and concentrated in vacuum to obtain the crude product. The crude product was purified by pre-TLC (thin-layer chromatography) to obtain the yellow solid product II-5-5 (300 mg, yield of 34.8%), MS (ESI) m/z: 479.0 [M+H]⁺.

Step 6: Synthesis of II-5-6 tert-Butyl 4-((methylsulfonyl)oxy)piperidine-1-carboxylate (329.35 mg, 1.18 mmol) and Cs₂CO₃ (384.68 mg, 1.18 mmol) were added to a mixture of II-5-5 (280 mg, 0.59 mmol) in DMF (10 mL). The reaction mixture was stirred for 4 hours at 70° C. until the reaction was complete. The reaction mixture was cooled to room temperature, added with ethyl acetate (30 mL) and water (30 mL), and extracted. The phases were separated, and the aqueous phase was extracted with ethyl acetate (30×3 mL). The combined organic phases were washed with brine (30×3 mL), dried over magnesium sulfate, filtered, and concentrated in vacuum to obtain the crude product. The crude product was purified by preparative HPLC to obtain the white solid product II-5-6 (44 mg, yield of 11.3%), MS (ESI) m/z: 662.0 [M+H]⁺.

Step 7: Synthesis of II-5C

II-5-6 (44 mg, 0.066 mmol) was added to 4 M HCl dioxane (3 mL) in portions at 0° C. After the addition was complete, the reaction mixture was stirred for 16 hours at room temperature until the reaction was complete. The reaction mixture was filtered, and the filter cake was washed thoroughly with ethyl ether. The filter cake was then dissolved with deionized water, and the mixture was lyophilized to obtain the white solid product II-5C (24 mg, yield of 80.0%), MS (ESI) m/z: 432.0 [M+H]⁺. ¹H NMR (400 MHz, DMSO-d₆) δ: 9.79 (s, 1H), 9.54-9.30 (m, 2H), 8.78 (d, J=6.4 Hz, 1H), 8.66 (s, 1H), 8.60 (s, 1H), 8.38 (s, 1H), 8.32 (d, J=6.4 Hz, 1H), 8.10 (s, 1H), 7.58 (s, 1H), 5.08-5.28 (m, 1H), 4.16 (s, 3H), 3.54-3.37 (m, 2H), 3.24-3.15 (m, 2H), 2.84 (s, 3H), 2.52-2.37 (m, 2H), 2.25-2.09 (m, 2H).

Example II-6: Synthesis of II-6

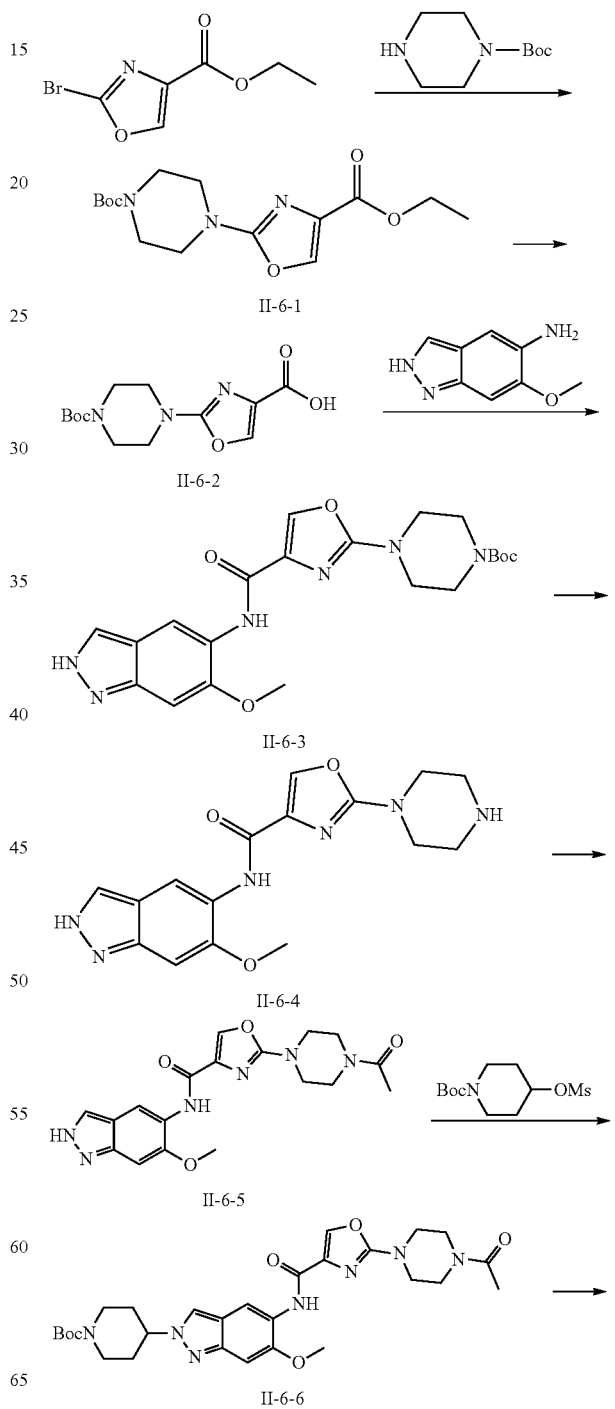

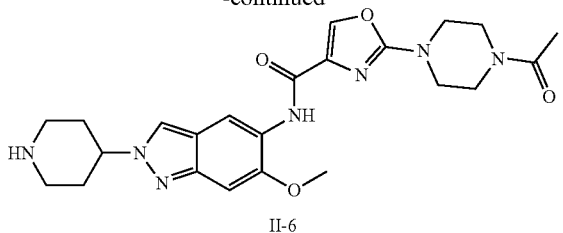

II-6

Step 1: Synthesis of II-6-1 tert-Butyl piperazine-1-carboxylate (4.65 g, 25 mmol) and TEA (6.9 g, 68.2 mmol) were added to a mixture of ethyl 2-bromooxazole-4-carboxylate (5 g, 22.7 mmol) and dioxane (54 mL). The resulting mixture was stirred for 1 hour at 120° C. until the reaction was complete. The reaction mixture was diluted with water, extracted with EtOAc (100 mL×2), and the combined organic phases were washed with brine, dried over sodium sulfate, filtered, and concentrated in vacuum to obtain the crude product. The crude product was purified by flash chromatography (PE/EtOAc=2/1) to obtain the yellow solid product II-6-1 (6.5 g, yield of 88.0%), MS (ESI) m/z: 326.1 $[M+H]^+$.

Step 2: Synthesis of II-6-2

LiOH (0.9 g, 36.6 mmol) and $H_2O$ (20 mL) were added to a mixture of II-6-1 (4 g, 12.2 mmol) in methanol (20 mL) and tetrahydrofuran (20 mL). The mixture was stirred for 16 hours at room temperature until the reaction was complete. The reaction mixture was concentrated in vacuum to obtain the white solid product II-6-2 (3.6 g, yield of 99.0%), MS (ESI) m/z: 298.2 $[M+H]^+$.

Step 3: Synthesis of II-6-3

A mixture of II-6-2 (3.6 g, 12 mmol), HATU (10.9 g, 28.8 mmol), DIPEA (6.2 g, 48 mmol), and DMF (70 mL) was stirred at room temperature for 10 minutes, then 6-methoxy-2H-indazol-5-amine (1.6 g, 9.6 mmol) was added thereto, and the mixture was stirred for another 16 hours at room temperature until the reaction was complete. The reaction mixture was diluted with water, extracted with EA (50 mL×3), and the combined organic phases were washed with brine, dried over sodium sulfate, filtered, and concentrated in vacuum to obtain the crude product. The crude product was purified by C18 chromatography column to obtain the yellow solid product II-6-3 (2.0 g, yield of 37.7%), MS (ESI) m/z: 443.1 $[M+H]^+$.

Step 4: Synthesis of II-6-4

TFA (trifluoroacetic acid, 12 mL) was added dropwise to a mixture of II-6-3 (2.0 g, 4.5 mmol) and DCM (80 mL) at 0° C., and the mixture was stirred for 0.5 hours at 0° C. until the reaction was complete. The mixture was concentrated to obtain the yellow solid product II-6-4 (1.4 g, yield of 93%), MS (ESI) m/z: 343.1 $[M+H]^+$.

Step 5: Synthesis of II-6-5

A mixture of II-6-4 (1.4 g, 4.0 mmol), $CH_3COOH$ (0.5 g, 8.0 mmol), EDCl (N-(3-dimethylaminopropyl)-N'-ethylcarbodiimide hydrochloride, 2.3 g, 12.0 mmol), HOBT (1-hydroxybenzotriazole, 1.6 g, 12.0 mmol), DIPEA (4.2 g, 32.0 mmol), and DMF (35 mL) was stirred for 16 hours at room temperature until the reaction was complete. MTBE (tert-butyl methyl ether) and DCM (MTBE: DCM=3:1) were added to the reaction mixture, and the reaction mixture was stirred vigorously for 1 hour and filtrated. The filter cake was washed and dried in vacuum to obtain the white solid product II-6-5 (0.33 g, yield of 21.4%), MS (ESI) m/z: 385.2 $[M+H]^+$.

Step 6: Synthesis of II-6-6

A mixture of II-6-5 (330 mg, 0.86 mmol), tert-butyl 4-((methylsulfonyl)oxy)piperidine-1-carboxylate (481 mg, 1.72 mmol), $Cs_2CO_3$ (841 mg, 2.58 mmol), and DMF (30 mL) was stirred for 4 hours at 70° C. until the reaction was complete. The reaction mixture was diluted with water, extracted with EtOAc (30 mL×2), and the combined organic phases were washed with brine, dried over sodium sulfate, filtered, and concentrated in vacuum to obtain the crude product. The crude product was purified by preparative HPLC to obtain the white solid product II-6-6 (100 mg, yield of 20.5%), MS (ESI) m/z: 568.2 $[M+H]_+$.

Step 7: Synthesis of II-6

HCl-dioxane (2 M, 7 mL) was added dropwise to a mixture of II-6-6 (150 mg, 0.26 mmol) in dioxane (7 mL) at 0° C., and after the dropwise addition was complete, the mixture was stirred for 1 hour at 0° C. until the reaction was complete. The reaction mixture was concentrated, and the crude product was purified by preparative HPLC to obtain the white solid product II-6 (16.69 mg, yield of 13.0%), MS (ESI) m/z: 468.2 $[M+H]^+$. $^1H$ NMR (400 MHz, DMSO-$d_6$) δ: 9.36 (s, 1H), 8.56 (s, 1H), 8.30 (s, 1H), 8.28 (s, 1H), 7.12 (s, 1H), 4.50-4.39 (m, 1H), 3.96 (s, 3H), 3.62-3.50 (m, 6H), 3.48-3.44 (m, 2H), 3.18-3.08 (m, 2H), 2.76-2.60 (m, 2H), 2.10-1.88 (m, 7H).

Example II-7C: Synthesis of II-7C

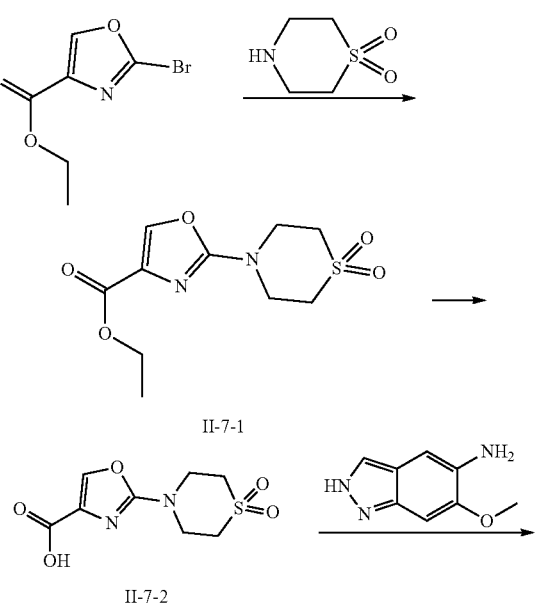

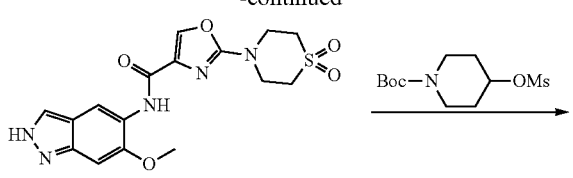

II-7-3

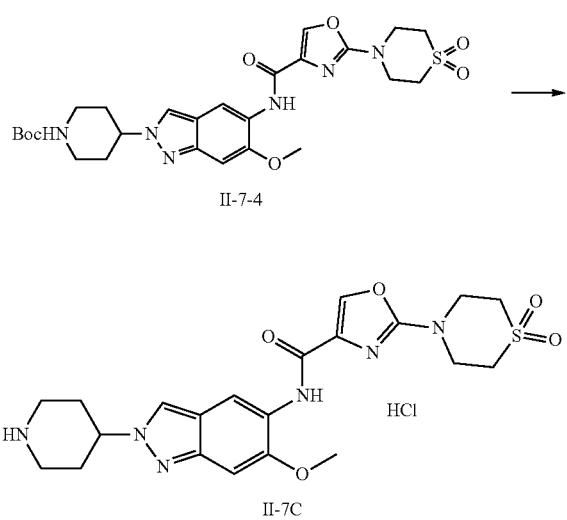

II-7-4

II-7C

Step 1: Synthesis of II-7-1

A mixture of ethyl 2-bromooxazole-4-carboxylate (5.0 g, 22.7 mmol), thiomorpholine 1,1-dioxide (5.2 g, 38.6 mmol), triethylamine (9.2 g, 90.8 mmol), and 1,4-dioxane (102 mL) was placed in a microwave reactor and reacted for 1 hour at 120° C. until the reaction was complete. The reaction mixture was added with water (100 mL) and extracted with ethyl acetate (3×200 mL). The combined organic phases were washed with sodium bicarbonate, dried over sodium sulfate, filtered and concentrated to obtain the yellow solid product II-7-1 (1.8 g, yield of 29%), MS (ESI) m/z: 275.0 [M+H]$^+$.

Step 2: Synthesis of II-7-2

LiOH (0.3 g, 13.1 mmol) and H$_2$O (20 mL) were added to a mixture of II-7-1 (1.2 g, 4.4 mmol) in methanol (20 mL) and tetrahydrofuran (20 mL), and the resulting mixture was stirred for 16 hours at room temperature until the reaction was complete. The reaction mixture was concentrated in vacuum to obtain the white solid product II-7-2 (0.6 g, yield of 56%), MS (ESI) m/z: 247.0 [M+H]$^+$.

Step 3: Synthesis of II-7-3

A mixture of II-7-2 (2 g, 8.0 mmol), HATU (7.3 g, 19.2 mmol), DIPEA (4.1 g, 32.1 mmol), and DMF (60 mL) was stirred at room temperature for 10 minutes, then 6-methoxy-2H-indazol-5-amine (0.65 g, 4.0 mmol) was added thereto, and the mixture was stirred for another 16 hours at room temperature until the reaction was complete. The reaction mixture was diluted with water (50 mL) and ethyl acetoacetate (3×100 mL), and the combined organic phases were washed with brine, dried over sodium sulfate, filtered, and concentrated in vacuum to obtain the crude product. The crude product was purified by flash chromatography (DCM/EtOAc=5/1) to obtain the yellow solid product II-7-3 (0.8 g, yield of 25%), MS (ESI) m/z: 392.0 [M+H]$^+$.

Step 4: Synthesis of II-7-4

A mixture of II-7-3 (800 mg, 2.1 mmol), tert-butyl 4-((methylsulfonyl)oxy)piperidine-1-carboxylate (1.2 g, 4.2 mmol), Cs$_2$CO$_3$ (2.0 g, 6.3 mmol), and DMF (20 mL) was stirred for 4 hours at 70° C. until the reaction was complete. The reaction mixture was diluted with water (30 mL) and ethyl acetoacetate (3×80 mL), and the combined organic phases were washed with brine, dried over sodium sulfate, filtered, and concentrated in vacuum to obtain the crude product. The crude product was purified by preparative HPLC to obtain the yellow solid product II-7-4 (40 mg, yield of 4%), MS (ESI) m/z: 575.2 [M+H]$^+$.

Step 5: Synthesis of II-7C

HCl-dioxane (1 mL) was added dropwise to a mixture of II-7-4 (31 mg, 0.05 mmol) in dioxane (2 mL) at 0° C., and after the dropwise addition was complete, the mixture was stirred for 4 hours at 0° C. until the reaction was complete. The reaction mixture was added with ethyl ether, filtered and dried in vacuum to obtain the white solid product II-7C (25.28 mg, yield of 99%), MS (ESI) m/z: 475.1 [M+H]$^+$. $^1$H NMR (400 MHz, DMSO-d$_6$) δ: 9.32 (s, 1H), 9.25-9.18 (br, 1H), 9.09-8.96 (br, 1H), 8.54 (s, 1H), 8.32 (s, 1H), 8.31 (s, 1H), 7.13 (s, 1H), 4.82-4.68 (m, 1H), 4.15-3.87 (m, 7H), 3.46-3.38 (m, 2H), 3.35-3.26 (m, 4H), 3.16-3.08 (m, 2H), 2.42-2.29 (m, 4H).

Example II-9C: Synthesis of II-9C

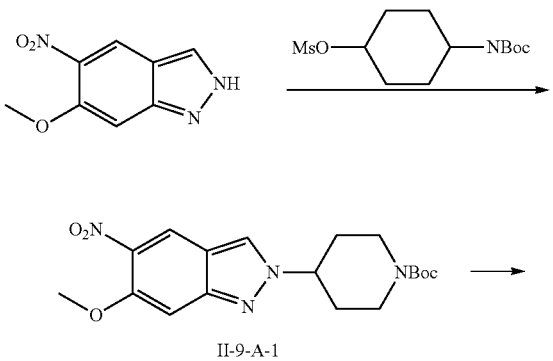

II-9-A-1

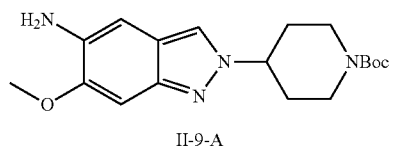

II-9-A

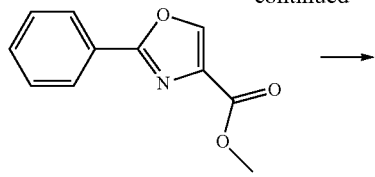

-continued

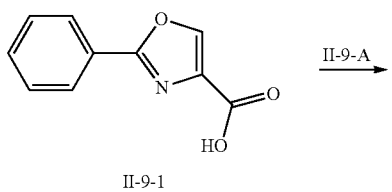

II-9-1

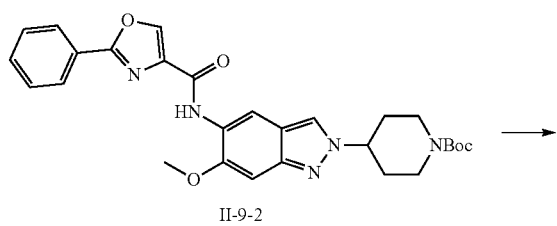

II-9-2

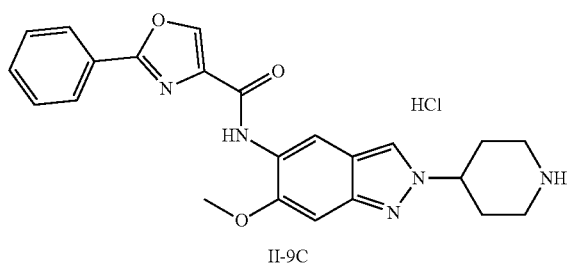

II-9C

Step 1: Synthesis of II-9-A-1

A mixture of 6-methoxy-5-nitro-2H-indazole (2.7 g, 13.98 mmol), tert-butyl 4-((methylsulfonyl)oxy)piperidine-1-carboxylate (5.47 g, 19.57 mmol), cesium carbonate (13.66 g, 41.93 mmol), and anhydrous N,N-dimethylformamide (12 mL) was heated to 110° C. and stirred for 0.5 hours under nitrogen atmosphere until the reaction was complete. Water (50 mL) was added to the reaction mixture, and the resulting mixture was extracted with ethyl acetate (30 mL×3) and washed with saturated brine (20 mL). The combined organic phases were then dried over anhydrous sodium sulfate and filtered, and the filtrate was concentrated in vacuum under reduced pressure to obtain the crude product. The crude product was purified by silica gel chromatography (mobile phase: 0 to 20% ethyl acetate/petroleum ether) to obtain the yellow solid product II-9-A-1 (1.5 g, yield of 28.51%). MS (ESI) m/z: 377.4 [M+H]$^+$.

Step 2: Synthesis of II-9-A

A mixture of II-9-A-1 (0.42 g, 1.12 mmol), ammonium chloride (596.85 mg, 11.16 mmol), iron powder (623.18 mg, 11.16 mmol), ethanol (3 mL) and water (1 mL) was heated to 70° C. and stirred for 4 hours under nitrogen atmosphere until the reaction was complete. The reaction mixture was filtered, the filter cake was washed with ethyl acetate (20 mL), and the filtrate was added with water (40 mL) and extracted with ethyl acetate (20 mL×3). The combined organic phases were washed with saturated brine (20 mL), dried over anhydrous sodium sulfate, filtered, and the filtrate was concentrated in vacuum under reduced pressure to obtain the crude product. The crude product was purified by silica gel chromatography (mobile phase: 100% ethyl acetate) to obtain the yellow solid product II-9-A (0.28 g, yield of 45.11%). MS (ESI) m/z: 347.4 [M+H]$^+$.

Step 3: Synthesis of II-9-1

Lithium hydroxide (49.50 mg, 2.07 mmol) was added to a mixture of methyl 2-phenyloxazole-4-carboxylate (210.00 mg, 1.03 mmol), H$_2$O (1 mL), and THF (3 mL), and the resulting mixture was stirred for 2 hours at 25° C. under nitrogen atmosphere until the reaction was complete. The reaction mixture was diluted with H$_2$O (10 mL), extracted with EA (10 mL×3) while stirring, and the combined organic phases were washed with brine (10 mL), dried over anhydrous Na$_2$SO$_4$, filtered, and concentrated in vacuum to obtain the white solid crude product II-9-1 (0.18 g), which was used directly in the next reaction step, MS (ESI) m/z: 190.0 [M+H]$^+$.

Step 4: Synthesis of II-9-2

A mixture of II-9-A (0.07 g, 202.07 μmol), II-9-1 (45.87 mg, 242.48 μmol), DIPEA (31.34 mg, 242.48 μmol, 42.23 μL), anhydrous DMF (5 mL), and PyBOP (210.31 mg, 404.13 μmol) was stirred for 4 hours at 25° C. under nitrogen atmosphere until the reaction was complete. The reaction mixture was diluted with H$_2$O (10 mL) and extracted with EA (10 mL×3) while stirring. The combined organic phases were washed with brine (10 mL), dried over anhydrous Na$_2$SO$_4$, filtered, and concentrated in vacuum to obtain the crude product. The crude product was purified by silica gel chromatography and eluted with PE/EA=1/1 to obtain the white solid product II-9-2 (0.07 g, yield of 64.87%), MS (ESI) m/z: 518.2 [M+H]$^+$.

Step 5: Synthesis of II-9C

HCl-dioxane (4 M, 676.23 μL) was added dropwise to a mixture of II-9-2 (0.07 g, 135.25 μmol) and DCM (2 mL), and the resulting mixture was stirred for 2 hours at 25° C. under nitrogen atmosphere after dropwise addition until the reaction was complete. The reaction mixture was concentrated in vacuum to obtain the white solid product II-9C (0.033 g, yield of 52.13%), MS (ESI) m/z: 418.1 [M+H]$^+$. $^1$H NMR (500 MHz, DMSO-d$_6$) δ: 9.57 (s, 1H), 9.39 (d, J=10.1 Hz, 1H), 9.27-9.15 (m, 1H), 8.94 (s, 1H), 8.60 (s, 1H), 8.37 (s, 1H), 8.13-8.04 (m, 2H), 7.66-7.59 (m, 3H), 7.20 (s, 1H), 4.80-4.74 (m, 1H), 4.03 (s, 3H), 3.48-3.38 (m, 2H), 3.16-3.06 (m, 2H), 2.39-2.25 (m, 4H).

Referring to Example II-8 and Example II-9C, the following products can finally be synthesized:

| Molecule ID | Structure | MS (ESI) m/z: [M + H]+ | 1H NMR |
|---|---|---|---|
| II-13C | 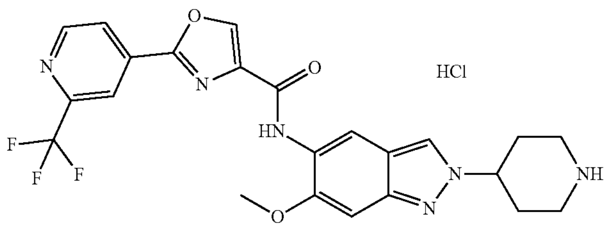 [SMILES: COc1cc2nn(C3CCNCC3)cc2cc1NC(=O)c1coc(-c2ccnc(C(F)(F)F)c2)n1 ; Cl] | 487.2 | (500 MHz, DMSO-d6) δ: 9.57 (s, 1H), 9.21 (d, J = 10.3 Hz, 1H), 9.15 (s, 1H), 9.06-8.98 (m, 2H), 8.53 (s, 1H), 8.36 (s, 1H), 8.35 (s, 1H), 8.33 (d, J = 5.0 Hz, 1H), 7.18 (s, 1H), 4.80-4.73 (m, 1H), 4.01 (s, 3H), 3.47-3.41 (m, 2H), 3.16-3.07 (m, 2H), 2.35-2.26 (m, 4H) |
| II-94C | 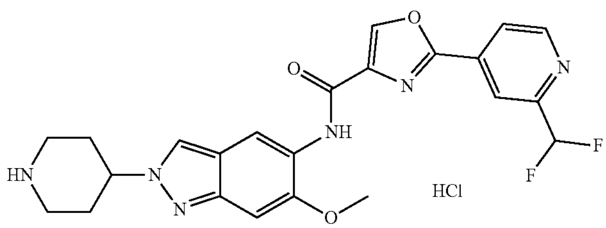 [SMILES: COc1cc2nn(C3CCNCC3)cc2cc1NC(=O)c1coc(-c2ccnc(C(F)F)c2)n1 ; Cl] | 469.2 | (400 MHz, DMSO-d6) δ 9.55 (s, 1H), 9.36 (d, J = 10.4 Hz, 1H), 9.18 (d, J = 10.4 Hz, 1H), 9.11 (s, 1H), 8.95 (d, J = 5.2 Hz, 1H), 8.54 (s, 1H), 8.35 (s, 1H), 8.22-8.15 (m, 2H), 7.20 (t, J = 27.6 Hz, 2H), 4.82-4.73 (m, 1H), 4.02 (s, 3H), 3.47-3.37 (m, 2H), 3.18-3.05 (m, 2H), 2.36-2.27 (m, 4H). |
| II-119C | 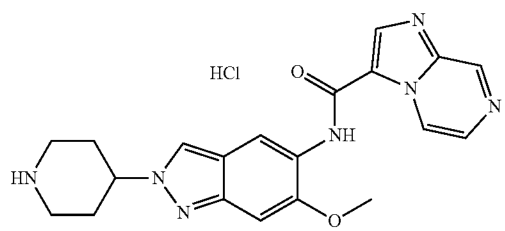 [SMILES: COc1cc2nn(C3CCNCC3)cc2cc1NC(=O)c1cnc2cnccn12 ; Cl] | 392.1 | (500 MHz, DMSO-d6) δ 9.89 (s, 1H), 9.36 (d, J = 4.5 Hz, 1H), 9.33 (s, 2H), 9.15 (d, J = 10 Hz, 1H), 8.82 (s, 1H), 8.35 (s, 1H), 8.18 (d, J = 4.5 Hz, 1H), 8.00 (s, 1H), 7.14 (s, 1H), 3.89 (s, 3H), 3.43 (d, J = 12.5 Hz, 2H), 3.12 (d, J = 11.0 Hz, 2H), 2.42-2.20 (m, 5H). |
| II-120C | 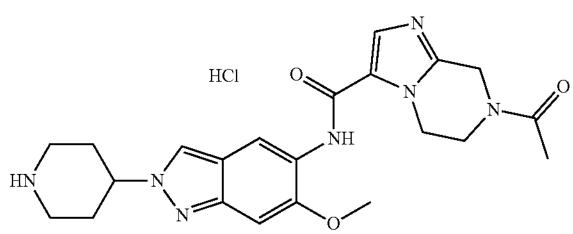 [SMILES: COc1cc2nn(C3CCNCC3)cc2cc1NC(=O)c1cnc2n1CCN(C(C)=O)C2 ; Cl] | 438.2 | (500 MHz, DMSO-d6) δ 9.93 (s, 1H), 9.40 (d, J = 9 Hz, 1H), 9.29 (m, 1H), 8.48 (s, 1H), 8.34 (s, 1H), 7.91 (d, J = 6 Hz, 1H), 7.13 (s, 1H), 5.04 (s, 1H), 4.95 (s, 1H), 4.82-4.75 (m, 1H), 4.52-4.48 (m, 1H), 4.00-3.95 (m, 1H), 3.86 (s, 3H), 3.42 (d, J = 12.5 Hz, 2H), 3.10 (q, J = 11 Hz, 2H), 2.40-2.23 (m, 4H), 2.16 (s, 3H), 1.39 (dd, J = 13, 6.5 Hz, 1H), 1.32-1.21 (m, 1H). |
Example II-10C: Synthesis of II-10C
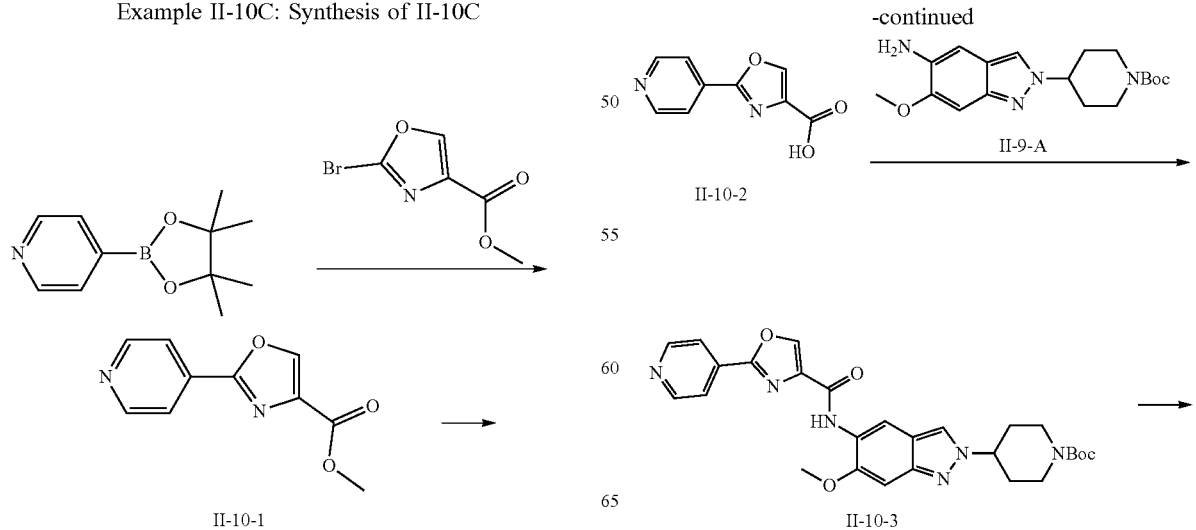

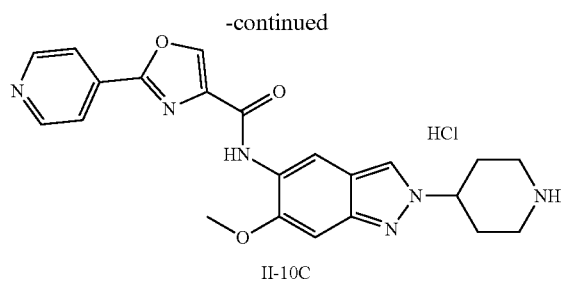

II-10C

Step 1: Synthesis of II-10-1

A mixture of 4-(4,4,5,5-tetramethyl-1,3,2-dioxobenzofuran-2-yl)pyridine (226.97 mg, 1.11 mmol), methyl 2-bromooxazole-5-carboxylate (0.19 g, 922.36 μmol), Pd(dppf)Cl$_2$ (33.74 mg, 46.12 μmol), cesium carbonate (601.04 mg, 1.84 mmol), and anhydrous dioxane (6 mL) was stirred for 4 hours at 80° C. under nitrogen atmosphere until the reaction was complete. The reaction mixture was diluted with H$_2$O (20 mL), and extracted with EA (15 mL×3) while stirring. The combined organic phases were washed with brine (20 mL), dried over anhydrous Na$_2$SO$_4$, filtered, and concentrated in vacuum to obtain the crude product. The crude product was purified by silica gel chromatography and eluted with DCM: MeOH=10/1 to obtain the brown solid product II-10-1 (0.22 g, yield of 62.15%), MS (ESI) m/z: 205.0 [M+H]$^+$.

Step 2: Synthesis of II-10-2

Lithium hydroxide (51.61 mg, 2.15 mmol) was added to a mixture of II-10-1 (220.00 mg, 1.08 mmol), H$_2$O (1 mL), and THF (3 mL), and the resulting mixture was stirred for 2 hours at 25° C. under nitrogen atmosphere until the reaction was complete. The reaction mixture was diluted with water (15 mL) and acidified while stirring until the pH of the mixture was adjusted to 3 to 4, and the mixture was extracted with EA (10 mL×3). The combined organic phases were washed with brine (20 mL), dried over anhydrous Na$_2$SO$_4$, filtered, and concentrated in vacuum to obtain the brown solid product II-10-2 (0.2 g, crude), which was used directly in the next step, MS (ESI) m/z: 191.0 [M+H]$^+$.

Step 3: Synthesis of II-10-3

A mixture of II-9-A (0.07 g, 202.07 μmol), II-10-2 (46.11 mg, 242.48 μmol), DIPEA (52.23 mg, 404.13 μmol, 70.39 μL), anhydrous DMF (5 mL), and PyBOP (126.18 mg, 242.48 μmol) was stirred for 4 hours at 25° C. under nitrogen atmosphere until the reaction was complete. The reaction mixture was diluted with H$_2$O (20 mL), and extracted with EA (20 mL×3) while stirring. The combined organic phases were washed with brine (20 mL), dried over anhydrous Na$_2$SO$_4$, filtered, and concentrated in vacuum to obtain the crude product. The crude product was purified by silica gel column chromatography to obtain the brown solid product II-10-3 (0.025 g, yield of 23.86%), MS (ESI) m/z: 519.2 [M+H]$^+$.

Step 4: Synthesis of II-10C

HCl-dioxane (4 M, 241.05 μL) was added dropwise to a mixture of II-10-3 (0.025 g, 48.21 μmol) in DCM (2 mL), and the reaction mixture was stirred for 2 hours at 25° C. under nitrogen atmosphere until the reaction was complete. The reaction mixture was concentrated in vacuum to obtain the crude product, and the crude product was purified by C18 chromatography column to obtain the white solid product II-10C (0.005 g, yield of 21.89%), MS (ESI) m/z: 419.1 [M+H]$^+$. $^1$H NMR (500 MHz, DMSO-d$_6$) δ: 9.72 (s, 1H), 9.57 (s, 1H), 9.06 (d, J=12.2 Hz, 1H), 8.89-8.81 (m, 2H), 8.58 (s, 1H), 8.36 (s, 1H), 8.04-7.95 (m, 2H), 7.18 (s, 1H), 5.38-5.26 (m, 1H), 4.02 (s, 3H), 3.64-3.52 (m, 2H), 3.41-3.37 (m, 2H), 2.15-1.77 (m, 5H).

Example II-11C: Synthesis of II-11C

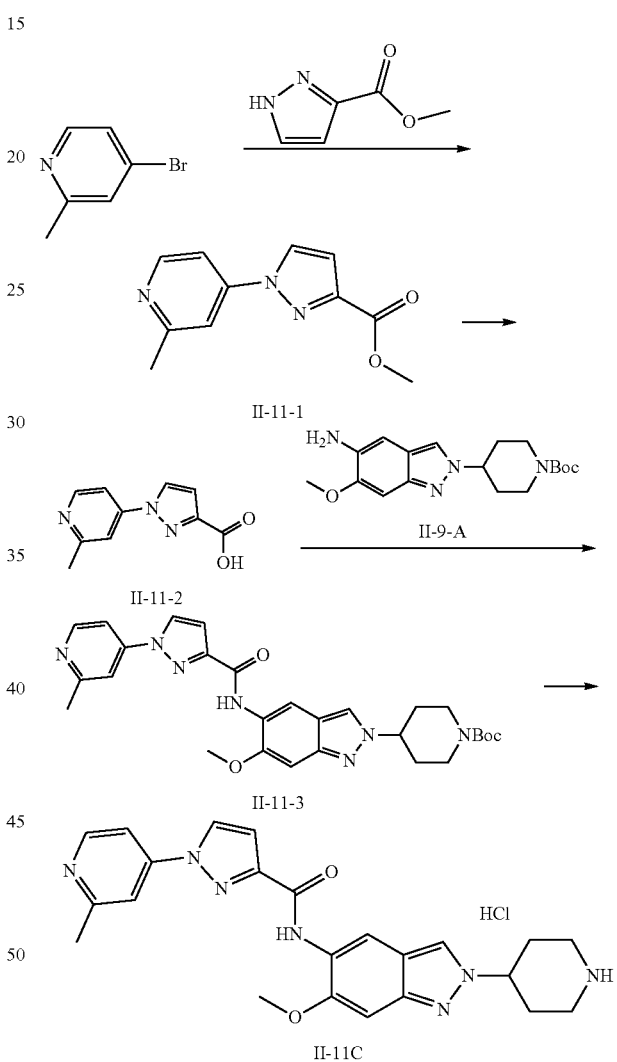

Step 1: Synthesis of II-11-1

A mixture of methyl 1H-pyrazole-3-carboxylate (275 mg, 2.18 mmol), 4-bromo-2-methylpyridine (375.11 mg, 2.18 mmol), potassium carbonate (602.74 mg, 4.36 mmol), copper iodide (41.53 mg, 218.06 μmol), (1 S,2S)-N1,N2-dimethylcyclohexane-1,2-diamine (124.07 mg, 872.23 μmol, 137.55 μL), and DMF (3 mL) was stirred for 3 hours at 110° C. under nitrogen atmosphere until the reaction was complete. The reaction mixture was cooled to 25° C. and concentrated in vacuum to obtain the crude product. The crude product was purified by silica gel column chromatography to obtain the white solid product II-II-1 (353 mg, yield of 74.52%), MS (ESI) m/z: 218.1 [M+H]⁺.

Step 2: Synthesis of II-II-2

LiOH (55.12 mg, 2.30 mmol) was added to a mixture of II-II-1 (100 mg, 460.36 μmol), methanol (4 mL), and H₂O (2 mL) at 0° C., and then after the addition, the resulting mixture was stirred for 3 hours at 25° C. under nitrogen atmosphere until the reaction was complete. The reaction mixture was concentrated in vacuum, diluted with water, and the mixture was acidified while stirring until the pH of the mixture was adjusted to 4, then concentrated in vacuum to obtain the white solid product II-II-2 (160 mg, crude), which was used directly in the next step, MS (ESI) m/z: 204.0 [M+H]⁺.

Step 3: Synthesis of II-II-3

DIPEA (235.04 mg, 1.82 mmol) was added dropwise to a mixture of II-9-A (210 mg, 606.20 μmol), II-II-2 (321.33 mg, 727.43 μmol), PyBOP (643.46 mg, 618.25 μmol), and THF (3.95 mL) at 0° C. under nitrogen atmosphere, and the resulting mixture was stirred for 1 hour at 25° C. after dropwise addition until the reaction was complete. The reaction mixture was concentrated in vacuum to obtain the crude product. The crude product was purified by silica gel column chromatography and eluted with DCM/CH₃OH=20/1 to obtain the white solid product II-II-3 (140 mg, yield of 39.10%), MS (ESI) m/z: 532.2 [M+H]⁺.

Step 4: Synthesis of II-11C

HCl-dioxane (4 M, 738.3 μL) was added dropwise to a mixture of II-II-3 (157 mg, 295.33 μmol) in DCM (5 mL) at 25° C., and the mixture was stirred for 1 hour at 25° C. after dropwise addition until the reaction was complete. The reaction mixture was filtered, and the filter cake was washed with DCM (20 mL) and dried in vacuum to obtain the white solid product II-11C (130 mg, yield of 89.36%), MS (ESI) m/z: 432.2 [M+H]⁺. ¹H NMR (500 MHz, DMSO-d₆) δ: 9.64 (s, 1H), 9.34-9.25 (m, 1H), 9.16-9.10 (m, 1H), 9.08 (d, J=2.6 Hz, 1H), 8.90 (d, J=6.5 Hz, 1H), 8.44 (s, 2H), 8.36 (s, 1H), 8.33 (d, J=6.2 Hz, 1H), 7.26 (d, J=2.6 Hz, 1H), 7.18 (s, 1H), 4.86-4.75 (m, 1H), 4.00 (s, 3H), 3.52-3.41 (m, 2H), 3.18-3.06 (m, 2H), 2.80 (s, 3H), 2.38-2.25 (m, 4H).

Example II-14C: Synthesis of II-14C

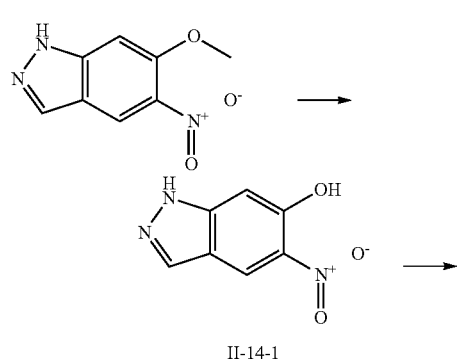

II-14-1

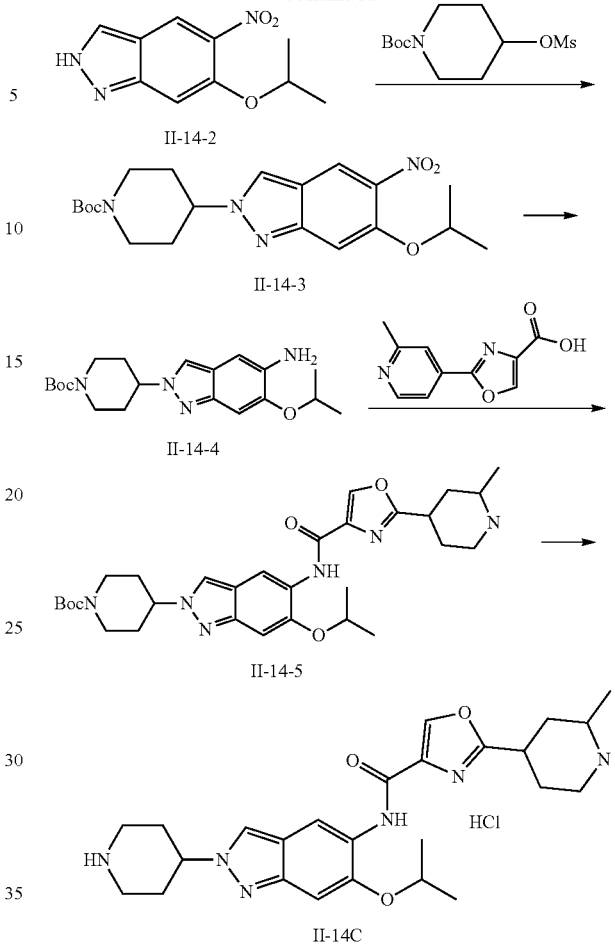

Step 1: Synthesis of II-14-1

AlCl₃ (10.3 g, 77.66 mmol) was added to a mixture of 6-methoxy-5-nitro-1H-indazole (5 g, 25.89 mmol) and DCM (150 mL) at 25° C., and the resulting mixture was stirred for 16 hours at 60° C. until the reaction was complete. The reaction mixture was diluted with H₂O (50 mL) and extracted with EA (80 mL×3). The combined organic phases were concentrated, and the crude product was purified by silica gel column to obtain the brown solid product II-14-1 (2.4 g, yield of 53%), MS (ESI) m/z: 180.1 [M+H]⁺.

Step 2: Synthesis of II-14-2

2-Iodopropane (3.41 g, 15.4 mmol) and K₂CO₃ (3.55 g, 25.6 mmol) were added to a mixture of II-14-1 (2.3 g, 12.8 mmol) in DMF (40 mL) at room temperature. The resulting mixture was stirred for 16 hours at room temperature until the reaction was complete. The reaction mixture was diluted with H₂O (50 mL) and extracted with EA (40 mL×3). The combined organic phases were concentrated, and the crude product was purified by silica gel column to obtain the brown solid product II-14-2 (2.2 g, yield of 72%), MS (ESI) m/z: 222.0 [M+H]⁺.

Step 3: Synthesis of II-14-3 tert-Butyl 4-((methylsulfonyl)oxy)piperidine-1-carboxylate (5.55 g, 19.91 mmol) was added to a mixture of II-14-2

(2.2 g, 9.95 mmol) and K$_2$CO$_3$ (9.74 g, 29.86 mmol) in DMF (120 mL) at 25° C. The resulting mixture was stirred for 4 hours at 70° C. until the reaction was complete. The reaction mixture was diluted with H$_2$O (50 mL) and extracted with EtOAc (40 mL×3). The combined organic phases were concentrated, and the crude product was purified by silica gel column to obtain the white solid product II-14-3 (0.9 g, yield of 43%), MS (ESI) m/z: 405.1 [M+H]$^+$.

Step 4: Synthesis of II-14-4

Pd/C (140 mg, purity: 10%) was added to a mixture of II-14-3 (700 mg, 1.732 mmol) in THF (10 mL) at room temperature. The resulting mixture was stirred for 16 hours at 25° C. under hydrogen atmosphere until the reaction was complete. The resulting mixture was filtered and concentrated to obtain the brown solid product II-14-4 (540 mg, yield of 76%), MS (ESI) m/z: 375.2 [M+H]$^+$.

Step 5: Synthesis of II-14-5

HATU (666.9 mg, 1.75 mmol), DIPEA (453.5 mg, 3.51 mmol), and 2-(2-methylpyridin-4-yl)oxazole-4-carboxylic acid (240.0 mg, 1.17 mmol) were added to a mixture of II-14-4 (440 mg, 1.17 mmol) in DMF (20 mL). The resulting mixture was stirred for 16 hours at 25° C. until the reaction was complete. The reaction mixture was diluted with H$_2$O (30 mL) and extracted with EA (30 mL×3). The combined organic phases were concentrated, and the crude product was purified by silica gel column to obtain the white solid product II-14-5 (450 mg, yield of 65%), MS (ESI) m/z: 561.1 [M+H]$^+$.

Step 6: Synthesis of II-14C

HCl-dioxane (2 M, 8 mL) was added to a mixture of II-14-5 (450 mg, 0.803 mmol) in EA (3 mL) at 0° C. The resulting mixture was stirred for 16 hours at 25° C. until the reaction was complete. The reaction mixture was added with ethyl ether (10 mL), filtered, and dried in vacuum to obtain the white solid product II-14C (394.51 mg, yield of 94%), MS (ESI) m/z: 460.2 [M+H]$^+$. $^1$H NMR (400 MHz, DMSO-d$_6$) δ: 9.77 (s, 1H), 9.14 (s, 1H), 9.08-8.99 (m, 1H), 8.97-8.85 (m, 1H), 8.82 (d, J=5.5 Hz, 1H), 8.62 (s, 1H), 8.35 (s, 1H), 8.05 (s, 1H), 7.95 (d, J=6.1 Hz, 1H), 7.22 (s, 1H), 4.90-4.81 (m, 1H), 4.80-4.71 (m, 1H), 3.49-3.38 (m, 2H), 3.19-3.04 (m, 2H), 2.70 (s, 3H), 2.35-2.24 (m, 4H), 1.48 (d, J=6.0 Hz, 6H).

Example II-15C: Synthesis of II-15C

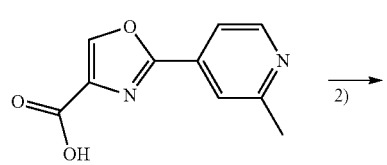

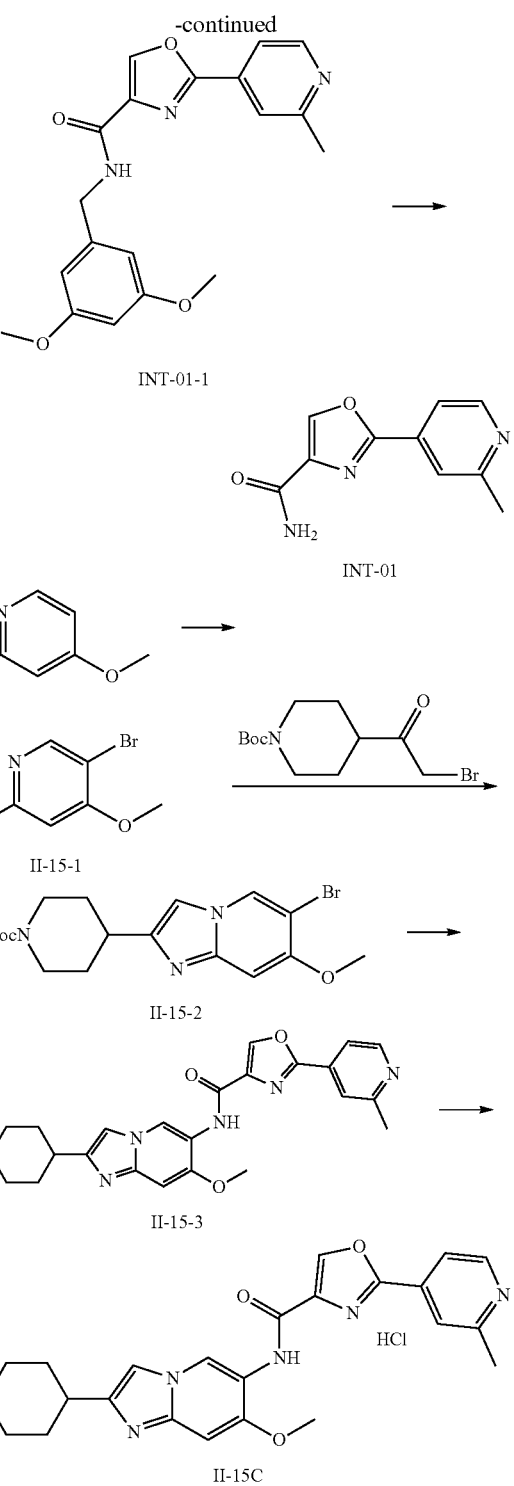

Step 1: Synthesis of INT-01-1

A mixture of 2-(2-methylpyridin-4-yl)oxazole-4-carboxylic acid (200.0 mg, 0.698 mmol) and SOCl$_2$ (5.0 mL) was stirred for 2 hours at 70° C. until the reaction was complete. The reaction mixture was concentrated under reduced pressure, the crude product was dissolved in DCM (5.0 mL), and the resulting mixture was added to a mixture of 3,5-dimethoxybenzylamine (245.0 mg 1.47 mmol) and Et$_3$N (297.0 mg, 2.94 mmol) in DCM (5.0 mL). The resulting mixture was refluxed and reacted for 1 hour until the reaction was complete. The reaction mixture was poured into water, and the mixture was extracted with EA. The combined organic phases were washed with brine, dried, and concentrated to obtain crude product. The crude product was purified by preparative TLC (eluent: EA/PE=1:1) to obtain INT-01-1 (132.0 mg, yield of 41%), MS (ESI) m/z: 354.1 [M+H]$^+$.

Step 2: Synthesis of INT-01

TFA (1.0 mL) was added to a mixture of INT-01-1 (132.0 mg, 0.40 mmol) and DCM (3.0 mL), and the resulting mixture was then stirred for 1 hour at room temperature. The reaction mixture was poured into a saturated NaHCO$_3$ solution and extracted with DCM. The combined organic phases were washed with brine, dried, and concentrated to obtain the crude product. The crude product was purified by preparative TLC (eluent: DCM/MeOH=20:1) to obtain the product INT-01 (65.0 mg, yield of 81%), MS (ESI) m/z: 204.0 [M+H]$^+$.

Step 3: Synthesis of II-15-1

NBS (17.8 g, 100.0 mmol) was added to a mixture of 4-methoxy-2-aminopyridine (9.5 g, 76.6 mmol) and MeCN (200.0 mL) in portions while stirring at 0° C. After the addition was completed, the resulting mixture was stirred for 1 hour at 10° C. to 15° C. until the reaction was complete. The reaction mixture was distilled under reduced pressure to remove solvent and added with DCM, washed with saturated Na$_2$CO$_3$ solution, dried, and concentrated to obtain the crude product. The crude product was purified by silica gel column chromatography (eluent: DCM/MeOH=300:1 to 50:1) to obtain the product II-15-1 (8.3 g, yield of 55%), MS (ESI) m/z: 203.0 [M+H]$^+$.

Step 4: Synthesis of II-15-2

A mixture of II-15-1 (1.3 g, 6.4 mol) and tert-butyl 4-(2-bromoacetyl)piperidine-1-carboxylate (2.0 g, 6.4 mol) in ethanol (40.0 mL) was refluxed and reacted for 16 hours until the reaction was complete. The resulting mixture was cooled to room temperature and concentrated under reduced pressure to obtain the crude product. The crude product was purified by silica gel column chromatography (eluent: DCM/MeOH=300:1 to 50:1) to obtain II-15-2 (1.4 g, yield of 54%), MS (ESI) m/z: 412.1 [M+H]$^+$.

Step 5: Synthesis of II-15-3

INT-01 (49.0 mg, 0.244 mmol), trans-dichlorobis(tri-o-tolylphosphine)palladium(II) (9.6 mg, 0.012 mmol), Xant-Phos (4,5-bis(diphenylphosphino)-9,9-dimethylxanthene, 7.09 mg, 0.012 mmol), and Cs$_2$CO$_3$ (119 mg, 0.366 mmol) were added to a mixture of II-15-2 (50.0 mg, 0.108 mmol) in dioxane (5.0 mL). The resulting mixture was heated and reacted at 120° C. for 4 hours under nitrogen atmosphere until the reaction was complete. The reaction mixture was filtered, the resulting filtrate was concentrated, and the crude product was purified by preparative TLC (eluent: DCM/MeOH=30:1) to obtain the product II-15-3 (35.0 mg, yield of 54.6%), MS (ESI) m/z: 533.2 [M+H]$^+$.

Step 6: Synthesis of II-15C

HCl/dioxane (4 M, 1.0 mL) was added to a mixture of II-15-3 (35.0 mg, 0.066 mmol) and DCM (3.0 mL), and then the resulting mixture was stirred for 1 hour at room temperature until the reaction was complete. The resulting mixture was concentrated and freeze-dried to obtain the white solid product II-15C (15.0 mg), MS (ESI) m/z: 433.1 [M+H]$^+$. $^1$H NMR (400 MHz, MeOD-d$_4$) δ: 9.70 (s, 1H), 9.00 (s, 1H), 8.89 (d, J=6.1 Hz, 1H), 8.57 (s, 1H), 8.48 (d, J=6.5 Hz, 1H), 7.99 (s, 1H), 7.41 (s, 1H), 4.28 (s, 3H), 3.70-3.63 (m, 1H), 3.59-3.53 (m, 2H), 3.28-3.17 (m, 2H), 2.91 (s, 3H), 2.45-2.32 (m, 2H), 2.10-1.99 (m, 2H).

Example II-28: Synthesis of II-28

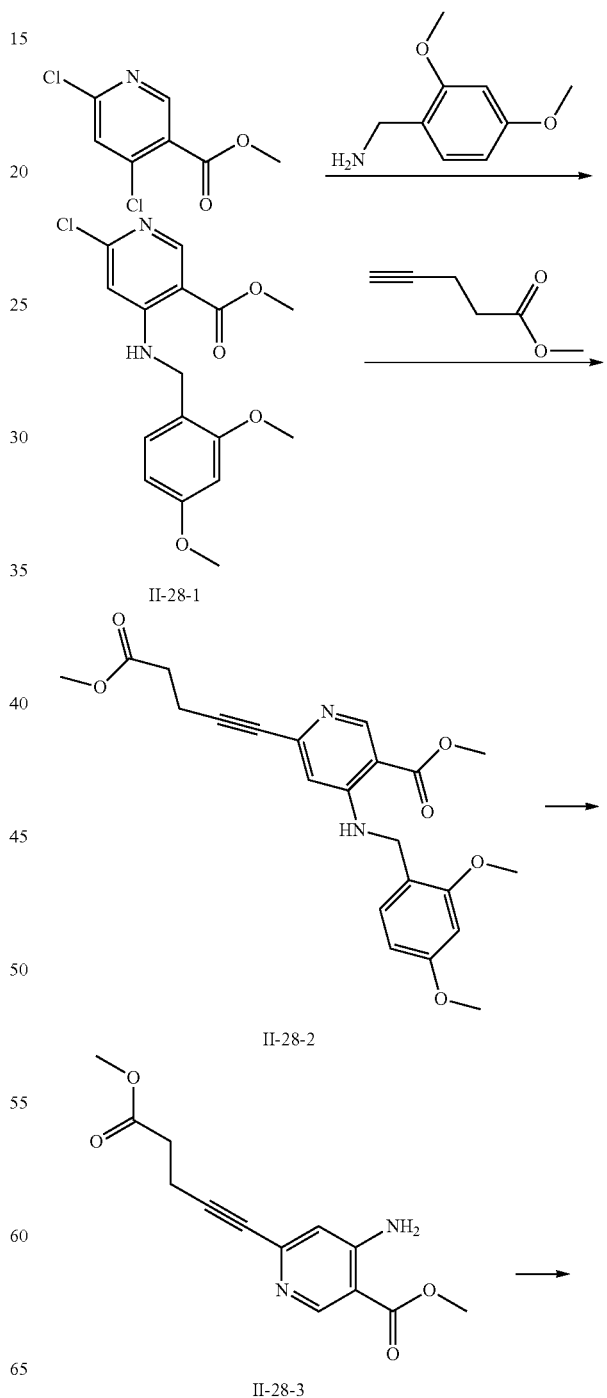

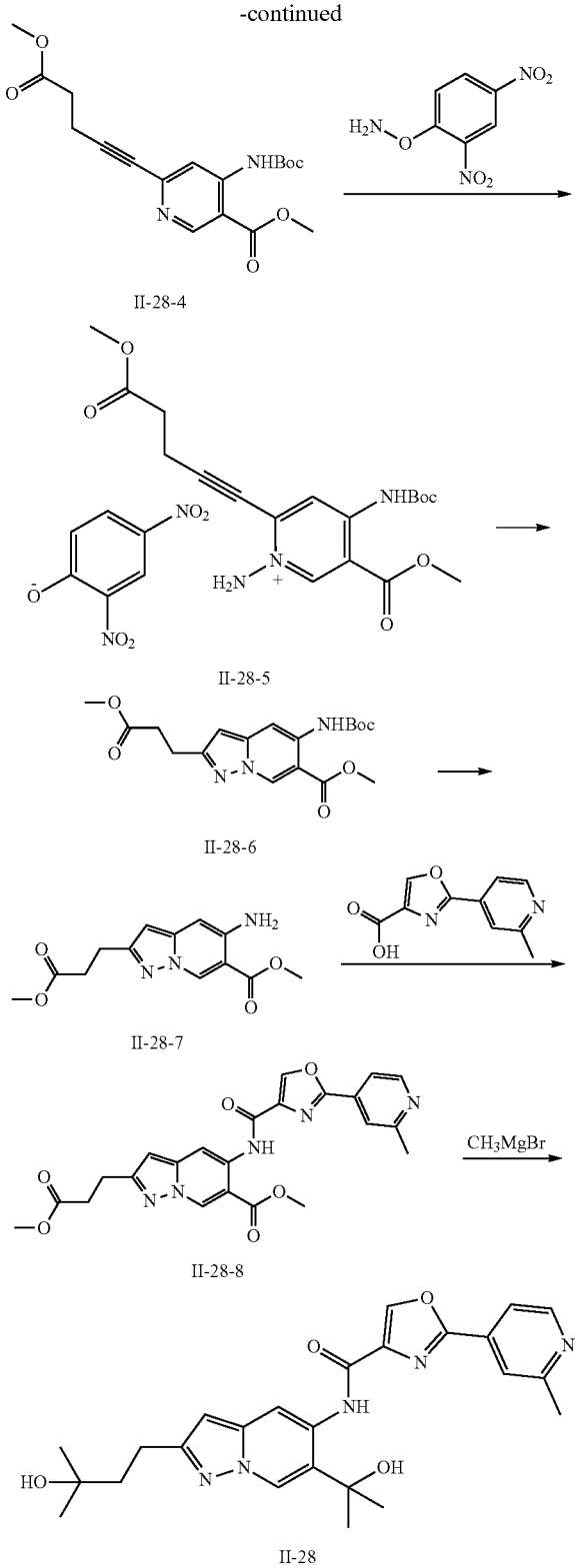

was stirred overnight at 25° C. The mixture was concentrated, and the residue was diluted with EA and saturated aqueous ammonium chloride solution while stirring, and extracted with EA (30 mL×3). The organic extracts were combined, dried over anhydrous sodium sulfate, filtered, and concentrated in vacuum. The crude residue was purified by silica gel chromatography (EA: heptane=3:1) to obtain the product II-28-1 (6.6 g, yield of 81%), which was used directly in the next step, MS (ESI) m/z: 337.8 $[M+H]^+$.

Step 2: Synthesis of II-28-2

II-28-1 (4.7 g, 140 mmol), methyl pent-4-ynoate (3.13 g, 280 mmol), TEA (19.8 g, 1.96 mol), $Pd(PPh_3)_2Cl_2$ (1.02 g, 14 mmol), and CuI (0.53 g, 28 mmol) were mixed in a solution of DMF (100.0 mL), and the mixture was stirred and reacted for 5 hours at 80° C. under nitrogen atmosphere. The reaction mixture was cooled to room temperature, added with saturated $NH_4C_1$ solution (50.0 mL), and extracted with EA (50.0 mL×3). The combined organic phases were dried over anhydrous $Na_2SO_4$, filtered, and concentrated in vacuum. The crude product was purified by silica gel column chromatography (PE/EA=10:1 to 1:1) to obtain the desired product II-28-2 (4 g, yield of 70%), MS (ESI) m/z: 413.2 $[M+H]^+$.

Step 3: Synthesis of II-28-3

TFA (10.0 mL) was slowly added dropwise to a stirred mixture of II-28-2 (3.0 g, 0.12 mmol) and DCM (3.0 mL) at 25° C., and the resulting mixture was stirred for another 1 hour after dropwise addition. The reaction mixture was concentrated to dryness in vacuum to obtain the desired product II-28-3 (1.9 g), MS (ESI) m/z: 263.1 $[M+H]^+$.

Step 4: Synthesis of II-28-4

DMAP (88.6 mg, 0.725 mol) and $Boc_2O$ (di-tert-butyl decarbonate, 10.0 g, 10.87 mol) were added to a mixture of II-28-3 (1.9 g, 7.25 mol), TEA (4.0 g, 21.7 mol), and THF (150.0 mL) at 25° C., and the resulting mixture was stirred for another 16 hours until the reaction was complete. The mixture was concentrated under reduced pressure, the residue was added with EA (30.0 mL) and water (50.0 mL), and the organic phase was separated. The aqueous phase was extracted with EA (100 mL×3), and the combined organic phases were dried over anhydrous $Na_2SO_4$, filtered, and concentrated under reduced pressure to obtain the residue. The residue was purified by silica gel column chromatography (PE: EA=30:1 to 5:1) to obtain II-28-4 (1.7 g, yield of 64.9%), MS (ESI) m/z: 363.1 $[M+H]^+$.

Steps 5 & 6: Synthesis of II-28-5 & II-28-6

II-28-4 (1.7 g, 4.7 mmol) was added to a mixture of O-(2,4-dinitrophenyl)hydroxylamine (3.7 g, 18.8 mmol) and ACN (60.0 mL), and the reaction mixture was stirred for 20 hours at 60° C. The mixture was evaporated to dryness to obtain the crude product II-28-5. Then DMF (50.0 mL) was added to the crude product, and the mixture was stirred for 16 hours at 80° C. until the reaction was complete. The reaction mixture was added with saturated $NaHCO_3$ solution and extracted with EA (100 mL×3). The combined organic phases were washed with saturated $NH_4C_1$ solution (200 mL), saturated brine (200 mL), dried over anhydrous $Na_2SO_4$, and concentrated. The residue was purified by silica gel column chromatography (DCM:MeOH=100:1 to Step 1: Synthesis of II-28-1

A mixture of (2,4-dimethoxyphenyl) formamide (3.8 mL, 29 mmol), methyl 4,6-dichloronicotinate (5.0 g, 24 mmol), triethylamine (4.1 mL, 30 mmol), and acetonitrile (50 mL)

50:1) to obtain the product II-28-6 (200 mg, yield of 11.3%). MS (ESI) m/z: 378.1 [M+H]⁺, ¹H NMR (400 MHz, CDCl₃) δ 10.01 (s, 1H), 9.11 (s, 1H), 8.32 (s, 1H), 6.17 (s, 1H), 3.94 (s, 3H), 3.71 (d, J=12.8 Hz, 3H), 3.13 (t, J=7.6 Hz, 2H), 2.79 (t, J=7.6 Hz, 2H), 1.54 (s, 9H).

Step 7: Synthesis of II-28-7

HCl-dioxane (4 M, 1.0 mL) was added to a mixture of II-28-6 (100.0 mg, 0.265 mmol) and DCM (3.0 mL) at 25° C., and then the resulting mixture was stirred for 1 hour. The reaction mixture was concentrated to dryness under reduced pressure, and the pH value of the residue was adjusted to 7 to 8 with a saturated NaHCO₃ solution. The mixture was then extracted with DCM (30 mL×3), and the combined organic phases were washed with saturated brine (50 mL), dried over anhydrous Na₂SO₄, and concentrated. The crude product was purified by preparative thin-layer chromatography (DCM:MeOH=50:1) to obtain II-28-7 (55.0 mg, yield of 69.4%), MS (ESI) m/z: 278.1 [M+H]⁺.

Step 8: Synthesis of II-28-8

A mixture of 2-(2-methylpyridin-4-yl)oxazole-4-carboxylic acid (122.0 mg, 0.54 mmol) and SOCl₂ (5.0 mL) was stirred for 2 hours at 70° C. The reaction mixture was concentrated under reduced pressure, the residue was added with DIPEA (92.8 mg, 0.72 mmol, dissolved in 5.0 mL of DCM), and the resulting mixture was added to a mixture of II-28-7 (50.0 mg, 0.18 mmol) and DCM (5.0 mL), and then the mixture was heated and refluxed for 1 hour. The reaction mixture was cooled to room temperature, poured into water (20.0 mL), and extracted with EA (20 mL×3). The combined organic phases were washed with saturated brine (50 mL), dried over anhydrous Na₂SO₄, filtered, and concentrated. The residue was purified by preparative thin-layer chromatography (DCM:MeOH=20:1) to obtain II-28-8 (50.0 mg, yield of 56%), MS (ESI) m/z: 464.1 [M+H]⁺.

Step 9: Synthesis of II-28

CH₃MgBr (1 M solution of THF, 1.3 mL, 1.29 mmol) was added to a mixture of II-28-8 (50.0 mg, 0.11 mmol) in THF (10.0 mL) at 0° C. The resulting mixture was stirred for 16 hours at 25° C. under nitrogen atmosphere. The reaction mixture was quenched with saturated NH₄Cl solution (10.0 mL) and extracted with DCM (15.0 mL×2). The combined organic phases were washed with saturated brine (20 mL), dried over anhydrous Na₂SO₄, filtered, and concentrated under reduced pressure. The residue was purified by preparative thin-layer chromatography (DCM/MeOH=20:1) to obtain the white solid product 11-28 (6.2 mg), MS (ESI) m/z: 464.2 [M+H]⁺, ¹H NMR (400 MHz, DMSO-d₆) δ 11.92 (s, 1H), 9.04 (s, 1H), 8.70 (d, J=5.1 Hz, 1H), 8.54 (s, 1H), 8.43 (s, 1H), 7.95-7.65 (m, 2H), 6.39 (s, 1H), 6.32 (s, 1H), 4.28 (s, 1H), 2.96-2.70 (m, 2H), 2.61 (s, 3H), 1.87-1.73 (m, 2H), 1.67 (s, 6H), 1.15 (s, 6H).

Referring to Example II-28, the following product can finally be synthesized:

| Molecule ID | Structure | MS (ESI) m/z: [M + H]⁺ | ¹H NMR |
|---|---|---|---|
| II-92 | 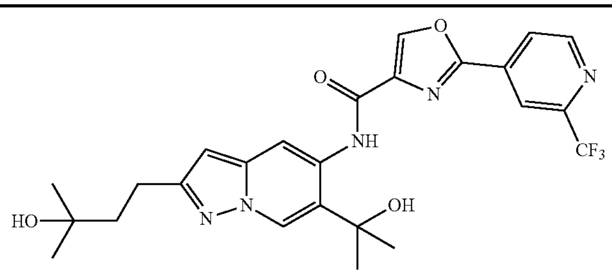 | 518.2 | (400 MHz, MeOD-d₄): δ 8.92 (d, J = 4.8 Hz, 1H), 8.75 (s, 1H), 8.60 (s, 1H), 8.43 (s, 1H), 8.36-8.33 (m, 2 H), 6.36 (s, 1H), 2.88-2.84 (m, 2 H), 1.96-1.86 (m, 2 H), 1.75 (s, 6H), 1.27 (s, 6H). |

Example II-49: Synthesis of II-49

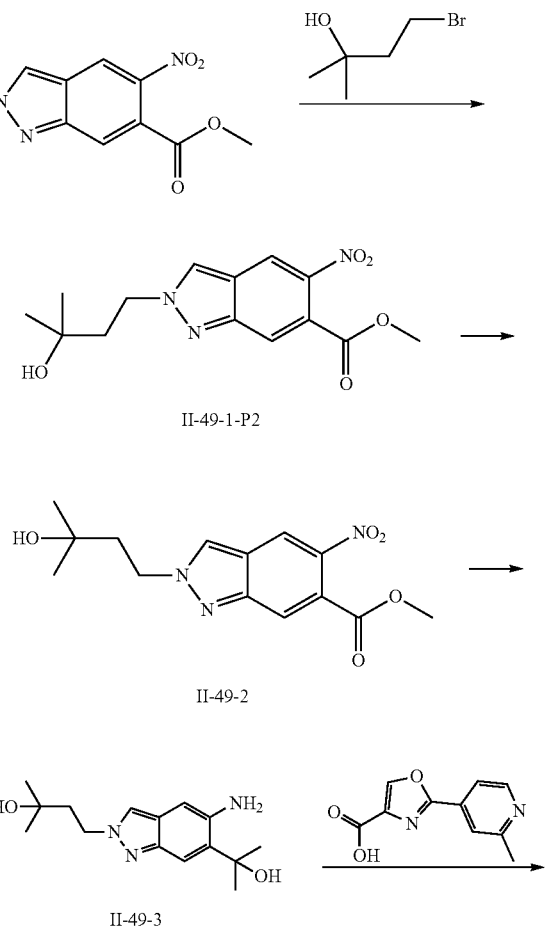

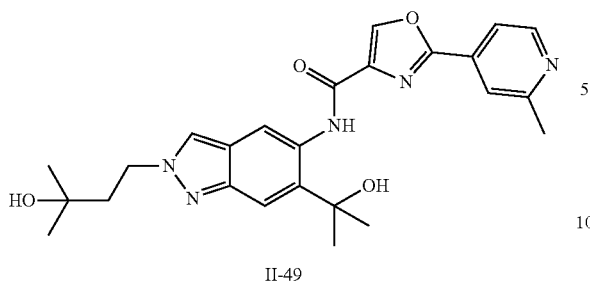

II-49

Step 1: Synthesis of II-49-1-P2

Cs$_2$CO$_3$ (2.62 g, 13.56 mmol) and 4-bromo-2-methyl-butan-2-ol (1.13 g, 6.78 mmol) were added to a mixture of methyl 5-nitro-2H-indazole-6-carboxylate (1 g, 4.52 mmol) and DMF (10 mL) at 25° C., and the resulting mixture was stirred for 16 hours at 100° C. The reaction mixture was cooled to room temperature, diluted with H$_2$O (30 mL), and extracted with EA (30 mL×3). The combined organic phases were washed with saturated brine (30 mL×3), dried over anhydrous Na$_2$SO$_4$, then filtered, and concentrated under reduced pressure to obtain the yellow solid crude product. The crude product was purified by silica gel column chromatography (PE: EtOAc=2:1) to obtain the light yellow solid product II-49-1-P2 (510.00 mg, 1.66 mmol, yield of 35.24%), MS (ESI) m/z: 308.1 [M+H]$^+$. II-49-1-P2: $^1$H NMR (400 MHz, CDCl$_3$) δ 8.40 (s, 1H), 8.23 (s, 1H), 8.01 (s, 1H), 4.68 (t, J=8.0 Hz, 2H), 3.92 (s, 3H), 2.22 (t, J=8.0 Hz, 2H), 1.30 (s, 6H).

Step 2: Synthesis of II-49-2

NH$_4$C$_1$ (43.00 mg, 811.32 μmol) and iron powder (908.72 mg, 16.27 mmol) were added to a mixture of II-49-1-P2 (0.5 g, 1.63 mmol), EtOH (6 mL), and H$_2$O (2.5 mL), and the resulting mixture was stirred for 16 hours at 80° C. The reaction mixture was cooled to room temperature, diluted with H$_2$O (20 mL), and extracted with EA (20 mL×3). The combined organic phases were washed with saturated brine (20 mL), dried over anhydrous Na$_2$SO$_4$, then filtered, and concentrated under reduced pressure. The yellow solid product II-49-2 (400.00 mg) was obtained, MS (ESI) m/z: 278.1 [M+H]$^+$.

Step 3: Synthesis of II-49-3

A mixture of methylmagnesium chloride in THF (1M, 7.21 mmol, 7.2 mL) was added to a stirred mixture of II-49-2 (400 mg, 1.44 mmol) and THF (10 mL) at 0° C., and the resulting mixture was stirred for another 16 hours. The reaction mixture was diluted with H$_2$O (20 mL), the pH of the mixture was adjusted to 7 to 8 with aqueous NH$_4$C$_1$ (1M), and then the mixture was extracted with EA (20 mL×3). The combined organic phases were washed with saturated brine (20 mL), dried over anhydrous Na$_2$SO$_4$, then filtered, and concentrated under reduced pressure. The crude product was subjected to reverse-phase preparative HPLC (Prep-C18, 5 μM XBridge column, 19×150 mm, where both solvents contained 0.1% ammonium bicarbonate) to obtain the yellow oily product II-49-3 (210.00 mg, 681.42 μmol, yield of 47.24%), MS (ESI) m/z: 278.2 [M+H]$^+$.

Step 4: Synthesis of II-49

II-49-3 (53.72 mg, 193.68 μmol), HATU (220.80 mg, 581.05 μmol), and DIPEA (25.18 mg, 1931.68 μmol) were added to a mixture of 2-(2-methylpyridin-4-yl)oxazole-4-carboxylic acid (50.00 mg, 193.68 μmol) and DCM (20 mL) at 25° C., and the resulting mixture was stirred for 1 hour. The reaction mixture was concentrated under reduced pressure, then diluted with H$_2$O (10 mL), and then extracted with DCM (10 mL×3). The combined organic phases were washed with saturated brine (10 mL), dried over anhydrous Na$_2$SO$_4$, then filtered, and concentrated under reduced pressure to obtain the crude product. The crude product was subjected to reverse-phase preparative HPLC (Prep-C18, 5 μM XBridge column, 19×150 mm, Waters; both solvents contained 0.1% ammonium bicarbonate) to obtain the yellow solid product II-49 (19.50 mg, 41.23 μmol, yield of 21.29%), MS (ESI) m/z: 464.2 [M+H]$^+$. $^1$H NMR (400 MHz, MeOD-d$_4$) δ 8.62 (s, 1H), 8.61 (s, 1H), 8.58 (d, J=6.0 Hz, 1H), 8.18 (s, 1H), 7.99 (s, 1H), 7.91 (s, 1H), 7.62 (s, 1H), 4.56-4.51 (m, 2H), 2.63 (s, 3H), 2.16-2.12 (m, 2H), 1.74 (s, 6H), 1.24 (s, 6H).

Referring to Examples II-1, 11-8, and Example II-49, the following products can finally be synthesized:

| Molecule ID | Structure | MS (ESI) m/z: [M + H]$^+$ | $^1$H NMR |
|---|---|---|---|
| II-93 | 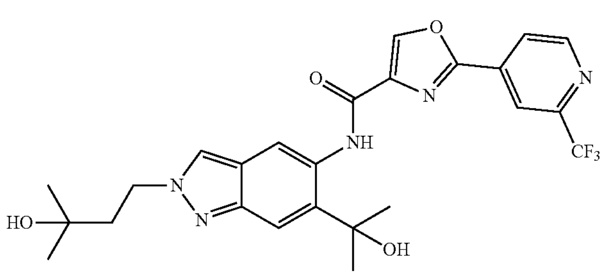 [SMILES: CC(C)(O)CCn1cc2cc(NC(=O)c3coc(-c4ccnc(C(F)(F)F)c4)n3)c(C(C)(C)O)cc2n1] | 518.2 | (400 MHz, CDCl$_3$) δ 11.38 (s, 1H), 8.91 (d, J = 4.0 Hz, 1H), 8.71 (s, 1H), 8.45 (s, 1H), 8.30 (s, 1H), 8.14 (dd, J = 4.0, 1.2 Hz, 1H), 7.90 (s, 1H), 7.68 (s, 1H), 4.57-4.51 (m, 2H), 2.68 (s, 1H), 2.37 (s, 1H), 2.18-2.12 (m, 2H), 1.79 (s, 6H), 1.31 (s, 6H). |

-continued

| Molecule ID | Structure | MS (ESI) m/z: [M + H]+ | 1H NMR |
|---|---|---|---|
| II-51 | 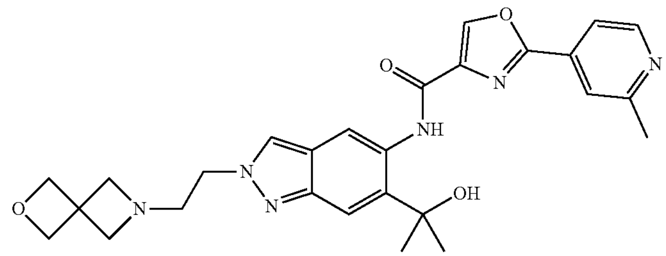 [SMILES: Cc1cc(-c2nc(C(=O)Nc3cc4cn(CCN5CC6(COC6)C5)nc4cc3C(C)(C)O)co2)ccn1] | 503.2 | (400 MHz, MeOD-d$_4$) δ 8.63 (s, 1H), 8.62 (s, 1H), 8.59 (d, J = 5.2 Hz, 1H), 8.18 (s, 1H), 8.02 (s, 1H), 7.92 (d, J = 5.2 Hz, 1H), 7.64 (s, 1H), 4.64 (s, 4H), 4.40 (t, J = 6.0 Hz, 2H), 3.30 (s, 4H), 3.00 (t, J = 6.0 Hz, 2H), 2.64 (s, 3H), 1.74 (s, 6H). |
| II-54 | 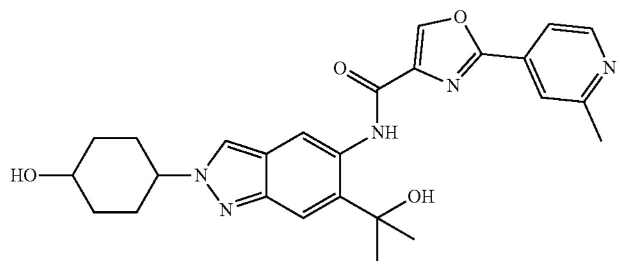 [SMILES: Cc1cc(-c2nc(C(=O)Nc3cc4cn(C5CCC(O)CC5)nc4cc3C(C)(C)O)co2)ccn1] | 476.2 | (400 MHz, MeOD-d$_4$) δ 8.63 (s, 1H), 8.62 (s, 1H), 8.59 (d, J = 8.0 Hz, 1H), 8.21 (s, 1H), 8.02 (s, 1H), 7.93 (d, J = 4 Hz, 1H), 7.63 (s, 1H), 4.49-4.42 (m, 1H), 3.73-3.67 (m, 1H), 2.64 (s, 3H), 2.24-2.19 (m, 2H), 2.14-2.01 (m, 4H), 1.74 (s, 6H), 1.58-1.52 (m, 2H). |
| II-56 | 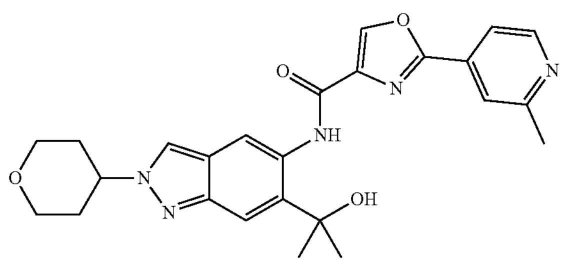 [SMILES: Cc1cc(-c2nc(C(=O)Nc3cc4cn(C5CCOCC5)nc4cc3C(C)(C)O)co2)ccn1] | 462.2 | (400 MHz, DMSO-d$_6$) δ 11.87 (s, 1H), 8.94 (s, 1H), 8.67 (d, J = 4 Hz, 1H), 8.60 (s, 1H), 8.38 (s, 1H), 7.80 (s, 1H), 7.79 (d, J = 4 Hz, 1H) 7.57 (s, 1H), 6.18 (s, 1H), 4.72-4.65 (m, 1H), 4.05-3.93 (m, 2H), 3.53-3.46 (m, 2H), 2.57 (s, 3H), 2.13-2.05 (m, 4H), 1.63 (s, 6H). |
| II-57 | 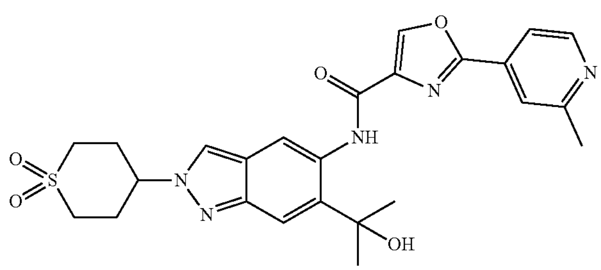 [SMILES: Cc1cc(-c2nc(C(=O)Nc3cc4cn(C5CCS(=O)(=O)CC5)nc4cc3C(C)(C)O)co2)ccn1] | 510.1 | (400 MHz, DMSO-d$_6$) δ 11.92 (s, 1H), 8.97 (s, 1H), 8.70 (d, J = 5.2 Hz, 1H), 8.64 (s, 1H), 8.43 (s, 1H), 7.83-7.81 (m, 2H), 7.61 (s, 1H), 6.22 (s, 1H), 4.98-4.82 (m, 1H), 3.48-3.39 (m, 2H), 3.28-3.18 (m, 2H), 2.61-2.57 (m, 5H), 2.44-2.41 (m, 2H), 1.67 (s, 6H). |
| II-59 | 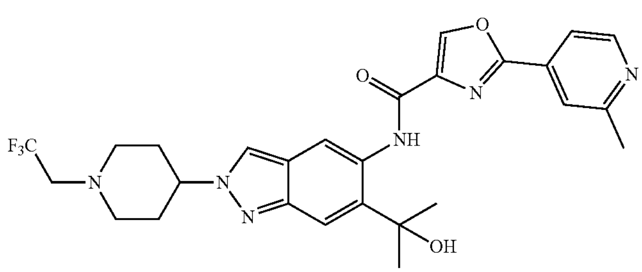 [SMILES: Cc1cc(-c2nc(C(=O)Nc3cc4cn(C5CCN(CC(F)(F)F)CC5)nc4cc3C(C)(C)O)co2)ccn1] | 543.2 | (400 MHz, CDCl$_3$) δ 11.36 (s, 1H), 8.71 (s, 1H), 8.65 (d, J = 4.0 Hz, 1H), 8.39 (s, 1H), 7.92 (s, 1H), 7.72-7.78 (m, 3H), 4.39-4.42 (m, 1H), 3.06-3.16 (m, 4H), 2.62-2.66 (m, 5H), 2.25-2.28 (m, 4H), 1.82 (s, 6H). |
| II-97 | 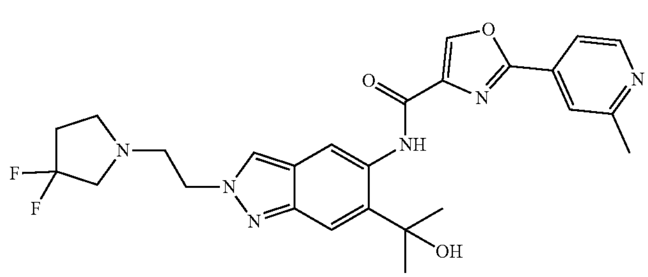 [SMILES: Cc1cc(-c2nc(C(=O)Nc3cc4cn(CCN5CCC(F)(F)C5)nc4cc3C(C)(C)O)co2)ccn1] | 511.2 | (400 MHz, DMSO-d$_6$) δ 11.89 (s, 1H), 8.99 (s, 1H), 8.70 (d, J = 4.8 Hz, 1H), 8.63 (s, 1H), 8.37 (s, 1H), 7.83-7.84 (m, 2H), 7.59 (s, 1H), 6.22 (s, 1H), 4.52 (t, J = 12.4 Hz, 2H), 3.01 (t, J = 6.0 Hz, 2H), 2.92 (t, J = 13.6 Hz, 2H), 2.72 (t, J = 6.8 Hz, 2H), 2.62 (s, 3H), 2.16-2.24 (m, 2H), 1.68 (s, 6H). |

-continued

| Molecule ID | Structure | MS (ESI) m/z: [M + H]+ | 1H NMR |
|---|---|---|---|
| II-99 | 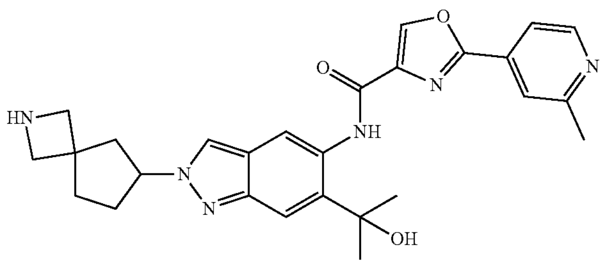 [SMILES: Cc1cc(-c2nc(C(=O)Nc3cc4cn(C5CCC6(CNC6)C5)nc4cc3C(C)(C)O)co2)ccn1] | 487.2 | (400 MHz, MeOD-d4) δ 8.63 (s, 1H), 8.60 (s, 1H), 8.59 (d, J = 5.2 Hz, 1H), 8.19 (s, 1H), 8.01 (s, 1H), 7.92 (d, J = 5.2 Hz, 1H), 7.63 (s, 1H), 5.03-4.84 (m, 1H), 3.86-3.59 (m, 4H), 2.64 (s, 3H), 2.63-2.53 (m, 1H), 2.45-2.40 (m, 1H), 2.38-2.14 (m, 3H), 2.09-2.04 (m, 1H), 1.74 (s, 6H). |
| II-100 | 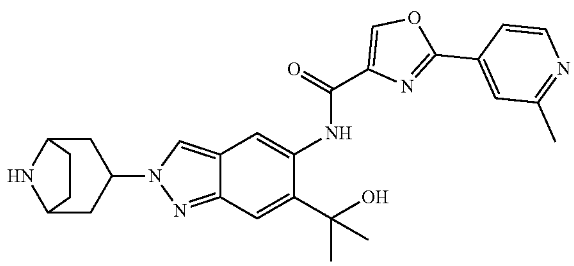 [SMILES: Cc1cc(-c2nc(C(=O)Nc3cc4cn(C5CC6CCC(C5)N6)nc4cc3C(C)(C)O)co2)ccn1] | 487.2 | (400 MHz, DMSO-d6) δ 11.93 (s, 1H), 8.99 (s, 1H), 8.77-8.60 (m, 3H), 7.86-7.84 (m, 2H), 7.62 (s, 1H), 6.25 (s, 1H), 4.86-4.78 (m, 1H), 4.04-3.85 (m, 2H), 3.76-3.64 (m, 2H), 3.03-2.91 (m, 2H), 2.62 (s, 3H), 2.06-1.92 (m, 2H), 1.69 (s, 6H), 1.60-1.53 (m, 2H). |
| II-101 | 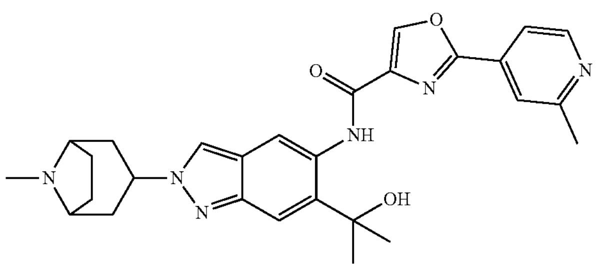 [SMILES: Cc1cc(-c2nc(C(=O)Nc3cc4cn(C5CC6CCC(C5)N6C)nc4cc3C(C)(C)O)co2)ccn1] | 501.2 | (400 MHz, MeOD-d4) δ 8.65 (d, J = 4.0 Hz, 2H), 8.61 (d, J = 5.2 Hz, 1H), 8.49 (s, 1H), 8.04 (s, 1H), 7.95 (d, J = 5.2 Hz, 1H), 7.71 (s, 1H), 3.97-3.90 (m, 2H), 3.78-3.69 (m, 1H), 3.59-3.53 (m, 2H), 2.80-2.75 (m, 5H), 2.66 (s, 3H), 2.18-2.05 (m, 2H), 1.98-1.89 (m, 2H), 1.77 (s, 6H). |
| II-103 | 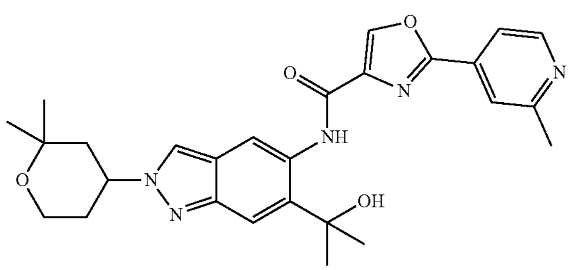 [SMILES: Cc1cc(-c2nc(C(=O)Nc3cc4cn(C5CCOC(C)(C)C5)nc4cc3C(C)(C)O)co2)ccn1] | 490.2 | (400 MHz, MeOD-d4) δ 8.63 (s, 2H), 8.59 (d, J = 4 Hz, 1H), 8.25 (s, 1H), 8.01 (s, 1H), 7.92 (d, J = 4 Hz, 1H), 7.64 (s, 1H), 4.92-4.87 (m, 1H), 3.91-3.88 (m, 2H), 2.64 (s, 3H), 2.17-2.00 (m, 4H), 1.74 (s, 6H), 1.37 (s, 3H), 1.29 (s, 3H). |
| II-104 | 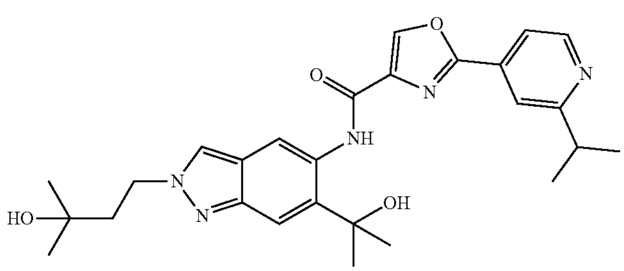 [SMILES: CC(C)c1cc(-c2nc(C(=O)Nc3cc4cn(CCC(C)(C)O)nc4cc3C(C)(C)O)co2)ccn1] | 492.2 | (400 MHz, MeOD-d4) δ 8.63 (s, 1H), 8.62 (s, 1H), 8.60 (s, 1H), 8.19 (s, 1H), 7.98 (s, 1H), 7.93 (d, J = 5.6 Hz, 1H), 7.63 (s, 1H), 4.54 (t, J = 7.6 Hz, 2H), 3.22-3.11 (m, 1H), 2.15 (t, J = 7.6 Hz, 2H), 1.74 (s, 6H), 1.36 (d, J = 7.2 Hz, 6H), 1.25 (s, 6H). |

-continued

| Molecule ID | Structure | MS (ESI) m/z: [M + H]+ | 1H NMR |
|---|---|---|---|
| II-105 | 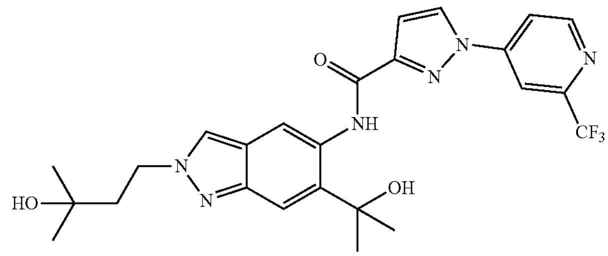 [SMILES: CC(C)(O)CCn1cc2cc(NC(=O)c3ccn(-c4ccnc(C(F)(F)F)c4)n3)c(C(C)(C)O)cc2n1] | 517.2 | (400 MHz, DMSO-d$_6$) δ 11.91 (s, 1 H), 9.01 (d, J = 2.8 Hz, 1 H), 8.90 (d, J = 5.6 Hz, 1 H), 8.61 (s, 1 H), 8.47 (d, J = 2.0 Hz, 1 H), 8.31(s, 1 H), 8.28 (dd, J = 5.6, 2.0 Hz, 1 H), 7.54 (s, 1 H), 7.10 (d, J = 2.4 Hz, 1 H), 6.23 (s, 1 H), 4.49 (s, 1 H), 4.45-4.41 (m, 2 H), 2.02-1.97 (m, 2 H), 1.65 (s, 6 H), 1.11 (s, 6 H). |
| II-106 | 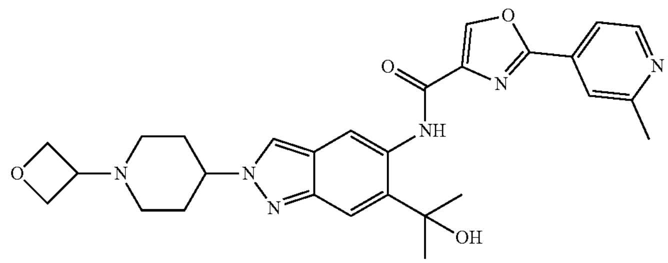 [SMILES: Cc1cc(-c2nc(C(=O)Nc3cc4cn(C5CCN(C6COC6)CC5)nc4cc3C(C)(C)O)co2)ccn1] | 517.2 | (400 MHz, DMSO-d$_6$) δ 11.87 (s, 1H), 8.93 (s, 1H), 8.66 (d, J = 5.2 Hz, 1H), 8.59 (s, 1H), 8.37 (s, 1H), 7.80 (s, 1H), 7.78 (d, J = 5.2 Hz, 1H), 7.55 (s, 1H), 6.18 (s, 1H), 4.53 (t, J = 6.0 Hz, 2H), 4.48-4.38 (m, 3H), 3.45-3.40 (m, 1H), 2.84-2.77 (m, 2H), 2.57 (s, 3H), 2.12-2.04 (m, 4H), 2.01-1.94 (m, 2H), 1.63 (s, 6H). |
| II-107 | 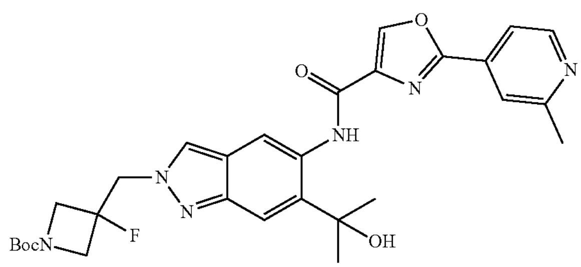 [SMILES: Cc1cc(-c2nc(C(=O)Nc3cc4cn(CC5(F)CN(C(=O)OC(C)(C)C)C5)nc4cc3C(C)(C)O)co2)ccn1] | 565.2 | (400 MHz, CDCl$_3$) δ 11.38 (s, 1H), 8.70 (s, 1H), 8.64 (d, J = 4 Hz, 1H), 8.38 (s, 1H), 7.93 (s, 1H), 7.76 (s, 1H), 7.73 (d, J = 4 Hz, 1H), 7.69 (s, 1H), 4.78 (d, J = 24 Hz, 2H), 4.23-4.16 (m, 2H), 4.09-4.01 (m, 2H), 2.79 (s, 1H), 2.65 (s, 3H), 1.81 (s, 6H), 1.43 (s, 9H). |
| II-108 | 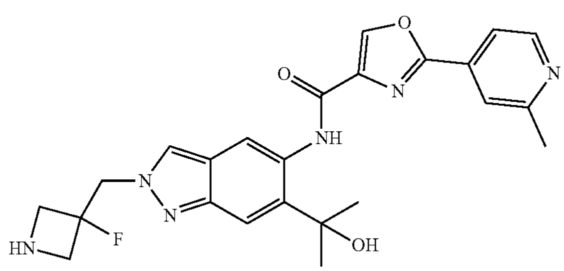 [SMILES: Cc1cc(-c2nc(C(=O)Nc3cc4cn(CC5(F)CNC5)nc4cc3C(C)(C)O)co2)ccn1] | 465.2 | (400 MHz, CDCl$_3$) δ 11.32 (s, 1H), 8.70 (s, 1H), 8.66 (d, J = 4 Hz, 1H), 8.39 (s, 1H), 7.96 (s, 1H), 7.78 (s, 1H), 7.75 (d, J = 4 Hz, 1H), 7.72 (s, 1H), 4.85 (d, J = 20 Hz, 2H), 3.89-3.81 (m, 2H), 3.74-3.68 (m, 2H), 2.66 (s, 3H), 1.81 (s, 6H). |
| II-109 | 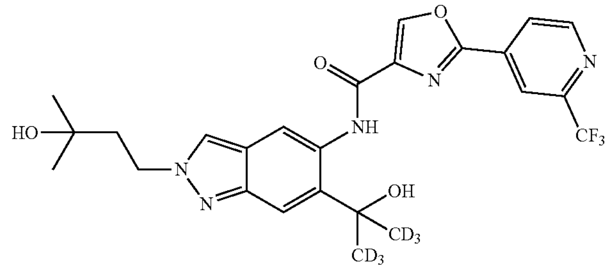 [SMILES: [2H]C([2H])([2H])C(O)(c1cc2nn(CCC(C)(C)O)cc2cc1NC(=O)c1coc(-c2ccnc(C(F)(F)F)c2)n1)C([2H])([2H])[2H]] | 524.2 | (400 MHz, CDCl$_3$) δ 11.37 (s, 1H), 8.90 (d, J = 8.0 Hz, 1H), 8.71 (s, 1H), 8.44 (s, 1H), 8.29 (s, 1H), 8.15 (d, J = 8.0 Hz, 1H), 7.90 (s, 1H), 7.67 (s, 1H), 4.57 (t, J = 8.0 Hz, 2H), 2.66 (s, 1H), 2.35 (s, 1H), 2.18 (t, J = 8 Hz, 2H), 1.30 (s, 6H). |

-continued

| Molecule ID | Structure | MS (ESI) m/z: [M + H]⁺ | ¹H NMR |
|---|---|---|---|
| II-110 | 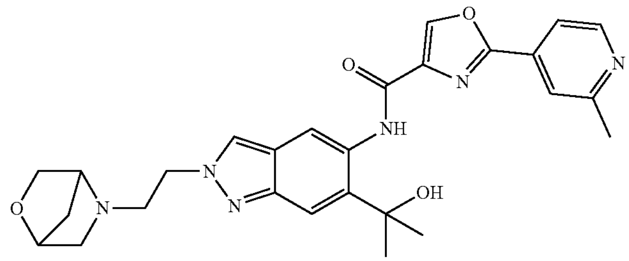 [SMILES: Cc1cc(-c2nc(C(=O)Nc3cc4cn(CCN5CC6CC5CO6)nc4cc3C(C)(C)O)co2)ccn1] | 503.2 | (400 MHz, MeOD-d₄) δ 8.63 (s, 1H), 8.62 (s, 1H), 8.59 (d, J = 4 Hz, 1H), 8.21 (s, 1H), 8.01 (s, 1H), 7.92 (d, J = 4 Hz, 1H), 7.64 (s, 1H), 4.51 (t, J = 6 Hz, 2H), 4.34 (s, 1H), 3.95 (d, J = 8 Hz, 1H), 3.56 (dd, J = 8, 1.6 Hz, 1H), 3.45 (s, 1H), 3.24-3.14 (m, 2H), 2.81 (dd, J = 10.3, 1.7 Hz, 1H), 2.64 (s, 3H), 2.57-2.48 (m, 1H), 1.83 (dd, J = 10.0, 1H), 1.74 (s, 6H), 1.71-1.59 (m, 1H). |
| II-112 | 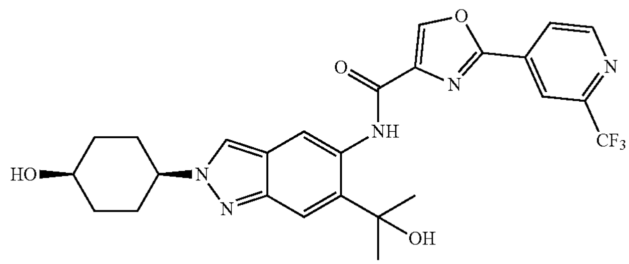 [SMILES: CC(C)(O)c1cc2nn([C@H]3CC[C@@H](O)CC3)cc2cc1NC(=O)c1coc(-c2ccnc(C(F)(F)F)c2)n1] | 530.2 | (400 MHz, DMSO-d₆) δ 11.94 (s, 1H), 9.06 (s, 1H), 9.04 (d, J = 4.9 Hz, 1H), 8.62 (s, 1H), 8.36 (s, 1H), 8.34-8.30 (m, 2H), 7.59 (s, 1H), 6.24 (s, 1H), 4.52 (d, J = 3.2 Hz, 1H), 4.50-4.40 (m, 1H), 3.92-3.86 (m, 1H), 2.36-2.24 (m, 2H), 1.92-1.74 (m, 4H), 1.67 (s, 6H), 1.66-1.57 (m, 2H). |
| II-113F | 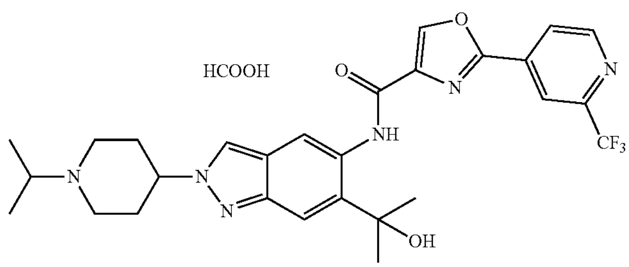 [SMILES: CC(C)N1CCC(n2cc3cc(NC(=O)c4coc(-c5ccnc(C(F)(F)F)c5)n4)c(C(C)(C)O)cc3n2)CC1 ; "HCOOH"] | 557.3 | (400 MHz, DMSO-d₆) δ 11.94 (s, 1H), 9.06 (s, 1H), 9.04 (d, J = 4.9 Hz, 1H), 8.62 (s, 1H), 8.39 (s, 1H), 8.33 (s, 1H), 8.31 (s, 1H), 8.19 (s, 1H), 7.58 (s, 1H), 6.24 (s, 1H), 4.50-4.36 (m, 1H), 2.94 (d, J = 11.2 Hz, 2H), 2.82-2.76 (m, 1H), 2.34 (m, 2H), 2.07 (m, 4H), 1.67 (s, 6H), 1.02 (d, J = 6.4 Hz, 6H). |
| II-114 | 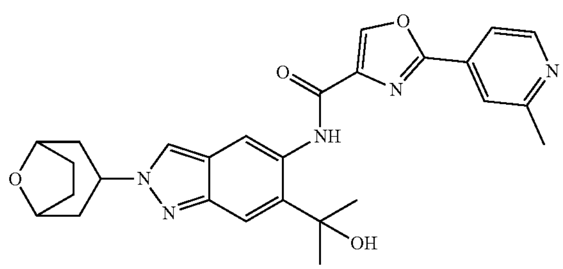 [SMILES: Cc1cc(-c2nc(C(=O)Nc3cc4cn(C5CC6CCC(C5)O6)nc4cc3C(C)(C)O)co2)ccn1] | 488.3 | (400 MHz, DMSO-d₆) δ 11.89 (s, 1H), 8.97 (s, 1H), 8.70 (d, J = 5.2 Hz, 1H), 8.64 (s, 1H), 8.58 (s, 1H), 7.87-7.78 (m, 2H), 7.61 (s, 1H), 6.19 (s, 1H), 4.76-4.55 (m, 1H), 4.38 (s, 2H), 2.60 (d, J = 7.6 Hz, 9H), 2.43 (m, 2H), 1.68 (s, 6H). |
| II-115 | 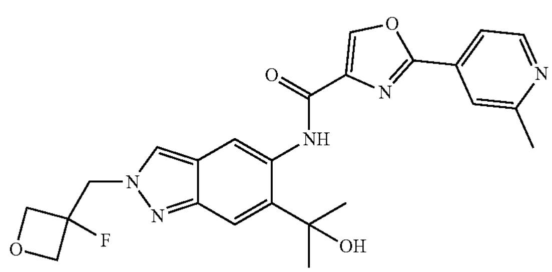 [SMILES: Cc1cc(-c2nc(C(=O)Nc3cc4cn(CC5(F)COC5)nc4cc3C(C)(C)O)co2)ccn1] | 466.2 | (400 MHz, DMSO-d₆) δ 11.90 (s, 1H), 8.97 (s, 1H), 8.70 (d, J = 5.2 Hz, 1H), 8.64 (s, 1H), 8.37 (s, 1H), 7.86-7.78 (m, 2H), 7.59 (s, 1H), 6.21 (s, 1H), 5.05 (s, 1H), 4.99 (s, 1H), 4.89 (dd, J = 21.4, 8.8 Hz, 2H), 4.66 (dd, J = 20.4, 8.4 Hz, 2H), 2.61 (s, 3H), 1.67 (s, 6H). |

| Molecule ID | Structure | MS (ESI) m/z: [M + H]+ | 1H NMR |
|---|---|---|---|
| II-116 | 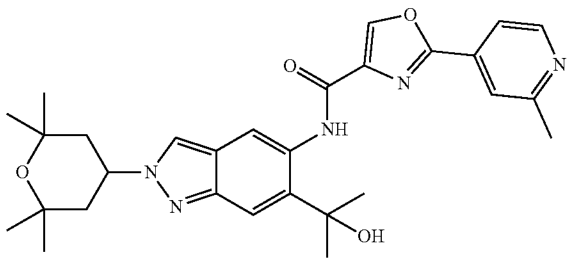 [SMILES: Cc1cc(-c2nc(C(=O)Nc3cc4cn(C5CC(C)(C)OC(C)(C)C5)nc4cc3C(C)(C)O)co2)ccn1] | 518.2 | NA |
| II-117 | 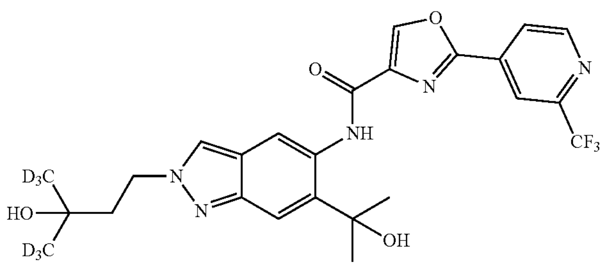 [SMILES: [2H]C([2H])([2H])C(O)(CCn1cc2cc(NC(=O)c3coc(-c4ccnc(C(F)(F)F)c4)n3)c(C(C)(C)O)cc2n1)C([2H])([2H])[2H]] | 524.5 | (500 MHz, DMSO-d6) δ 11.93 (s, 1H), 9.06 (s, 1H), 9.04 (d, J = 5.0 Hz, 1H), 8.61 (d, J = 3.5 Hz, 1H), 8.35 (s, 1H), 8.32 (d, J = 7.0 Hz, 2H), 7.57 (s, 1H), 6.25 (s, 1H), 4.50 (s, 1H), 4.49-4.44 (m, 2H), 2.05-2.00 (m, 2H), 1.67 (s, 6H). |
| II-118 | 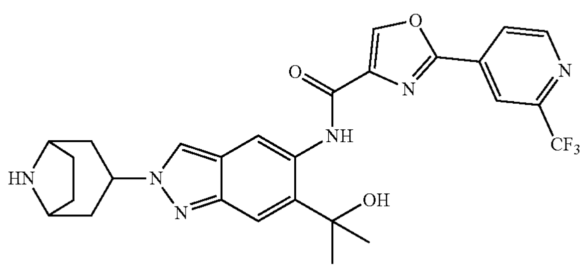 [SMILES: CC(C)(O)c1cc2nn(C3CC4CCC(C3)N4)cc2cc1NC(=O)c1coc(-c2ccnc(C(F)(F)F)c2)n1] | 541.5 | (500 MHz, DMSO-d6) δ 11.94 (s, 1H), 9.07 (s, 1H), 9.05 (d, J = 5.0 Hz, 1H), 8.63 (s, 1H), 8.55 (s, 1H), 8.34-8.29 (m, 2H), 7.60 (s, 1H), 6.25 (s, 1H), 4.76-4.67 (m, 1H), 3.60 (s, 2H), 2.58-2.54 (m, 2H), 2.43-2.35 (m, 3H), 1.68 (s, 6H), 1.62-1.57 (m, 2H), 1.51-1.44 (m, 2H). |
| II-121 | 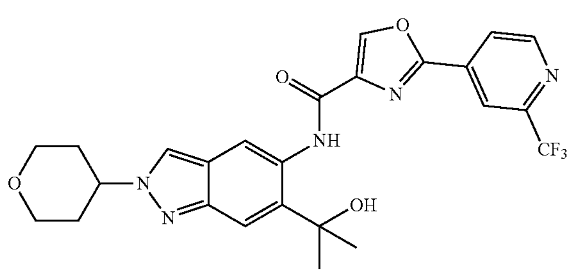 [SMILES: CC(C)(O)c1cc2nn(C3CCOCC3)cc2cc1NC(=O)c1coc(-c2ccnc(C(F)(F)F)c2)n1] | 516.4 | (500 MHz, CDCl3) δ 11.40 (s, 1H), 8.91 (d, J = 5.0 Hz, 1H), 8.73 (s, 1H), 8.46 (s, 1H), 8.30 (s, 1H), 8.15 (d, J = 4.5 Hz, 1H), 7.95 (s, 1H), 7.73 (s, 1H), 4.72-4.50 (m, 1H), 4.17 (d, J = 10.5 Hz, 2H), 3.61 (t, J = 10.8 Hz, 2H), 2.36-2.16 (m, 5H), 1.82 (s, 6H). |
Example II-64: Synthesis of II-64
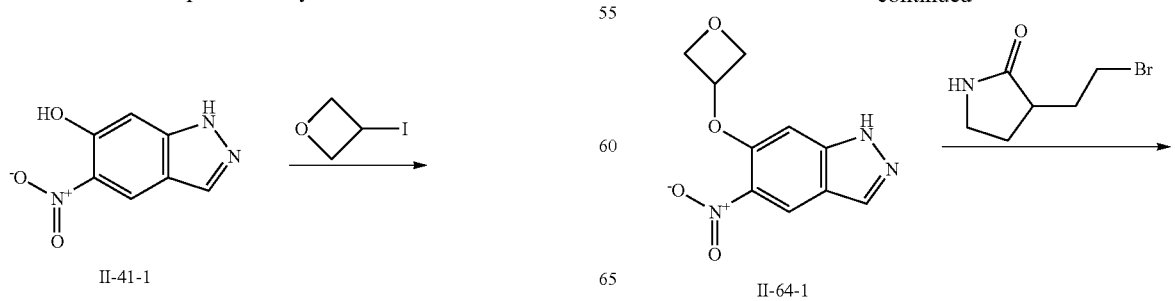

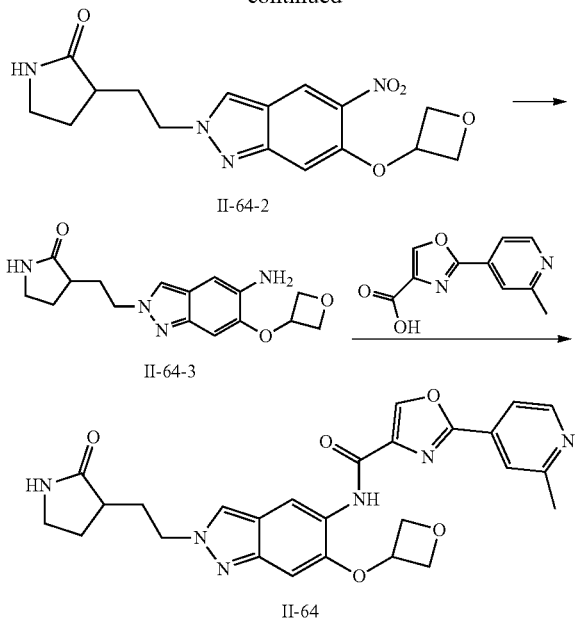

Step 1: Synthesis of II-64-1

K₂CO₃ (3.08 g, 22.34 mmol) was added to a mixture of II-14-1 (2 g, 11.17 mmol), 3-iodooxetane (3.08 g, 16.76 mmol), and DMF (50 mL), and the resulting mixture was stirred for 24 hours at 50° C. The reaction mixture was cooled to room temperature, diluted with H₂O (80 mL), and extracted with chloroform: isopropanol=3:1 (30 mL×3), and the combined organic phases were dried over anhydrous Na₂SO₄, filtered, and concentrated to obtain the crude product. The crude product was purified by flash silica gel column chromatography and preparative TLC to obtain the brown solid product II-64-1 (230 mg, yield of 9%), MS (ESI) m/z: 236.1 [M+H]⁺.

Step 2: Synthesis of II-64-2

Cs₂CO₃ (832 mg, 2.553 mmol) was added to a mixture of II-64-1 (300 mg, 1.276 mmol), KI (21 mg, 0.128 mmol), 3-(2-bromoethyl)pyrrolidin-2-one (490 mg, 2.553 mmol), and DMF (6 mL) at 25° C., and the resulting mixture was stirred for 16 hours at 60° C. The reaction mixture was cooled to room temperature, diluted with H₂O (80 mL), and extracted with EA (20 mL×3), and the combined organic phases were dried over anhydrous Na₂SO₄, filtered, and concentrated to obtain the crude product. The crude product was purified by preparative thin-layer chromatography to obtain the white solid product II-64-2 (120 mg, yield of 27%), MS (ESI) m/z: 347.1 [M+H]⁺.

Step 3: Synthesis of II-64-3

Na₂S₂O₄ (629 mg, 3.613 mmol) was added to a mixture of II-64-2 (250 mg, 0.722 mmol) and THF/H₂O (5/5 mL) at 25° C., and the resulting mixture was stirred for 4 hours until the reaction was complete. The resulting mixture was concentrated to obtain the crude product, and the crude product was purified by reversed-phase column chromatography to obtain the brown solid product II-64-3 (45 mg, yield of 20%), MS (ESI) m/z: 317.1 [M+H]⁺.

Step 4: Synthesis of II-64

DIEA (74 mg, 0.569 mmol) was added to a mixture of II-64-3 (30 mg, 0.095 mmol), 2-(2-methylpyridin-4-yl)oxazole-4-carboxylic acid (58 mg, 0.285 mmol), HATU (108 mg, 0.285 mol), and DMF (3 mL) at 25° C., and the resulting mixture was stirred for 16 hours until the reaction was complete. The reaction mixture was diluted with H₂O (30 mL) and extracted with EA (10 mL×3), and the combined organic phases were dried over anhydrous Na₂SO₄, filtered, and concentrated to obtain the crude product. The crude product was purified by preparative thin-layer chromatography and preparative HPLC to obtain the white solid product II-64 (5.31 mg, yield of 11%), MS (ESI) m/z: 503.1 [M+H]⁺.

Example II-95: Synthesis of II-95

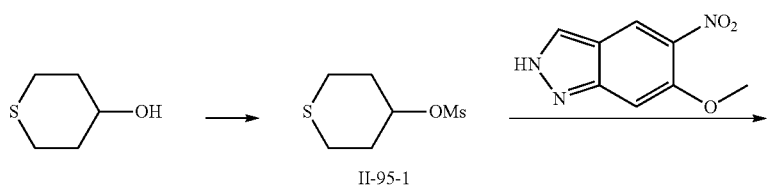

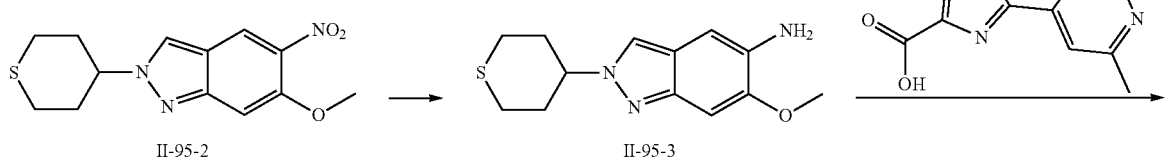

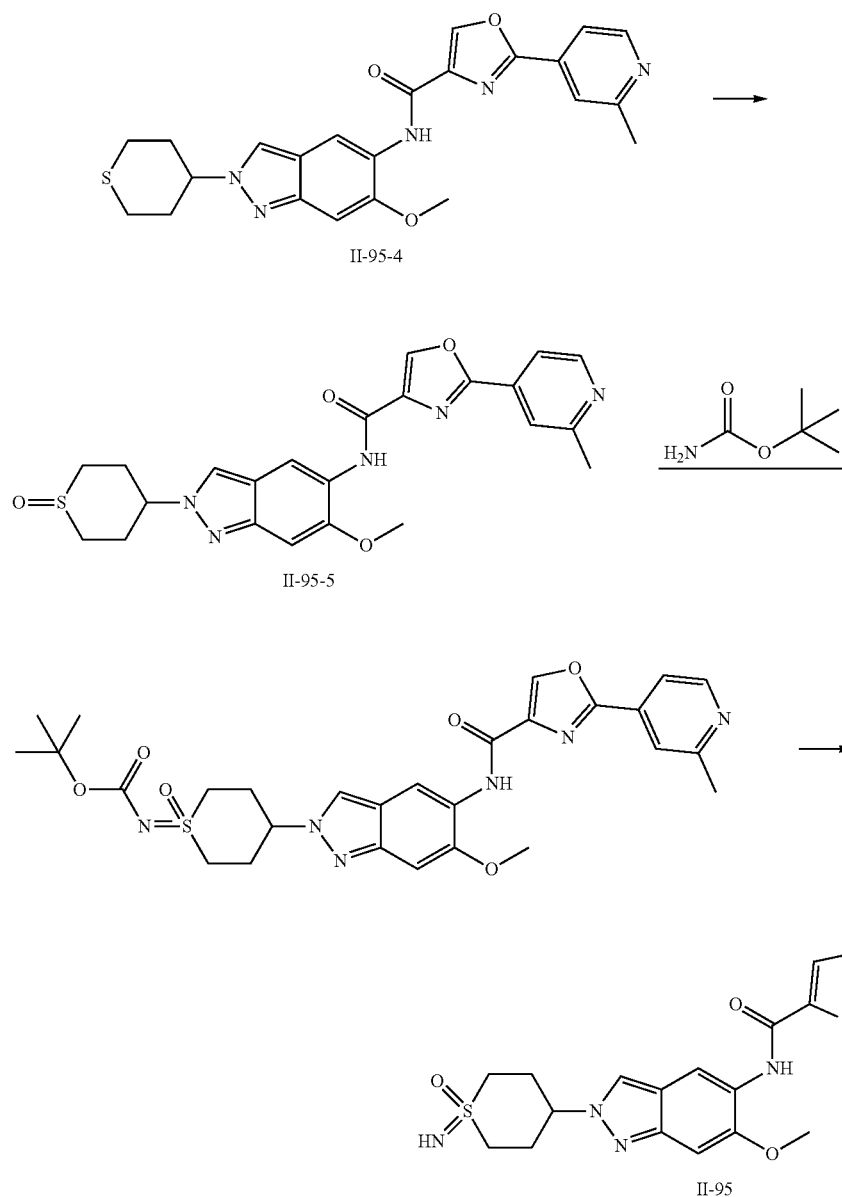

Step 1: Synthesis of II-95-1

TEA (12.83 g, 127.03 mmol) was added to a mixture of tetrahydro-2H-thiopyran-4-ol (5.0 g, 42.30 mmol), MsCl (methanesulfonyl chloride, 6.24 g, 54.47 mmol), and DCM (50 mL) at 0° C., and the resulting mixture was stirred for 16 hours at 25° C. The resulting mixture was diluted with H$_2$O (100 mL) and extracted with DCM (200 mL). The combined organic phases were dried over anhydrous Na$_2$SO$_4$, filtered, and concentrated to obtain the yellow solid product II-95-1 (7.9 g), which was directly used in the next reaction step without purification.

Step 2: Synthesis of II-95-2

Cs$_2$CO$_3$ (17.604 g, 54.00 mmol) was added to a mixture of 6-methoxy-5-nitro-2H-indazole (5.32 g, 27.01 mmol), II-95-1 (7.9 g, 40.93 mmol), and DMF (40 mL), and the resulting mixture was stirred for 16 hours at 70° C. The resulting mixture was diluted with H$_2$O (150 mL) and extracted with EtOAc (300 mL). The combined organic phases were dried over anhydrous Na$_2$SO$_4$, filtered, and concentrated to obtain crude product. The crude product was purified by flash silica gel column chromatography and reversed-phase column chromatography to obtain the yellow solid product II-95-2 (0.63 g, yield of 8%), MS (ESI) m/z: 294.0 [M+H]$^+$.

Step 3: Synthesis of II-95-3

NH$_4$Cl (610 mg, 11.40 mmol) and H$_2$O (5 mL) were added to a mixture of II-95-2 (670 mg, 2.28 mmol), DMF (10 mL), and EtOH (20 mL), the resulting mixture was heated to 60° C., and iron powder (640 mg, 11.43 mmol) was added thereto. The resulting mixture was stirred for 2 hours at 90° C. The reaction mixture was filtered, and the filtrate was concentrated to obtain the crude product. The crude was diluted with H₂O (40 mL) and extracted with EtOAc (80 mL), and the combined organic phases were dried over anhydrous Na₂SO₄, filtered, and concentrated to obtain the yellow solid product II-95-3 (500 mg, yield of 83%), MS (ESI) m/z: 264.1 [M+H]⁺.

Step 4: Synthesis of II-95-4

HATU (1.73 g, 4.55 mmol) was added to a mixture of II-95-3 (500 mg, 1.89 mmol), 2-(2-methylpyridin-4-yl)oxazole-4-carboxylic acid (582 mg, 2.84 mmol), DIEA (733 mg, 5.26 mmol), and DMF (8 mL) at 25° C., and the resulting mixture was stirred for 4 hours. The reaction mixture was diluted with H₂O (40 mL) and extracted with DCM (80 mL). The combined organic phases were dried over anhydrous Na₂SO₄, filtered, and concentrated, and the residue was washed with DMF (2 mL) to obtain a white solid crude product, and the filtrate was purified by reversed-phase column chromatography to obtain the white solid product II-95-4 (200 mg, yield of 24%), MS (ESI) m/z: 450.1 [M+H]⁺.

Step 5: Synthesis of II-95-5

A mixture of NaIO4 (240 mg, 1.17 mmol) and H₂O (2.0 mL) was added to a mixture of II-95-4 (500 mg, 1.11 mmol), MeOH (10 mL), and DCM (10 mL) at 25° C., and the mixture was stirred for 16 hours. The reaction mixture was quenched with Na₂SO₃ (saturated, 15 mL), diluted with H₂O (20 mL), and extracted with DCM (80 mL). The combined organic phases were dried over anhydrous Na₂SO₄, filtered, and concentrated to obtain the white solid product II-95-5 (250 mg, yield of 48%), MS (ESI) m/z: 466.1 [M+H]⁺.

Step 6: Synthesis of II-95-6

Rh₂(OAc)₄ (122 mg, 0.27 mmol) was added to a mixture of II-95-5 (50 mg, 0.11 mmol), tert-butyl carbamate (25 mg, 0.21 mmol), PhI(OAc)₂ (53 mg, 0.16 mmol), MgO (18 mg, 0.45 mmol), and DCM (5 mL), and the resulting mixture was stirred for 3 hours at 40° C. The reaction mixture was diluted with H₂O (30 mL) and extracted with DCM (80 mL), and the combined organic phases were concentrated and purified by reversed-phase column chromatography to obtain the white solid product II-95-6 (20 mg, yield of 31%), MS (ESI) m/z: 581.0 [M+H]⁺.

Step 7: Synthesis of II-95

II-95-6 (20 mg, 0.03 mmol) was added to HCl-dioxane (1 M, 2 mL) at 25° C., and the mixture was stirred for 3 hours until the reaction was complete. The reaction mixture was filtered, and the filter cake was washed with a small amount of dioxane, and dried in vacuum to obtain the yellow solid product II-95 (7.26 mg, yield of 50%), MS (ESI) m/z: 481.1 [M+H]⁺. ¹H NMR (400 MHz, DMSO-d₆) δ 9.55 (s, 1H), 9.19 (s, 1H), 8.85 (d, J=5.6 Hz, 1H), 8.56 (d, J=5.6 Hz, 1H), 8.43 (d, J=12.4 Hz, 1H), 8.26 (s, 1H), 8.15 (d, J=5.2 Hz, 1H), 7.21 (d, J=7.6 Hz, 1H), 5.06-4.97 (m, 1H), 4.29-4.08 (m, 4H), 4.03 (d, J=5.2 Hz, 3H), 2.78 (s, 3H), 2.69-2.57 (m, 4H).

Example II-96: Synthesis of II-96

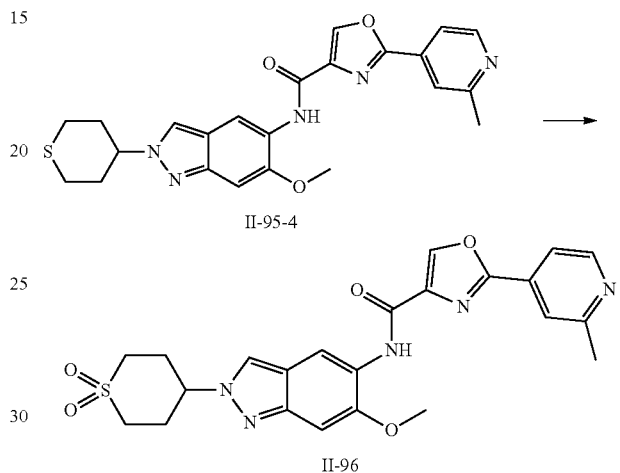

m-CPBA (28 mg, 0.17 mmol) was added to a mixture of II-95-4 (50 mg, 0.11 mmol) and DCM (4 mL) at 0° C., and the resulting mixture was stirred for 2 hours at 25° C. The resulting mixture was quenched with saturated Na₂SO₃ aqueous solution (30 mL) and extracted with DCM (60 mL), and the combined organic phases were dried over anhydrous Na₂SO₄, filtered, and concentrated to obtain the crude product. The crude product was purified by preparative HPLC to obtain the yellow solid product II-96 (5.94 mg, yield of 11%), MS (ESI) m/z: 482.1 [M+H]⁺. ¹H NMR (400 MHz, DMSO-d₆) δ 9.54 (s, 1H), 9.05 (s, 1H), 8.70 (d, J=5.2 Hz, 1H), 8.56 (s, 1H), 8.39 (s, 1H), 7.87 (s, 1H), 7.80 (d, J=5.2 Hz, 1H), 7.19 (s, 1H), 4.91-4.82 (m, 1H), 4.03 (s, 3H), 3.50-3.41 (m, 2H), 3.28-3.23 (m, 2H), 2.62 (s, 3H), 2.60-2.54 (m, 2H), 2.45-2.38 (m, 2H).

Referring to Example II-95, the following product can finally be synthesized:

| Molecule ID | Structure | MS (ESI) m/z: [M + H]⁺ | ¹H NMR |
|---|---|---|---|
| II-12 | 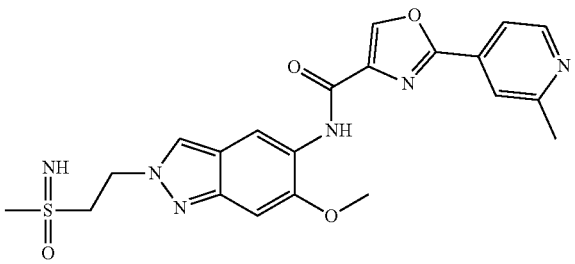 [SMILES: COc1cc2nn(CCS(C)(=N)=O)cc2cc1NC(=O)c1coc(-c2ccnc(C)c2)n1] | 455.1 | (500 MHz, DMSO-d₆) δ 9.54 (s, 1H), 9.07 (s, 1H), 8.70 (d, J = 4.5 Hz, 1H), 8.56 (s, 1H), 8.38 (s, 1H), 7.87 (s, 1H), 7.80 (d, J = 3.0 Hz, 1H), 7.16 (s, 1H), 4.79 (d, J = 5.5 Hz, 2H), 4.03 (s, 3H), 3.84-3.70 (m, 2H), 2.80 (s, 3H), 2.62 (s, 3H), 2.02-1.93 (m, 1H). |

Example II-98: Synthesis of II-98

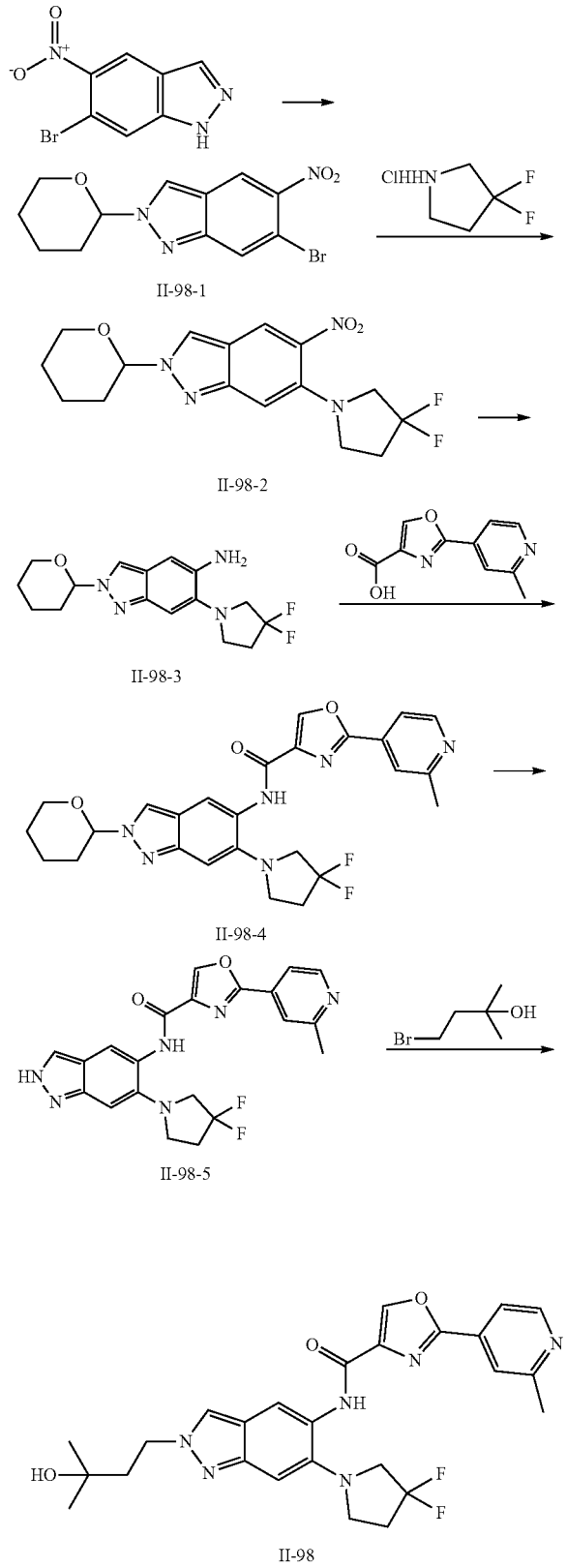

Step 1: Synthesis of II-98-1

TsOH (p-toluenesulfonic acid, 627 mg, 3.3 mmol) was added to a mixture of 6-bromo-5-nitro-1H-indazole (4 g, 16.7 mmol), DHP (3,4-dihydro-2H-pyran, 2.8 g, 33.3 mmol), and DCM (50 mL) at 0° C., and the resulting mixture was stirred for 0.5 hours at 0° C. The reaction mixture was diluted with $H_2O$ (120 mL) and extracted with EA (30 mL×3). The combined organic phases were dried over anhydrous $Na_2SO_4$, filtered, and concentrated to obtain the crude product. The crude product was purified by silica gel column chromatography to obtain the yellow solid product II-98-1 (4.8 g, yield of 88%), MS (ESI) m/z: 326.0 $[M+H]^+$. $^1H$ NMR: (400 MHz, DMSO-$d_6$) δ 8.63 (s, 1H), 8.38 (s, 2H), 6.0-5.98 (m, 1H), 3.89 (d, J=11.6 Hz, 1H), 3.80-3.78 (m, 1H), 2.38-2.35 (m, 1H), 2.05-1.97 (m, 2H), 1.75-1.71 (m, 1H), 1.60-1.57 (m, 2H).

Step 2: Synthesis of II-98-2

$Cs_2CO_3$ (1.5 mg, 4.62 mmol) was added to a mixture of II-98-1 (500 mg, 1.54 mmol), 3,3-difluoropyrrolidine hydrochloride (220 mg, 1.54 mmol), Xantphos (179 mg, 0.31 mmol), $Pd_2(dba)_3$ (tris(dibenzylideneacetone)dipalladium, 137 mg, 0.15 mmol), and dioxane (15 mL) at 25° C., and the resulting mixture was reacted for 1 hour at 140° C. under microwave irradiation. The reaction mixture was diluted with $H_2O$ (80 mL) and extracted with EA (30 mL×3), and the combined organic phases were dried over anhydrous $Na_2SO_4$, filtered, and concentrated to obtain the crude product. The crude product was purified by flash silica gel column chromatography to obtain the brown solid product II-98-2 (70 mg, yield of 12%), MS (ESI) m/z: 353.1 $[M+H]^+$.

Step 3: Synthesis of II-98-3

Iron powder (486 mg, 9.088 mmol) was added to a mixture of II-98-2 (800 mg, 2.272 mmol), $NH_4C_1$ (508 mg, 9.088 mmol), and $EtOH/H_2O$ (20/5 mL) at 60° C., and the resulting mixture was stirred for 2 hours at 90° C. The reaction mixture was diluted with $H_2O$ (50 mL) and extracted with EA (10 mL×3). The combined organic phases were dried over anhydrous $Na_2SO_4$, filtered, and concentrated to obtain the crude product. The crude product was purified by reversed-phase column chromatography to obtain the white solid product II-98-3 (100 mg, yield of 14%), MS (ESI) m/z: 323.0 $[M+H]^+$.

Step 4: Synthesis of II-98-4

DIEA (160 mg, 1.24 mmol) was added to a mixture of II-98-3 (100 mg, 0.31 mmol), 2-(2-methylpyridin-4-yl)oxazole-4-carboxylic acid (126 mg, 0.62 mmol), HATU (283 mg, 0.74 mmol), and DMF (6 mL) at 25° C. The resulting mixture was stirred for 16 hours. The reaction mixture was diluted with $H_2O$ (30 mL) and extracted with EA (10 mL×3). The combined organic phases were dried over anhydrous $Na_2SO_4$, filtered, and concentrated to obtain the crude product. The crude product was purified by preparative thin-layer chromatography to obtain the brown solid product II-98-4 (120 mg, yield of 76%), MS (ESI) m/z: 509.2 $[M+H]^+$.

Step 5: Synthesis of II-98-5

HCl-1,4-dioxane (1 M, 5 mL) was added to a mixture of II-98-4 (120 mg, 0.236 mmol) and 1,4-dioxane (1 mL) at 0° C., and the resulting mixture was stirred for 16 hours at 25° C. The reaction mixture was concentrated under reduced pressure to obtain the white solid product II-98-5 (80 mg, yield of 80%), MS (ESI) m/z: 425.1 [M+H]$^+$.

Step 6: Synthesis of II-98

$K_2CO_3$ (97.7 mg, 0.708 mmol) was added to a mixture of II-98-5 (100 mg, 0.236 mmol), KI (19.5 mg, 0.118 mmol), and 4-bromo-2-methylbutan-2-ol (78 mg, 0.472 mmol), and DMF (5 mL) at 25° C. The resulting mixture was stirred for 16 hours. The reaction mixture was diluted with $H_2O$ (30 mL) and extracted with EA (10 mL×3), and the combined organic phases were dried over anhydrous $Na_2SO_4$, filtered, and concentrated to obtain the crude product. The crude product was purified by preparative thin-layer chromatography and reversed-phase column chromatography to obtain the white solid product II-98 (5.58 mg, yield of 4%), MS (ESI) m/z: 511.2 [M+H]$^+$. $^1$H NMR (400 MHz, DMSO-$d_6$) δ 10.07 (s, 1H), 9.04 (s, 1H), 8.71 (d, J=5.2 Hz, 1H), 8.56 (s, 1H), 8.36 (s, 1H), 7.87 (s, 1H), 7.76 (d, J=5.2 Hz, 1H), 7.57 (s, 1H), 4.51 (s, 1H), 4.47-4.43 (m, 2H), 3.58 (t, J=12.4 Hz, 2H), 3.35-3.31 (m, 2H), 2.62-2.57 (m, 5H), 2.04-1.96 (m, 2H), 1.15 (s, 6H).

Referring to Example II-98, the following product can finally be synthesized:

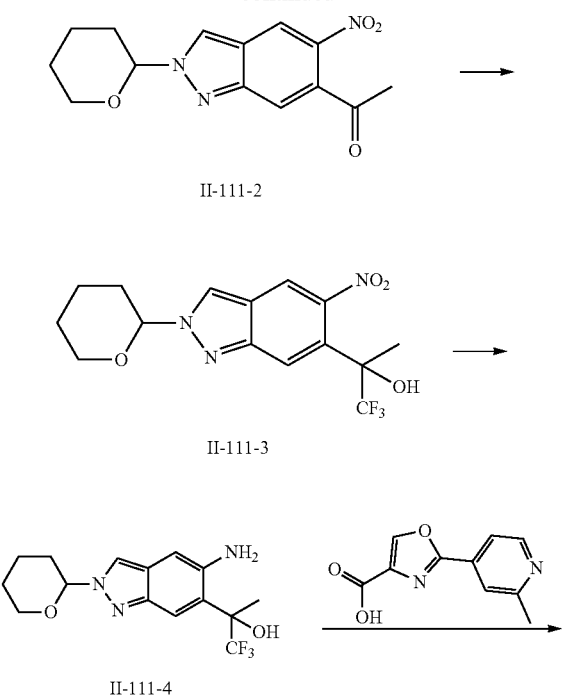

| Molecule ID | Structure | MS (ESI) m/z: [M + H]$^+$ | $^1$H NMR |
|---|---|---|---|
| II-102 | 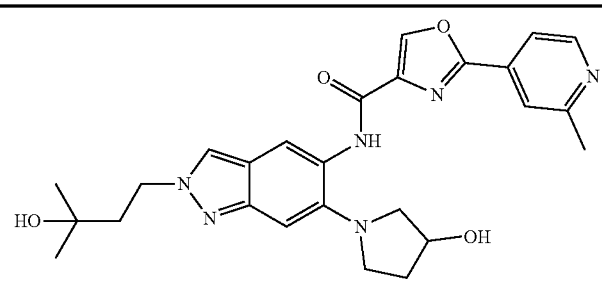 | 491.2 | (400 MHz, DMSO-$d_6$) δ 10.05 (s, 1H), 9.04 (s, 1H), 8.69 (d, J = 5.2 Hz, 1H), 8.44 (s, 1H), 8.31 (s, 1H), 7.93 (s, 1H), 7.81 (d, J = 4.8 Hz, 1H), 7.32 (s, 1H), 5.10 (d, J = 3.2 Hz, 1H), 4.53 (s, 1H), 4.48-4.38 (m, 2H), 3.81-3.60 (m, 2H), 3.11-2.96 (m, 2H), 2.60 (s, 3H), 2.35-2.23 (m, 2H), 2.05-1.87 (m, 3H), 1.23 (s, 3H), 1.15 (s, 3H). |

Example II-111: Synthesis of II-111

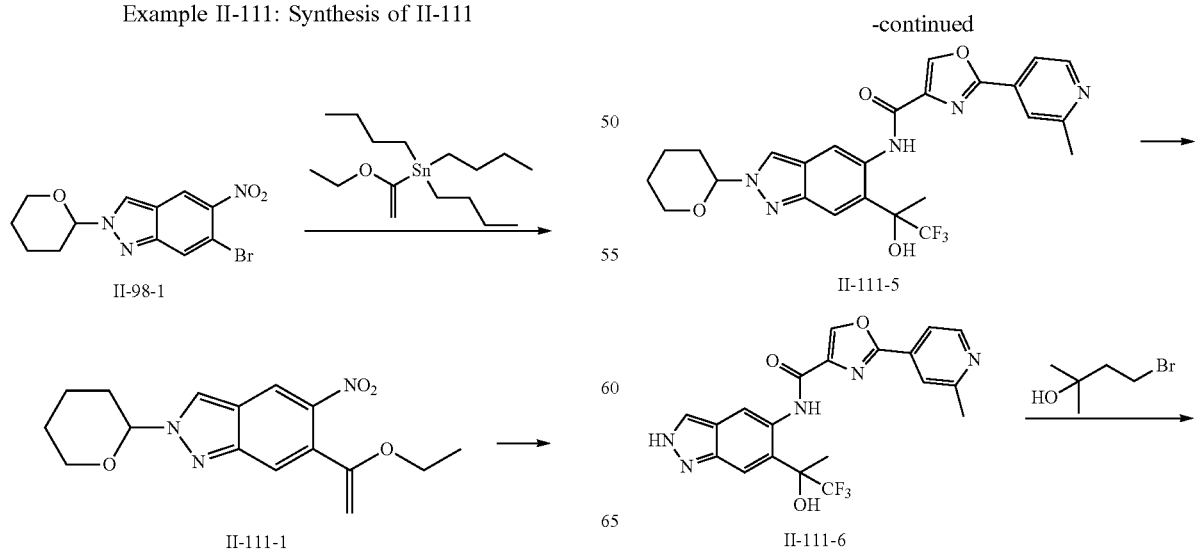

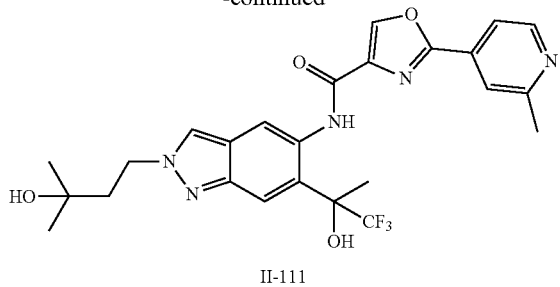

II-111

Step 1: Synthesis of II-111-1

Tributyl(1-ethoxyvinyl)stannane (5.45 g, 15.1 mmol) and TEA (3.2 g, 31.5 mmol) were added to a mixture of II-98-1 (4.1 g, 15.6 mmol) and 1,4-dioxane (15 mL), the resulting mixture was stirred for 15 minutes at 25° C. under nitrogen atmosphere, then Pd(PPh$_3$)$_2$Cl$_2$ (0.9 g, 1.3 mmol) was added thereto, and the resulting mixture was stirred for 16 hours at 100° C. The reaction mixture was cooled to room temperature and diluted with saturated potassium fluoride aqueous solution (50 mL). The insoluble material was removed by filtration, and the filtrate was extracted with EtOAc (60 mL×3). The combined organic phases were dried over anhydrous Na$_2$SO$_4$ and concentrated, and the crude product was purified by silica gel column chromatography (PE: EtOAc=3:1) to obtain the yellow oily product II-111-1 (2.9 g, yield of 72.7%), MS (ESI) m/z: 318.1 [M+H]$^+$. $^1$H NMR (400 MHz, DMSO-d$_6$) δ 8.47 (s, 1H), 8.36 (s, 1H), 7.94 (s, 1H), 6.03 (dd, J=9.2, 2.0 Hz, 1H), 4.62 (d, J=2.4 Hz, 1H), 4.48 (d, J=2.4 Hz, 1H), 3.83 (m, 4H), 2.37 (m, 1H), 2.01 (s, 2H), 1.75 (m, 1H), 1.64-1.54 (m, 2H), 1.19 (t, J=7.2 Hz, 3H).

Step 2: Synthesis of II-111-2

TsOH (0.15 g, 0.8 mmol) was added to a mixture of II-111-1 (2.5 g, 7.9 mmol), acetone (15 mL), and water (15 mL), and the resulting mixture was stirred for 2 hours at 50° C. The resulting mixture was diluted with water (30 mL) and extracted with ethyl acetate (50 mL×3). The combined organic phases were washed with saturated brine (100 mL), dried over anhydrous Na$_2$SO$_4$, filtered, and concentrated to obtain the white solid product II-111-2 (1.8 g, yield of 78.8%), MS (ESI) m/z: 290.1 [M+H]$^+$.

Step 3: Synthesis of II-111-3

A mixture of trifluoromethyltrimethylsilane (2.04 mL, 13.84 mmol) in THF (27.6 mL) was added to a mixture of II-111-2 (2.0 g, 6.92 mmol) and THF (20 mL) at 25° C., and the resulting mixture was stirred for 15 minutes, then added with tetrabutylammonium fluoride (TBAF) (6.92 mL, 6.92 mmol), and reacted under microwave irradiation for 16 hours at room temperature until the reaction was complete. The reaction mixture was poured into saturated NH$_4$Cl solution and then extracted with ethyl acetate (50 mL×2). The combined organic phases were washed with saturated brine (100 mL), dried over anhydrous Na$_2$SO$_4$, filtered, and concentrated in vacuum. The crude product was purified by flash silica gel column chromatography (petroleum ether: ethyl acetate=2:1) to obtain the yellow solid product II-111-3 (1.4 g, yield of 22.5%), MS (ESI) m/z: 360.1 [M+H]$^+$.

Step 4: Synthesis of II-111-4

Pd/C (0.3 g, purity: 10%) was added to a mixture of II-111-3 (0.6 g, 1.7 mmol) and MeOH (10 mL) at 25° C., and the resulting mixture was replaced with H$_2$ three times while stirring and then stirred for another 16 hours under H$_2$ atmosphere. The resulting mixture was filtered and concentrated to obtain the brown solid product II-111-4 (0.5 g, yield of 91%), MS (ESI) m/z: 330.1 [M+H]$^+$.

Step 5: Synthesis of II-111-5

DIEA (0.4 g, 3.1 mmol) was added to a mixture of II-111-4 (0.5 g, 1.6 mmol), 2-(2-methylpyridin-4-yl)oxazole-4-carboxylic acid (0.3 g, 1.6 mmol), HATU (0.7 g, 1.9 mmol), and DMF (5.0 mL) at 25° C., and the resulting mixture was stirred for 16 hours. The reaction mixture was diluted with H$_2$O (20 mL) and extracted with EtOAc (20 mL×3). The combined organic phases were dried over anhydrous Na$_2$SO$_4$, filtered, and concentrated to obtain the crude product. The crude product was purified by flash silica gel column chromatography (DCM:MeOH=20:1) to obtain the yellow solid product II-111-5 (0.44 g, yield of 54%), MS (ESI) m/z: 516.1 [M+H]$^+$.

Step 6: Synthesis of II-111-6

TFA (2.0 mL) was added dropwise to a mixture of II-111-5 (200 mg, 0.39 mmol) and DCM (10 mL) at 0° C., and the resulting mixture was stirred for 16 hours at 25° C. The reaction mixture was concentrated to dryness and added with water (10 mL) and EtOAc (30 mL), and the organic phase was separated. The organic phase was washed with saturated brine (20 mL), dried over anhydrous Na$_2$SO$_4$, filtered, and concentrated. The crude product was purified by silica gel column chromatography (DCM: MeOH=10:1) to obtain the yellow solid product II-111-6 (82 mg, yield of 48.6%), MS (ESI) m/z: 432.1 [M+H]$^+$.

Step 7: Synthesis of II-111

NaH (28.0 mg, 0.6 mmol) was added to a mixture of II-111-6 (100.0 mg, 0.2 mmol) and DMF (5 mL) at 0° C., and the resulting mixture was stirred for 1 hour under nitrogen atmosphere, then added with a mixture of 4-bromo-2-methylbutan-2-ol (41.7 mg, 0.25 mmol) in DMF (1 mL) at 0° C., and the resulting reaction mixture was stirred for 16 hours at 25° C. The reaction mixture was diluted with water (10 mL) and extracted with EtOAc (30 mL×3). The combined organic phases were washed with saturated brine (50 mL), dried over anhydrous Na$_2$SO$_4$, filtered, and concentrated. The crude product was purified by preparative HPLC to obtain the white solid product II-111 (21.16 mg, yield of 20.4%), MS (ESI) m/z: 518.2 [M+H]$^+$. $^1$H NMR (400 MHz, DMSO-d$_6$) δ 11.74 (s, 1H), 8.96 (s, 1H), 8.76-8.68 (m, 2H), 8.42 (s, 1H), 7.99 (s, 1H), 7.83 (s, 1H), 7.80 (d, J=5.2 Hz, 2H), 4.54-4.46 (m, 3H), 2.61 (s, 3H), 2.08-2.02 (m, 2H), 1.98 (s, 3H), 1.16 (s, 6H).

Example II-122: Synthesis of II-122

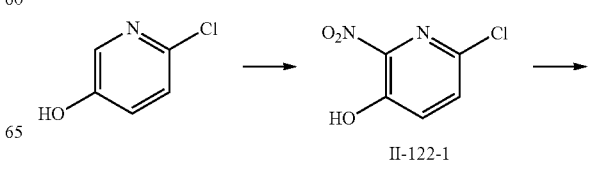

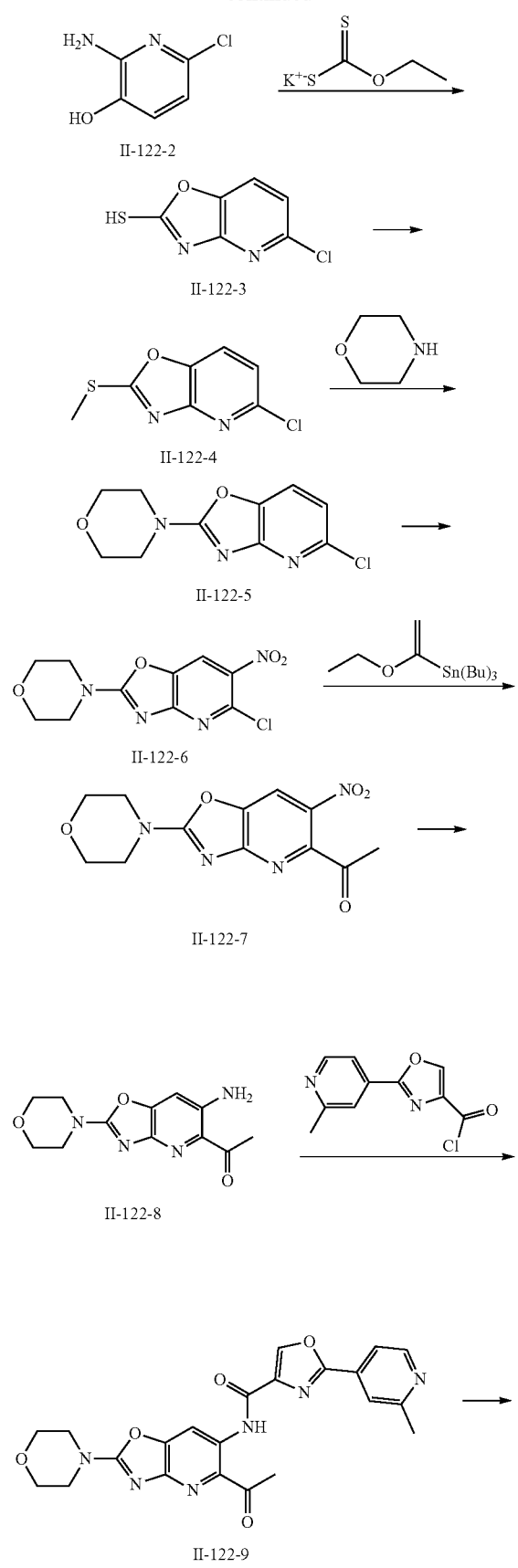

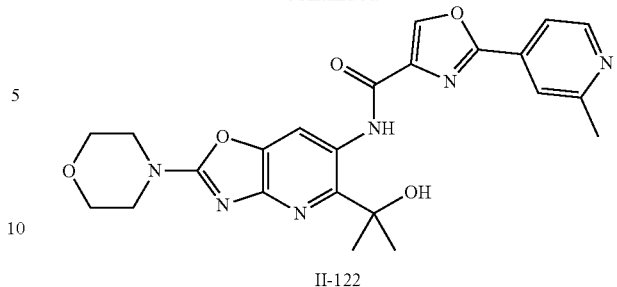

Step 1: Synthesis of II-122-1

Concentrated sulfuric acid (125 mL) was cooled to 0° C. and added with 6-chloropyridin-3-ol (25 g, 0.195 mol) in portions while stirring. The mixture was kept at 0° C. and added with potassium nitrate (35.5 g, 0.351 mol) in portions, and the resulting mixture was stirred for 4 hours at 25° C. After the reaction was complete, the reaction mixture was quenched with ice water (100 mL), and the resulting solid was filtered and dried in vacuum to obtain the product II-122-1 (26 g, yield of 92%), MS (ESI) m/z: 174.9 [M+H]$^+$.

Step 2: Synthesis of II-122-2

II-122-1 (15 g, 85.7 mmol) was dissolved in methanol (150 mL), and Raney nickel (wet, 7.0 g) was added thereto. The mixture was replaced with hydrogen three times and then stirred for 16 hours at 25° C. under hydrogen atmosphere (about 1 to 2 atmospheres). After the reaction was complete, the reaction mixture was filtered through diatomite, and the filtrate was concentrated in vacuum to obtain the crude product II-122-2 (17 g), MS (ESI) m/z: 145.1 [M+H]$^+$.

Step 3: Synthesis of II-122-3

Potassium ethylxanthate (21.6 g, 0.300 mol) was added to a mixture of II-122-2 (14.5 g, 0.100 mol) and pyridine (150 mL) at 25° C., and the resulting mixture was stirred for 12 hours at 100° C. under nitrogen atmosphere. The reaction mixture was quenched with ice water (30 mL), pyridine was removed in vacuum, and the reaction mixture was acidified with concentrated HCl until the pH of the mixture was adjusted to about 1.0. The reaction mixture was filtered and dried in vacuum to obtain the desired product II-122-3 (18 g, yield of 95%), MS (ESI) m/z: 186.9 [M+H]$^+$.

Step 4: Synthesis of II-122-4

$K_2CO_3$ (8.10 g, 58.8 mmol) was added to a mixture of II-122-3 (11.0 g, 58.8 mmol) and ethyl acetate (150 mL), and iodomethane (8.35 g, 58.8 mmol) was added thereto. The resulting mixture was stirred for 3 hours at 25° C. After the reaction was complete, the reaction mixture was added with water (100 mL) and ethyl acetate (200 mL), and extracted, and the phases were separated. The combined organic phases were dried over anhydrous $Na_2SO_4$ and concentrated to obtain the crude product. The crude product was slurried with ethyl acetate: n-hexane=1:9 to obtain the off-white solid compound of II-122-4 (5.0 g, yield of 42%), MS (ESI) m/z: 201.1 [M+H]⁺. ¹H NMR (CDCl₃, 400 MHz): δ 7.65 (d, J=8.4 Hz, 1H), 7.20 (d, J=8.4 Hz, 1H), 2.79 (s, 3H).

Step 5: Synthesis of II-122-5

Morpholine (5.73 g, 65.7 mmol) was added to a mixture of II-122-4 (2.20 g, 10.9 mmol) and THF (50 mL) at 25° C., and the resulting mixture was stirred and refluxed for 12 hours. After the reaction was complete, the reaction mixture was concentrated under reduced pressure to remove THF, and then the reaction was quenched with ice water (20 mL). The reaction mixture was filtered and dried in vacuum to obtain the product II-122-5 (2.20 g, yield of 84%), MS (ESI) m/z: 240.1 [M+H]⁺. ¹H NMR (CDCl₃, 400 MHz): δ 7.38 (d, J=8.4 Hz, 1H), 6.94 (d, J=8.0 Hz, 1H), 3.83-3.81 (m, 4H), 3.77-3.75 (m, 4H).

Step 6: Synthesis of II-122-6

Concentrated sulfuric acid (15 mL) was cooled to 0° C., added with II-122-5 (2.20 g, 9.17 mmol) in batches, and then added with potassium nitrate (1.76 g, 17.41 mmol) in batches, and the resulting mixture was stirred for 12 hours at 25° C. After the reaction was complete, the reaction mixture was quenched with ice water (100 mL). The resulting solid was filtered and dried in vacuum to obtain the product II-122-6 (2.0 g, yield of 76%), MS (ESI) m/z: 285.1 [M+H]⁺. ¹H NMR (DMSO-d₆, 300 MHz): δ 8.60 (s, 1H), 3.75 (s, 8H).

Step 7: Synthesis of II-122-7

Tributyl(1-ethoxyvinyl)tin (2.03 g, 5.63 mmol) and Pd(PPh₃)Cl₂ (197 mg, 0.281 mmol) were added to a mixture of II-122-6 (800 mg, 2.81 mmol) and anhydrous DMF (10 mL), and the resulting mixture was stirred for 2 hours at 110° C. After the reaction was complete, the reaction mixture was cooled to 0° C. and added with THF (10 mL), and 2N HCl (10 mL) was added thereto. The resulting mixture was stirred for 2 hours at 25° C. and basified with saturated NaHCO₃ until the pH of the mixture was adjusted to 8 to 9. The mixture was filtered through diatomite, the aqueous phase was extracted with EtOAc (30 mL×3), and the combined organic phases were washed with saturated brine (50 mL), dried over anhydrous Na₂SO₄, filtered, and concentrated. The crude product was purified by silica gel column chromatography (10% to 100% ethyl acetate/heptane) to obtain the light yellow solid product II-122-7 (600 mg, yield of 73%), MS (ESI) m/z: 293.1 [M+H]⁺.

Step 8: Synthesis of II-122-8

Iron powder (334 mg, 5.97 mmol) and ammonium chloride (193 mg, 3.57 mmol) were added to a mixture of II-122-7 (350 mg, 1.19 mmol), EtOH (10 mL), and water (2.5 mL). The resulting mixture was stirred for 3 hours at 60° C. under nitrogen atmosphere. After the reaction was complete, the mixture was filtered through diatomite and washed with DCM (containing 10% MeOH, 30 mL×3). The filtrate was washed with saturated brine (50 mL), dried over anhydrous Na₂SO₄, filtered, and concentrated to obtain the crude product II-122-8 (310 mg, yield of 88%), and the crude product was directly used in the next step, MS (ESI) m/z: 263.1 [M+H]⁺. ¹H NMR (DMSO-d₆, 400 MHz): δ 7.24 (s, 1H), 7.15 (s, 1H), 3.73 (s, 4H), 3.61 (s, 4H), 2.53 (s, 3H).

Step 9: Synthesis of II-122-9

2-(2-Methylpyridin-4-yl)oxazole-4-carbonyldichloride (203 mg, 0.912 mmol) was added to a mixture of II-122-8 (120 mg, 0.456 mol) and pyridine (5.0 mL), then the system was heated to 80° C., and the reaction mixture was stirred for 12 hours. After the reaction was complete, the reaction mixture was evaporated to dryness by rotary evaporation, and the crude product was purified by silica gel column chromatography (10% to 100% ethyl acetate/heptane) to obtain the brown solid product II-122-9 (100 mg, yield of 49%), MS (ESI) m/z: 449.1 [M+H]⁺.

Step 10: Synthesis of II-122

A solution of methylmagnesium bromide (2.7 mL, 2.67 mmol) was added to a mixture of II-122-9 (120 mg, 0.267 mmol) and anhydrous THF (10 mL) in an ice water bath. The resulting mixture was stirred for 3 hours at 25° C. and quenched with saturated ammonium chloride solution. The resulting mixture was extracted with EtOAc (30 mL×3), and the combined organic phases were washed with saturated brine (50 mL), dried over anhydrous Na₂SO₄, filtered, and concentrated. The crude product was purified by preparative HPLC to obtain the yellow solid II-122 (30 mg, yield of 24%), MS (ESI) m/z: 465.1 [M+H]⁺. ¹H NMR (DMSO-d₆, 400 MHz): δ 12.09 (s, 1H), 9.01 (s, 1H), 8.74 (s, 1H), 8.70 (d, J=5.2 Hz, 1H), 7.91-7.72 (m, 2H), 6.44 (s, 1H), 3.84-3.72 (m, 4H), 3.72-3.61 (m, 4H), 2.61 (s, 3H), 1.60 (s, 6H).

Referring to Example II-122, the following products can finally be synthesized:

| Molecule ID | Structure | MS (ESI) m/z: [M + H]⁺ | ¹H NMR |
|---|---|---|---|
| II-123 | 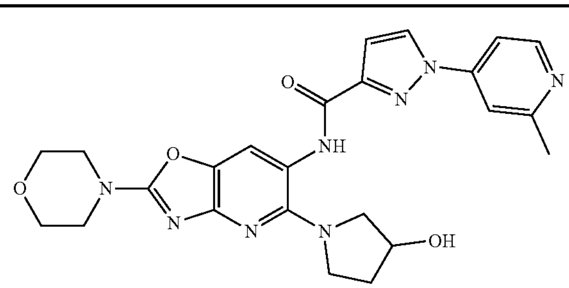 | 491.2 | (400 MHz, DMSO-d₆): δ 9.96 (s, 1H), 8.87 (s, 1H), 8.63 (d, J = 5.6 Hz, 1H), 8.00 (s, 1H), 7.90 (d, J = 5.6 Hz, 1H), 7.73 (s, 1H), 7.14 (s, 1H), 4.94 (s, 1H), 4.34 (s, 1H), 3.92-3.73 (m, 4H), 3.73-3.61 (m, 6H), 3.55-3.46 (m, 1H), 3.33 (d, J = 10.0 Hz, 1H), 2.62 (s, 3H), 1.96-1.83 (m, 2H). |

-continued

| Molecule ID | Structure | MS (ESI) m/z: [M + H]+ | 1H NMR |
|---|---|---|---|
| II-124 | 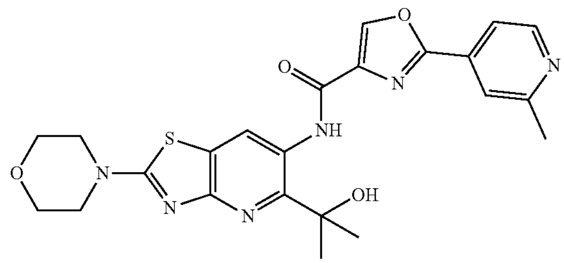 [SMILES: Cc1cc(-c2nc(C(=O)Nc3cc4sc(N5CCOCC5)nc4nc3C(C)(C)O)co2)ccn1] | 481.1 | (400 MHz, DMSO-d6): δ 12.02 (s, 1H), 9.14 (s, 1H), 9.02 (s, 1H), 8.71 (d, J = 5.2 Hz, 1H), 7.86-7.78 (m, 2H), 6.46 (s, 1H), 3.84-3.72 (m, 4H), 3.71-3.56 (m, 4H), 2.62 (s, 3H), 1.62 (s, 6H). |
| II-125 | 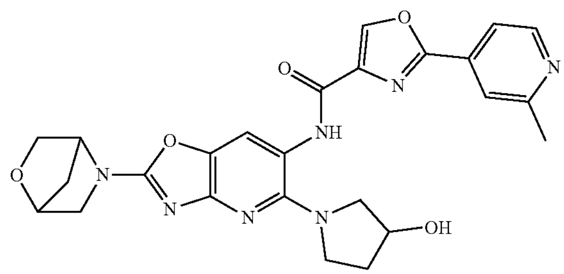 [SMILES: Cc1cc(-c2nc(C(=O)Nc3cc4oc(N5CC6CC5CO6)nc4nc3N3CCC(O)C3)co2)ccn1] | 504.2 | (400 MHz, DMSO-d6): δ 9.74 (s, 1H), 8.89 (s, 1H), 8.61 (d, J = 5.2 Hz, 1H), 7.80 (s, 1H), 7.71 (d, J = 4.8 Hz, 1H), 7.59 (s, 1H), 4.80 (d, J = 2.4 Hz, 1H), 4.67 (d, J = 10.8 Hz, 2H), 4.22 (s, 1H), 3.75 (s, 2H), 3.60-3.40 (m, 5H), 3.23-3.10 (m, 1H), 2.53 (s, 3H), 1.97-1.71 (m, 4H). |
| II-126 | 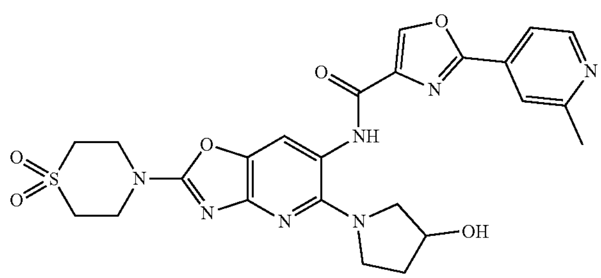 [SMILES: Cc1cc(-c2nc(C(=O)Nc3cc4oc(N5CCS(=O)(=O)CC5)nc4nc3N3CCC(O)C3)co2)ccn1] | 540.1 | (400 MHz, DMSO-d6): δ 9.86 (s, 1H), 8.98 (s, 1H), 8.68 (d, J =5.2 Hz, 1H), 7.87 (s, 1H), 7.78 (d, J = 5.2 Hz, 1H), 7.71 (s, 1H), 4.88 (d, J=2.4 Hz, 1H), 4.29 (s, 1H), 4.20-4.03 (s, 4H), 3.61-3.57 (m, 2H), 3.46-3.43 (m, 4H), 3.26-3.23 (m, 2H), 2.60 (s, 3H), 1.94-1.91 (m, 1H), 1.89-1.76 (m, 1H). |
| II-127 | 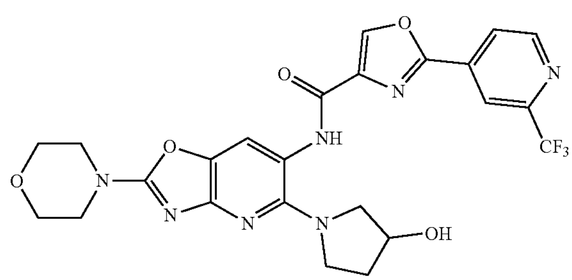 [SMILES: O=C(Nc1cc2oc(N3CCOCC3)nc2nc1N1CCC(O)C1)c1coc(-c2ccnc(C(F)(F)F)c2)n1] | 546.1 | (400 MHz, CDCl3): δ 9.48 (s, 1H), 8.94 (d, J = 5.2 Hz, 1H), 8.53 (s, 1H), 8.46 (s, 1H), 8.35 (s, 1H), 8.15 (dd, J = 5.2, 1.6 Hz, 1H), 4.59 (s, 1H), 3.83 (dd, J = 5.6, 3.6 Hz, 4H), 3.75 (dd, J = 5.6, 3.6 Hz, 4H), 3.62-3.54 (m, 1H), 3.51 (d, J = 2.4 Hz, 2H), 3.48-3.43 (m, 1H), 2.77 (br, 1H), 2.34-2.23 (m, 1H), 2.10-1.98 (m, 1H). |
| II-128 | 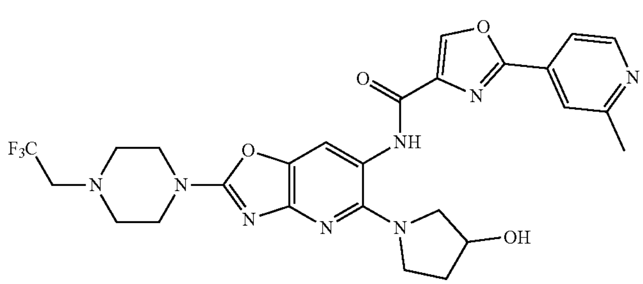 [SMILES: Cc1cc(-c2nc(C(=O)Nc3cc4oc(N5CCN(CC(F)(F)F)CC5)nc4nc3N3CCC(O)C3)co2)ccn1] | 573.2 | (400 MHz, CDCl3): δ 9.46 (s, 1H), 8.69 (d, J = 5.2 Hz, 1H), 8.51 (s, 1H), 8.40 (s, 1H), 7.81 (s, 1H), 7.74 (d, J = 4.8 Hz, 1H), 4.58 (s, 1H), 3.84-3.71 (m, 4H) (m, 4H), 3.64-3.54 (m, 1H), 3.54-3.49 (m, 2H), 3.49-3.40 (m, 1H), 3.12-2.99 (m, 2H), 2.89-2.76 (m, 5H), 2.68 (s, 3H), 2.28-2.25 (m, 1H), 2.05-2.00 (m, 1H). |

-continued

| Molecule ID | Structure | MS (ESI) m/z: [M + H]+ | 1H NMR |
|---|---|---|---|
| II-129 | 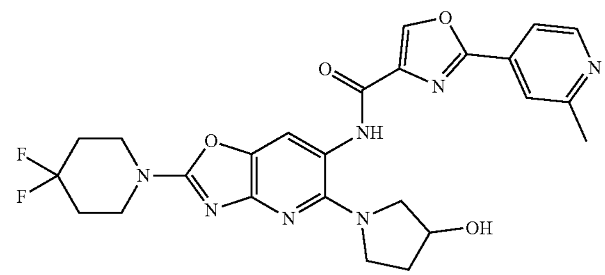 [SMILES: Cc1cc(-c2nc(C(=O)Nc3cc4oc(N5CCC(F)(F)CC5)nc4nc3N3CCC(O)C3)co2)ccn1] | 526.2 | (400 MHz, CDCl3): δ 9.44 (s, 1H), 8.69 (d, J = 4.8 Hz, 1H), 8.53 (s, 1H), 8.40 (s, 1H), 7.81 (s, 1H), 7.74 (d, J = 4.8 Hz, 1H), 4.59 (s, 1H), 3.96-3.84 (m, 4H), 3.64-3.44 (m, 4H), 2.86-2.73 (m, 1H), 2.68 (s, 3H), 2.31-2.25 (m, 1H), 2.17-2.00 (m, 5H). |
| II-130 | 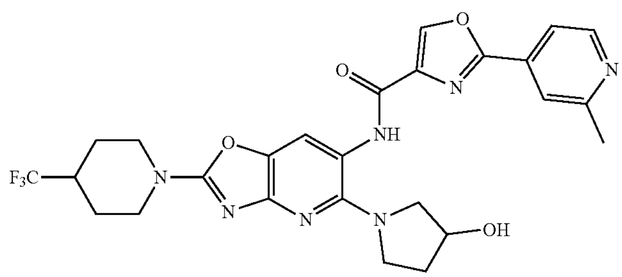 [SMILES: Cc1cc(-c2nc(C(=O)Nc3cc4oc(N5CCC(C(F)(F)F)CC5)nc4nc3N3CCC(O)C3)co2)ccn1] | 558.2 | (400 MHz, DMSO-d6): δ 9.74 (s, 1H), 8.89 (s, 1H), 8.60 (d, J = 4.4 Hz, 1H), 7.79 (s, 1H), 7.70 (d, J = 3.6 Hz, 1H), 7.59 (s, 1H), 4.82 (s, 1H), 4.20-4.16 (m, 3H), 3.53-3.51 (m, 2H), 3.38-3.32 (m, 2H), 3.18-3.09 (m, 3H), 2.43 (s, 3H), 1.89-1.86 (m, 3H), 1.76-1.65 (m, 1H), 1.47-1.45 (m, 2H). |
| II-132 | 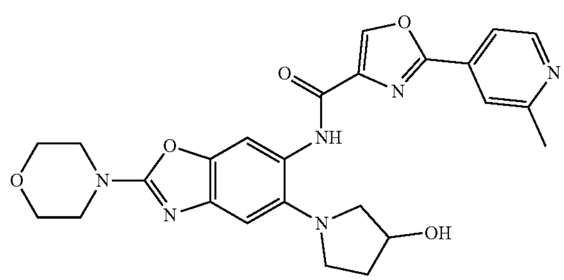 | 491.2 | (400 MHz, DMSO-d6) δ 10.10 (s, 1H), 9.01 (s, 1H), 8.68 (d, J = 5.2 Hz, 1H), 8.26 (s, 1H), 7.90 (s, 1H), 7.79 (d, J = 5.2 Hz, 1H), 7.25 (s, 1H), 5.04 (d, J = 3.6 Hz, 1H), 4.48 (br, 1H), 3.77-3.68 (m, 4H), 3.60-3.53 (m, 4H), 3.29-3.20 (m, 2H), 3.04-2.92 (m, 2H), 2.59 (s, 3H), 2.26 (m, 1H), 1.96-1.73 (m, 1H). |
| II-133 | 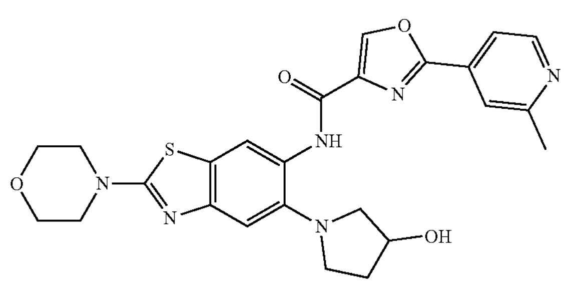 [SMILES: Cc1cc(-c2nc(C(=O)Nc3cc4sc(N5CCOCC5)nc4cc3N3CCC(O)C3)co2)ccn1] | 507.2 | (400 MHz, DMSO-d6) δ 9.89 (s, 1H), 9.00 (s, 1H), 8.68 (d, J = 5.2 Hz, 1H), 8.28 (s, 1H), 7.90 (s, 1H), 7.79 (d, J = 5.2 Hz, 1H), 7.24 (s, 1H), 5.00 (d, J = 3.6 Hz, 1H), 4.42 (br, 1H), 3.79-3.69 (m, 4H), 3.58-3.51 (m, 4H), 3.17-2.96 (m, 4H), 2.59 (s, 3H), 2.24-2.12 (m, 1H), 1.96-1.81 (m, 1H). |

Example II-131: Synthesis of II-131

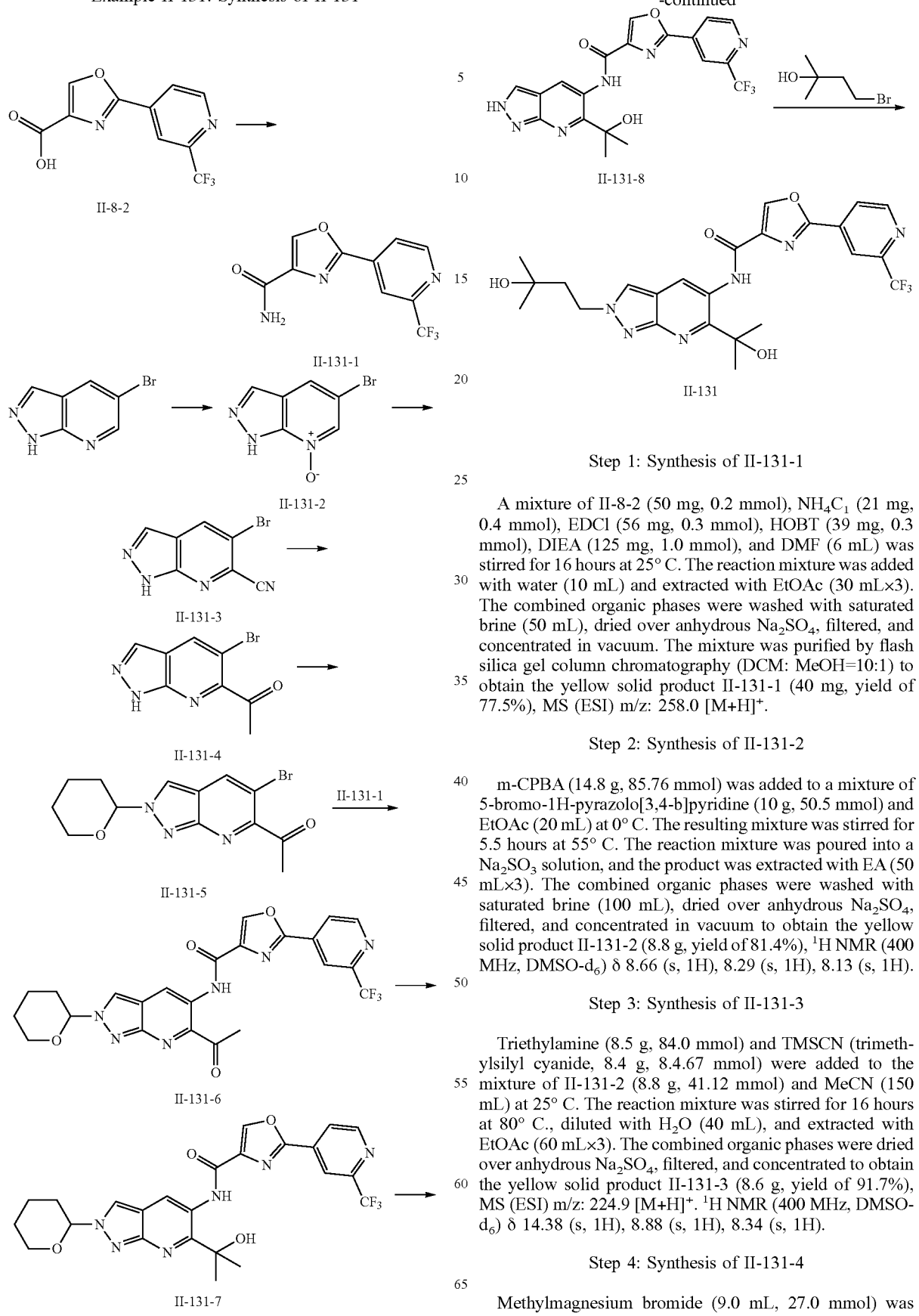

Step 1: Synthesis of II-131-1

A mixture of II-8-2 (50 mg, 0.2 mmol), $NH_4C_1$ (21 mg, 0.4 mmol), EDCl (56 mg, 0.3 mmol), HOBT (39 mg, 0.3 mmol), DIEA (125 mg, 1.0 mmol), and DMF (6 mL) was stirred for 16 hours at 25° C. The reaction mixture was added with water (10 mL) and extracted with EtOAc (30 mL×3). The combined organic phases were washed with saturated brine (50 mL), dried over anhydrous $Na_2SO_4$, filtered, and concentrated in vacuum. The mixture was purified by flash silica gel column chromatography (DCM: MeOH=10:1) to obtain the yellow solid product II-131-1 (40 mg, yield of 77.5%), MS (ESI) m/z: 258.0 $[M+H]^+$.

Step 2: Synthesis of II-131-2 m-CPBA (14.8 g, 85.76 mmol) was added to a mixture of 5-bromo-1H-pyrazolo[3,4-b]pyridine (10 g, 50.5 mmol) and EtOAc (20 mL) at 0° C. The resulting mixture was stirred for 5.5 hours at 55° C. The reaction mixture was poured into a $Na_2SO_3$ solution, and the product was extracted with EA (50 mL×3). The combined organic phases were washed with saturated brine (100 mL), dried over anhydrous $Na_2SO_4$, filtered, and concentrated in vacuum to obtain the yellow solid product II-131-2 (8.8 g, yield of 81.4%), $^1$H NMR (400 MHz, DMSO-$d_6$) δ 8.66 (s, 1H), 8.29 (s, 1H), 8.13 (s, 1H).

Step 3: Synthesis of II-131-3

Triethylamine (8.5 g, 84.0 mmol) and TMSCN (trimethylsilyl cyanide, 8.4 g, 8.4.67 mmol) were added to the mixture of II-131-2 (8.8 g, 41.12 mmol) and MeCN (150 mL) at 25° C. The reaction mixture was stirred for 16 hours at 80° C., diluted with $H_2O$ (40 mL), and extracted with EtOAc (60 mL×3). The combined organic phases were dried over anhydrous $Na_2SO_4$, filtered, and concentrated to obtain the yellow solid product II-131-3 (8.6 g, yield of 91.7%), MS (ESI) m/z: 224.9 $[M+H]^+$. $^1$H NMR (400 MHz, DMSO-$d_6$) δ 14.38 (s, 1H), 8.88 (s, 1H), 8.34 (s, 1H).

Step 4: Synthesis of II-131-4

Methylmagnesium bromide (9.0 mL, 27.0 mmol) was added to a mixture of II-131-3 (2 g, 9.0 mmol) and THF (20.0 mL) at 0° C. The resulting mixture was stirred for 3 hours at 25° C. The reaction mixture was diluted with H$_2$O (40 mL) and extracted with EtOAc (60 mL×3). The combined organic phases were dried over anhydrous Na$_2$SO$_4$, filtered, and concentrated to obtain the yellow solid product II-131-4 (1.0 g, yield of 46.3%). $^1$H NMR (400 MHz, DMSO-d$_6$) δ 8.70 (s, 1H), 8.23 (s, 1H), 2.66 (s, 3H).

Step 5: Synthesis of II-131-5

TsOH (0.2 g, 1.2 mmol) was added to a mixture of II-131-4 (1.4 g, 5.8 mmol), DHP (1.0 g, 11.7 mmol), and DCM (15 mL) at 0° C. The resulting mixture was stirred for 0.5 hours at 0° C. The reaction mixture was diluted with H$_2$O (20 mL) and extracted with EtOAc (30×3 mL). The combined organic phases were dried over anhydrous Na$_2$SO$_4$, filtered, and concentrated to obtain a crude product. The crude product was purified by flash silica gel column chromatography (PE: EtOAc=5:1) to obtain the white solid product II-131-5 (1.6 g, yield of 85.1%), MS (ESI) m/z: 324.1 [M+H]$^+$.

Step 6: Synthesis of II-131-6

A mixture of II-131-5 (126.0 mg, 0.39 mmol), II-131-1 (300.0 mg, 1.2 mmol), Xantphos (34.0 mg, 0.06 mmol), Cs$_2$CO$_3$ (381.0 mg, 1.2 mm ol), Pd$_2$(dba)$_3$ (36 mg, 0.04 mmol), and 1,4-dioxane (10.0 mL) was reacted for 1 hour at 140° C. under microwave irradiation. The reaction mixture was cooled to room temperature, poured into water, and then extracted with ethyl acetate (20 mL×3). The combined organic phases were washed with saturated brine (50 mL), dried over anhydrous Na$_2$SO$_4$, filtered, and concentrated. The crude product was purified by flash silica gel column chromatography (DCM:MeOH=10:1) to obtain the yellow solid product II-131-6 (90 mg, yield of 46.0%), MS (ESI) m/z: 501.1 [M+H]$^+$.

Step 7: Synthesis of II-131-7

A mixture of 2M methylmagnesium bromide in tetrahydrofuran (2.0 mL, 4.0 mmol) was added to a mixture of II-131-6 (200 mg, 0.4 mmol) and THF (5.0 mL) at 0° C. The resulting mixture was stirred for 5 hours at 70° C. The reaction mixture was cooled to room temperature, diluted with H$_2$O (20 mL) and extracted with EtOAc (20 mL×3). The combined organic phases were dried over anhydrous Na$_2$SO$_4$, filtered, and concentrated to obtain a crude product. The mixture was purified by flash silica gel column chromatography (DCM:MeOH=10:1) to obtain the yellow solid product II-131-7 (150 mg, yield of 72.8%), MS (ESI) m/z: 517.1 [M+H]$^+$.

Step 8: Synthesis of II-131-8

TFA (2.0 mL) was added to a mixture of II-131-7 (200 mg, 0.39 mmol) and DCM (10 mL) at 0° C., and the resulting mixture was stirred for 16 hours at 25° C. The mixture was concentrated, water (10 mL) was added to the residue, the pH of the mixture was adjusted to 8 while stirring, and the mixture was extracted with EtOAc (10 mL×3). The combined organic phases were washed with saturated brine (30 mL), dried over anhydrous Na$_2$SO$_4$, filtered, and concentrated to obtain the yellow solid product II-131-8 (50 mg, yield of 29.6%), MS (ESI) m/z: 433.1 [M+H]$^+$.

Step 9: Synthesis of II-131

NaH (15.0 mg, 0.3 mmol) was added to a mixture of II-131-8 (50.0 mg, 0.1 mmol) and DMF (5 mL) at 0° C., the resulting mixture was stirred for 1 hour under nitrogen atmosphere, and then a solution of 4-bromo-2-methylbutanol (25.0 mg, 0.2 mmol) in DMF (1 mL) was added to the resulting mixture at 0° C. The reaction mixture was stirred for 16 hours at 25° C. The reaction mixture was extracted with water (10 mL) and EtOAc (30 mL×3), and the combined organic phases were washed with saturated brine (50 mL), dried over anhydrous Na$_2$SO$_4$, filtered, and concentrated. The crude product was purified by preparative high performance liquid chromatography to obtain the white solid product II-131 (2.5 mg, yield of 4.3%), MS (ESI) m/z: 519.2 [M+H]$^+$.

Evaluation of Compound Inhibition on Kinase Activity

Based on the experimental method of fluorescence microfluidic mobility shift assay, the IC$_{50}$ value of the compound for competitive binding of ATP to kinases IRAK4 and FLT3 was determined. The initial detection concentration of the compound was 10 μM, which was diluted to 0.38 nM with a 4-fold gradient and assayed in duplicate. In this case, commercially available staurosporine was the standard control for the assay.

Information on reagents and consumables is as follows:
IRAK4 kinase (Carna, Cat. No. 09-145, Lot. No. 14CBS-0020 H)
FLT3 kinase (Carna, Cat. No. 08-154, Lot. No. 07CBS-2350)
Substrate peptide FAM-P2 (GL Biochem, Cat. No. 112394, Lot. No. P131014-XP112394)
Substrate peptide FAM-P8 (GL Biochem, Cat. No. 112396, Lot. No. P170731-SY112396)
ATP (adenosine triphosphate, Sigma, Cat. No. A7699-1G, CAS No. 987-65-5)
DMSO (dimethyl sulfoxide, Sigma, Cat. No. D2650)
EDTA (ethylenediaminetetraacetic acid, Sigma, Cat. No. E5134, CAS No. 60-00-4)
Staurosporine (Selleckchem, Cat. No. 51421)
HEPES (4-(2-Hydroxyethyl)-1-piperazineethanesulfonic acid, Gibco, Cat. No. 15630-080)
Brij-35 solution (Polyoxyethylene lauryl ether, Sigma, Cat. No. B41840-100 mL)
DTT (dithiothreitol, Sigma, Cat. No. D0632-20G)
0.2% Coating Reagent #3 (0.2% coating reagent, Perkin Elmer, Cat. No. 760050)
96-well plate (Corning, Cat. No. 3365)
384-well plate (Corning, Cat. No. 3573)

Experimental operation method:
1) FLT3 and IRAK4 kinases were dissolved in the kinase buffer (50 mM HEPES pH 7.5, 10 mM MgCl$_2$, 2 mM DTT, and 0.01% Brij-35) at final concentrations of 0.9 nM, 30 nM, and 6 nM, respectively.
2) The substrate peptide FAM-P2 and the substrate peptide FAM-P8, together with ATP, were dissolved in the above kinase buffer, respectively, where the final concentrations of the substrate peptide FAM-P2 and ATP for the determination of FLT3 were 3 μM and 97 μM, respectively; and the final concentrations of the substrate peptide FAM-P8 and ATP for the determination of IRAK4 were 3 μM and 10 μM, respectively.
3) Compound dilution: The compound was first diluted to 50 μM, and then diluted downward with DMSO in a 4-fold gradient. In this case, the solution without compound and kinase served as the blank control, corresponding to the "minimum value" shown below; the solution without compound but containing kinase, adenosine triphosphate, DMSO, and the buffer served as the positive control, corresponding to the "maximum value" shown below.

4) Kinase reaction and termination: 10 μL of the kinase buffer was added to a 384-well plate containing 5 μL of the compound to be tested, and the mixture was incubated for 10 minutes at room temperature; another 10 μL, of buffer containing the substrate peptide and adenosine triphosphate was added to the 384-well plate, and after incubation for one hour at 28° C., 25 μL, of termination solution (100 mM HEPES pH 7.5, 50 mM EDTA, 0.2% Coating Reagent #3, and 0.015% Brij-35) was added to each well for reaction termination.

5) Data reading: CaliperEZ Reader II instrument was used to read the conversion rate data. Setting conditions: downstream voltage as −500 V, upstream voltage as −2250 V, base pressure as −0.5 PSI, and screening pressure as −1.2 PSI.

6) Data calculation: the conversion rate data was copied from CaliperEZ Reader II, and the conversion rate was converted into inhibition rate data. The calculation formula is as follows:

Inhibition percentage (%)=(maximum value−conversion rate)/(maximum value−minimum value)*100%

$IC_{50}$ values were fitted with XLFit excel add-in version 5.4.0.8.

Y=Bottom+(Top−Bottom)/(1+($IC_{50}$/X)^HillSlope)  Fitting formula:

The activity data of kinase are shown in Table 1

TABLE 1

| Serial No. | FLT3 $IC_{50}$ (nM) | IRAK4 $IC_{50}$ (nM) |
|---|---|---|
| II-1 | 0.34 | 11 |
| II-2 | 0.52 | 8.4 |
| II-3F | 2.3 | 6 |
| II-4 | 12 | 72 |
| II-5C | 0.19 | 3.5 |
| II-6 | ND | 178 |
| II-7C | 100 | 94 |
| II-8 | 9.5 | 25 |
| II-9C | ND | 9.4 |
| II-10C | 2.9 | 25 |
| II-11C | 0.75 | 6.9 |
| II-12 | 0.44 | 10 |
| II-13C | 0.44 | 6.4 |
| II-14C | 0.72 | 7.5 |
| II-15C | 1.3 | 6.5 |
| II-28 | 0.79 | 16 |
| II-49 | 0.32 | 5.1 |
| II-51 | 0.32 | 6.5 |
| II-54 | 0.78 | 23 |
| II-56 | 0.24 | 3.4 |
| II-57 | 0.3 | 6.5 |
| II-59 | 0.63 | 4.9 |
| II-64 | 0.2 | 4.5 |
| II-92 | 15.53 | 4.86 |
| II-93 | 2.2 | 2.7 |
| II-94C | 0.44 | 8 |
| II-95 | 0.47 | 12 |
| II-96 | 0.22 | 3.7 |
| II-97 | 0.53 | 6.9 |
| II-98 | 0.44 | 5.2 |
| II-99 | 0.26 | 5.5 |
| II-100 | 0.62 | 22 |
| II-101 | 0.48 | 22 |
| II-102 | 0.85 | 21 |
| II-103 | 0.35 | 3.2 |
| II-104 | 2.31 | 5.3 |

TABLE 1-continued

| Serial No. | FLT3 $IC_{50}$ (nM) | IRAK4 $IC_{50}$ (nM) |
|---|---|---|
| II-105 | 39 | 2.63 |
| II-106 | 0.41 | 3.3 |
| II-107 | 0.73 | 9.22 |
| II-108 | 0.29 | 11.7 |
| II-109 | 4.2 | 6.48 |
| II-110 | 0.36 | 8.16 |
| II-111 | 0.42 | 4.94 |
| II-112 | 2.8 | 6.96 |
| II-113F | 0.38 | 4.6 |
| II-114 | 0.26 | 5.9 |
| II-115 | 0.25 | 11 |
| II-116 | ND | 7.54 |
| II-117 | 4 | 5.54 |
| II-118 | 0.44 | 12.24 |
| II-121 | 3.5 | 9.1 |
| II-122 | 6.23 | 14.1 |
| II-123 | ND | 122 |
| II-124 | 0.31 | 4.8 |
| II-125 | ND | 81.98 |
| II-128 | 13 | 44 |
| II-129 | 11 | 57 |
| II-130 | 8.9 | 26 |
| II-131 | ND | 20 |
| II-132 | 0.35 | 7.18 |
| II-133 | 0.26 | 4.84 |

"ND" in the above table refers to not detected.

Determination of the $IC_{50}$ Value of the Compound's Cytotoxicity Against MV4-11 Cells Information on reagents and consumables is as follows:
MV4-11 cells (ATCC, Cat. No. CRL-9591)
DPBS (Dulbecco's Phosphate Buffered Saline, Biosera, Cat. No. LM-52041/500)
IMDM medium (Thermo, Cat. No. 12440053)
Fetal bovine serum (Biological, Cat. No. 04-002-1A)
Penicillin-streptomycin solution (Invitrogen, Cat. No. 15140122)
Dimethyl sulfoxide (Sigma, Cat. No. D2650)
CellTiter-Glo Luminescent Cell Viability Assay (CellTiter-Glo chemiluminescent cell viability assay, Promega, Cat. No. G7573)
96-well plate (Corning, Cat. No. 3903)

CTG Experimental Steps

1. MV-4-11 cells were cultured with IMDM complete medium (IMDM+10% fetal bovine serum+1% Penicillin-Streptomycin, a mixture of penicillin-streptomycin).
2. MV-4-11 cells in good condition were collected and washed twice with DPBS (Duchenne phosphate buffered saline solution).
3. MV-4-11 cells were resuspended with IMDM complete medium, the cell density was adjusted to 1.11×10^6 cells/mL, and the MV-4-11 cells were added to 96-well plates at 90 μL per well.
4. A compound solution with 10-fold concentration was prepared with IMDM complete medium, 10 μL of the compound solution with 10-fold concentration was added to the cells in the 96-well plate, mixed well, and then the 96-well plate was placed in a 5% $CO_2$ incubator at 37° C. and incubated for 72 hours.
5. After the incubation, the 96-well plate was taken out and equilibrated for 30 minutes at room temperature. Then 100 μL of CellTiter Glo reagent was added to each well and mixed on a horizontal shaker for 2 minutes.
6. The 96-well plate was removed, equilibrated at room temperature for 10 minutes, and the chemiluminescence value was detected on a microplate reader.

183

The cytotoxic activity data are shown in Table 2

TABLE 2

| Serial No. | MV4-11 IC$_{50}$ (nM) |
|---|---|
| II-1 | 19.4 |
| II-2 | 14.8 |
| II-3F | 15 |
| II-5C | 0.78 |
| II-10C | 4.3 |
| II-11C | 4.6 |
| II-12 | 17.9 |
| II-13C | 14.6 |
| II-14C | 0.25 |
| II-15C | 8.2 |
| II-28 | 3.1 |
| II-49 | 5 |
| II-51 | 16 |
| II-54 | 35.3 |
| II-56 | 4.6 |
| II-57 | 13 |
| II-59 | 12.5 |
| II-64 | 1.3 |
| II-92 | 63.2 |
| II-93 | 21 |
| II-94C | 10.6 |
| II-95 | 18 |
| II-96 | 6.5 |
| II-97 | 13.7 |
| II-98 | 0.3 |
| II-99 | 10.9 |
| II-100 | 9 |
| II-101 | 7 |
| II-102 | 8 |
| II-103 | 3 |
| II-104 | 21 |
| II-106 | 8 |
| II-108 | 22 |
| II-109 | 15.2 |
| II-111 | 0.8 |
| II-112 | 11.9 |
| II-113F | 6.0 |
| II-114 | 1.3 |
| II-115 | 2.5 |
| II-116 | 27.3 |
| II-117 | 23.2 |
| II-118 | 6.2 |
| II-121 | 33 |
| II-122 | 33 |
| II-124 | 5 |
| II-129 | 49.6 |
| II-132 | 1.2 |
| II-133 | 0.2 |

What is claimed is:

1. A five-membered-fused six-membered compound of formula II, or a pharmaceutically acceptable salt thereof,

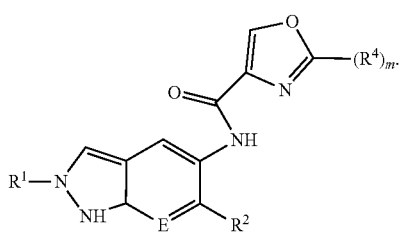

II wherein m is 1, 2, or 3;
E is N or CH;
$R^1$ is unsubstituted 3- to 11-membered heterocycloalkyl, 3- to 11-membered heterocycloalkyl substituted by one or more than one $R^{1-1}$, 3- to 10-membered cycloalkyl substituted by one or more than one $R^{1-2}$, $C_{1-6}$ alkyl substituted by one or more than one $R^{1-4}$; and the heteroatom of the 3- to 11-membered heterocycloalkyl is selected from one or more than one of N, S, and O, and the number of heteroatoms is 1, 2 or 3;
$R^{1-1}$, $R^{1-2}$, and $R^{1-4}$ are each independently deuterium, halogen, oxo,

hydroxyl, unsubstituted 3- to 11-membered heterocycloalkyl, 3- to 11-membered heterocycloalkyl substituted by one or more than one $R^{1-1-1}$, cyano, unsubstituted $C_{1-6}$ alkoxy, $C_{1-6}$ alkoxy substituted by one or more than one $R^{1-1-3}$,

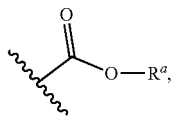

unsubstituted $C_{1-6}$ alkyl, $C_{1-6}$ alkyl substituted by one or more than one $R^{1-1-4}$ unsubstituted 3- to 10-membered cycloalkyl, 3- to 10-membered cycloalkyl substituted by one or more than one $R^{1-1-5}$, -SO$_2$-R$^a$, or

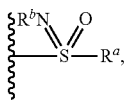

and the heteroatom of the 3- to 11-membered heterocycloalkyl is selected from one or more than one of N, S, and O, and the number of heteroatoms is 1, 2, or 3;
$R^{1-1-1}$, $R^{1-1-3}$, $R^{1-1-4}$, and $R^{1-1-5}$, are each independently deuterium, unsubstituted $C_{1-6}$ alkyl, $C_{1-6}$ alkyl substituted by one or more than one halogen, oxo,

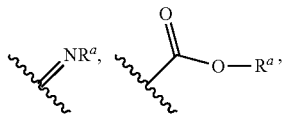

or hydroxyl;
$R^a$ and $R^b$ are each independently H or unsubstituted $C_{1-6}$ alkyl;
$R^2$ is unsubstituted 3- to 11-membered heterocycloalkyl, 3- to 11-membered heterocycloalkyl substituted by one or more than one $R^{2-1}$, unsubstituted $C_{1-6}$ alkoxy, $C_{1-6}$ alkoxy substituted by one or more than one $R^{2-7}$, hydroxyl substituted by $R^{2-8}$, or $C_{1-6}$ alkyl substituted by one or more than one $R^{2-4}$; the heteroatom of the 3- to 11-membered heterocycloalkyl is selected from one or more than one of N, S, and O, and the number of heteroatoms is 1, 2, or 3;
$R^{2-1}$ is deuterium, halogen, or hydroxyl;
$R^{2-4}$ is deuterium, halogen, or hydroxyl;
$R^{2-7}$ is deuterium, hydroxyl, halogen, oxo, unsubstituted $C_{1-6}$ alkyl, $C_{1-6}$ alkyl substituted by one or more than one halogen;

$R^{2-8}$ is 3- to 10-membered cycloalkyl, 6- to 10-membered aryl, 3- to 11-membered heterocycloalkyl, or 5- to 10-membered heteroaryl; the heteroatom of the 3- to 11-membered heterocycloalkyl is selected from one or more than one of N, S, and O, and the number of heteroatoms is 1, 2, or 3; the heteroatom of the 5- to 10-membered heteroaryl is selected from one or more than one of N, S, and O, and the number of heteroatoms is 1, 2, or 3;

$R^4$ is unsubstituted 5- to 10-membered heteroaryl, 5- to 10-membered heteroaryl substituted by one or more than one $R^{4-1}$, unsubstituted 6- to 10-membered aryl, 6- to 10-membered aryl substituted by one or more than one $R^{4-5}$, the heteroatom of the 5- to 10-membered heteroaryl is selected from one or more than one of N, S, and O, and the number of heteroatoms is 1, 2, or 3;

$R^{4-1}$ and $R^{4-5}$ are each independently halogen, unsubstituted $C_{1-6}$ alkoxy, $C_{1-6}$ alkoxy substituted by one or more than one $R^{4-1-1}$, cyano, oxo, hydroxyl, unsubstituted $C_{1-6}$ alkyl, $C_{1-6}$ alkyl substituted by one or more than one $R^{4-1-3}$;

$R^{4-1-1}$, and $R^{4-1-3}$ are each independently halogen, hydroxyl, unsubstituted $C_{1-6}$ alkyl, $C_{1-6}$ alkyl substituted by one or more than one halogen, unsubstituted $C_{1-6}$ alkoxy, or $C_{1-6}$ alkoxy substituted by one or more than one halogen.

2. The five-membered-fused six-membered compound of formula II, or the pharmaceutically acceptable salt thereof according to claim 1, wherein the five-membered-fused six-membered compound satisfies one or more than one of the following conditions:

(1) when $R^1$ is unsubstituted 3- to 11-membered heterocycloalkyl or 3- to 11-membered heterocycloalkyl substituted by one or more than one $R^{1-1}$, the 3- to 11-membered heterocycloalkyl is 3- to 9-membered heterocycloalkyl; each $R^1$-1 is independently halogen, hydroxyl, oxo,

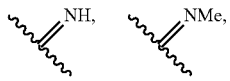

or $C_{1-6}$ alkyl substituted by one or more than one halogen or heterocycloalkyl;

(2) when $R^1$ is 3- to 10-membered cycloalkyl substituted by one or more than one $R^{1-2}$, the 3- to 10-membered cycloalkyl is $C_{3-6}$ cycloalkyl; each $R^{1-2}$ is independently -SO$_2$-R$^a$, halogen, or hydroxyl, R$^a$ is $C_{1-6}$ alkyl;

(3) when $R^1$ is $C_{1-6}$ alkyl substituted by one or more than one $R^{1-4}$, the $C_{1-6}$ alkyl is methyl, ethyl, n-propyl, isopropyl, n-butyl, isobutyl, primary butyl, sec-butyl, tert-butyl, n-pentyl, isopentyl, primary pentyl, sec-pentyl, tert-pentyl, or neopentyl; each $R^{1-4}$ is independently deuterium, halogen, hydroxyl, —SO$_2$-R$^a$,

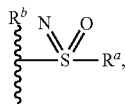

3- to 6-membered cycloalkyl substituted by hydroxyl, 3- to 8-membered heterocycloalkyl substituted by hydroxyl, 3- to 8-membered heterocycloalkyl substituted by oxo, 3- to 8-membered heterocycloalkyl substituted by halogen and Boc, or 3- to 8-membered heterocycloalkyl substituted by halogen; and the heteroatom of the 3- to 8-membered heterocycloalkyl is N and/or O, the number of heteroatoms is 1 or 2, R$^a$ is $C_{1-6}$ alkyl, and R$^b$ is hydrogen;

(4) when $R^{1-1}$, $R^{1-2}$, and $R^{1-4}$ are each independently halogen, the halogen is fluorine, chlorine, bromine, or iodine;

(5) when $R^{1-1}$, $R^{1-2}$, and $R^{1-4}$ are each independently unsubstituted 3- to 11-membered heterocycloalkyl or 3- to 11-membered heterocycloalkyl substituted by one or more than one $R^{1-1-1}$, the 3- to 11-membered heterocycloalkyl is 3- to 7-membered heterocycloalkyl;

(6) when $R^{1-1}$, $R^{1-2}$, and $R^{1-4}$ are each independently unsubstituted $C_{1-6}$ alkyl or $C_{1-6}$ alkyl substituted by one or more than one $R^{1-1-4}$, the $C_{1-6}$ alkyl is $C_{1-4}$ alkyl;

(7) when each $R^{1-1-1}$ is independently $C_{1-6}$ alkyl, the $C_{1-6}$ alkyl is $C_{1-4}$ alkyl;

(8) when $R^2$ is unsubstituted 3- to 11-membered heterocycloalkyl or 3- to 11-membered heterocycloalkyl substituted by one or more than one $R^{2-1}$, the 3- to 11-membered heterocycloalkyl is 3- to 8-membered heterocycloalkyl; each $R^{2-1}$ is independently halogen or hydroxyl;

(9) when $R^2$ is $C_{1-6}$ alkyl substituted by one or more than one $R^{2-4}$, the $C_{1-6}$ alkyl is methyl, ethyl, n-propyl, isopropyl, n-butyl, isobutyl, primary butyl, sec-butyl, tert-butyl, n-pentyl, isopentyl, primary pentyl, sec-pentyl, tert-pentyl, or neopentyl; each $R^{2-4}$ is independently deuterium, halogen, or hydroxyl;

(10) when $R^2$ is unsubstituted $C_{1-6}$ alkoxy or $C_{1-6}$ alkoxy substituted by one or more than one $R^{2-7}$, the $C_{1-6}$ alkoxy is $C_{1-4}$ alkoxy; each $R^{2-7}$ is independently deuterium or halogen;

(11) when $R^2$ is hydroxyl substituted by $R^{2-8}$, $R^{2-8}$ is 3- to 6-membered cycloalkyl or 3- to 6-membered heterocycloalkyl, and the heteroatom of the 3- to 6-membered heterocycloalkyl is oxygen, the number of heteroatoms is 1;

(12) when $R^{2-1}$, $R^{2-4}$, and $R^{2-7}$ are each independently halogen, the halogen is fluorine, chlorine, bromine, or iodine;

(13) when $R^4$ is unsubstituted 5- to 10-membered heteroaryl or 5- to 10-membered heteroaryl substituted by one or more than one $R^{4-1}$, the 5- to 10-membered heteroaryl is 6-membered heteroaryl; each $R^{4-1}$ is independently $C_{1-6}$ alkyl or $C_{1-6}$ alkyl substituted by one or more than one halogen;

(14) when $R^{4-1}$ is unsubstituted $C_{1-6}$ alkyl or $C_{1-6}$ alkyl substituted by one or more than one halogen, the $C_{1-6}$ alkyl is $C_{1-4}$ alkyl; the halogen is fluorine, chlorine, bromine, or iodine.

3. The five-membered-fused six-membered compound of formula II, or the pharmaceutically acceptable salt thereof according to claim 2, wherein the five-membered-fused six-membered compound satisfies one or more than one of the following conditions:

(1) when $R^1$ is unsubstituted 3- to 11-membered heterocycloalkyl or 3- to 11-membered heterocycloalkyl substituted by one or more than one $R^{1-1}$, the unsubstituted 3- to 11-membered heterocycloalkyl or the 3- to 11-membered heterocycloalkyl substituted by one or more than one $R^1$-1 is

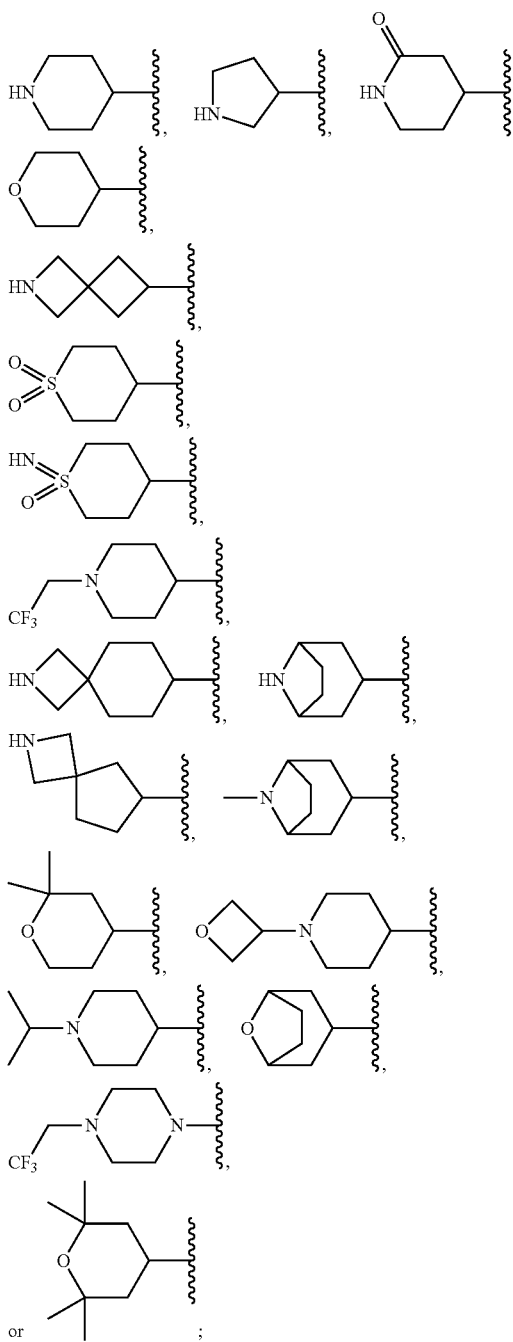

(2) when $R^1$ is 3- to 10-membered cycloalkyl substituted by one or more than one $R^{1-2}$, the 3- to 10-membered cycloalkyl substituted by one or more than one $R^{1-2}$ is

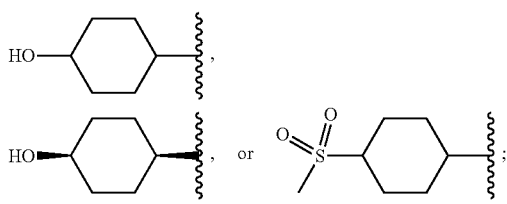

(3) when $R^1$ is $C_{1-6}$ alkyl substituted by one or more than one $R^{1-4}$, the $C_{1-6}$ alkyl substituted by one or more than one $R^{1-4}$ is

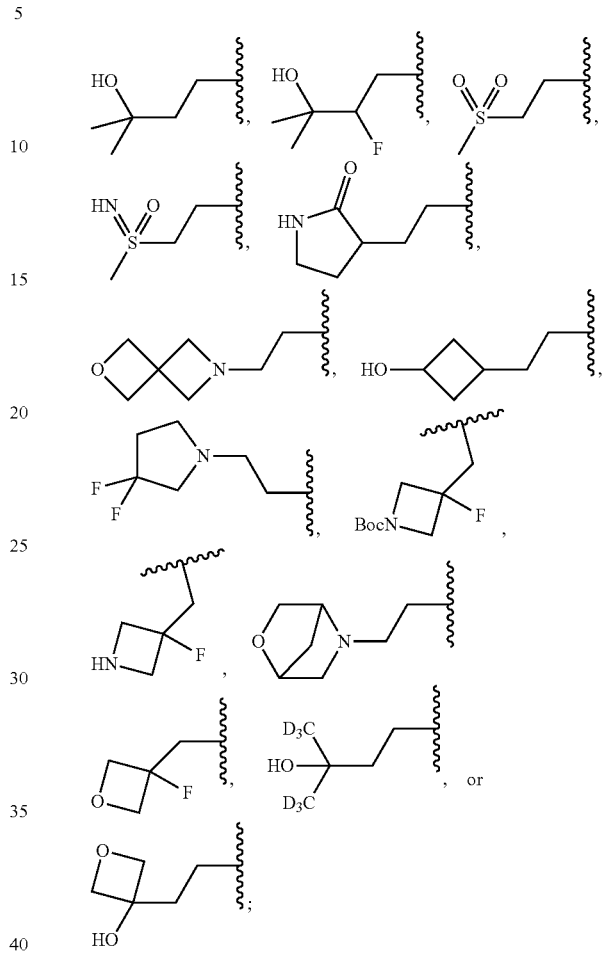

(4) when $R^{1-1}$, $R^{1-2}$, and $R^{1-4}$ are each independently halogen, the halogen is fluorine;

(5) when $R^{1-1}$, $R^{1-2}$, and $R^{1-4}$ are each independently unsubstituted 3- to 11-membered heterocycloalkyl or 3- to 11-membered heterocycloalkyl substituted by one or more than one $R^{1-1-1}$, the 3- to 11-membered heterocycloalkyl is

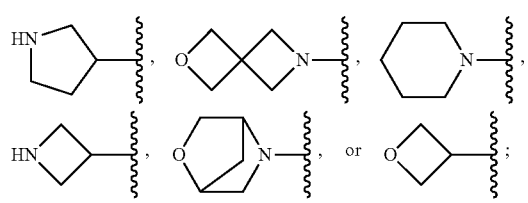

(6) when $R^{1-1}$, $R^{1-2}$, and $R^{1-4}$ are each independently $C_{1-6}$ alkyl substituted by one or more than one $R^{1-1-4}$, the $C_{1-6}$ alkyl is isopropyl, methyl or ethyl;

(7) when each $R^{1-1-1}$ is independently $C_{1-6}$ alkyl, the $C_{1-6}$ alkyl is methyl or ethyl;

(8) when $R^2$ is unsubstituted 3- to 11-membered heterocycloalkyl or 3- to 11-membered heterocycloalkyl substituted by one or more than one $R^{2-1}$, the 3- to 11-membered heterocycloalkyl is 3- to 8-membered heterocycloalkyl, and the unsubstituted 3- to 8-membered heterocycloalkyl or the 3- to 8-membered heterocycloalkyl substituted by one or more than one $R^{2-1}$ is

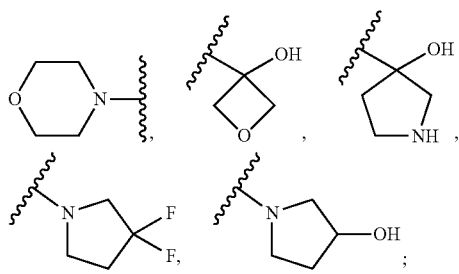

(9) when $R^2$ is $C_{1-6}$ alkyl substituted by one or more than one $R^{2-4}$, the $C_{1-6}$ alkyl substituted by one or more than one $R^{2-4}$ is

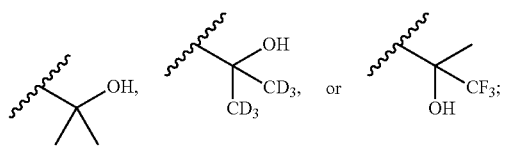

(10) when $R^2$ is unsubstituted $C_{1-6}$ alkoxy or $C_{1-6}$ alkoxy substituted by one or more than one $R^{2-7}$, the unsubstituted $C_{1-6}$ alkoxy or $C_{1-6}$ alkoxy substituted by one or more than one $R^{2-7}$ is methoxy, isopropoxy, deuterated methoxy, or trifluoromethoxy;

(11) when $R^2$ is hydroxyl substituted by $R^{2-8}$, the hydroxyl substituted by $R^{2-8}$ is

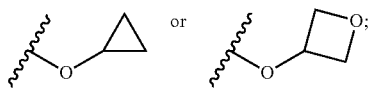

(12) when $R^{2-1}$, and $R^{2-7}$ are each independently halogen, the halogen is fluorine;

(13) when $R^4$ is unsubstituted 5- to 10-membered heteroaryl or 5- to 10-membered heteroaryl substituted by one or more than one $R^{4-1}$, the unsubstituted 5- to 10-membered heteroaryl or 5- to 10-membered heteroaryl substituted by one or more than one $R^{4-1}$ is

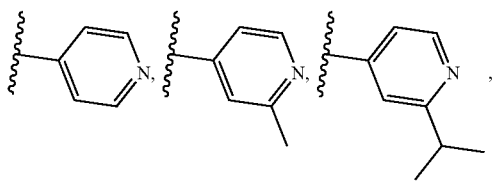

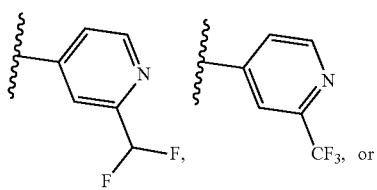

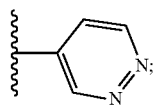

(14) when $R^4$ is unsubstituted 6- to 10-membered aryl or 6- to 10-membered aryl substituted by one or more than one $R^{4}$-5, the 6- to 10-membered aryl is phenyl, each $R^{4-5}$ is independently $C_{1-6}$ alkyl or $C_{1-6}$ alkyl substituted by one or more than one halogen.

4. The five-membered-fused six-membered compound of formula II, or the pharmaceutically acceptable salt thereof according to claim 1, wherein the five-membered-fused six-membered compound of formula I satisfies one or more than one of the following conditions:

(1) $R^{1-1}$, $R^{1-2}$, and $R^{1-4}$ are each independently deuterium, oxo, hydroxyl,

halogen,

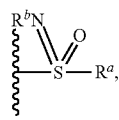

—$SO_2$-$C_{1-6}$ alkyl, unsubstituted $C_{1-6}$ alkyl, $C_{1-6}$ alkyl substituted by one or more than one $R^{1-1-4}$, unsubstituted 3- to 10-membered cycloalkyl, 3- to 10-membered cycloalkyl substituted by one or more than one $R^{1-1-5}$, unsubstituted 3- to 10-membered heterocycloalkyl, or 3- to 10-membered heterocycloalkyl substituted by one or more than one $R^{1-1-1}$; the heteroatom of the 3- to 10-membered heterocycloalkyl is one or more than one of N, O, or S, and the number of heteroatoms is 1, 2, or 3;

(2) each $R^{1-1-1}$ is independently oxo, halogen, or hydroxyl;

(3) each $R^{1-1-4}$ is independently halogen;

(4) each $R^{1-1-5}$ is independently hydroxyl;

(5) $R^2$ is unsubstituted 3- to 6-membered heterocycloalkyl, 3- to 6-membered heterocycloalkyl substituted by one or more than one $R^{2-1}$, unsubstituted $C_{1-6}$ alkoxy, $C_{1-6}$ alkoxy substituted by one or more than one $R^{2-7}$, $C_{1-6}$ alkyl substituted by one or more than one $R^{2-4}$, or hydroxyl substituted by $R^{2-8}$; the heteroatom of the 3- to 6-membered heterocycloalkyl is selected from one or two of N and O, and the number of heteroatoms is 1 or 2;

(6) $R^{2-8}$ is 3- to 6-membered cycloalkyl or 3- to 6-membered heterocycloalkyl; the heteroatom of the 3- to 6-membered heterocycloalkyl is selected from one of N and O, and the number of heteroatoms is 1;

(7) each $R^{2-1}$ is independently hydroxyl or halogen;

(8) each $R^{2-4}$ is independently deuterium, halogen, or hydroxyl;

(9) each $R^{2-7}$ is independently deuterium or halogen;

(10) each $R^4$ is independently unsubstituted 5- to 6-membered heteroaryl, 5-to 6-membered heteroaryl substituted by one or more than one $R^{4-1}$ unsubstituted phenyl, phenyl substituted by one or more than one $R^{4-5}$, the heteroatom of the 5- to 6-membered heteroaryl is N, and the number of heteroatoms is 1, 2, or 3; and

(11) $R^{4-1}$ and $R^4$-5 are each independently unsubstituted $C_{1-6}$ alkyl or $C_{1-6}$ alkyl substituted by one or more than one halogen.

5. The five-membered-fused six-membered compound of formula II, or the pharmaceutically acceptable salt thereof according to claim 4, wherein the five-membered-fused six-membered compound of formula I satisfies one or more than one of the following conditions:

(1) $R^{1-4}$ is hydroxyl, or halogen, or 3- to 11-membered heterocycloalkyl substituted by one or more than one $R^{1-1-1}$, the 3- to 11-membered hetrocycloalkyl is

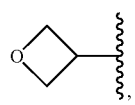

and $R^{1-1-1}$ is halogen;
(2) $R^{2-4}$ is hydroxyl; and
(3) $R^{2-7}$ is halogen.

6. The five-membered-fused six-membered compound of formula II, or the pharmaceutically acceptable salt thereof according to claim 1, wherein
$R^1$ is

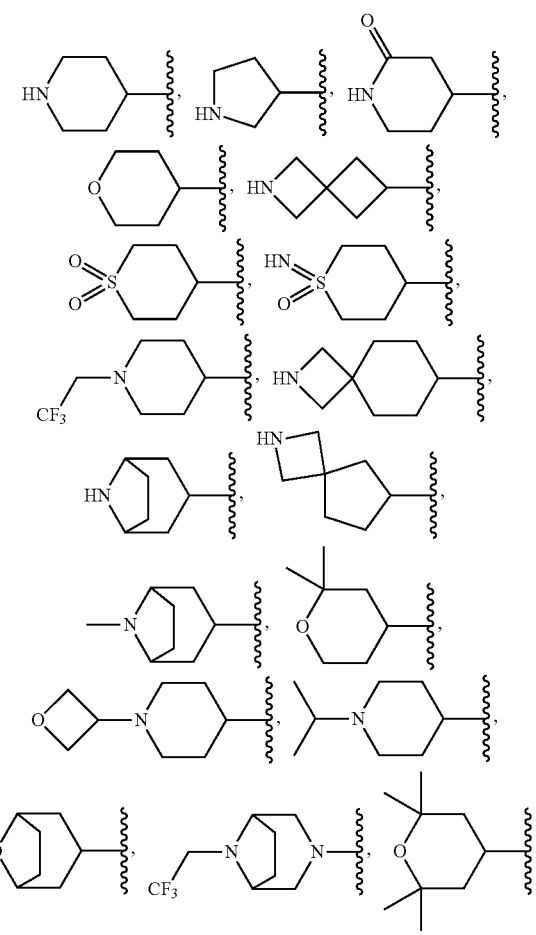

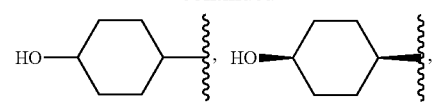

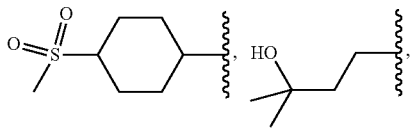

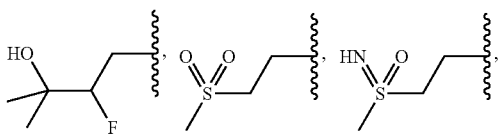

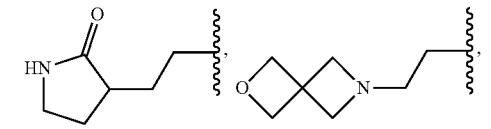

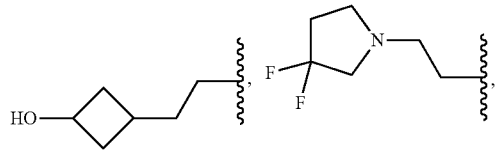

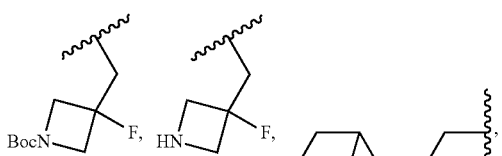

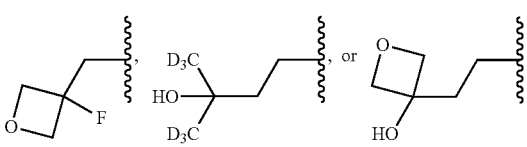

7. The five-membered-fused six-membered compound of formula II, or the pharmaceutically acceptable salt thereof according to claim 1, wherein
$R^2$ is

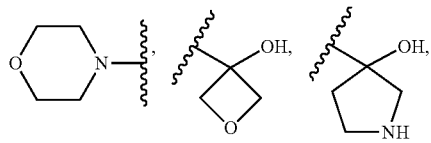

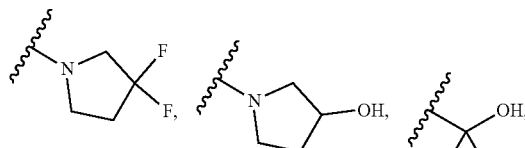

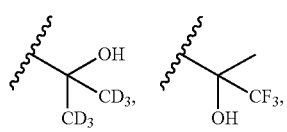

methoxy, isopropoxy, deuterated methoxy, trifluoromethoxy,

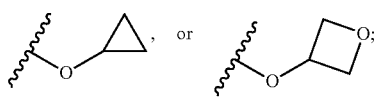 [SMILES: *OC1CC1 ; *OC1COC1]

(2) R⁴ is

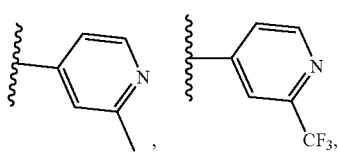

phenyl,

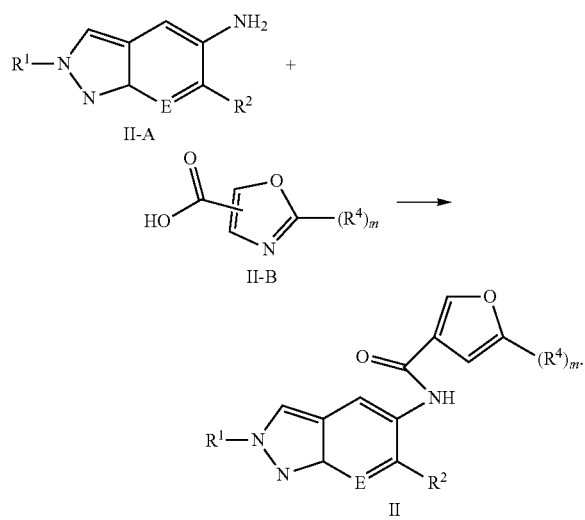

8. A preparation method for a five-membered-fused six-membered compound of formula II according to claim 1, wherein
the preparation method for the five-membered-fused six-membered compound of formula II comprises the following steps: a compound of formula II-A and a compound of formula II-B undergo a condensation reaction as shown below in a solvent with the presence of a base and a condensing agent,

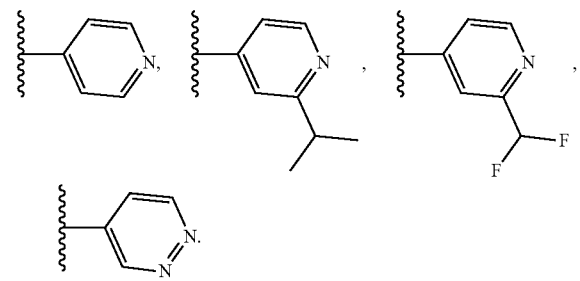

9. A pharmaceutical composition comprising the five-membered-fused six-membered compound of formula II, or the pharmaceutically acceptable salt thereof according to claim 1, and a pharmaceutically acceptable carrier.

10. A method for inhibiting an FMS-like tyrosine kinase 3 (FLT3) kinase activity in a subject comprising administering to the subject a therapeutically effective amount of the five-membered-fused six-membered compound of formula II, or the pharmaceutically acceptable salt thereof according to claim 1.

11. A method for inhibiting an interleukin-1 receptor-associated kinase 4 (IRAK4) kinase activity in a subject comprising administering to the subject a therapeutically effective amount of the five-membered-fused six-membered compound of formula II, or the pharmaceutically acceptable salt thereof according to claim 1.

12. A five-membered-fused six-membered compound of formula II, or the pharmaceutically acceptable salt thereof, having one of the following structures,

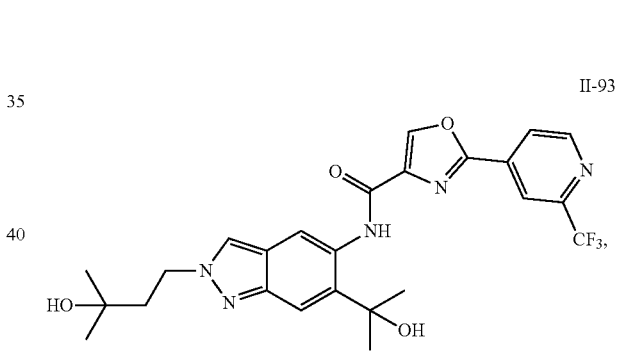

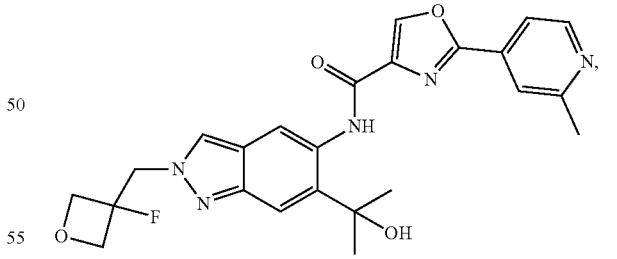

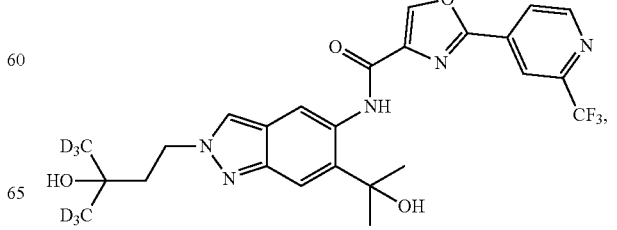

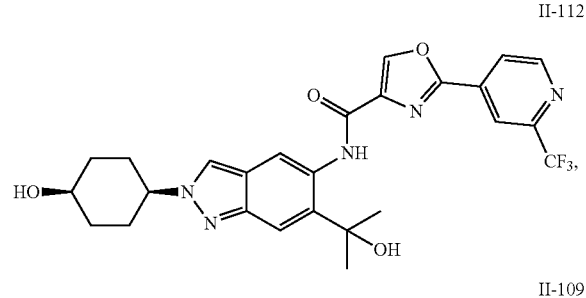
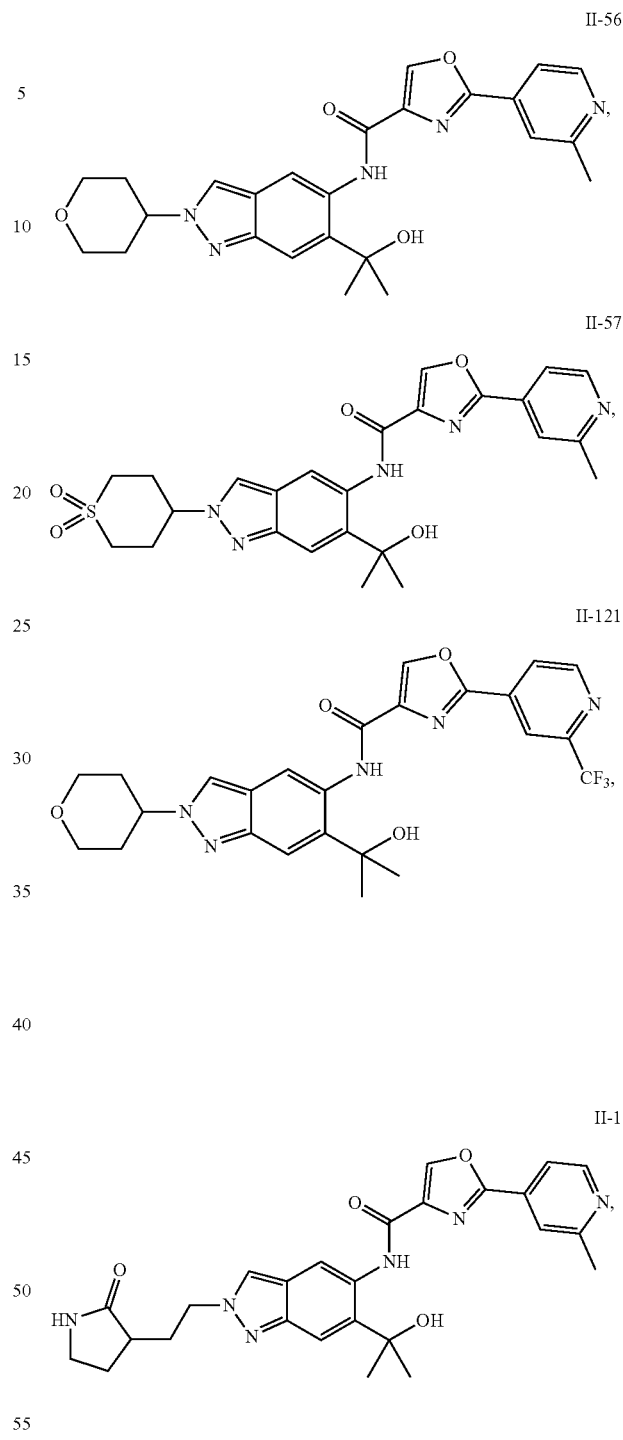
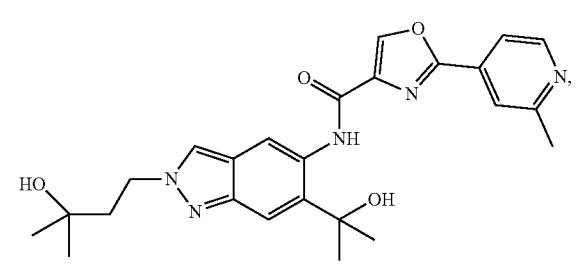

-continued
II-8
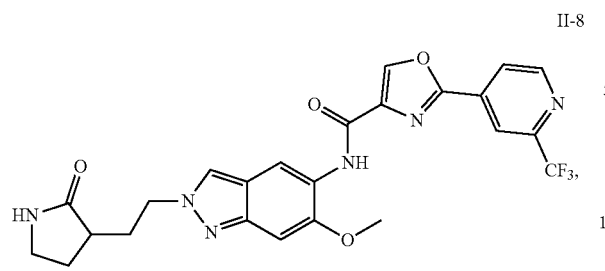
II-13
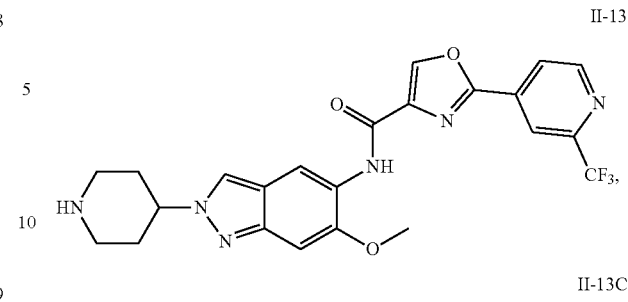
II-9
II-13C
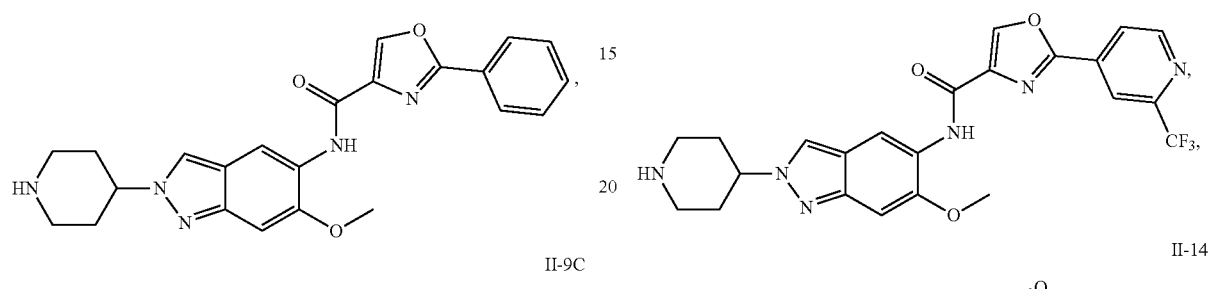
II-9C
II-14
II-10
II-14C
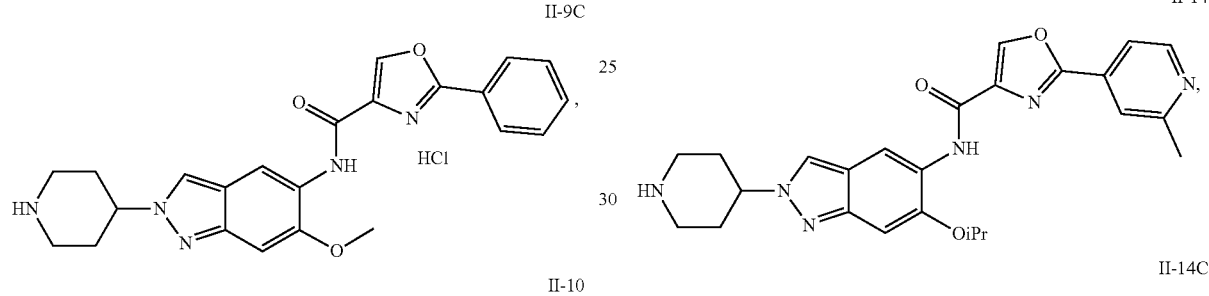
II-10C
II-51
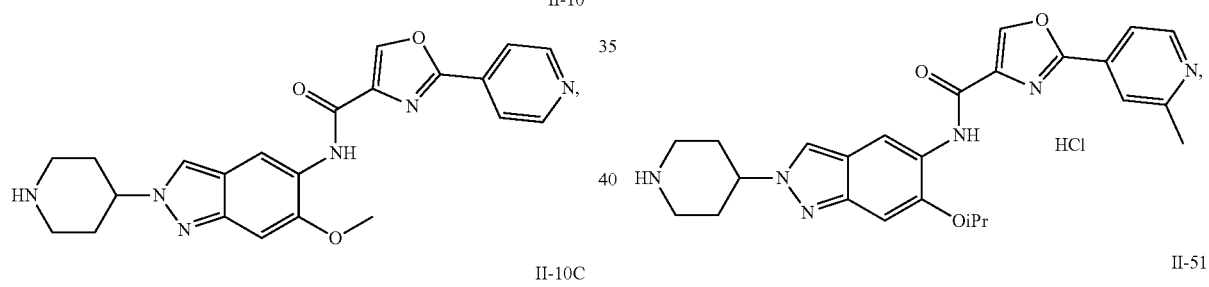
II-12
II-54
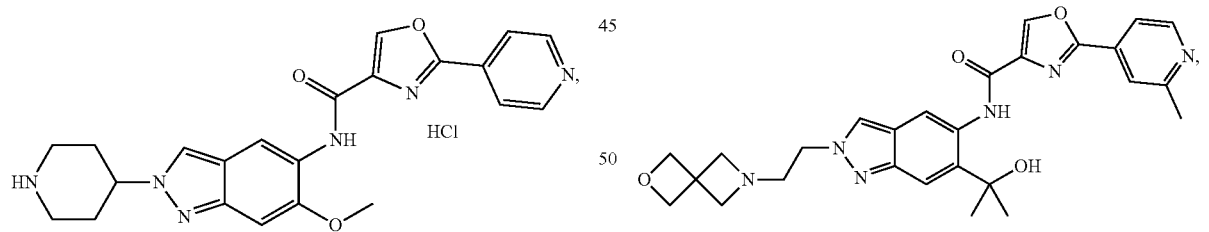
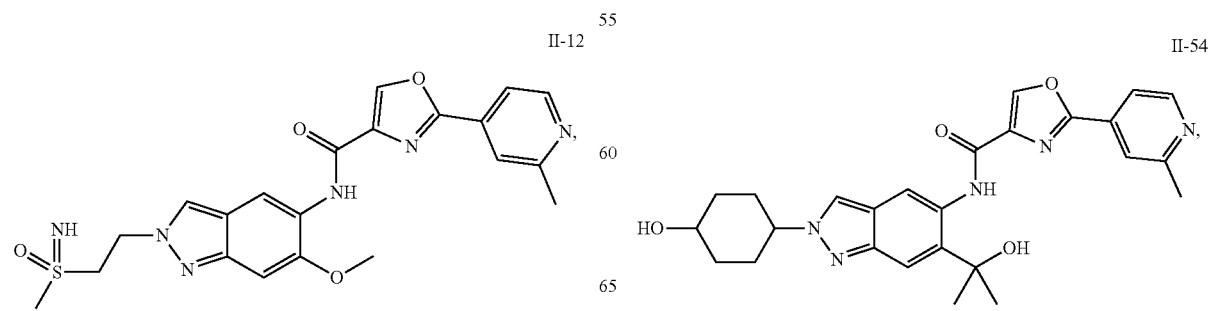

II-59
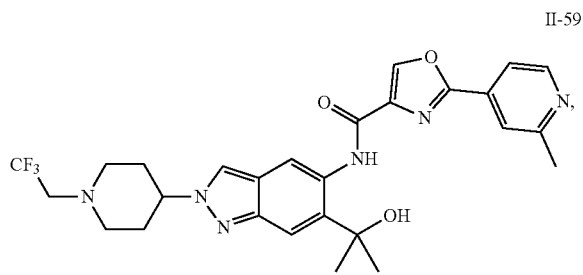
II-64
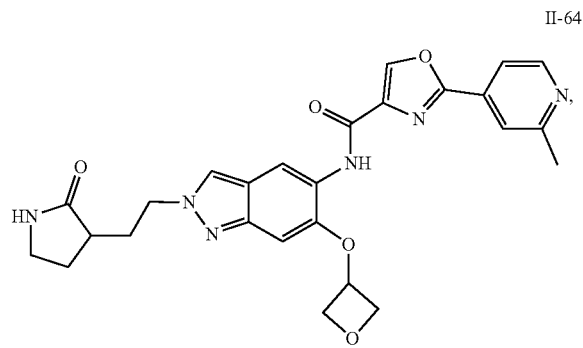
II-94
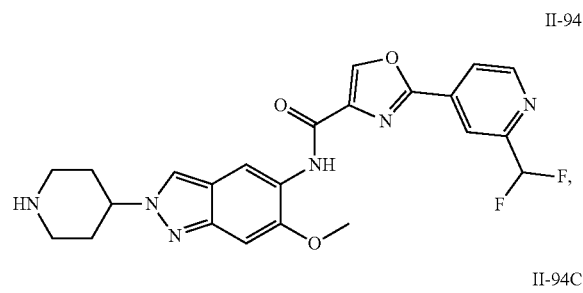
II-94C
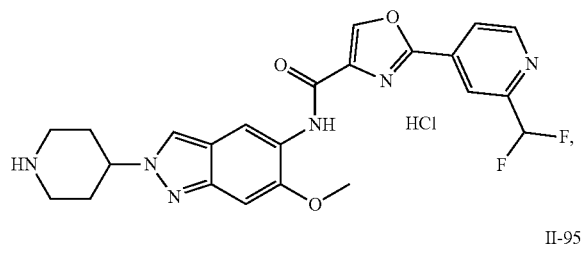
II-95
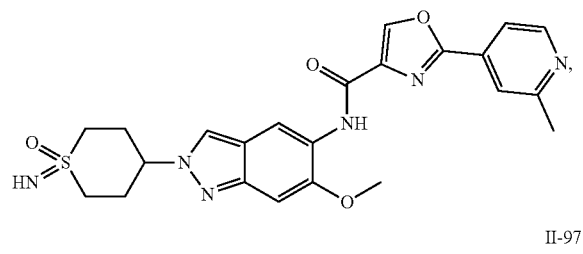
II-97
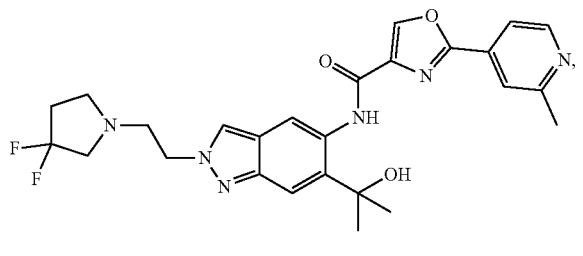
II-99
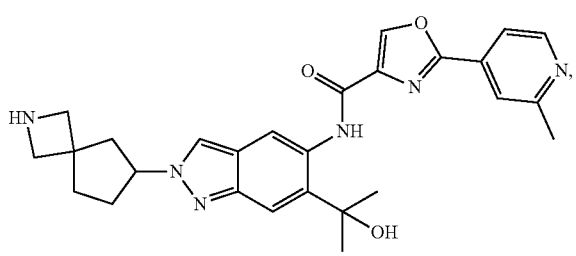
II-100
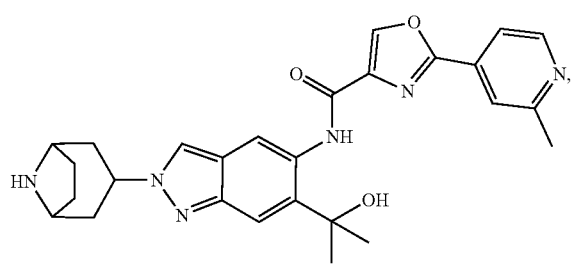
II-101
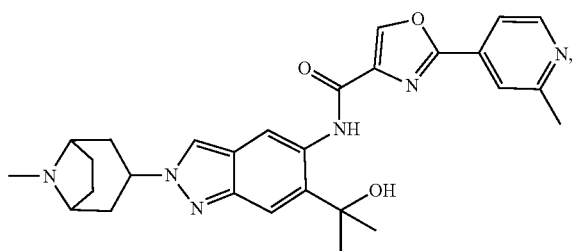
II-103
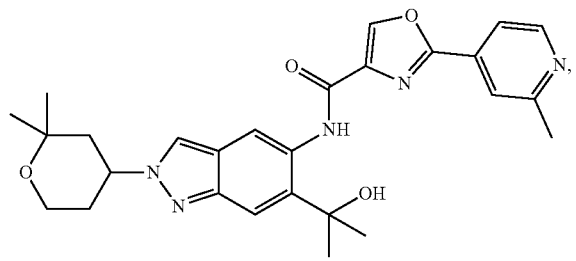
II-104
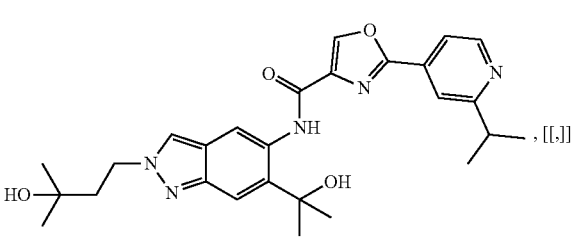
II-106
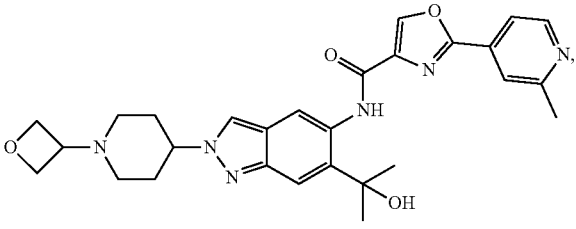

II-107
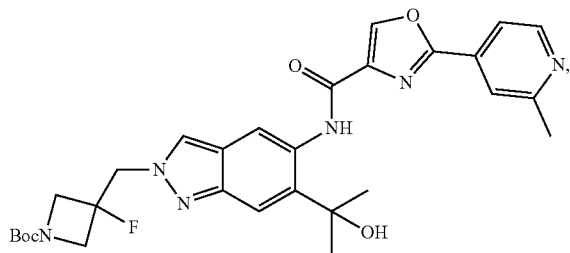
II-114
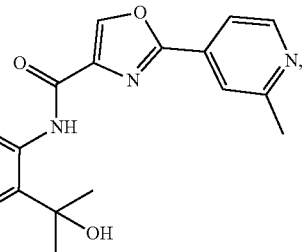
II-108
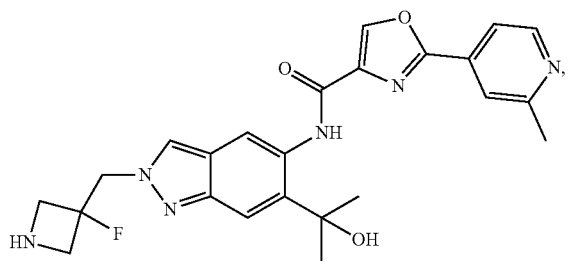
II-116
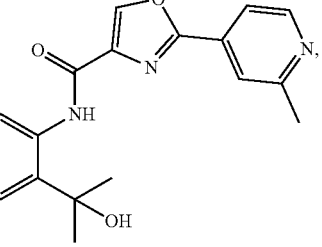
II-110
II-118
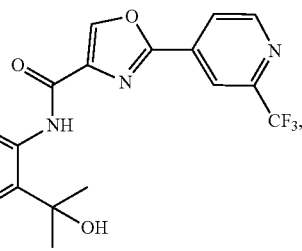
II-111
II-50
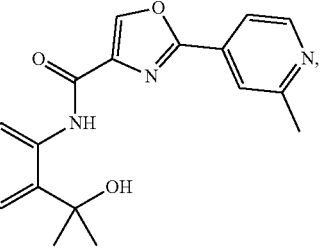
II-113
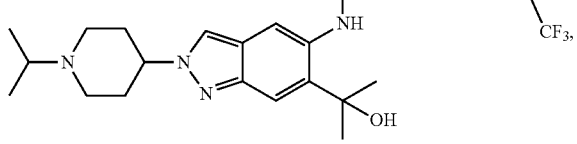
II-113F
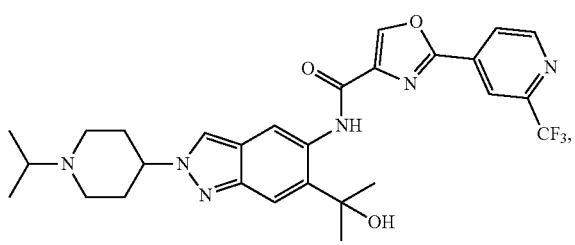
II-52
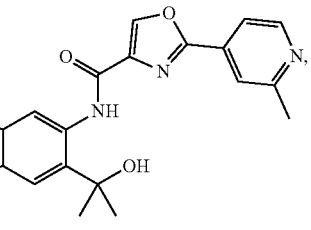

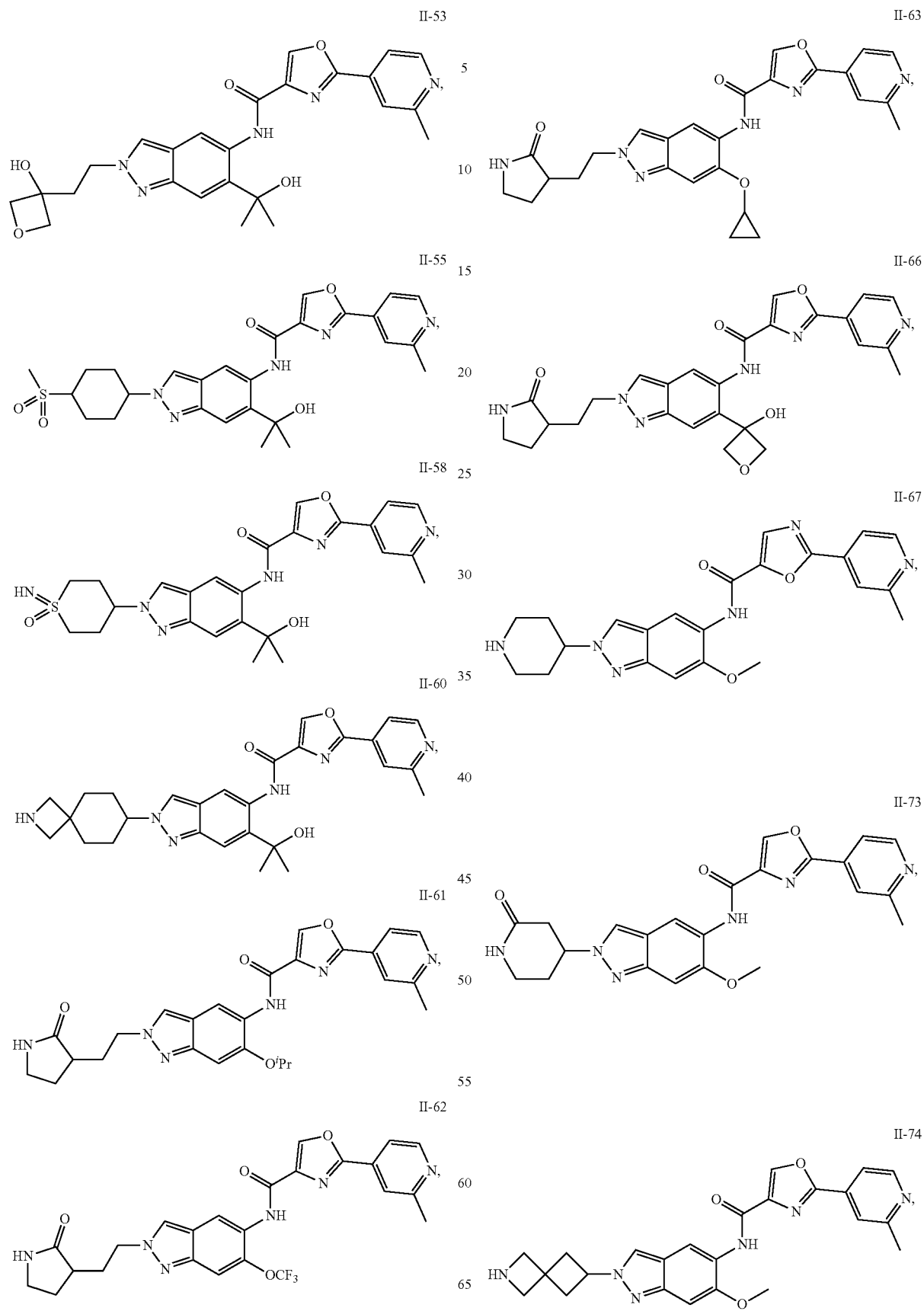

II-75
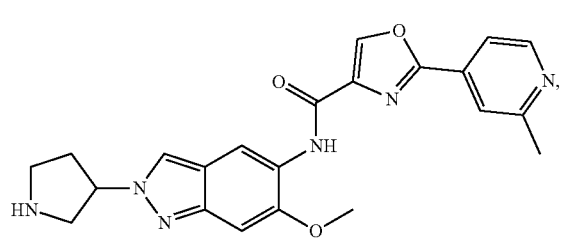
II-76
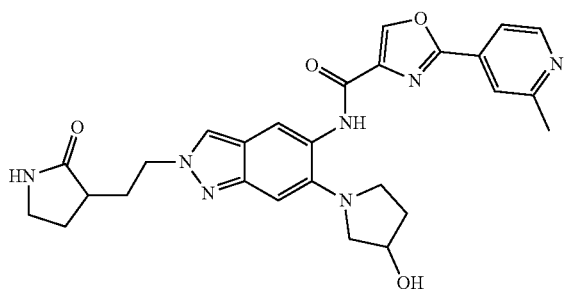
II-77
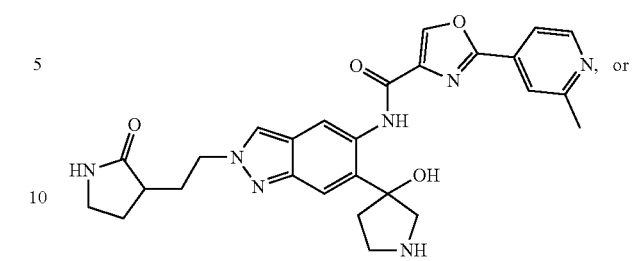
or
II-78
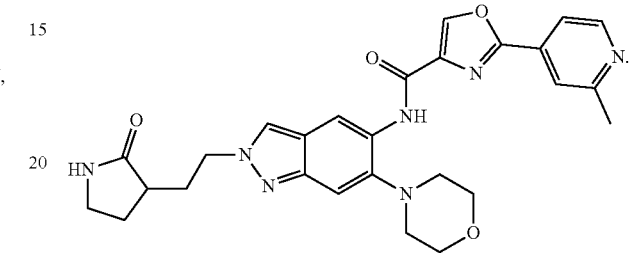
* * * * *